(12) United States Patent
Van Rensburg et al.

(10) Patent No.: US 11,819,382 B2
(45) Date of Patent: Nov. 21, 2023

(54) TISSUE BORNE FIXATION SYSTEM, DEVICE, AND METHODS OF MAKING AND USING SAME

(71) Applicant: DDS Company, Inc., Durham, NC (US)

(72) Inventors: Cornelis J. Janse Van Rensburg, Durham, NC (US); Brian Lee, Durham, NC (US); Matthew Vrhovac, Durham, NC (US); Richard Meaney, Chapel Hill, NC (US); Louis Costanzo, Chapel Hill, NC (US)

(73) Assignee: DDS Company, Inc., Durham, NC (US)

( * ) Notice: Subject to any disclaimer, the term of this patent is extended or adjusted under 35 U.S.C. 154(b) by 485 days.

(21) Appl. No.: 16/869,717

(22) Filed: May 8, 2020

(65) Prior Publication Data

US 2020/0352679 A1    Nov. 12, 2020

Related U.S. Application Data

(60) Provisional application No. 62/912,821, filed on Oct. 9, 2019, provisional application No. 62/872,829, filed
(Continued)

(51) Int. Cl.
*A61F 2/46*     (2006.01)
*A61F 2/28*     (2006.01)
(Continued)

(52) U.S. Cl.
CPC .......... *A61C 8/0089* (2013.01); *A61B 17/176* (2013.01); *A61C 1/082* (2013.01);
(Continued)

(58) Field of Classification Search
CPC ..... A61C 1/082; A61C 8/0069; A61C 8/0028; A61C 13/2656; A61C 13/225;
(Continued)

(56) References Cited

U.S. PATENT DOCUMENTS

| 1,417,237 A | 5/1922 | Evans |
| 5,542,847 A | 8/1996 | Margulies |

(Continued)

FOREIGN PATENT DOCUMENTS

| CN | 105852931 A | * | 8/2016 | ........... A61B 17/176 |
| CN | 105852931 A |   | 8/2016 | |

(Continued)

OTHER PUBLICATIONS

Alzoubi et al., "Bone Reduction to Facilitate Immediate Implant Placement and Loading Using CAD/CAm Surgical Guides for Patients with Terminal Dentition", Journal of Oral Implantology, 2016, 36 pages.
(Continued)

*Primary Examiner* — Heidi M Eide
*Assistant Examiner* — Lina Faraj
(74) *Attorney, Agent, or Firm* — Ward and Smith, P.A.; Ryan K. Simmons

(57) ABSTRACT

A surgical guide foundation system, device, and methods of making and using same. The surgical guide foundation system may include one or more foundation devices. The one or more foundation devices may include a main body portion, one or more fixation ports formed in the main body portion and forming a passage therethrough, and one or more carrier connectors (e.g., plug connector style latches) formed on the main body portion. The surgical guide foundation system may further include a guide component. The guide component may be configured to be engageable with one or more of the one or more carrier connectors. The main
(Continued)

body portion may include protrusions formed on an inner facing surface of the main body portion and extending in a generally perpendicular direction therefrom.

50 Claims, 105 Drawing Sheets

Related U.S. Application Data on Jul. 11, 2019, provisional application No. 62/845,540, filed on May 9, 2019.

(51) Int. Cl.

| | | |
|---|---|---|
| *A61B 34/10* | (2016.01) | |
| *A61C 1/08* | (2006.01) | |
| *A61C 8/00* | (2006.01) | |
| *A61B 17/17* | (2006.01) | |
| *A61F 2/30* | (2006.01) | |
| *A61C 9/00* | (2006.01) | |
| *A61B 17/56* | (2006.01) | |

(52) U.S. Cl.
CPC ............ *A61C 1/084* (2013.01); *A61C 8/0028* (2013.01); *A61C 8/0069* (2013.01); *A61B 2017/568* (2013.01); *A61B 2034/102* (2016.02); *A61B 2034/105* (2016.02); *A61B 2034/108* (2016.02); *A61C 9/0046* (2013.01)

(58) Field of Classification Search
CPC ..... A61C 13/10; A61C 13/26; A61C 13/0019; A61C 13/34; A61C 13/001; A61C 8/0089; A61C 1/084; A61C 1/085; A61C 8/009; A61B 34/10; A61B 17/176; A61F 2/4603; A61F 2002/4687
See application file for complete search history.

(56) References Cited

U.S. PATENT DOCUMENTS

| | | | |
|---|---|---|---|
| 6,926,525 B1* | 8/2005 | Rønvig | A61C 1/084 433/76 |
| D655,816 S | 3/2012 | Llop et al. | |
| 8,398,396 B2 | 3/2013 | Taormina | |
| 8,419,426 B2 | 4/2013 | Paris et al. | |
| 8,491,301 B2* | 7/2013 | Cho | A61C 1/085 433/76 |
| 8,585,402 B2 | 11/2013 | Vogel et al. | |
| 8,714,975 B2 | 5/2014 | Stumpel | |
| 8,777,612 B2 | 7/2014 | Suttin et al. | |
| 8,794,964 B2 | 8/2014 | Haber | |
| 8,899,984 B2 | 12/2014 | Llop et al. | |
| 8,956,158 B2 | 2/2015 | Schmalzle et al. | |
| 9,004,919 B2 | 4/2015 | Llop | |
| 9,226,801 B2 | 1/2016 | Groscurth et al. | |
| 9,504,533 B2* | 11/2016 | Groscurth | A61B 34/10 |
| 9,687,327 B2 | 6/2017 | Prestipino | |
| 9,693,834 B2 | 7/2017 | Llop | |
| 9,763,757 B2 | 9/2017 | Llop et al. | |
| 9,795,458 B2 | 10/2017 | Llop | |
| 10,034,722 B2 | 7/2018 | Groscurth et al. | |
| 10,213,275 B2 | 2/2019 | Groscurth et al. | |
| 10,278,789 B2 | 5/2019 | Llop et al. | |
| 10,307,226 B2 | 6/2019 | Llop et al. | |
| 10,363,115 B2 | 7/2019 | Groscurth et al. | |
| 10,398,530 B2 | 9/2019 | Llop et al. | |
| 10,405,945 B2 | 9/2019 | Llop | |
| 10,517,694 B2 | 12/2019 | Llop | |
| 10,639,129 B2* | 5/2020 | Llop | A61C 13/0004 |
| 11,160,639 B2* | 11/2021 | Palmer | A61C 13/34 |
| 11,173,016 B2* | 11/2021 | Watson | A61C 8/0068 |
| 11,553,985 B2* | 1/2023 | Fisker | A61B 34/10 |
| 2008/0124672 A1* | 5/2008 | Sussman | A61C 1/084 433/76 |
| 2009/0298008 A1 | 12/2009 | Groscurth et al. | |
| 2010/0022604 A1* | 1/2010 | Nakao | C07D 413/04 548/131 |
| 2010/0124731 A1 | 5/2010 | Groscurth et al. | |
| 2010/0203479 A1* | 8/2010 | Bulloch | A61C 8/0089 433/215 |
| 2011/0045431 A1 | 2/2011 | Groscurth et al. | |
| 2011/0045432 A1 | 2/2011 | Groscurth et al. | |
| 2011/0287381 A1* | 11/2011 | Sanders | A61C 8/0018 433/173 |
| 2012/0022604 A1* | 1/2012 | Polley | A61B 17/176 606/86 R |
| 2012/0029574 A1* | 2/2012 | Furrer | A61B 17/8061 606/280 |
| 2012/0046914 A1 | 2/2012 | Gao | |
| 2012/0191421 A1* | 7/2012 | Greenberg | A61C 1/084 703/1 |
| 2013/0071811 A1 | 3/2013 | Groscurth et al. | |
| 2014/0154638 A1* | 6/2014 | Kats | A61C 9/0006 433/49 |
| 2014/0272778 A1* | 9/2014 | Llop | A61C 1/084 433/173 |
| 2014/0358246 A1* | 12/2014 | Levy | A61F 2/4611 623/23.47 |
| 2015/0010881 A1 | 1/2015 | Llop | |
| 2015/0056575 A1 | 2/2015 | Groscurth et al. | |
| 2015/0272704 A1 | 10/2015 | Watson et al. | |
| 2015/0272705 A1 | 10/2015 | Watson et al. | |
| 2015/0308609 A1* | 10/2015 | Moens | F16M 11/121 901/50 |
| 2016/0038255 A1 | 2/2016 | Llop | |
| 2016/0106517 A1* | 4/2016 | Groscurth | A61C 9/0046 433/75 |
| 2016/0278878 A1 | 9/2016 | Watson et al. | |
| 2016/0331489 A1* | 11/2016 | Sanders | A61C 1/082 |
| 2016/0338714 A1* | 11/2016 | Schoenefeld | A61B 17/7055 |
| 2016/0346062 A1 | 12/2016 | Lococo | |
| 2016/0374778 A1* | 12/2016 | Grobbee | A61C 13/01 433/74 |
| 2017/0112365 A1* | 4/2017 | Ostrovsky | A61B 1/31 |
| 2017/0112591 A1 | 4/2017 | Llop | |
| 2017/0112592 A1 | 4/2017 | Groscurth et al. | |
| 2017/0265963 A1* | 9/2017 | Yau | A61C 1/084 |
| 2017/0290646 A1 | 10/2017 | Prestipino | |
| 2018/0036103 A1 | 2/2018 | Llop | |
| 2018/0221109 A1* | 8/2018 | Chung | A61B 17/17 |
| 2018/0263727 A1 | 9/2018 | Pellerito | |
| 2018/0333229 A1 | 11/2018 | Watson | |
| 2019/0000590 A1 | 1/2019 | Groscurth et al. | |
| 2019/0038378 A1* | 2/2019 | Nulty | A61C 8/009 |
| 2019/0209267 A1* | 7/2019 | Massoels | A61C 8/0089 |
| 2019/0216577 A1 | 7/2019 | Llop et al. | |
| 2019/0216581 A1 | 7/2019 | Watson | |
| 2019/0216851 A1* | 7/2019 | Xiao | A61P 35/00 |
| 2019/0223988 A1* | 7/2019 | Palmer | A61C 8/001 |
| 2019/0262107 A1 | 8/2019 | Jusuf et al. | |
| 2019/0314114 A1 | 10/2019 | Watson | |
| 2019/0380783 A1* | 12/2019 | Gemon | A61B 17/1757 |
| 2019/0388184 A1 | 12/2019 | Jusuf et al. | |
| 2019/0388185 A1 | 12/2019 | Jusuf et al. | |
| 2020/0015934 A1* | 1/2020 | Llop | A61B 17/176 |
| 2020/0146770 A1* | 5/2020 | Schmälzle | A61C 9/004 |
| 2020/0155271 A1 | 5/2020 | Groscurth et al. | |
| 2020/0163740 A1 | 5/2020 | Llop | |
| 2020/0352736 A1* | 11/2020 | Van Rensburg | B33Y 80/00 |
| 2021/0369402 A1* | 12/2021 | Jusuf | A61C 1/084 |
| 2021/0369407 A1* | 12/2021 | Groscurth | A61C 1/084 |
| 2022/0031364 A1* | 2/2022 | Frey | A61B 17/88 |
| 2022/0071671 A1* | 3/2022 | Little | A61B 17/8004 |
| 2022/0079709 A1* | 3/2022 | Van Rensburg | A61C 8/085 |
| 2022/0362023 A1* | 11/2022 | Toranto | A61F 2/2803 |

FOREIGN PATENT DOCUMENTS

| | | |
|---|---|---|
| EP | 1502556 A2 | 2/2005 |
| EP | 2229909 A1 | 9/2010 |

(56) References Cited

FOREIGN PATENT DOCUMENTS

| FR | 2942953 A1 | 9/2010 | | |
|---|---|---|---|---|
| KR | 2019-0041668 A | 4/2019 | | |
| WO | WO-2009115617 A1 * | 9/2009 | ............. | A61C 1/084 |
| WO | 2010061124 A1 | 6/2010 | | |
| WO | 2014/072919 A1 | 5/2014 | | |
| WO | WO-2016012223 A1 * | 1/2016 | ........... | A61B 17/176 |
| WO | 2017/069797 A1 | 4/2017 | | |
| WO | 2017/143107 A1 | 8/2017 | | |
| WO | 2017/203419 A1 | 11/2017 | | |
| WO | 2018/213817 A1 | 11/2018 | | |
| WO | 2019/144163 A1 | 7/2019 | | |
| WO | WO-2019240691 A1 * | 12/2019 | ............. | A61C 1/084 |

OTHER PUBLICATIONS

IBUR Early Stackable, "Surgical Guide Options", 2016, 2017, 1 page.

IBUR Early Stackable, "Mandible Virtually Planned Surgery", 2016, 2017, 4 pages.

Charette et al., "Cone Beam Computed Tomography Imaging as a Primary Diagnostic Tool for Computer-Guided Surgery", The Journal of Prosthetic Dentistry, 2016, 9 pages.

Hu et al., "Computer-Designed Surgical Guide Template", Medicine, 2017, 6 pages.

Pikos et al., "Guided Full-Arch Immediate-Function Treatment Modality for the Edentulous and Terminal Dentition Patient", nSequence Compendium, 2015, 6 pages, vol. 36, Issue 2.

Zhang et al., "Accuracy of Virtual Surgical Planning in Two-Jaw Orthognathic Surgery: Comparison of Planned and Actual Results", Oral and Maxillofacial Surgery, 2016, 9 pages.

Wong, "Predictable Immediate Implant Prosthetics Using Guided Surgery and Guided Prosthetics: A Case Report", Oral Health Group, 2016, available on https://www.oralhealthgroup.com/features/1003918999/, retrieved from web on Aug. 10, 2021, 21 pages.

Salama et al., "The Scalloped Guide: A Proof-of-Concept Technique for a Digitally Streamlined, Pink-Free Full-Arch Implant Protocol", The International Journal of Periodontics & Restorative Dentistry, 2018, vol. 38, No. 6, 9 pages.

Cowellmedi Co. Ltd.,"Cowell® Direct Surgical Guide Kit", available on web https://pdf.medicalexpo.com/pdf/cowellmedi/cowell-direct-surgical-guide-kit/102495-178350-_3.html, retrieved from web on Jun. 29, 2020, 2019, 13 pages.

Trobough et al., "Surgical Guide Techniques for Dental Implant Placement", Decisions in Dentistry, available on https://decisionsindentistry.com/article/surgical-guide-techniques-for-dental-implant-placement/, retrieved from web on Jun. 29, 2020, Jul. 24, 2018, 11 pages.

* cited by examiner

TISSUE BORNE FIXATION SYSTEM, DEVICE, AND METHODS OF MAKING AND USING SAME

RELATED APPLICATIONS

This application is related and claims priority to U.S. Provisional Patent Application Nos.: 62/912,821, entitled "Tissue Borne Fixation (TBF) System, Device, and Methods of Making and Using Same" filed on Oct. 9, 2019; 62/872,829, entitled "Unilateral Key Fixation (UKF) System, Device, and Methods of Making and Using Same" filed on Jul. 11, 2019; and 62/845,540, entitled "Tissue Borne Stackable Foundation Guide" filed on May 9, 2019, the applications of which are incorporate herein by reference in their entirety.

TECHNICAL FIELD

The presently disclosed subject matter relates generally to systems and methods for performing intraoral guided surgery and more particularly to a tissue borne fixation (TBF) system, device, and methods of making and using same.

In another embodiment, the presently disclosed subject matter relates generally to systems and methods for performing intraoral guided surgery and more particularly to a unilateral key fixation (UKF) system, device, and methods of making and using same.

SUMMARY

In one embodiment, a surgical guide foundation system is provided. The surgical guide foundation system, device, and methods of making and using the same. The surgical guide foundation system may include one or more foundation devices. The one or more foundation devices may include a main body portion, one or more fixation ports formed in the main body portion and forming a passage therethrough, and one or more carrier connectors (e.g., plug connector style latches) formed on the main body portion. The surgical guide foundation system may further include a guide component. The guide component may be configured to be engageable with one or more of the one or more carrier connectors. The main body portion may include protrusions formed on an inner facing surface of the main body portion and may extend in a generally perpendicular direction therefrom. The protrusions may include generally conical shaped bodies tapering to a point at a distal end. The one or more of the protrusions may be disposed proximate to the one or more fixation ports. The protrusions may be localized in groups proximal to one or more of the one or more fixation ports. The protrusions may include a length, such that when the foundation device is seated on a patient's gum tissue, the distal most ends of the protrusions are at a depth slightly less than or equal to a thickness of the patient's gum tissue. The one or more fixation ports may be configured to receive a fixation mechanism therethrough, and wherein the fixation mechanism may be configured for anchoring the foundation device to a maxillary or mandibular bone of a patient. The fixation mechanism may include one or more of a fixation pin and fixation screw. The main body portion may include two carrier connectors, and wherein a first one of the two carrier connectors extends laterally from a first side of the main body portion and a second one of the two carrier connectors extends laterally from a second opposing side of the main body portion. Each of the one or more carrier connectors may include a connection sleeve, and the connection sleeve may include a lengthwise passageway therethrough. Each of the one or more carrier connectors may include a coupling hole, and the coupling hole may include a widthwise passageway therethrough, and wherein the coupling hole may intersect with the lengthwise passageway of the connection sleeve. An inner facing surface of the main body portion may be configured to be generally of the same contour as that of a gum tissue surface of a patient. The system may further include a connector bridge (e.g., latch bridge), wherein the connector bridge may be configured to connect two adjacent foundation devices together. The connector bridge may be configured to engage with one of the one or more carrier connectors of one foundation device and an adjacent one of the one or more carrier connectors of an adjacent foundation device. The connector bridge may include a crossbar portion and two connector pins positioned at opposing end portions of the crossbar, and wherein the two connector pins extend generally perpendicular relative to the crossbar portion. The connector bridge may include a crossbar portion; two openings formed through opposing end portions of the crossbar portion; and removable bridge pins, wherein the bridge pins may be configured to be inserted at least partially through the openings. The guide component may include a component body portion and one or more component connectors. The component connectors may be spaced about an outer edge portion of the component body portion. The component connectors each may include a coupling hole, and the coupling hole may include a widthwise passageway therethrough. The carrier connectors and component connectors may be configured such that when engaged the component connectors seat into voids formed in corresponding ones of the carrier connectors, and wherein when the component connectors are seated into corresponding carrier connectors, their respective coupling holes are substantially aligned. The guide component may be securable to one or more of the one or more foundation devices via one or more coupling mechanisms inserted through their aligned coupling holes. The guide component may be configured to facilitate a dental procedure. The guide component may include any of a surgical/dental procedure guide, an alignment guide, or a prosthetic. The guide component may include a hingeable component and may include one or more hinged members, wherein the one or more hinged members may be configured to engage with one or more foundation devices via one or more carrier connectors. The one or more hinged members may include one or more carrier connectors, and wherein the one or more component connectors may be configured to be engageable with the one or more carrier connectors. The hingeable component further may include a releasable component body hingeably attached to the one or more hinged members. The releasable component body may include an alignment guide.

In another embodiment, a surgical guide foundation device is provided. The surgical guide foundation device may include a main body portion; one or more fixation ports formed in the main body portion and forming a passage therethrough; and one or more carrier connectors (e.g., plug connector style latches) formed on the main body portion. The device may further include protrusions formed on an inner facing surface of the main body portion and extending in a generally perpendicular direction therefrom. The protrusions may include generally conical shaped bodies tapering to a point at a distal end. The protrusions may be disposed proximate to the one or more fixation ports. The protrusions may be localized in groups proximal to one or more of the one or more fixation ports. The protrusions may include a length, such that when the foundation device is seated on a patient's gum tissue, the distal most ends of the protrusions are at a depth slightly less than or equal to a thickness of the patient's gum tissue. The one or more fixation ports are configured to receive a fixation mechanism therethrough, and wherein the fixation mechanism may be configured for anchoring the foundation device to a maxillary or mandibular bone of a patient. The fixation mechanism may include one or more of a fixation pin and/or fixation screw. The main body portion may include two carrier connectors, and wherein a first one of the two carrier connectors may extend laterally from a first side of the main body portion and a second one of the two carrier connectors may extend laterally from a second opposing side of the main body portion. Each of the one or more carrier connectors may include a connection sleeve, and the connection sleeve may include a lengthwise passageway therethrough. Each of the one or more carrier connectors may include a coupling hole, and the coupling hole may include a widthwise passageway therethrough, and wherein the coupling hole intersects with the lengthwise passageway of the connection sleeve. An inner facing surface of the main body portion may be configured to be generally of the same contour as that of a gum tissue surface of a patient. The one or more carrier connectors may be configured to be engageable with a guide component. The guide component may include a component body; and component connectors spaced about an outer edge portion of the guide body, wherein the component connectors are configured to engage with the carrier connectors. The guide component may include a hingeable component, and may include one or more hinged members, wherein the one or more hinged members are configured to be engageable with the one or more carrier connectors.

In yet another embodiment, a connector bridge (e.g., latch bridge) is provided. The connector bridge may be configured to connect two adjacent surgical guide foundation devices together. The connector bridge may be configured to engage with a carrier connector of a first one of the two adjacent foundation devices and an adjacent carrier connector of a second one of the two adjacent foundation devices. The connector bridge may include a crossbar portion and two connector pins positioned at opposing end portions of the crossbar, and wherein the two connector pins may extend outward generally perpendicular relative to the crossbar portion. The connector bridge may include a crossbar portion; two openings formed through opposing end portions of the crossbar portion; and removable bridge pins, and wherein the bridge pins may be configured to be inserted at least partially through the openings.

In still yet another embodiment, a method of making a surgical guide foundation system component is provided. The method may include modeling a patient's mouth; planning a desired surgical procedure; designing and fabricating a surgical guide foundation device. The designed surgical guide foundation device may include a main body portion; one or more fixation ports formed in the main body portion and forming a passage therethrough; and one or more carrier connectors (e.g., plug connector style latches) formed on the main body portion. The surgical guide foundation device further may include protrusions formed on an inner facing surface of the main body portion and extending in a generally perpendicular direction therefrom. The protrusions may include generally conical shaped bodies tapering to a point at a distal end. The protrusions may include a length, such that when the foundation device is seated on a patient's gum tissue, the distal most ends of the protrusions are at a depth slightly less than or equal to a thickness of the patient's gum tissue. The method may further include designing and fabricating one or more corresponding guide components as required based on the planned surgical procedure. The one or more guide components may be configured to be engageable with the foundation guide. The method may further include testing the fabricated surgical guide foundation device and/or one or more corresponding guide components.

In still yet another embodiment, a method of using a surgical guide foundation system is provided. The method may include positioning one or more foundation devices in a patient's oral cavity. The one or more foundation devices may include a main body portion; one or more fixation ports formed in the main body portion and forming a passage therethrough; and one or more carrier connectors (e.g., plug connector style latches) formed on the main body portion. The method may further include seating and fixating the one or more foundation devices on the patient's gum tissues; positioning and securing a guide component to the foundation guide as required for a planned procedure; conducting the planned procedure; and removing the guide component and the one or more foundation devices from the patient's oral cavity. The surgical guide foundation device further may include protrusions formed on an inner facing surface of the main body portion and extending in a generally perpendicular direction therefrom. The protrusions may include generally conical shaped bodies tapering to a point at a distal end. The protrusions may include a length, such that when the foundation device is seated on a patient's gum tissue, the distal most ends of the protrusions are at a depth slightly less than or equal to a thickness of the patient's gum tissue.

BACKGROUND

Currently, intraoral guided surgery procedures, such as, but not limited to, intraoral dental implant surgical procedures, utilize dental surgical guides and methods. However, certain drawbacks may exist when using these surgical guides and methods. For example, in dental implant surgery, the dental practitioner may use a traditional mechanical torque wrench/value based off resistance force to measure the depth and tightness of the guide screws to seat the guide. However, these values can vary greatly depending on a particular patient's bone thickness, density, and so on. Consequently, these values do not effectively account for the patient's actual gum tissue thickness, swelling, location, and so on. As a result, it is very common for a dental practitioner to overtighten the guide screws when seating the guide. Overtightening the guide screws can result in the patient's gum tissue becoming overly compressed by the guide. Compression of the gum tissue under the guide causes the blood flow to be cut off and can cause necrosis, killing or permanently damage the patient's gum tissue. Accordingly, new approaches are needed in intraoral guided surgery procedures that prevent practitioners from over tightening guide screws when seating a guide and damaging a patient's gum tissue.

Further, many current guides require that the guide to be seated directly on the patient's bone (i.e., bone borne guides) or "float" off the bone, and thereby require reflection or cutback of the patient's gum tissue. The procedure for reflection or cutback of the patient's gum tissue adds additional procedure time, complexity, and patient risk. Reflection or cutback of the patient's gum tissue is a very invasive, and can increase the patient's discomfort during and after the procedure, overall recovery time, and potential for complications. Accordingly, new approaches are needed in intraoral guided surgery procedures that are less invasive, faster, and safer, and that overall provide better patient care and recovery as compared with current methods.

In traditional intraoral guided surgery procedures, such as, but not limited to, intraoral dental implant surgical procedures, "paperclip" (buccolingual) guides and/or buccal bone engaging base or foundation guides are used for example. However, certain drawbacks exist when using in these methods. In one example, a significant amount of surgical tissue reflection is required to stabilize the guides and intraoral surgical devices. Namely, paperclip guides require significant buccal as well as lingual tissue reflection. Further, the invasive nature of intraoral guided surgery procedures and protocols can lead to high patient morbidity and extended post-surgical recovery time. Accordingly, new approaches are needed with respect to performing intraoral guided surgery procedures, such as intraoral dental implant surgical procedures.

BRIEF DESCRIPTION OF THE DRAWINGS

Figure 5:
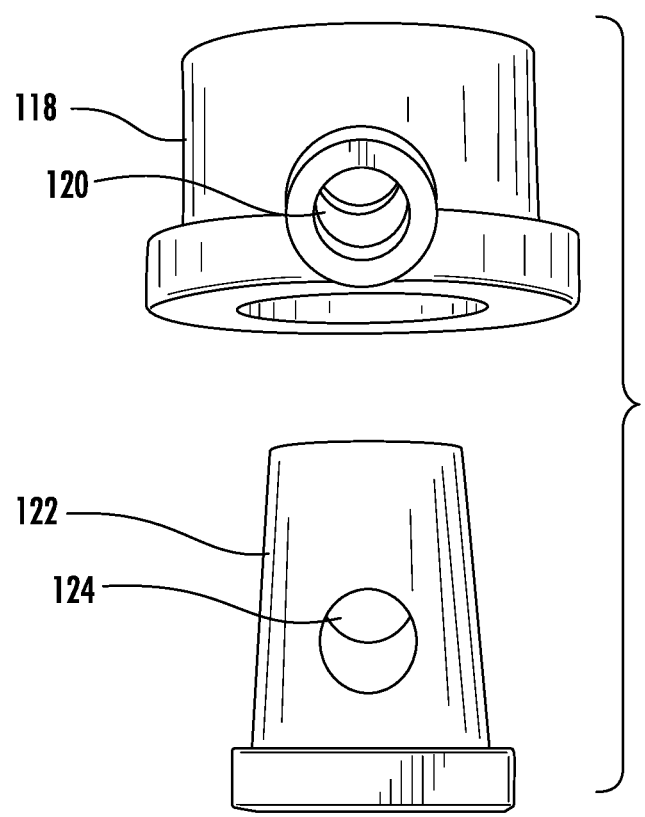
Figure 6:
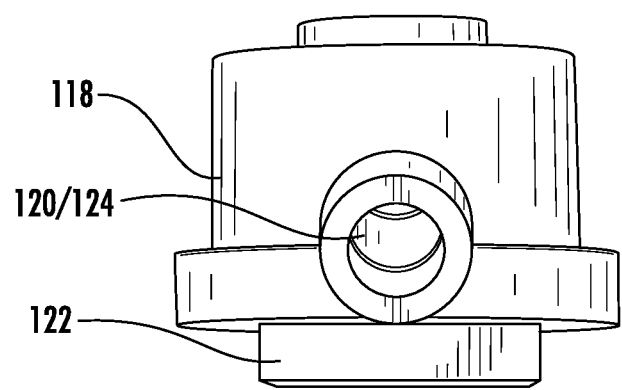
Figure 7A:
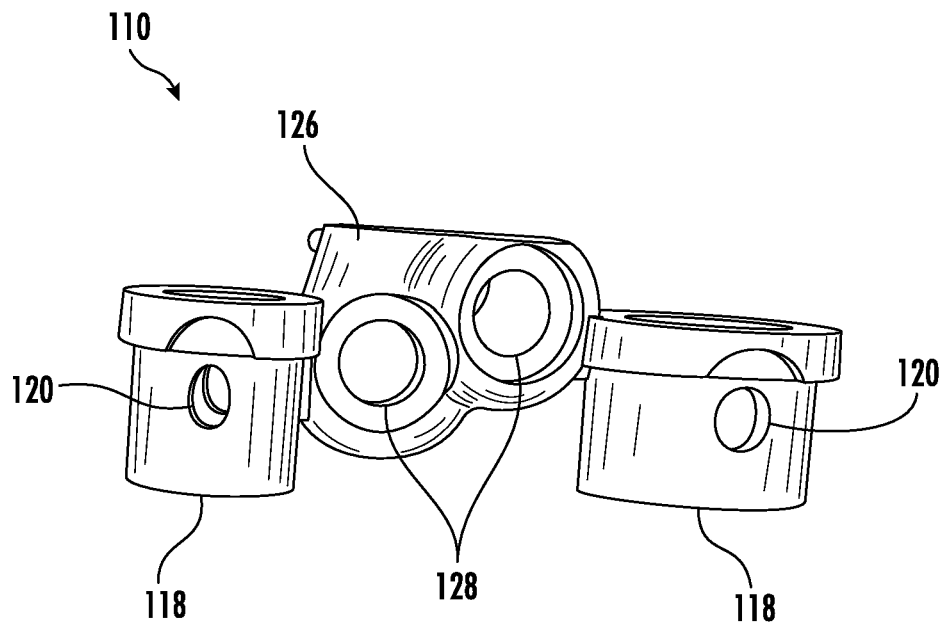
Figure 7B:
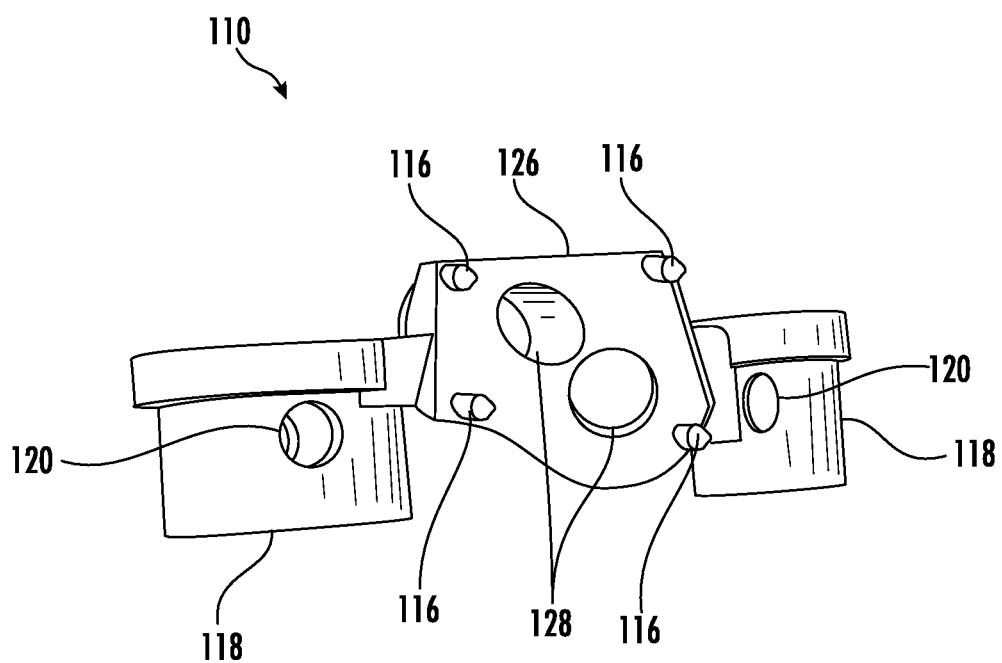
Figure 7C:
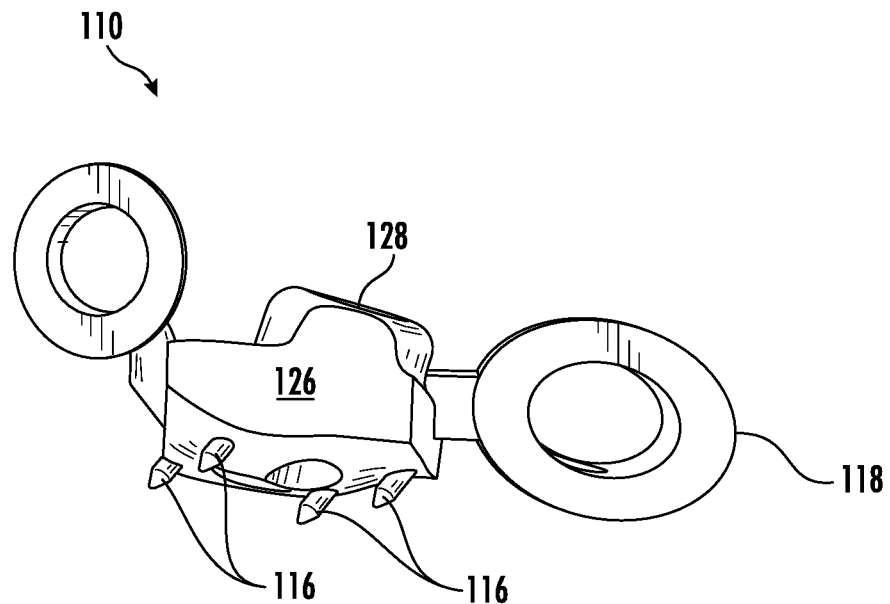
Figure 8:
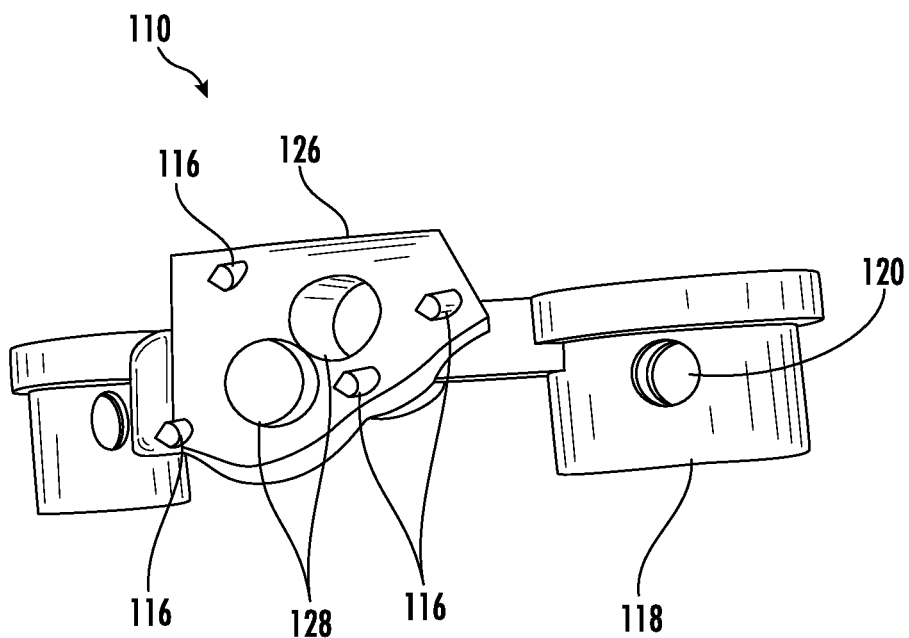
Figure 10A:
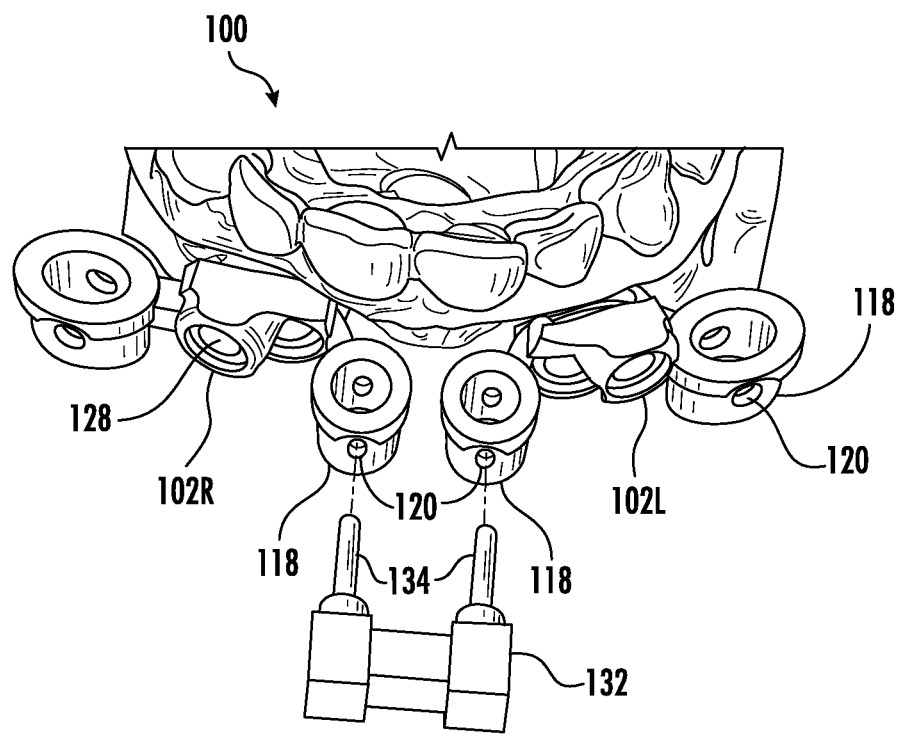
Figure 10B:
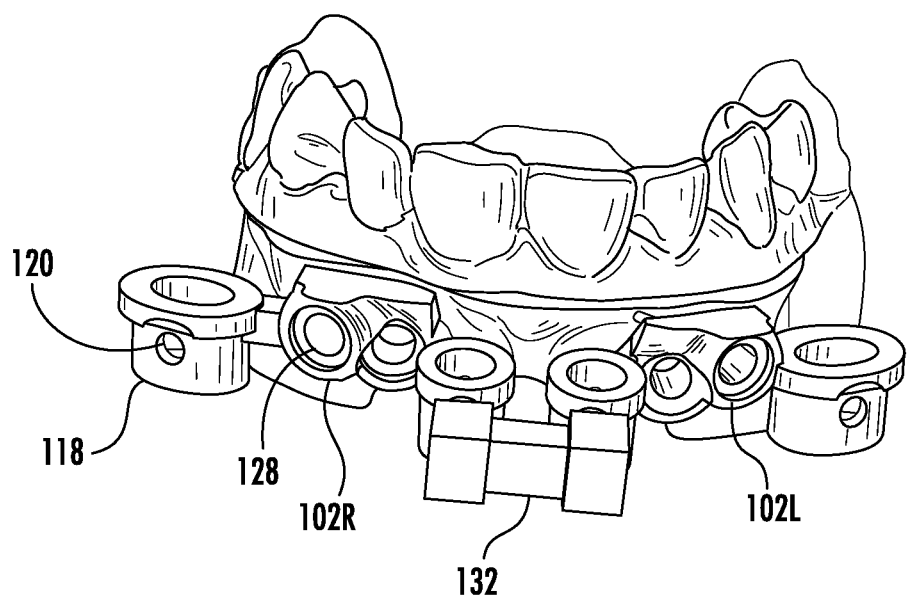
Figure 11:
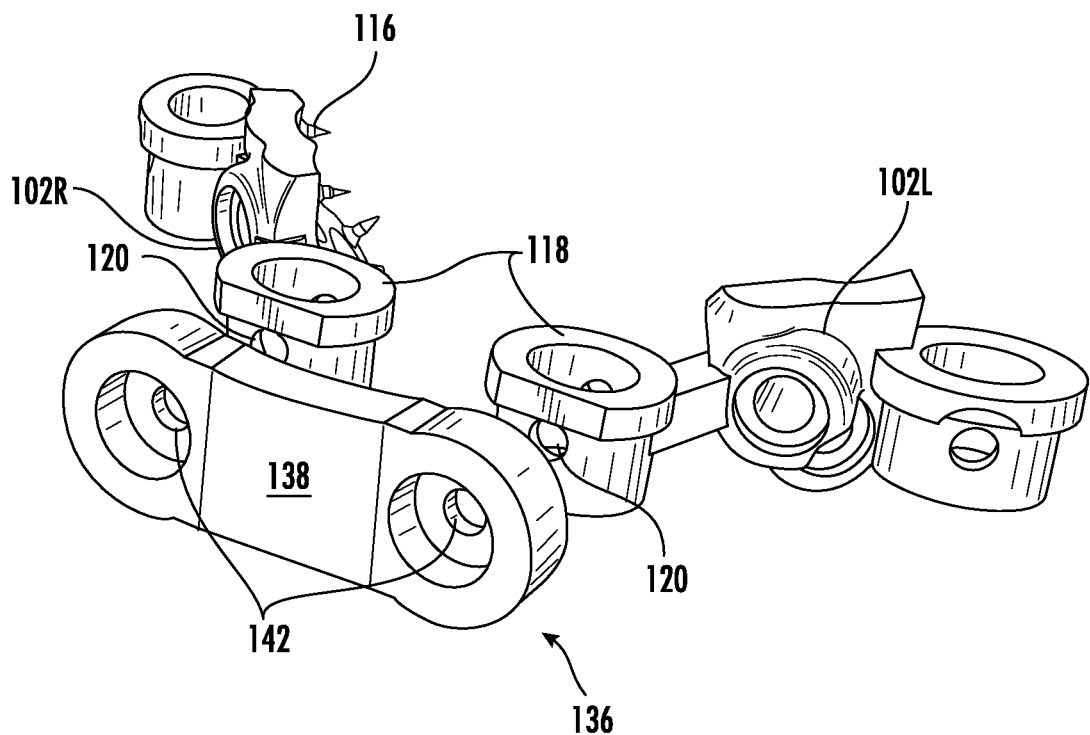
Figure 12:
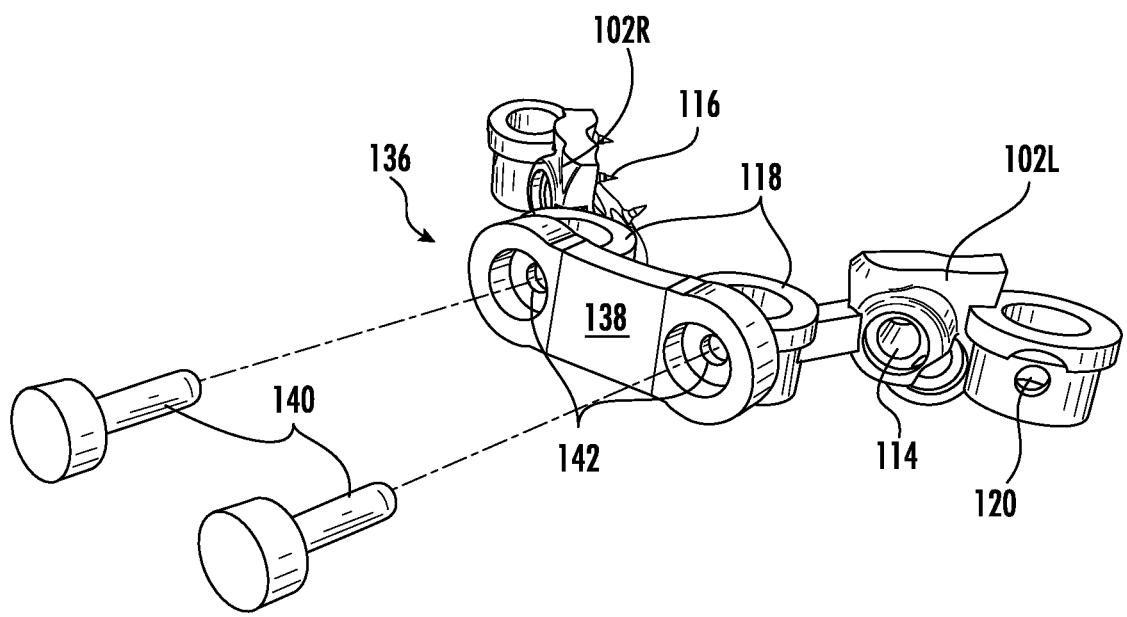
Figure 13:
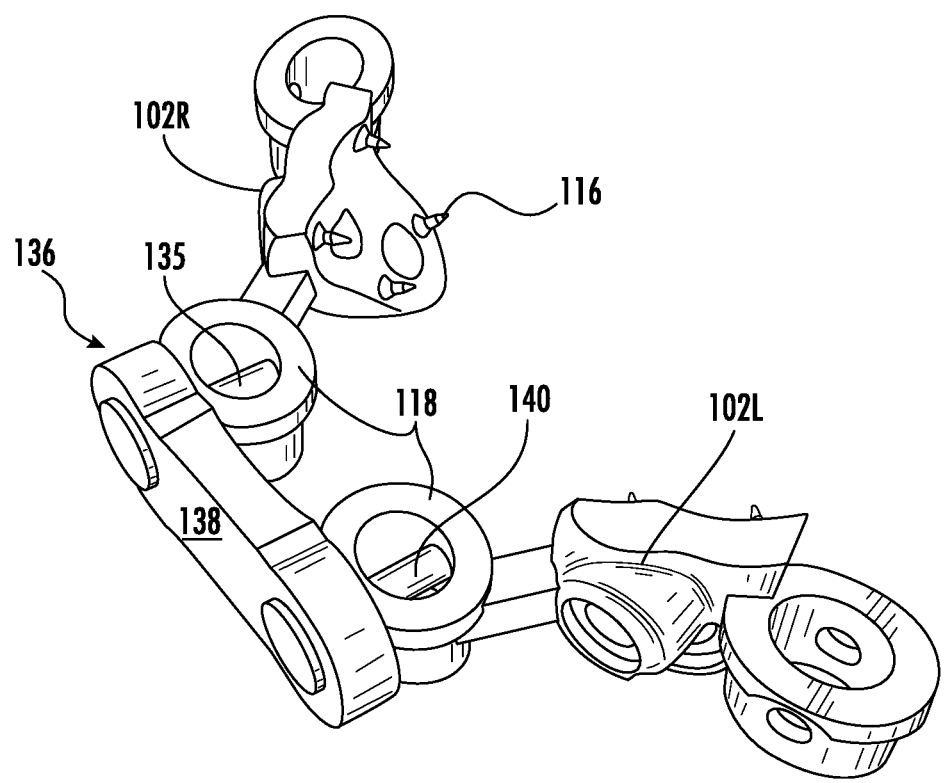
Figure 14:
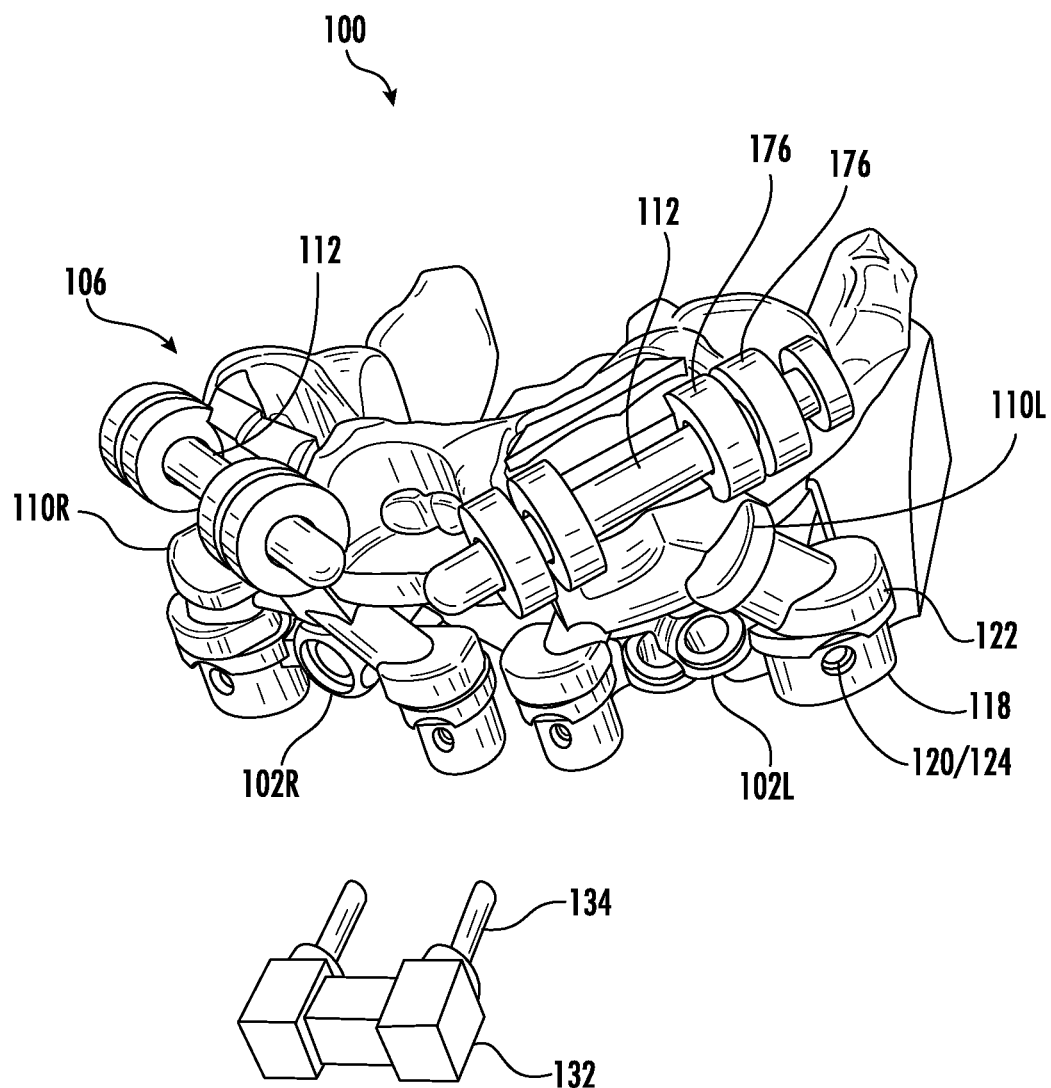
Figure 15A:
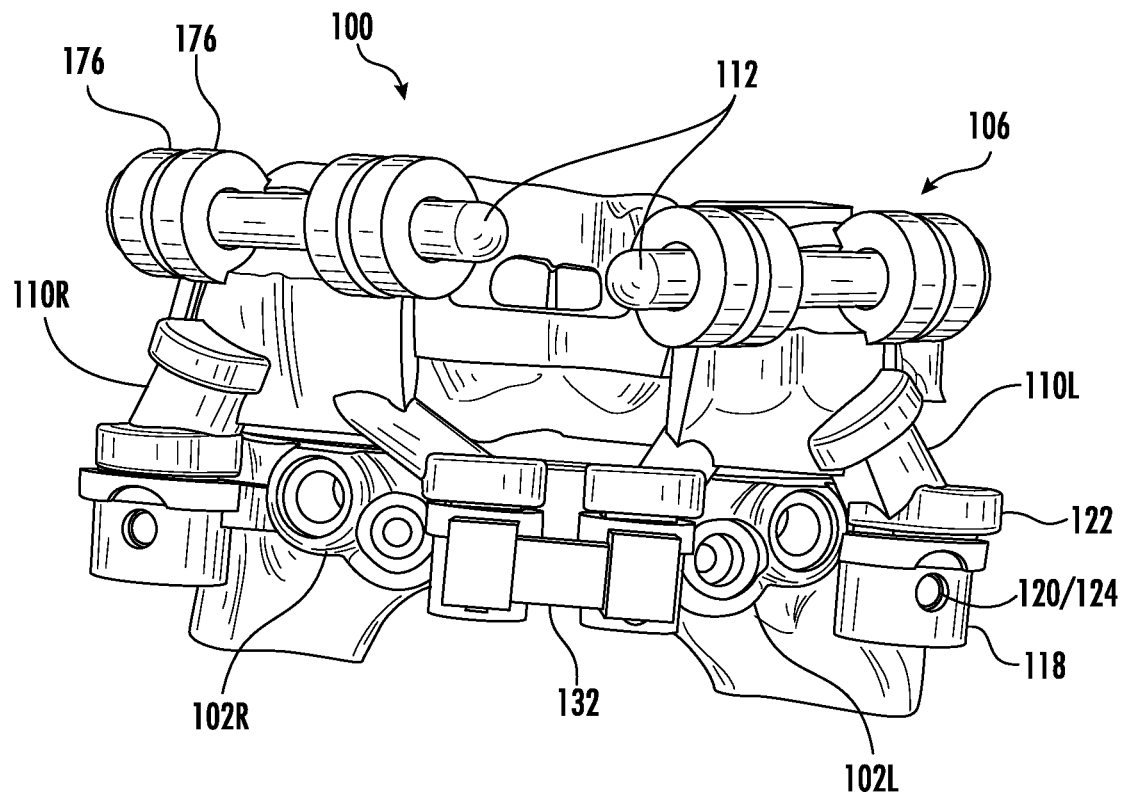
Figure 15B:
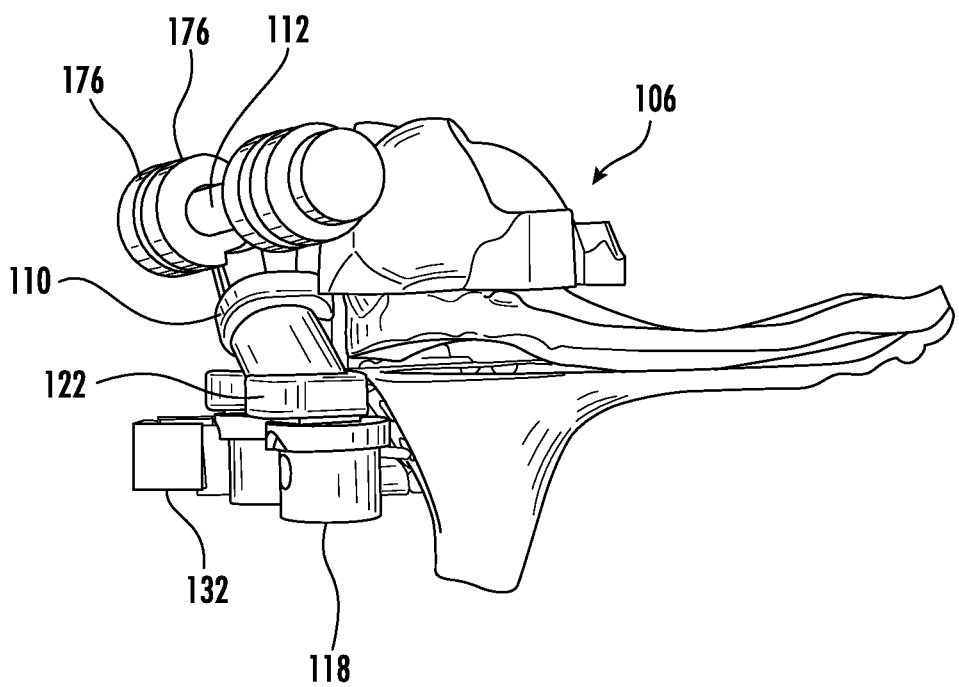
Figure 16A:
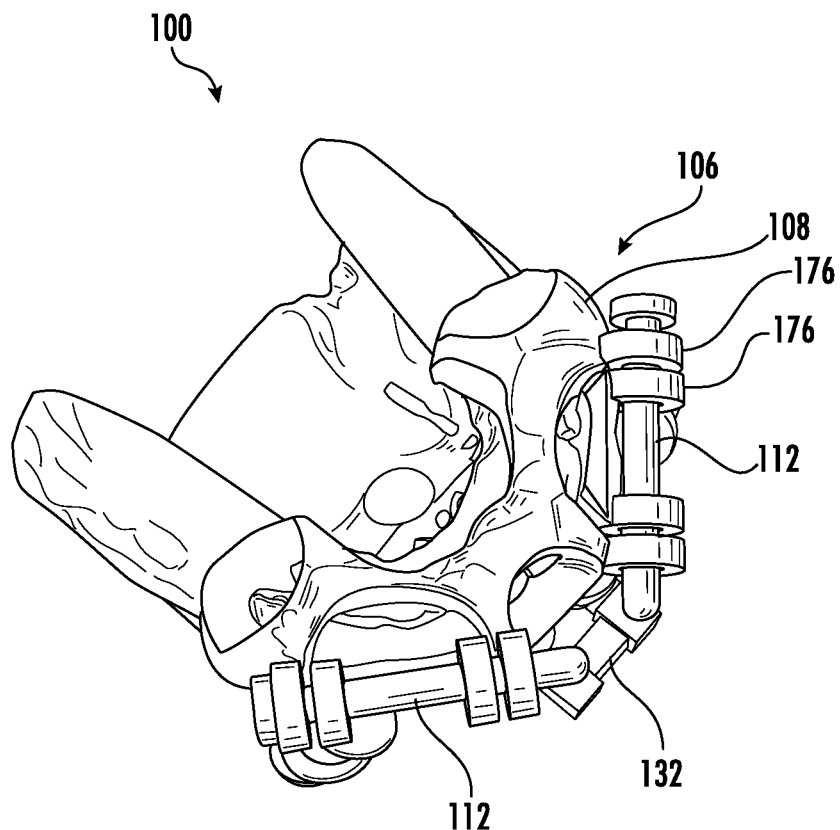
Figure 16B:
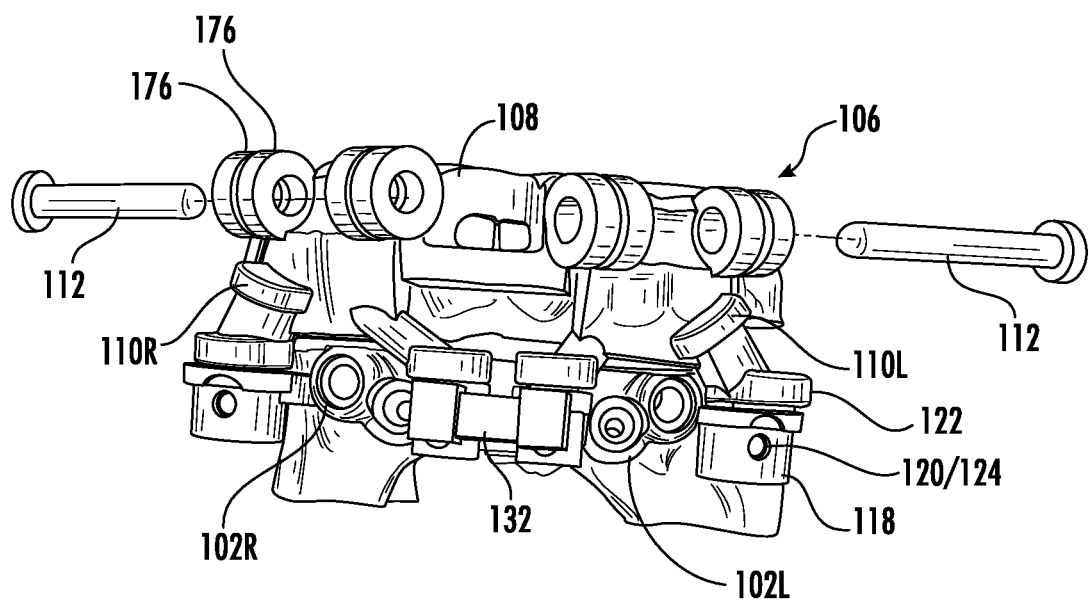
Figure 17:
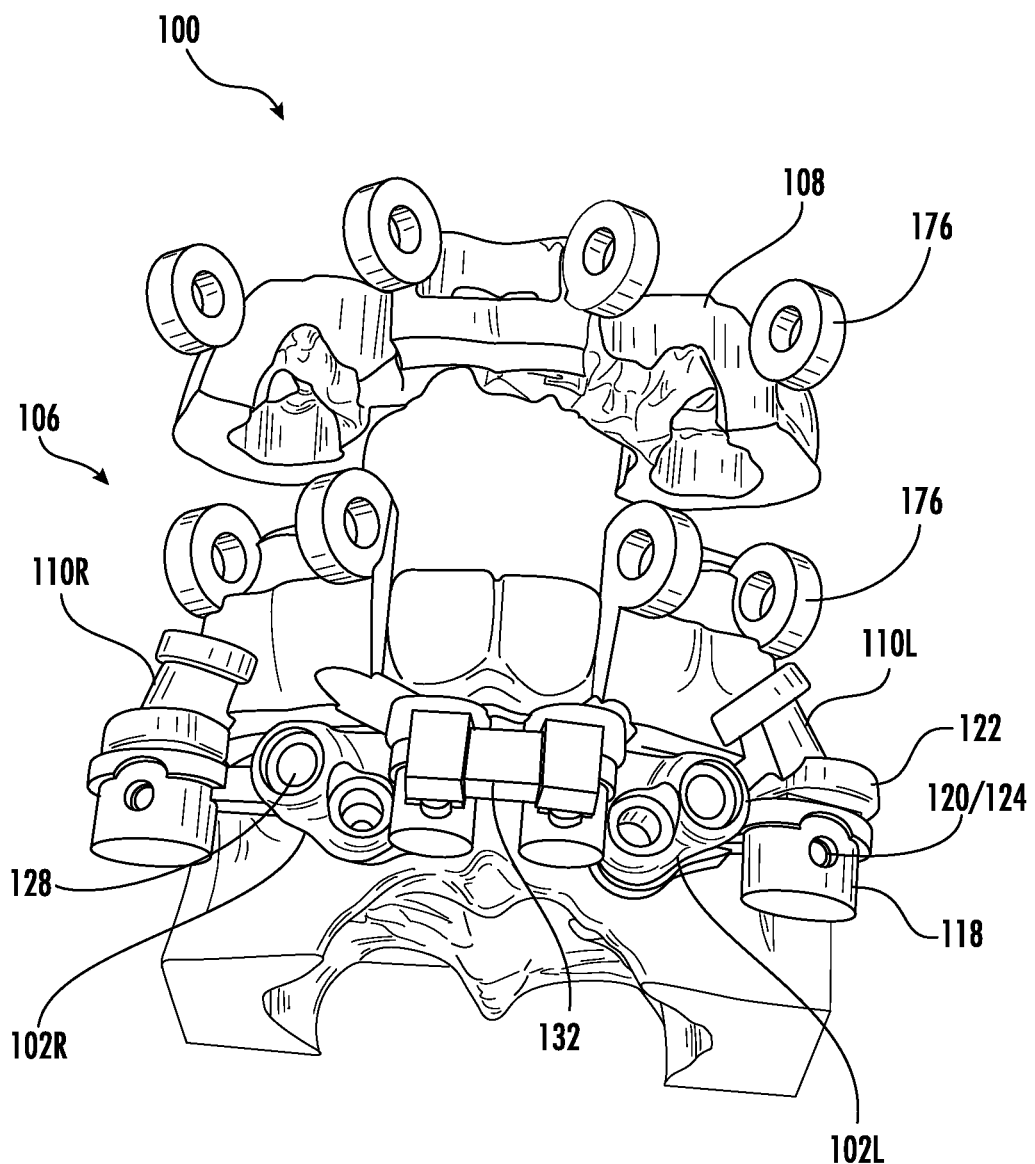
Figure 18A:
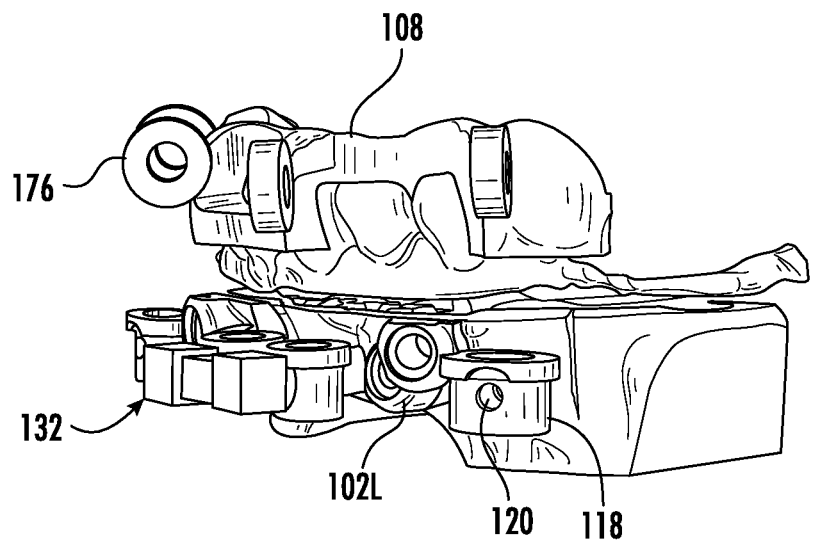
Figure 18B:
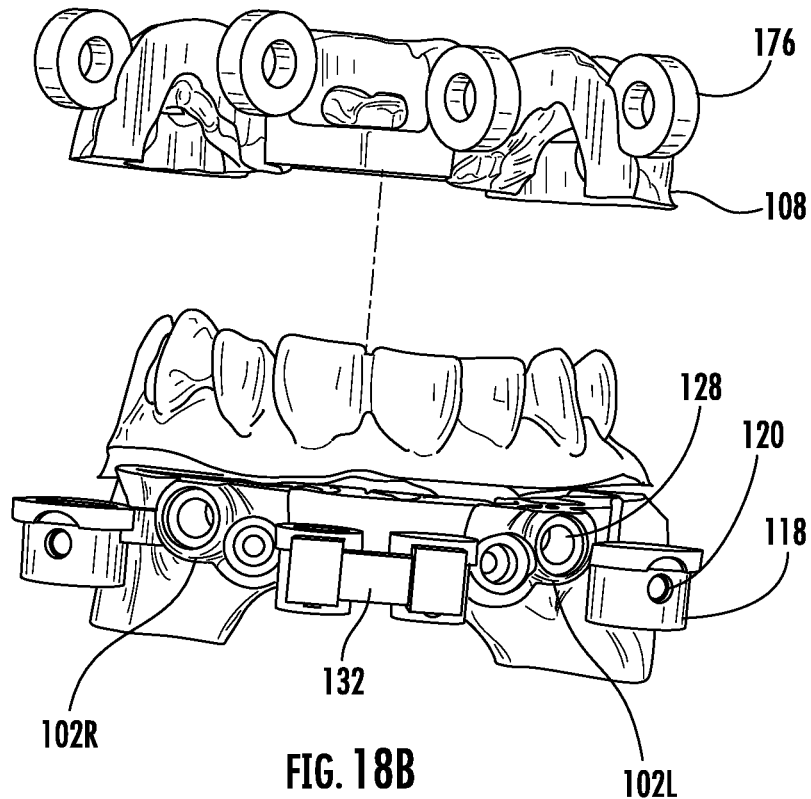
Figure 19A:
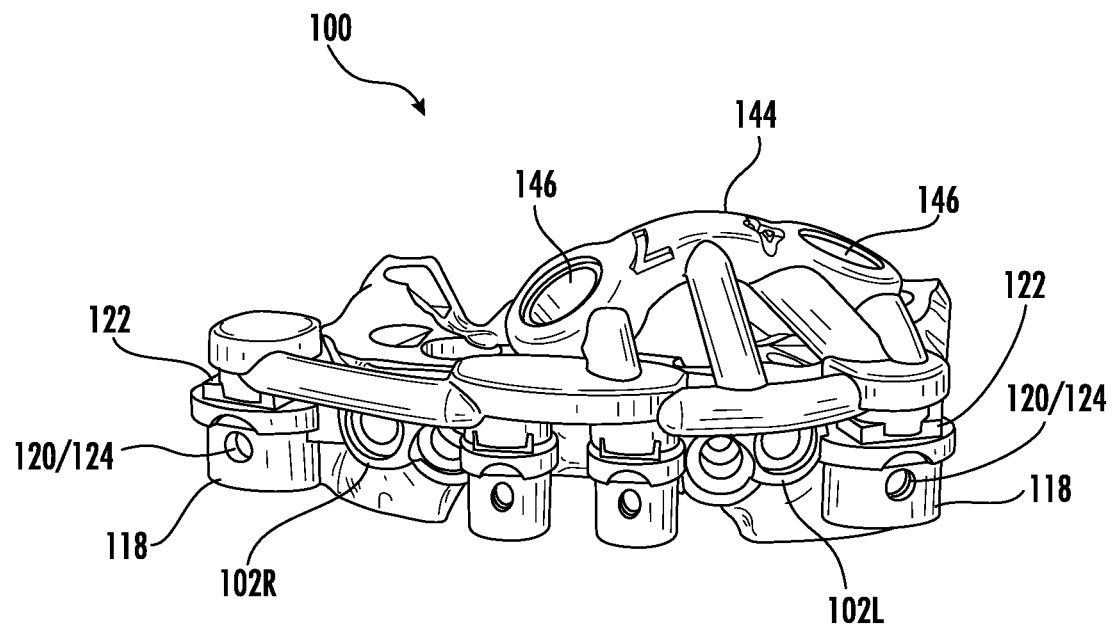
Figure 19B:
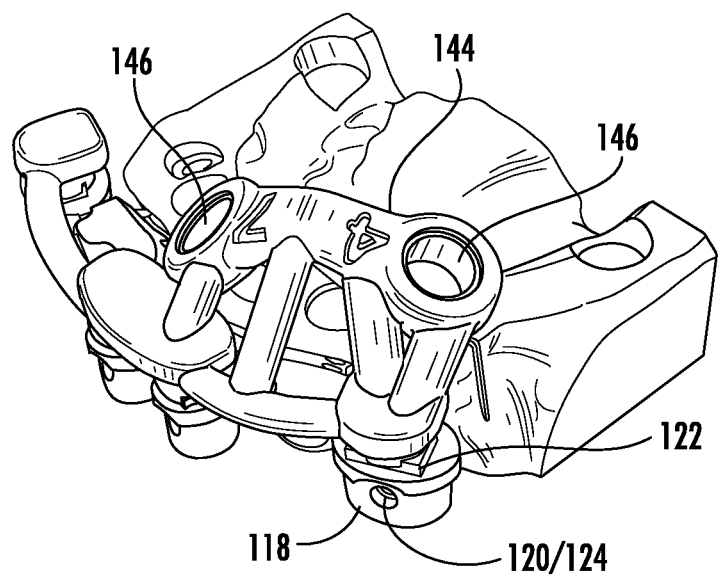
Figure 20A:
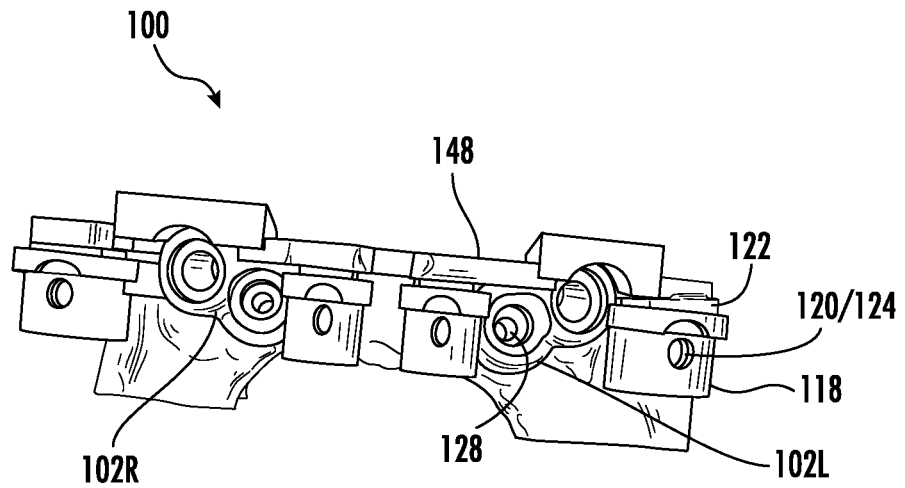
Figure 20B:
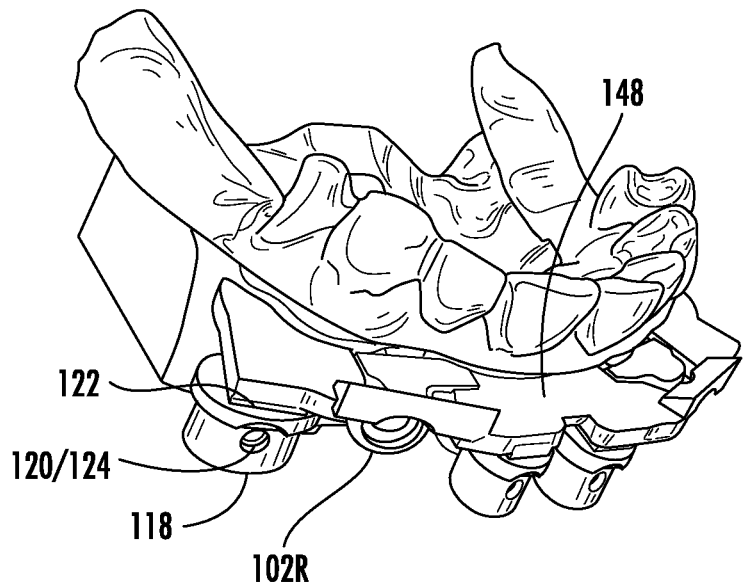
Figure 21:
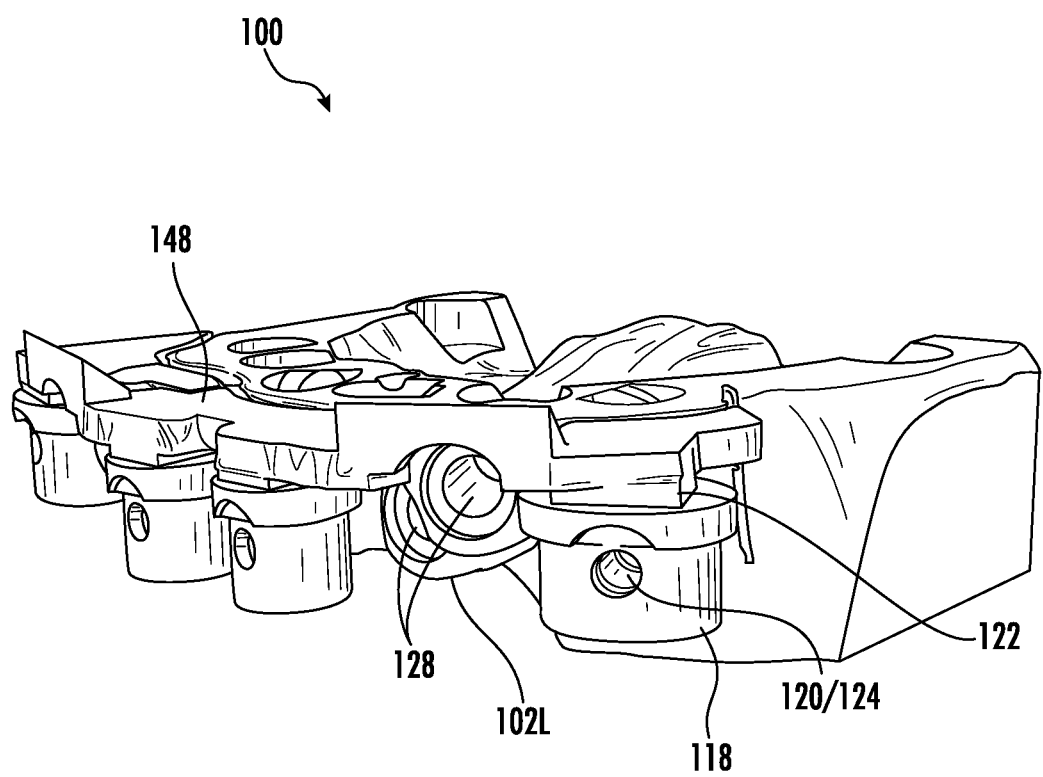
Figure 22:
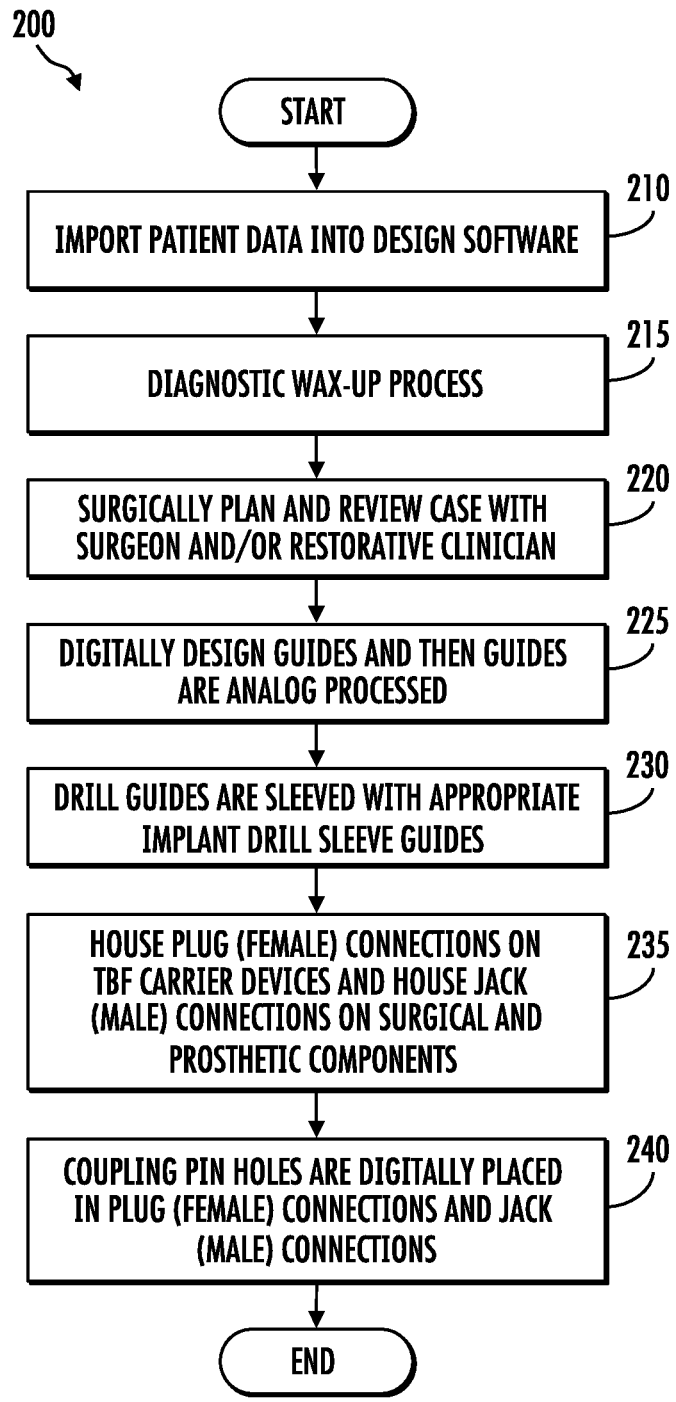
Figure 23:
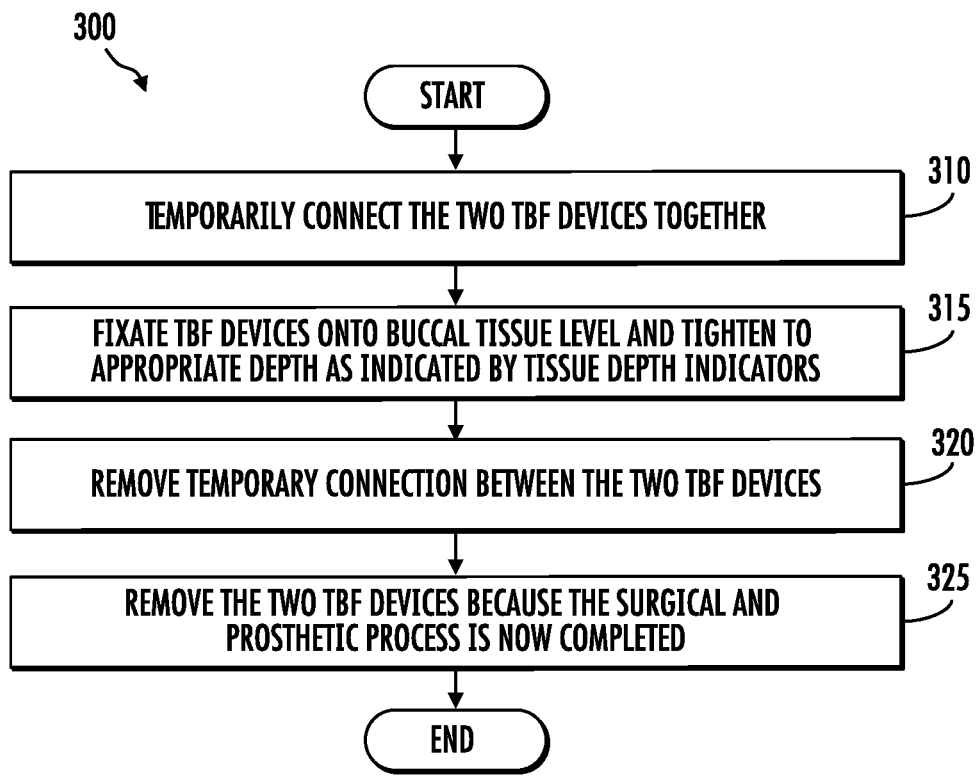
Figure 24A:
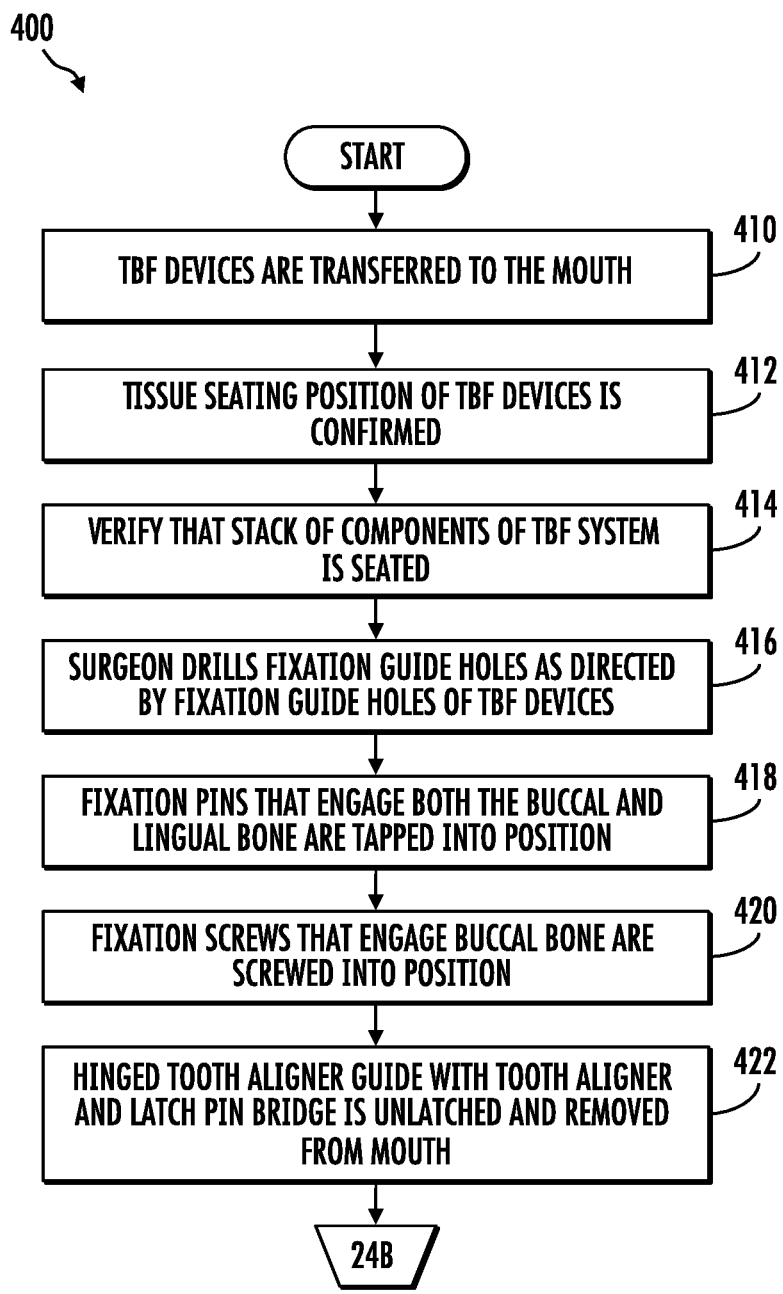
Figure 24B:
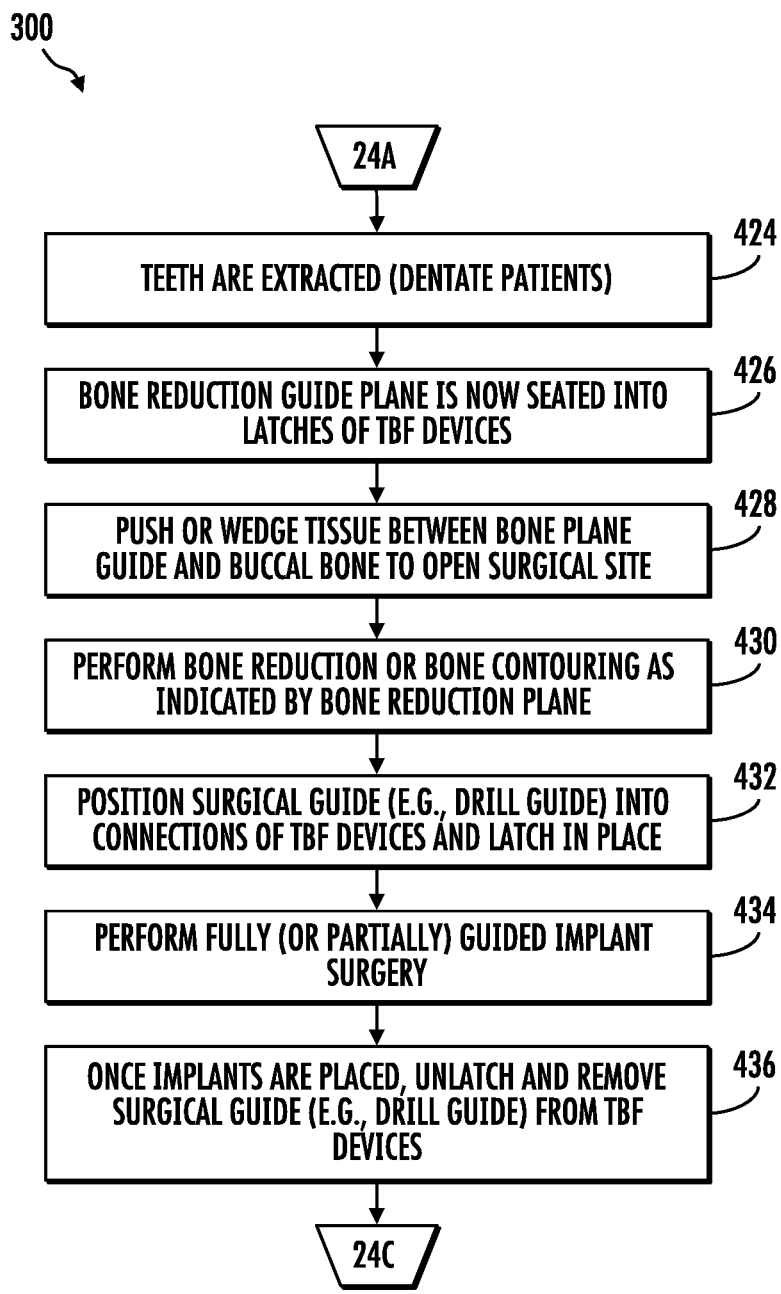
Figure 24C:
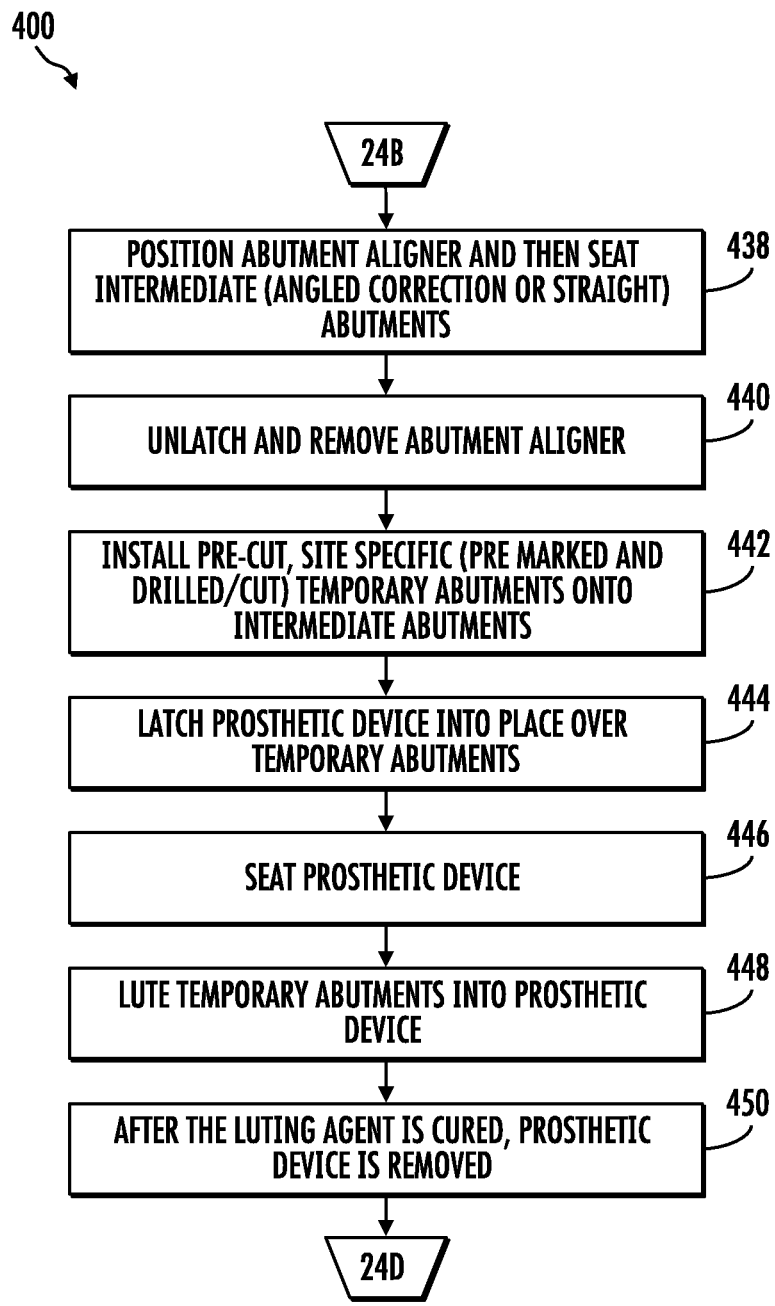
Figure 24D:
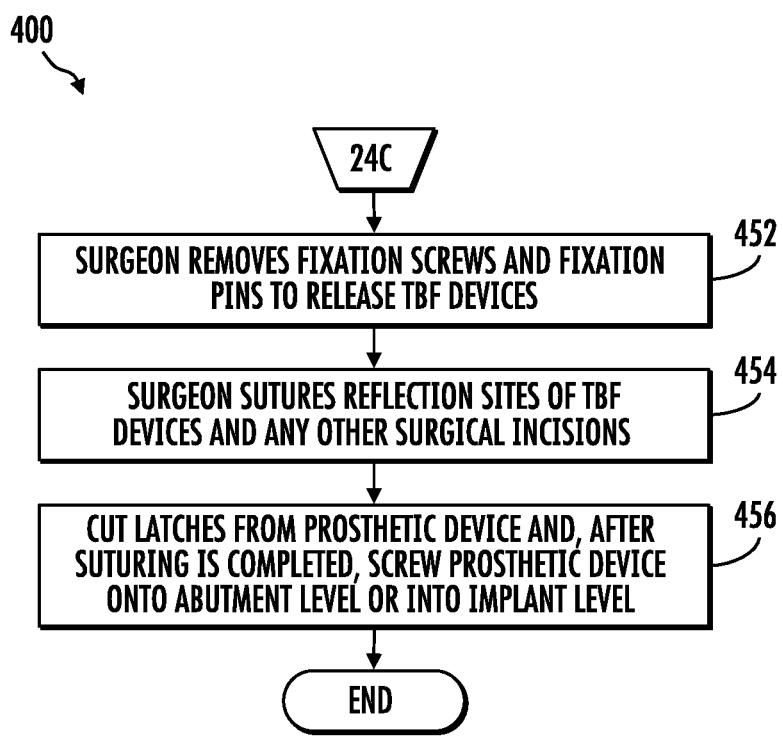
Figure 25:
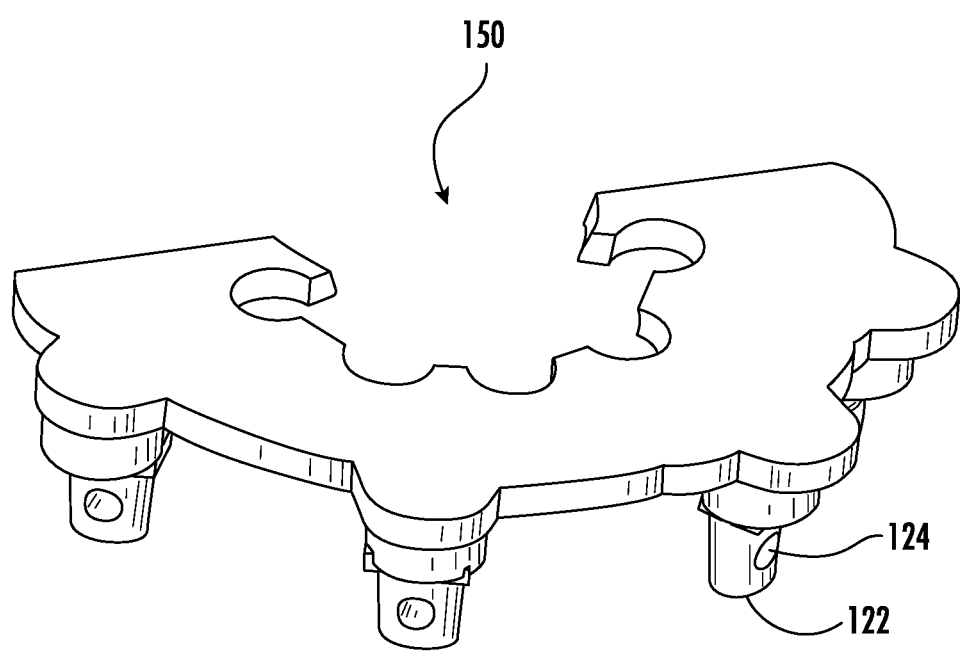
Figure 26:
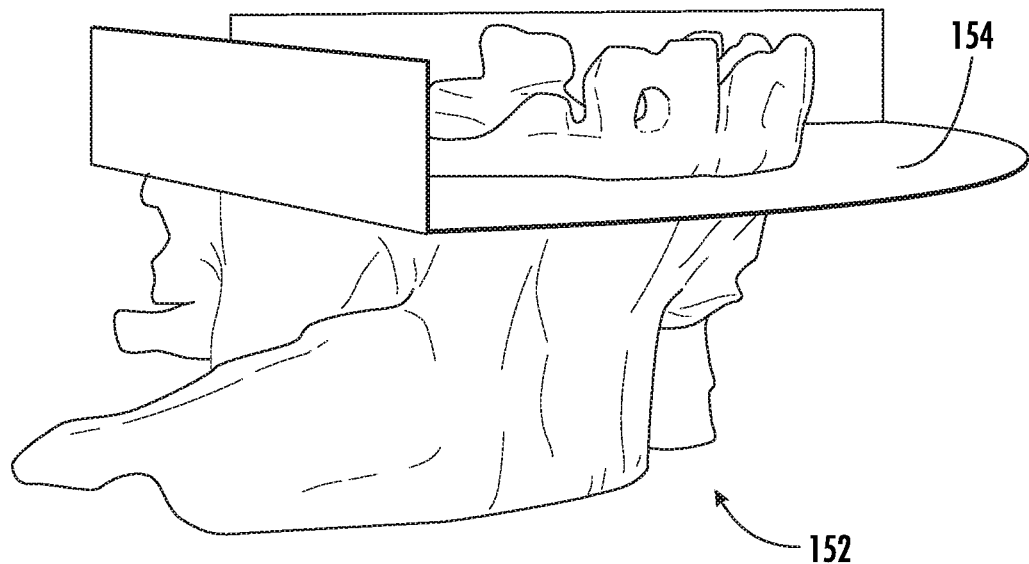
Figure 27:
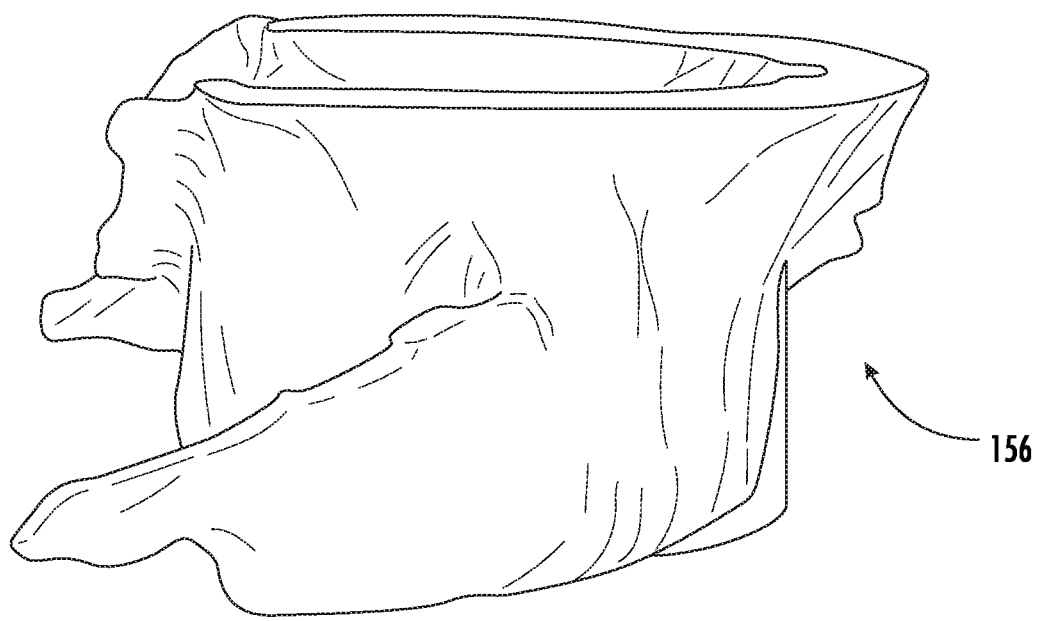
Figure 28:
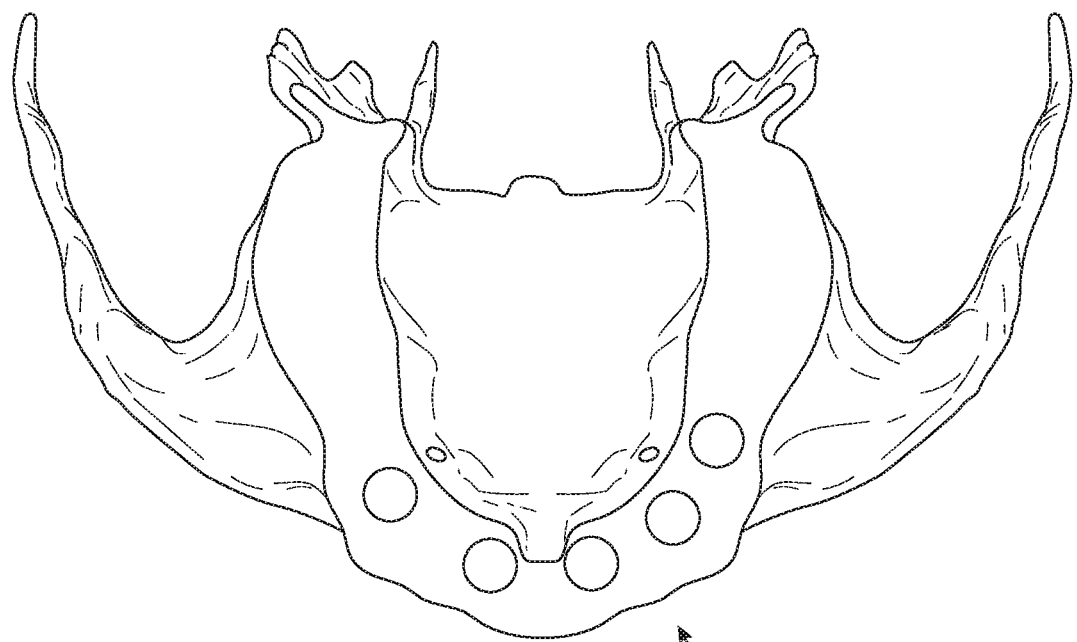
Figure 29:
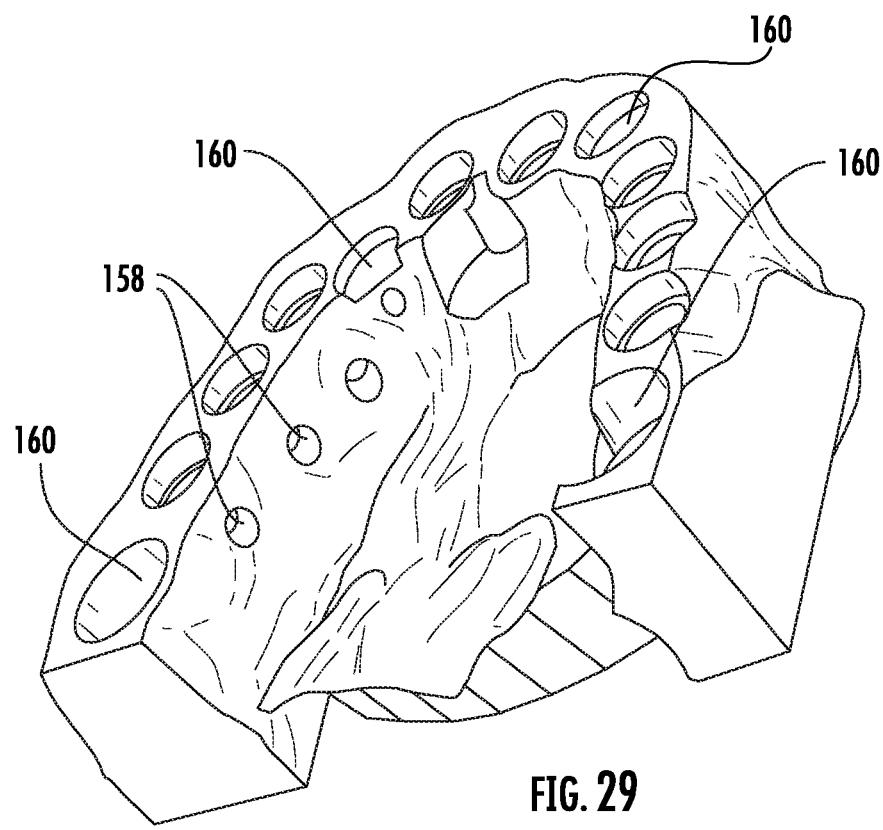
Figure 30:
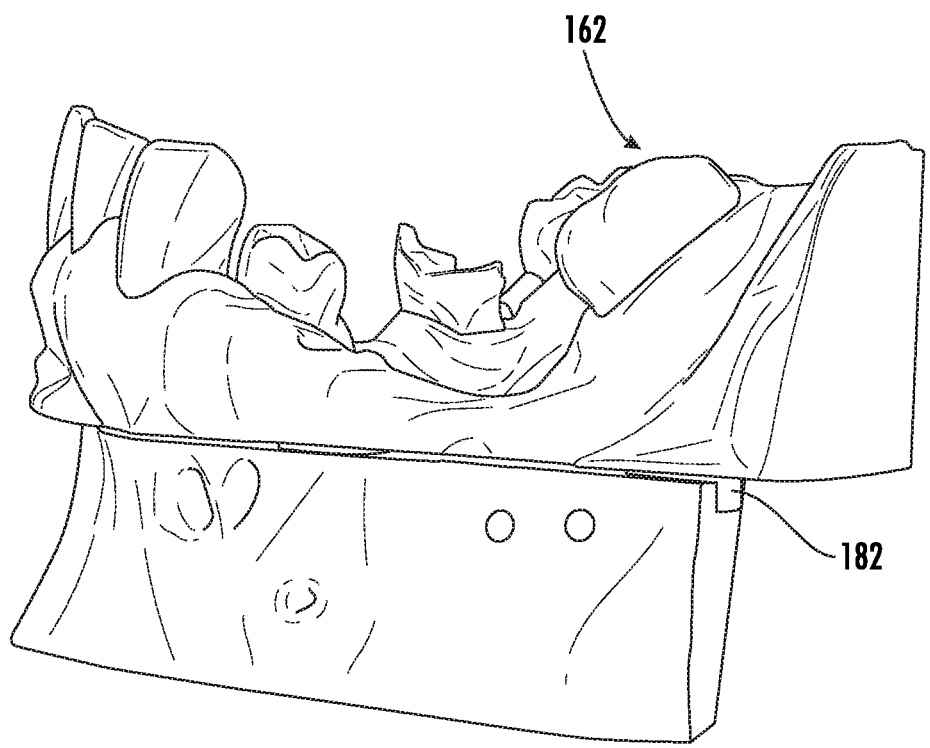
Figure 31:
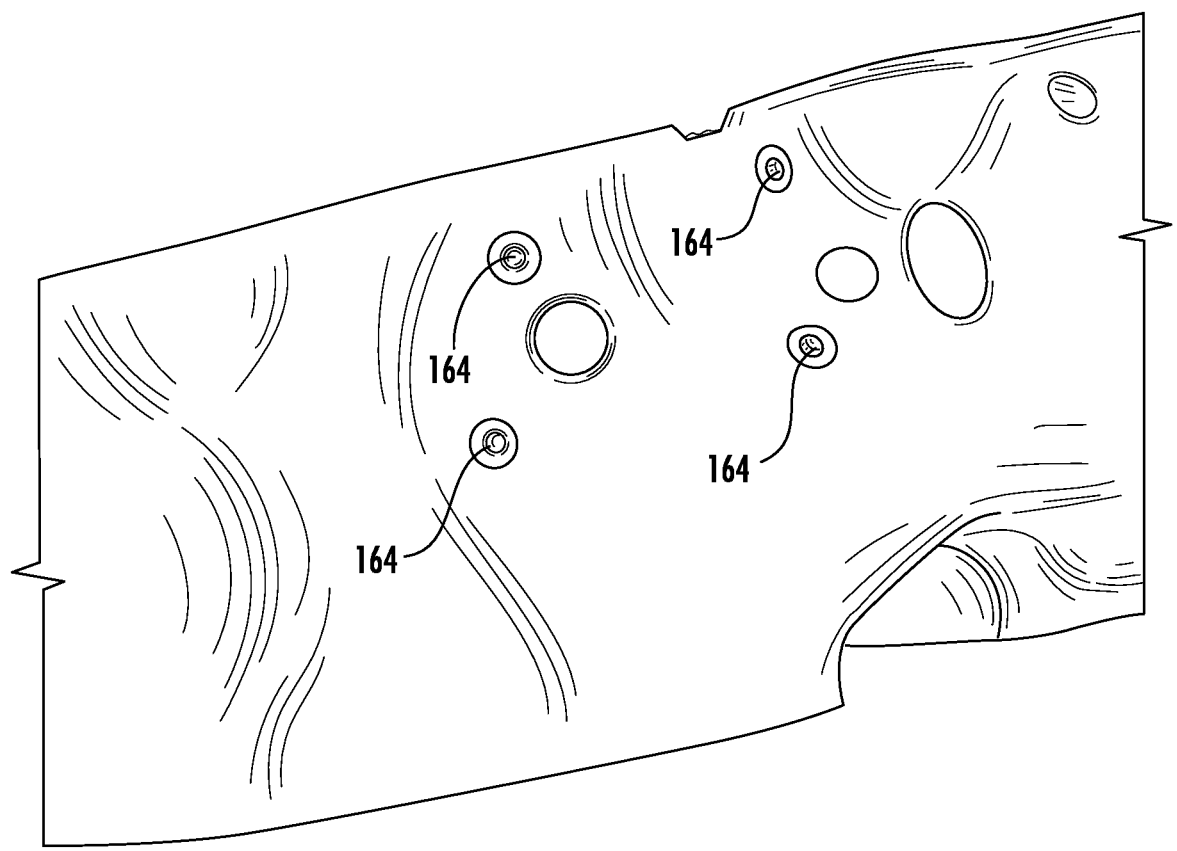
Figure 32:
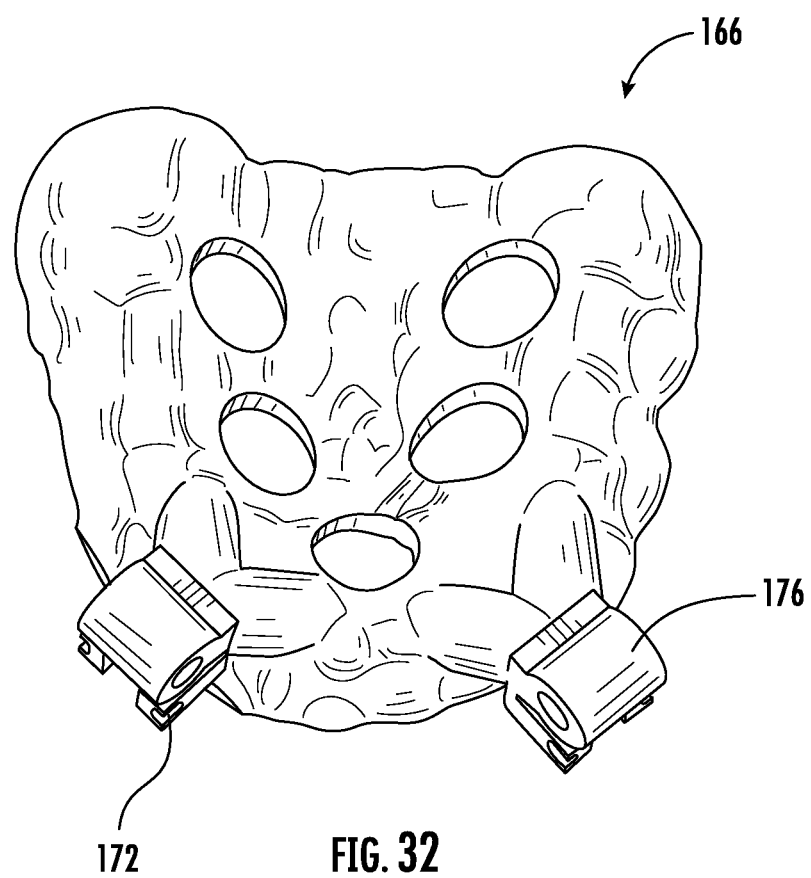
Figure 33:
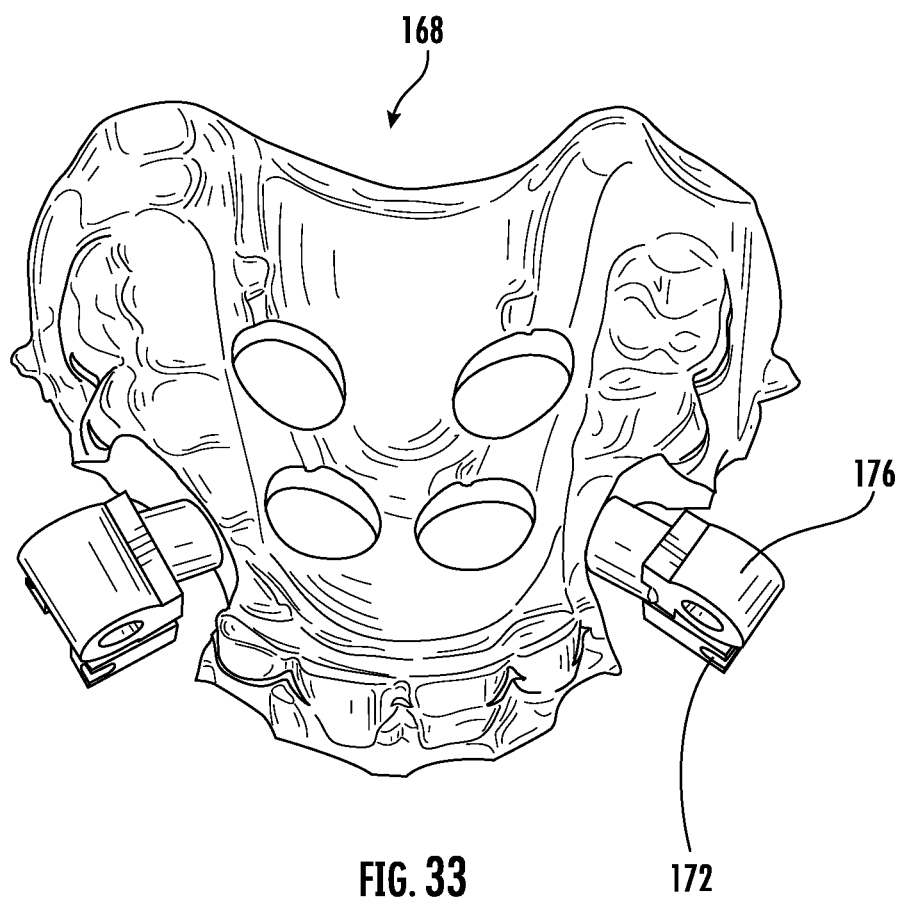
Figure 34:
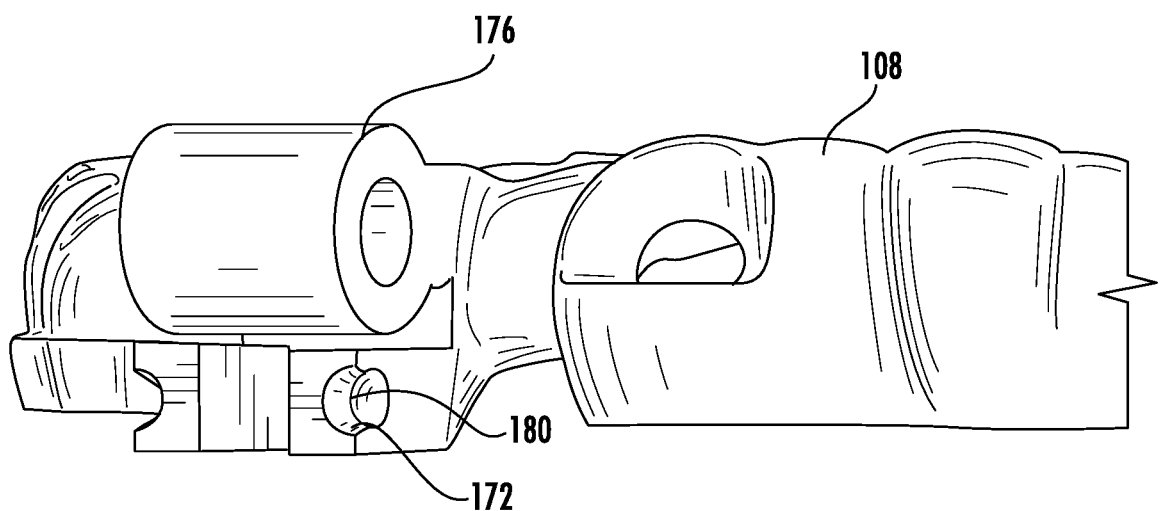
Figure 35:
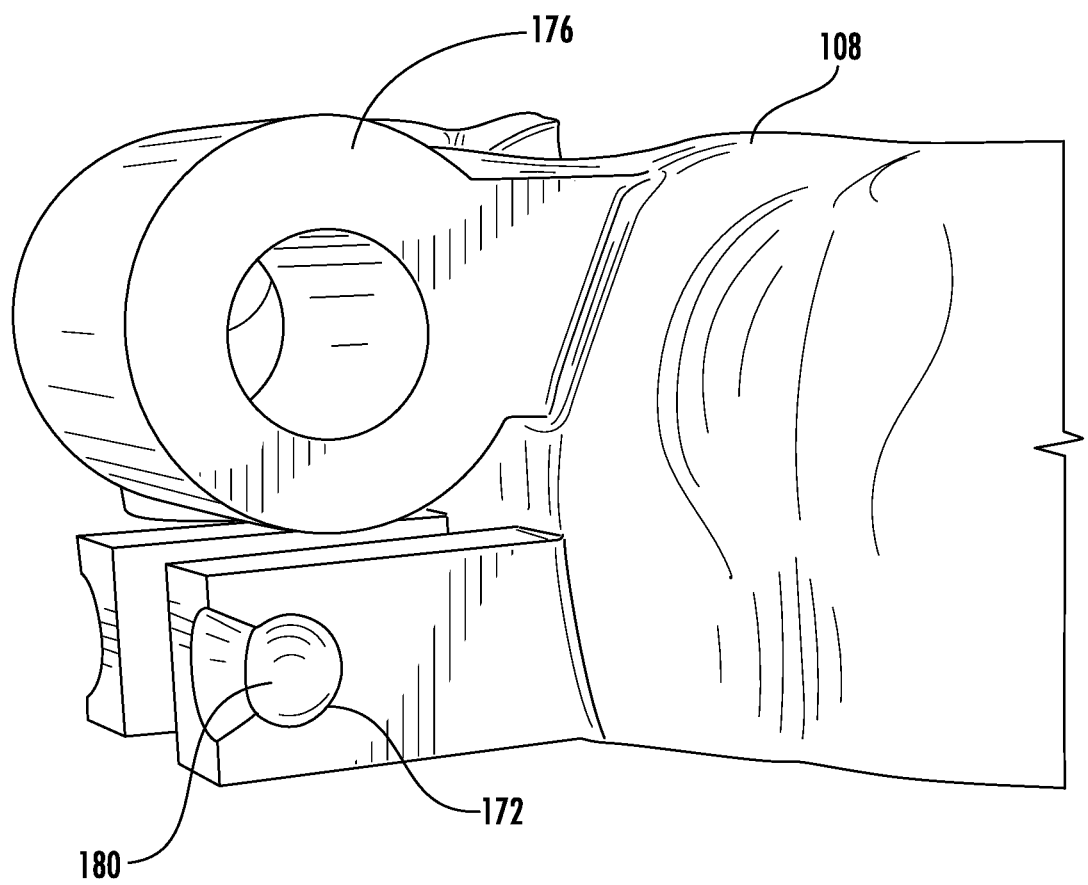
Figure 36:
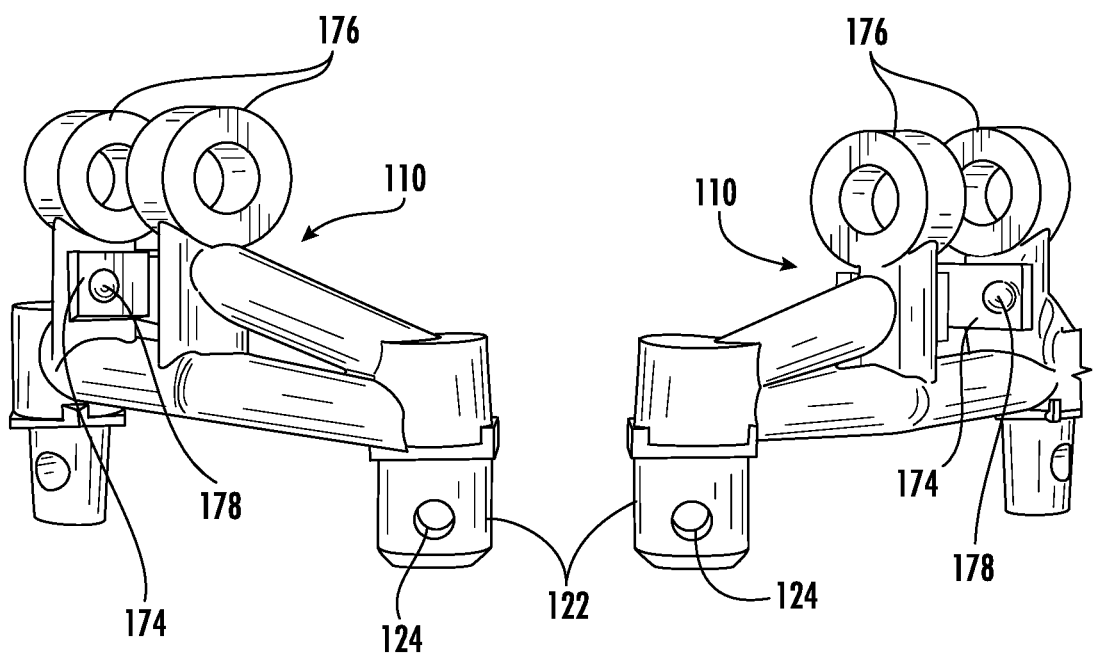
Figure 37:
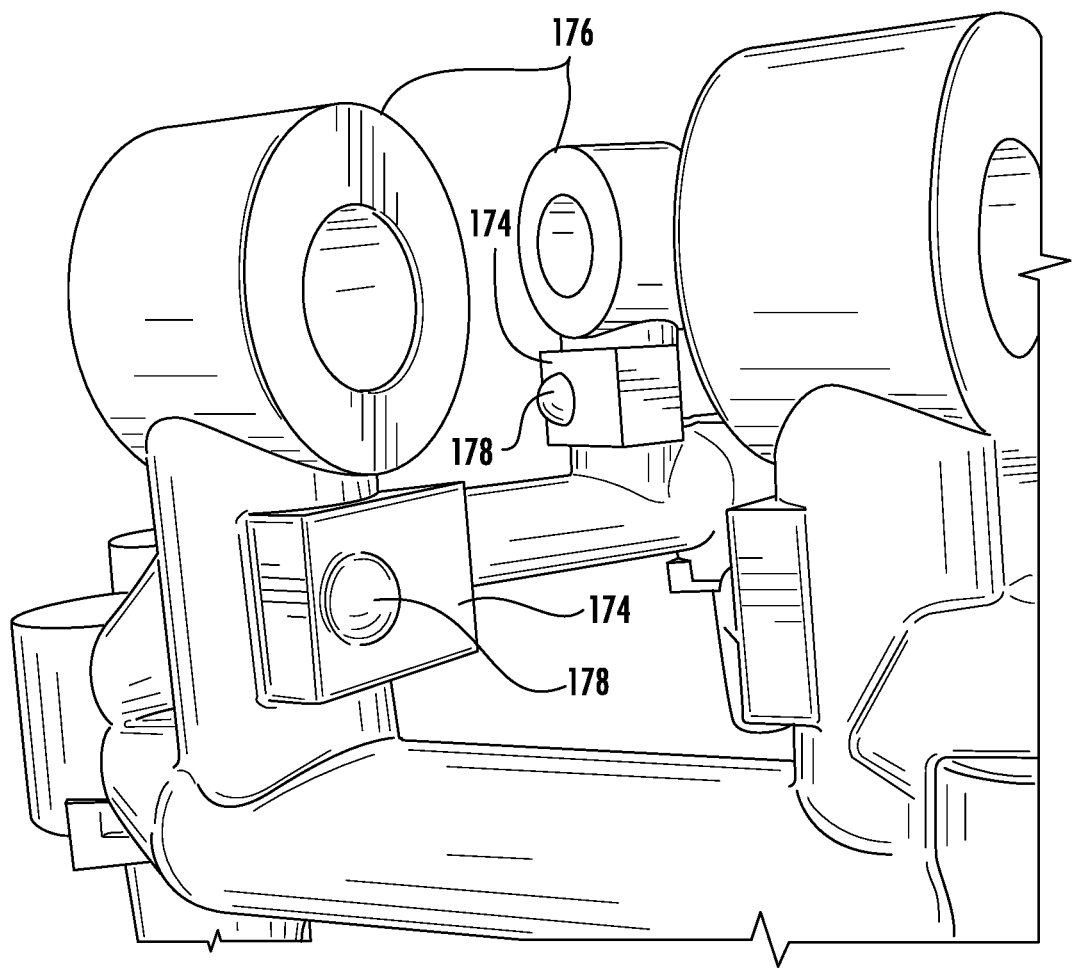
Figure 38:
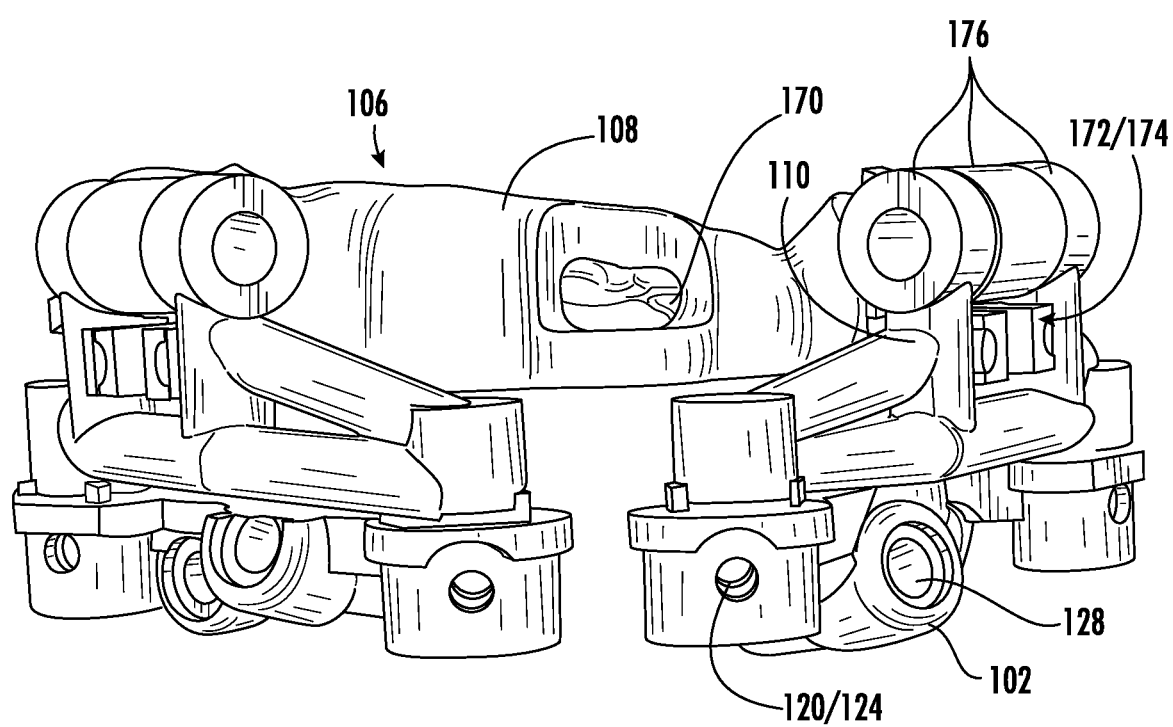
Figure 39:
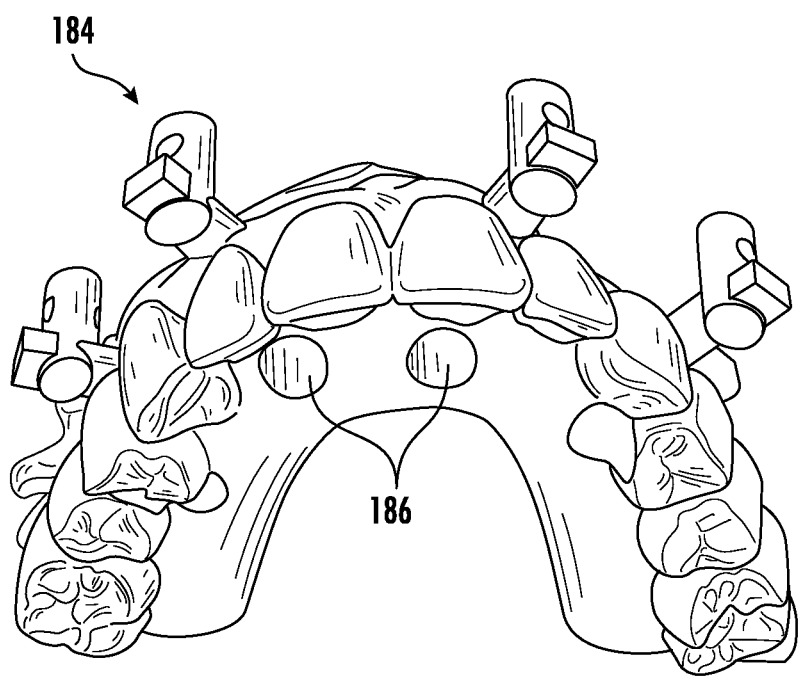
Figure 40:
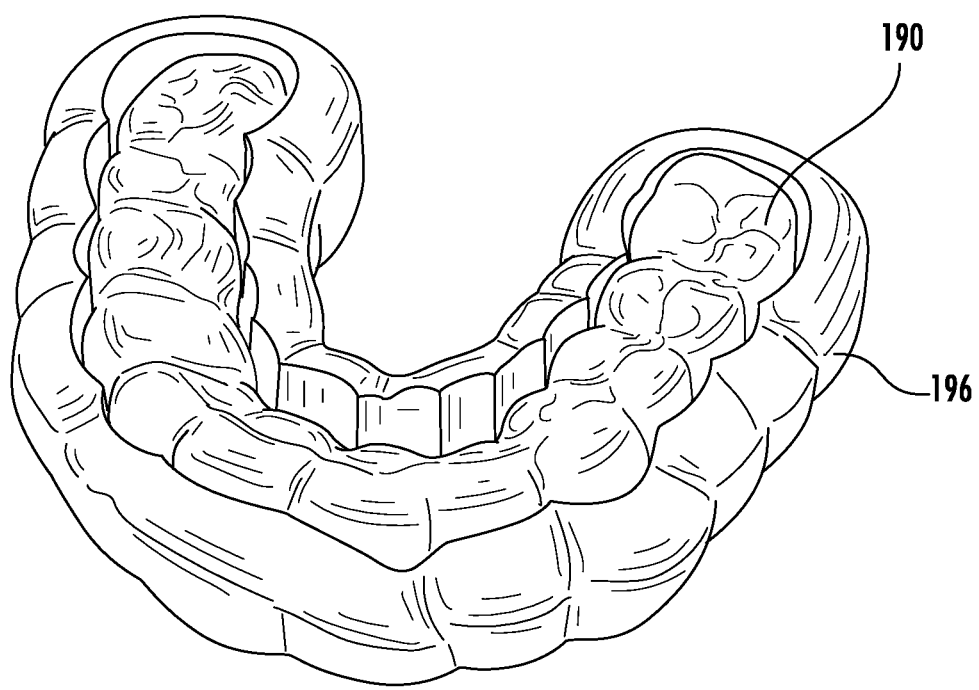
Figure 41:
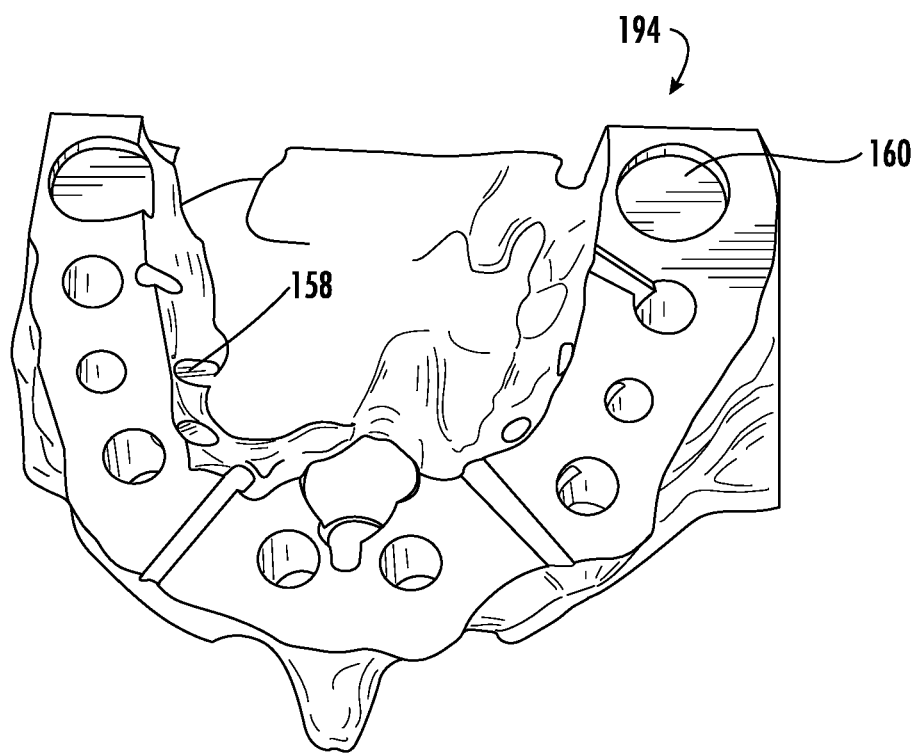
Figure 42:
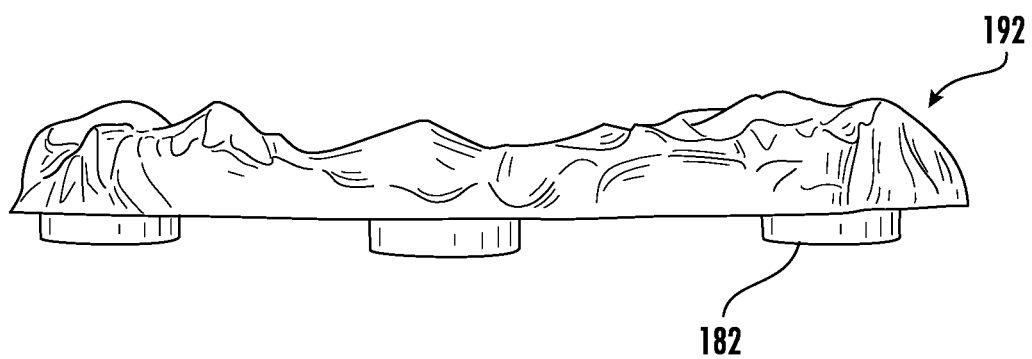
Figure 43:
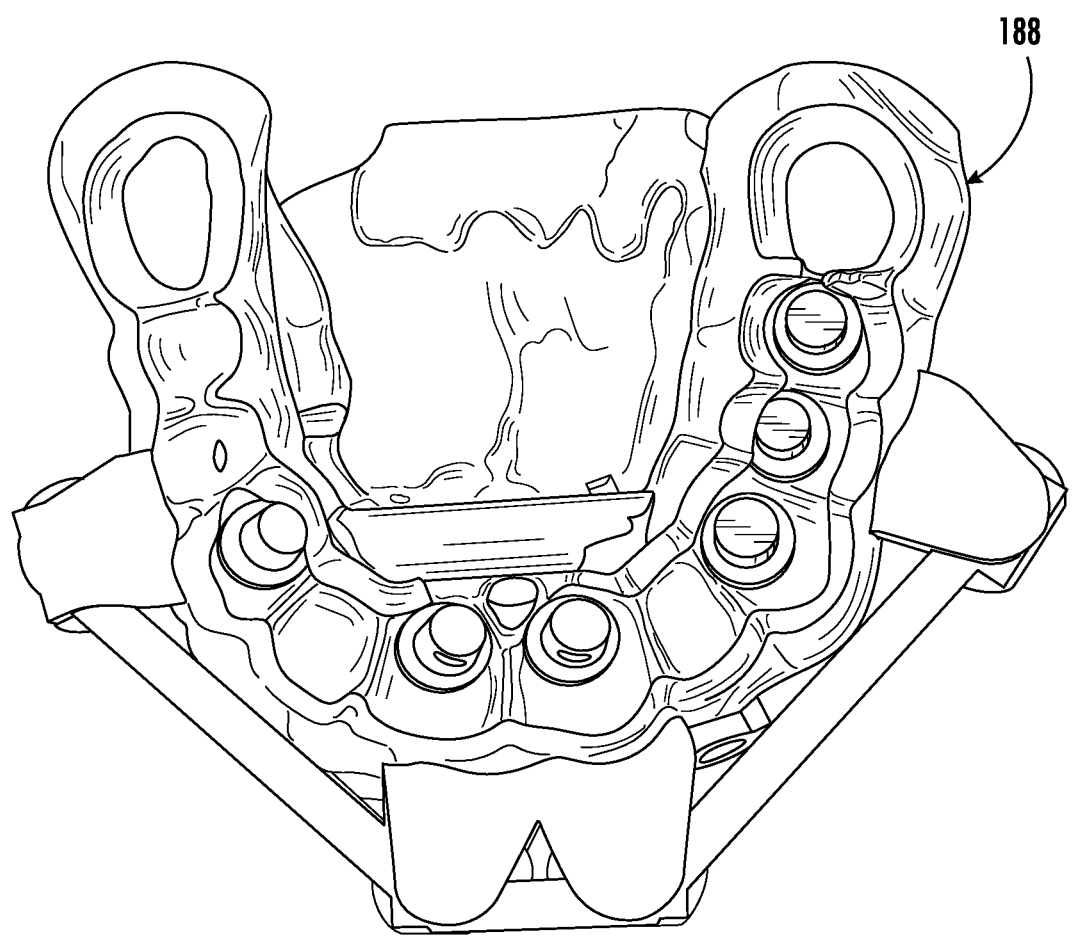
Figure 44:
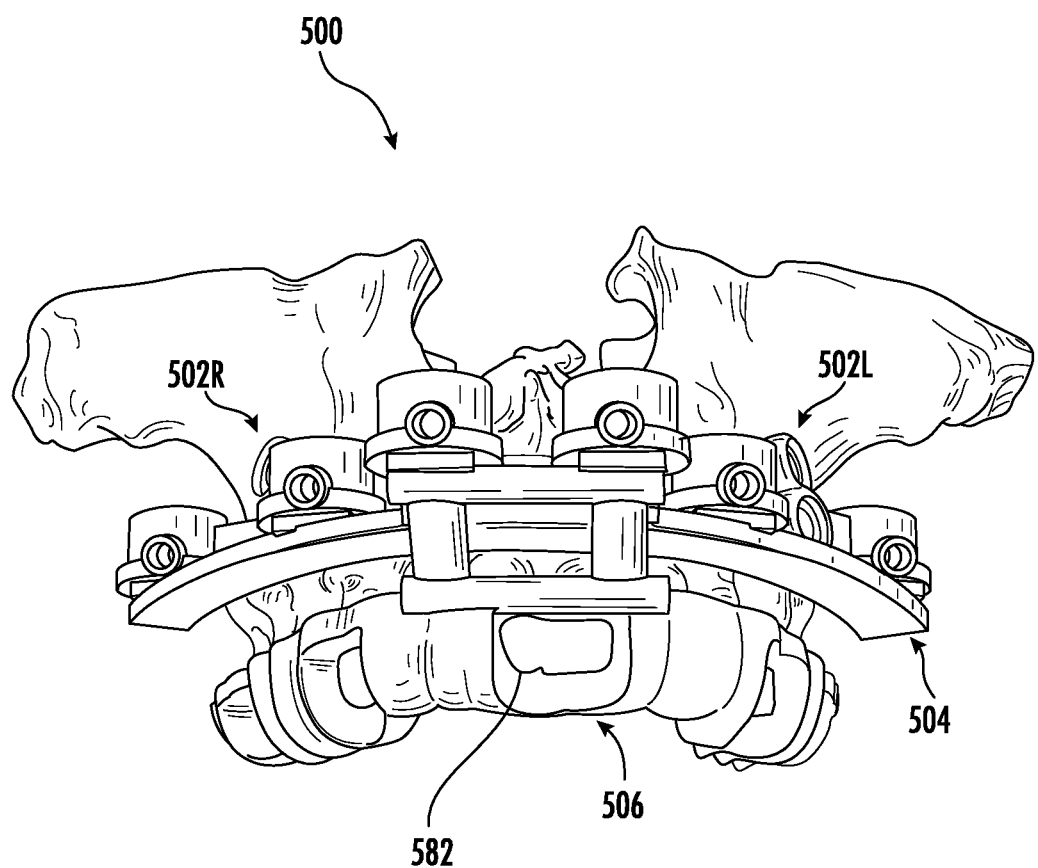
Figure 45:
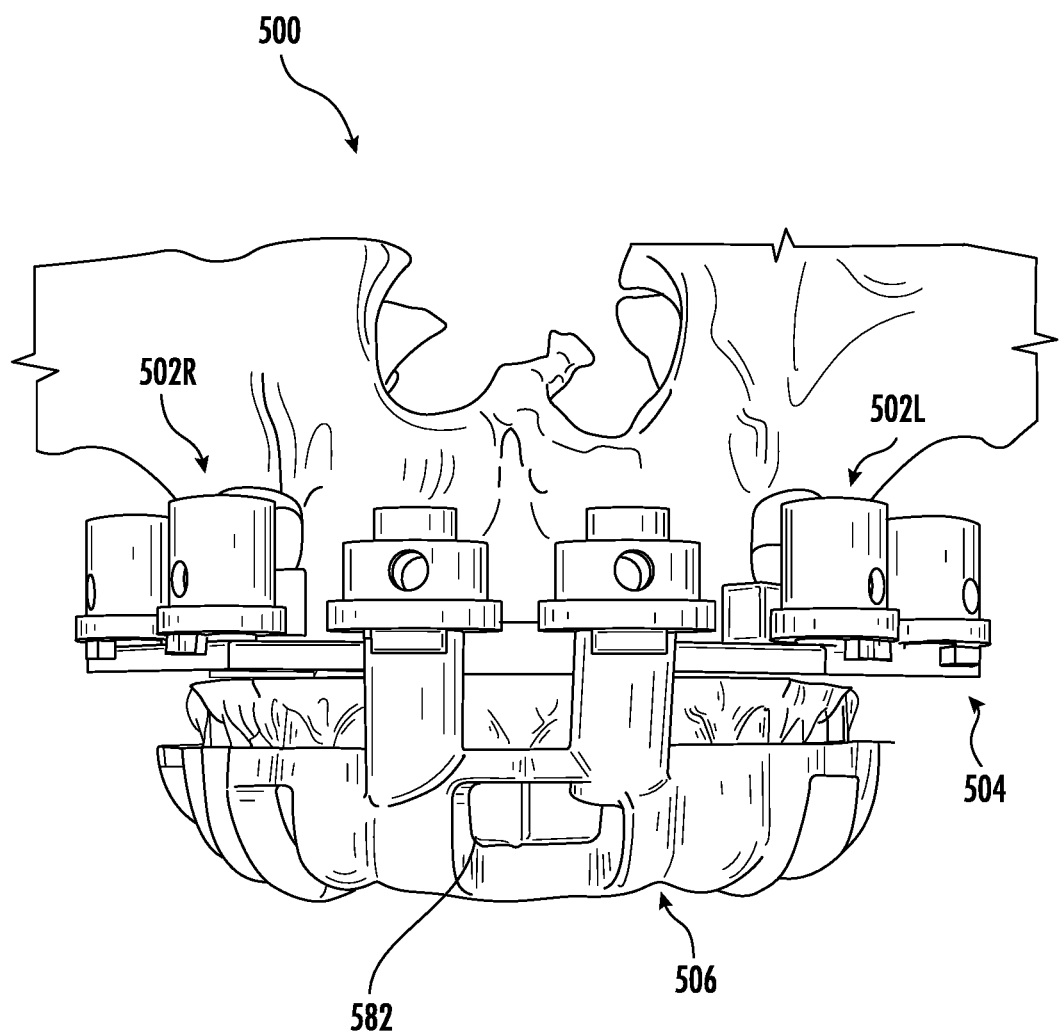
Figure 46:
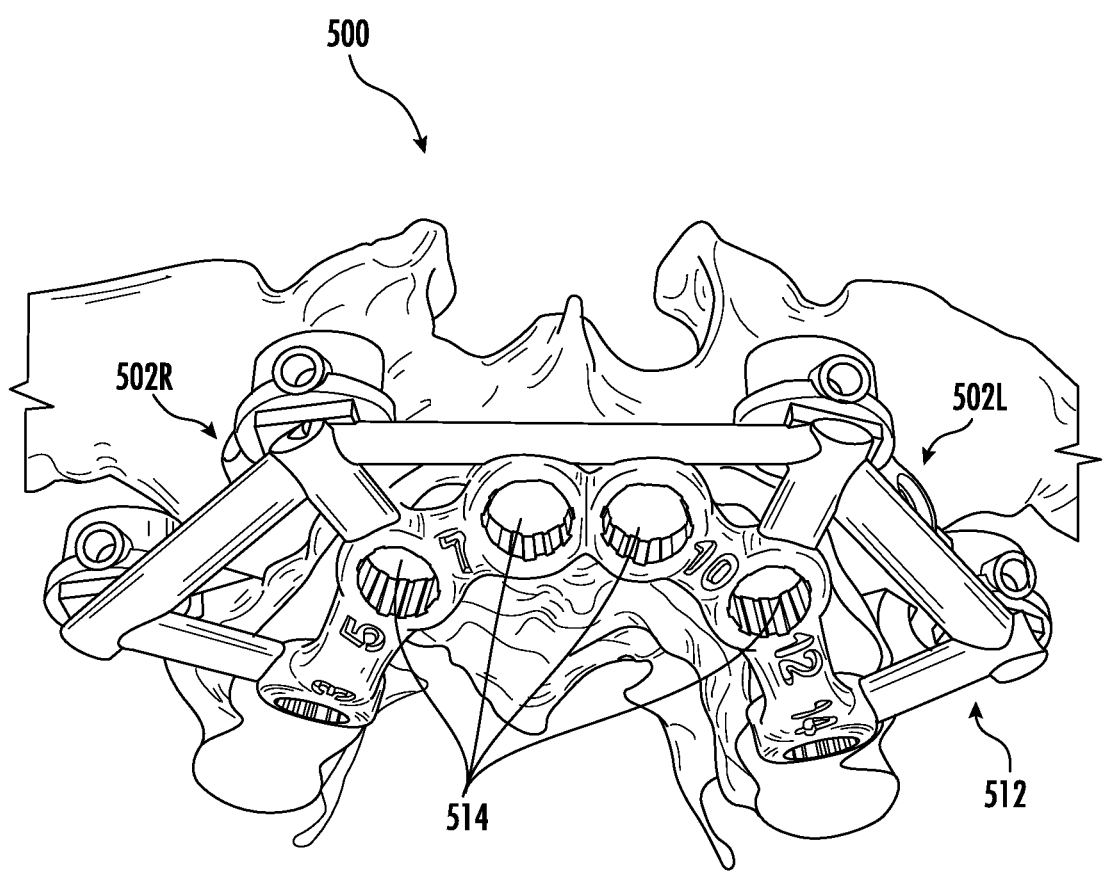
Figure 47:
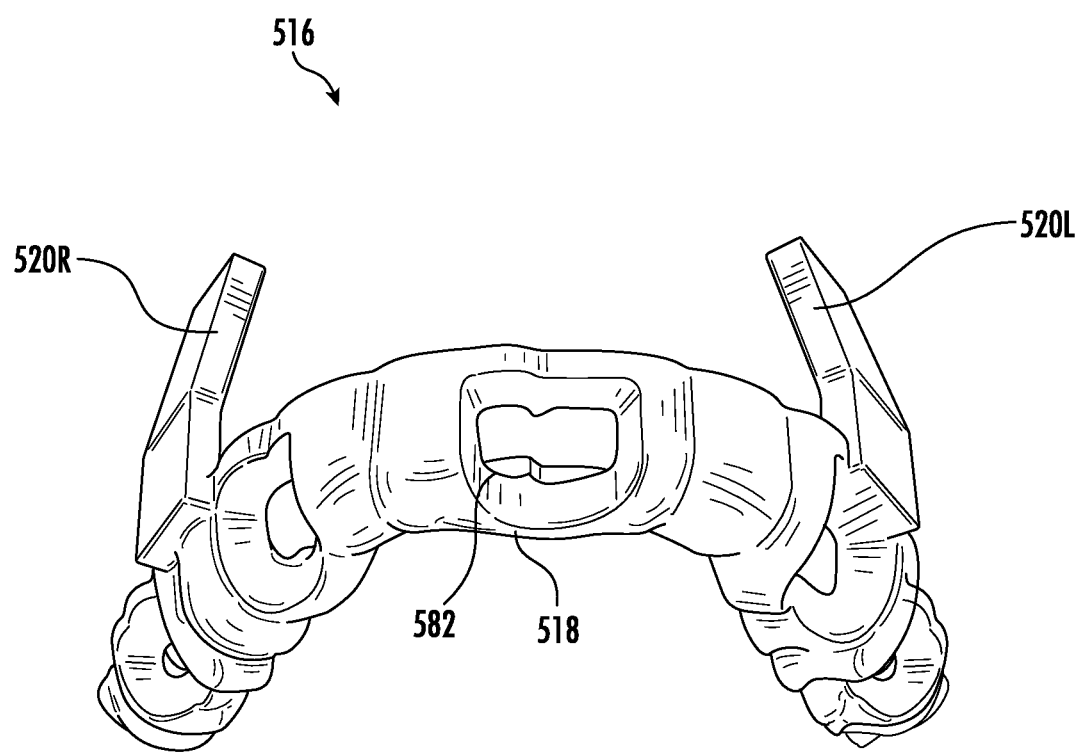
Figure 48:
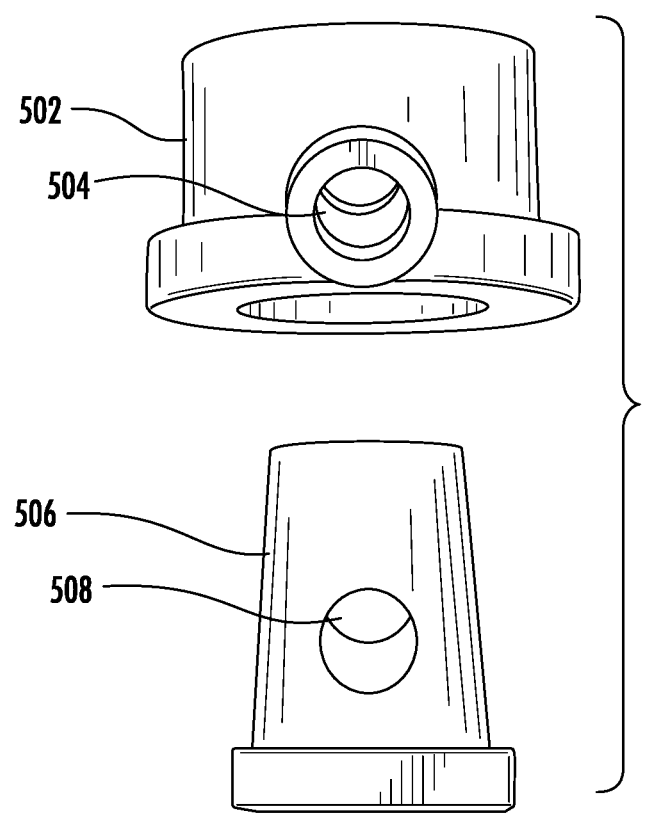
Figure 49:
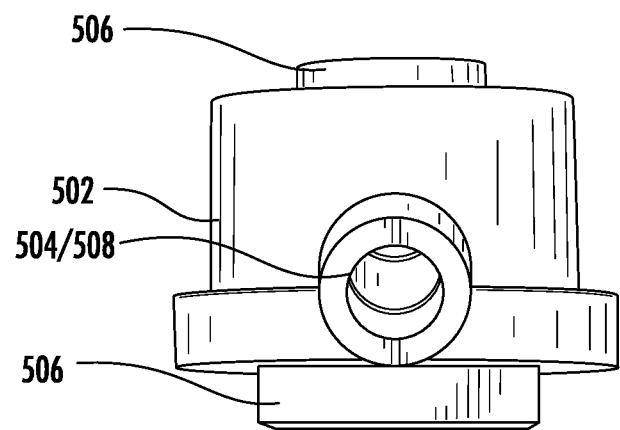
Figure 50:
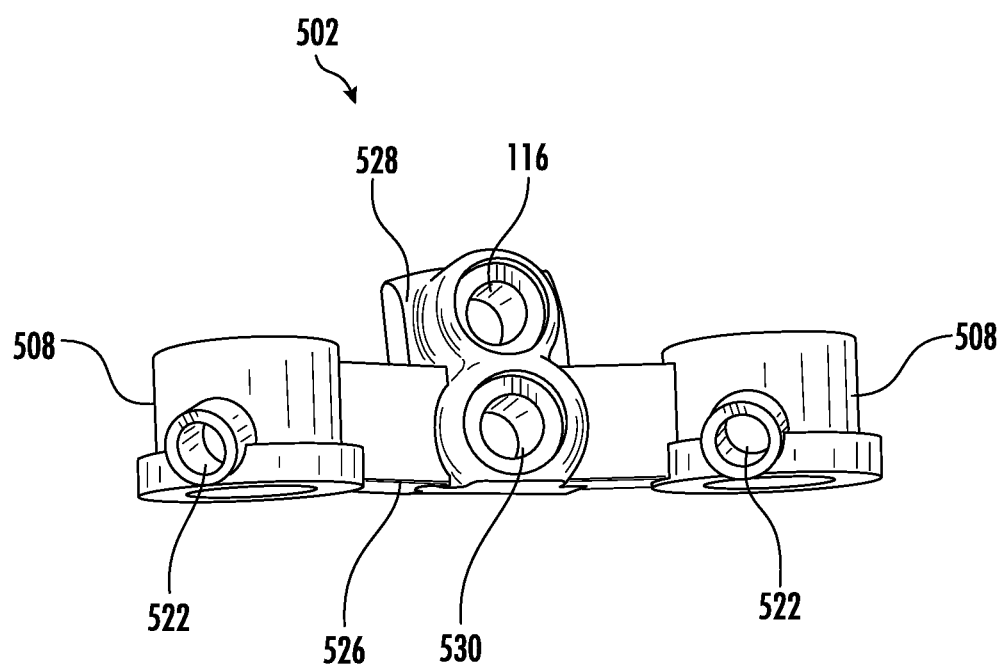
Figure 51:
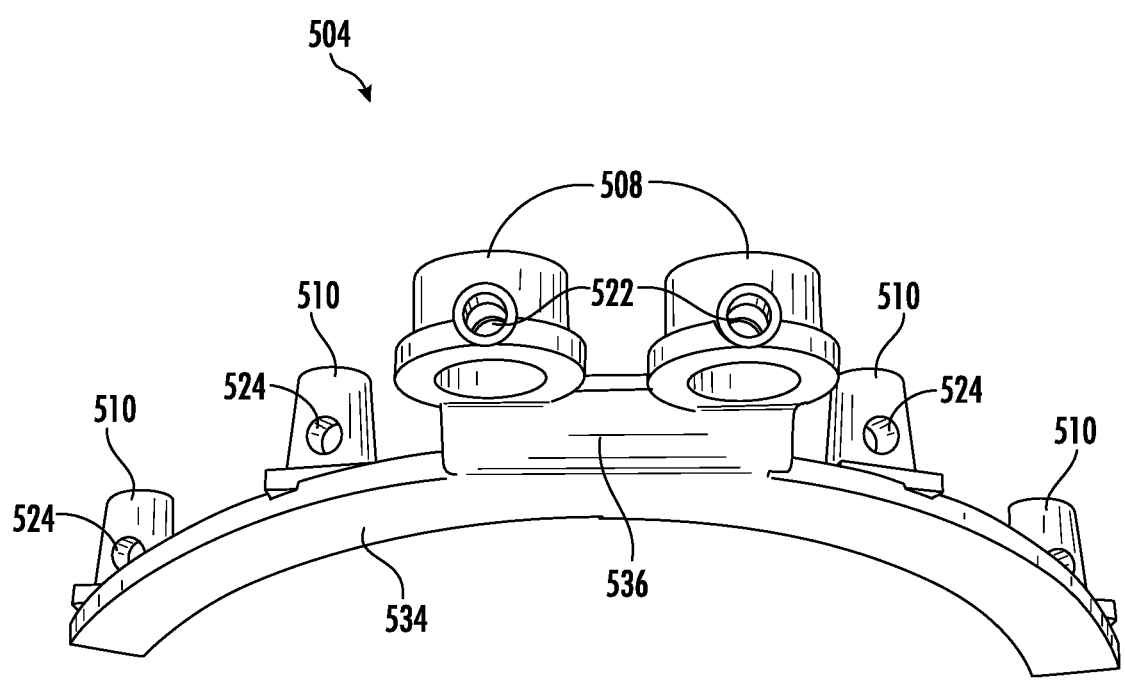
Figure 52:
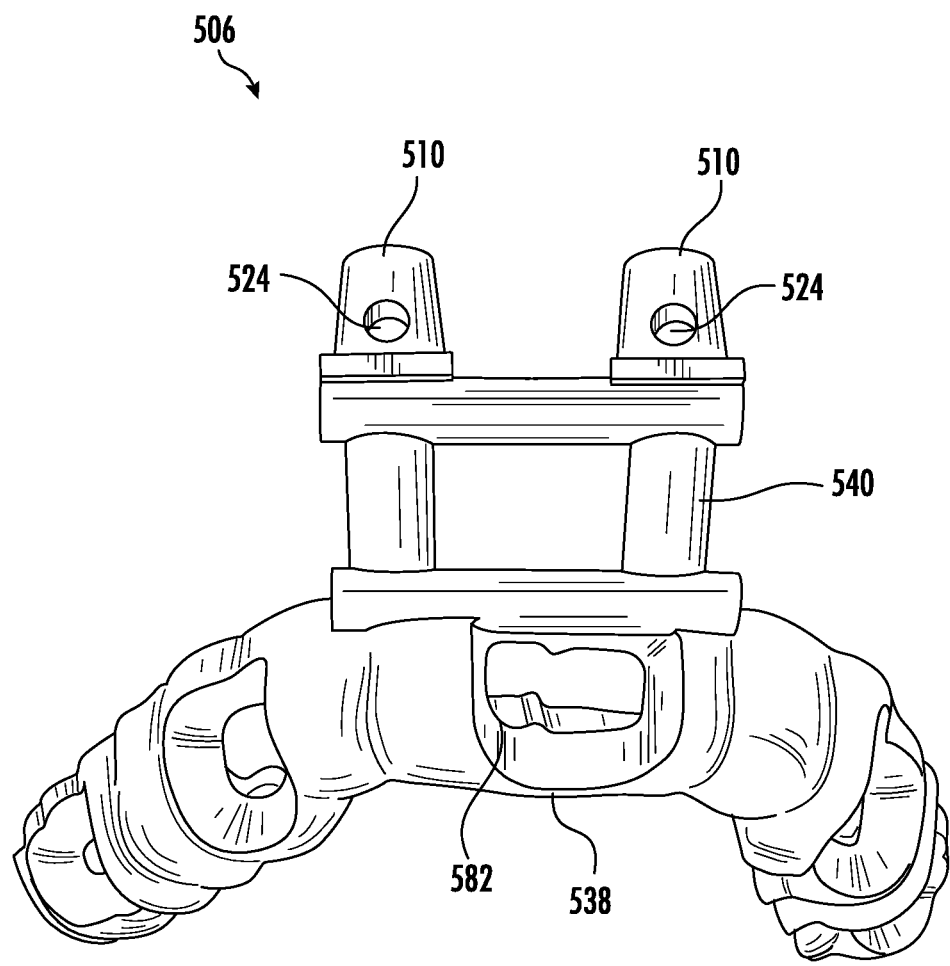
Figure 53:
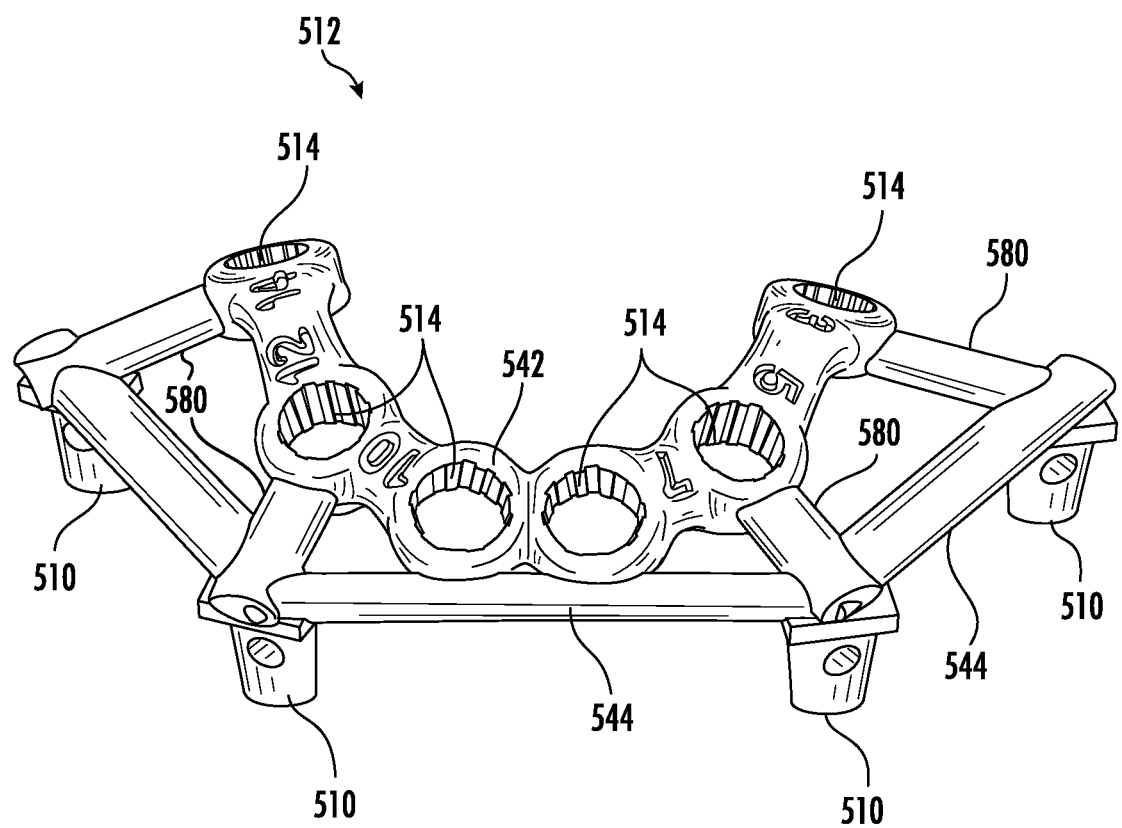
Figure 54:
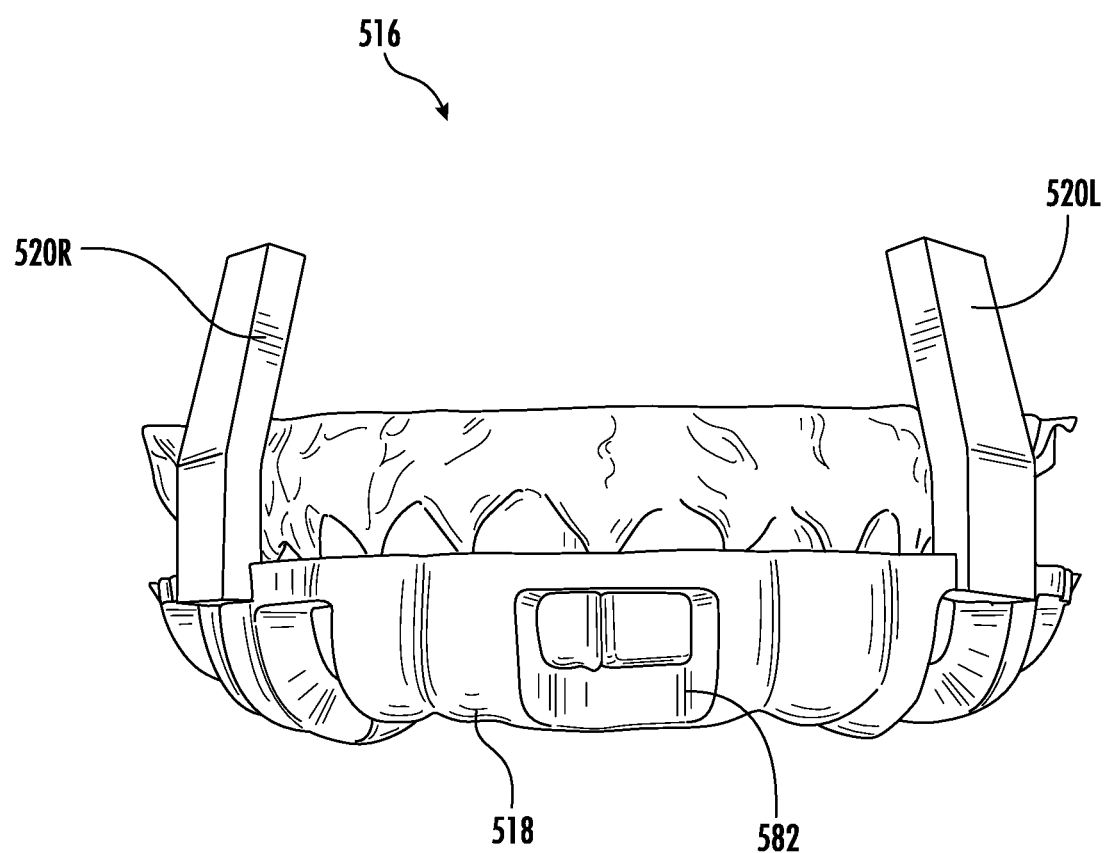
Figure 55:
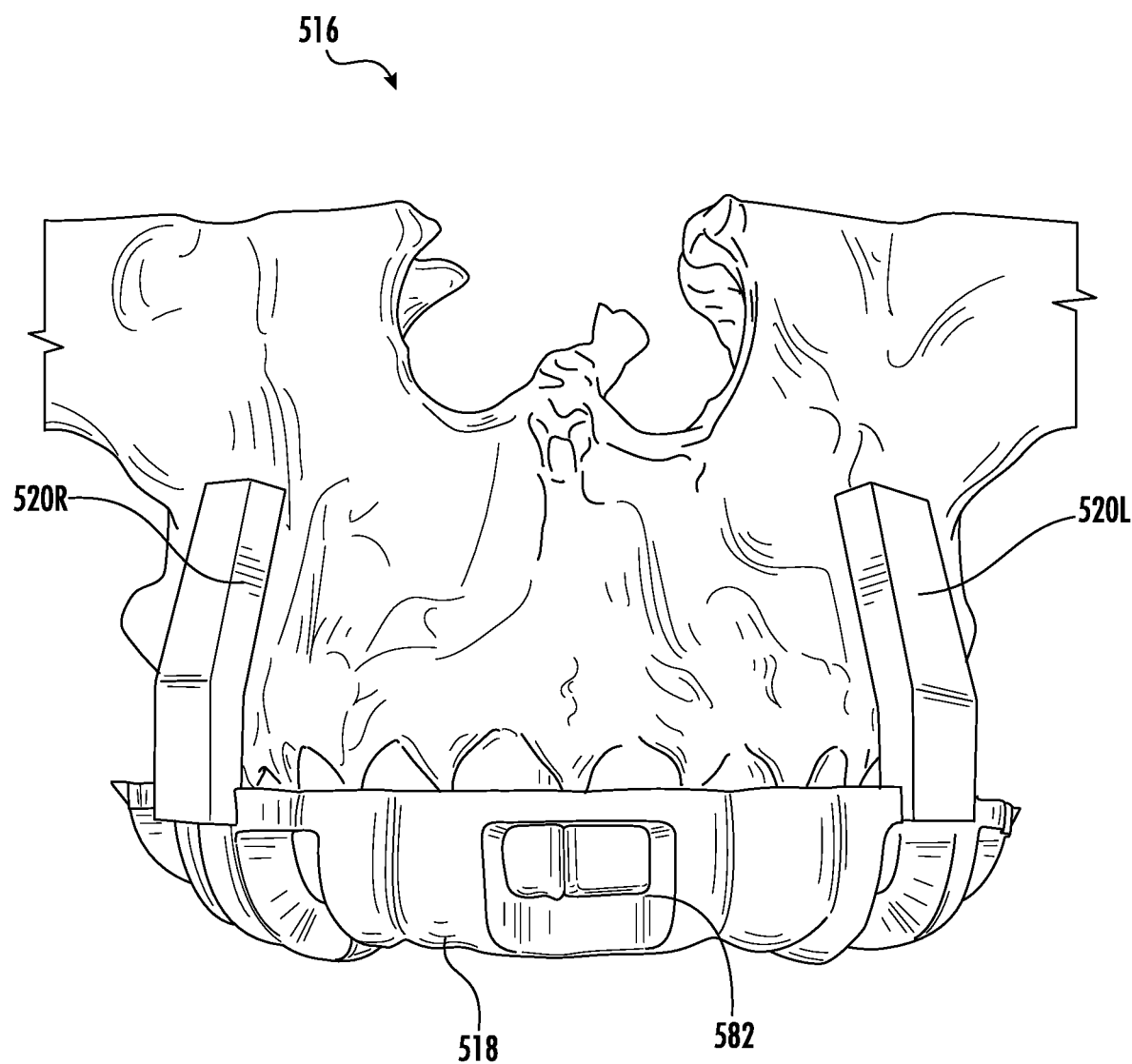
Figure 58:
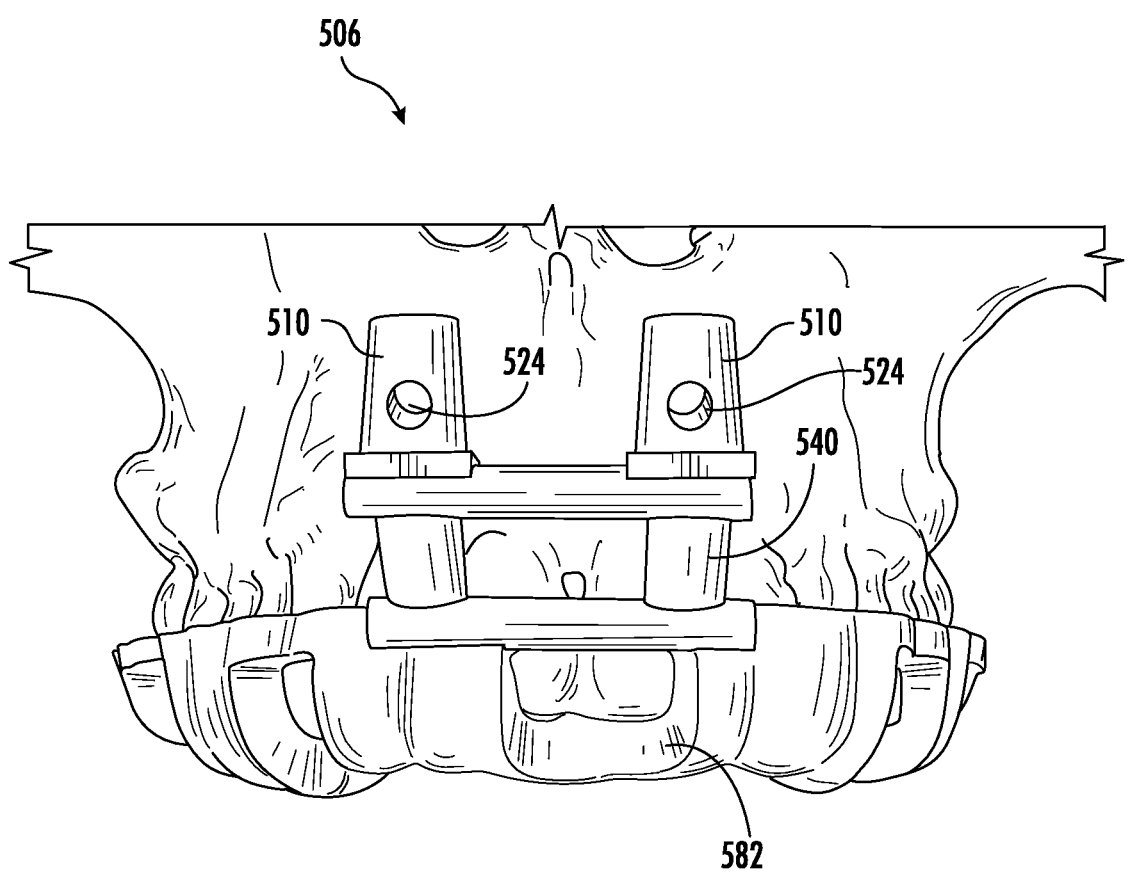
Figure 59:
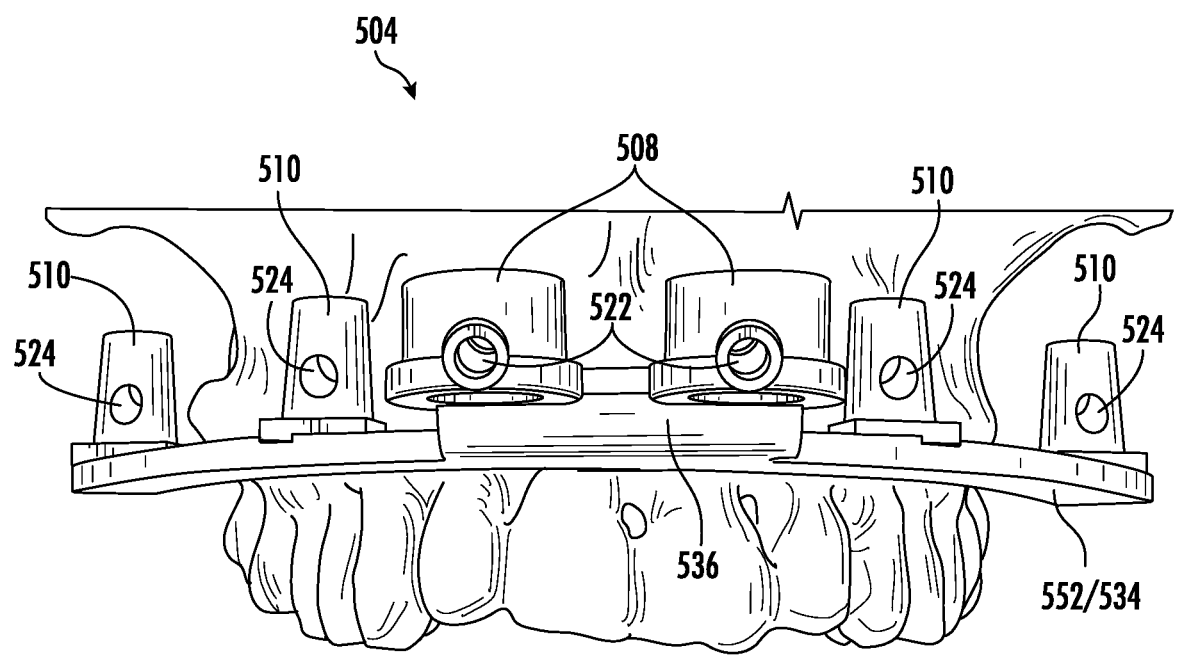
Figure 60:
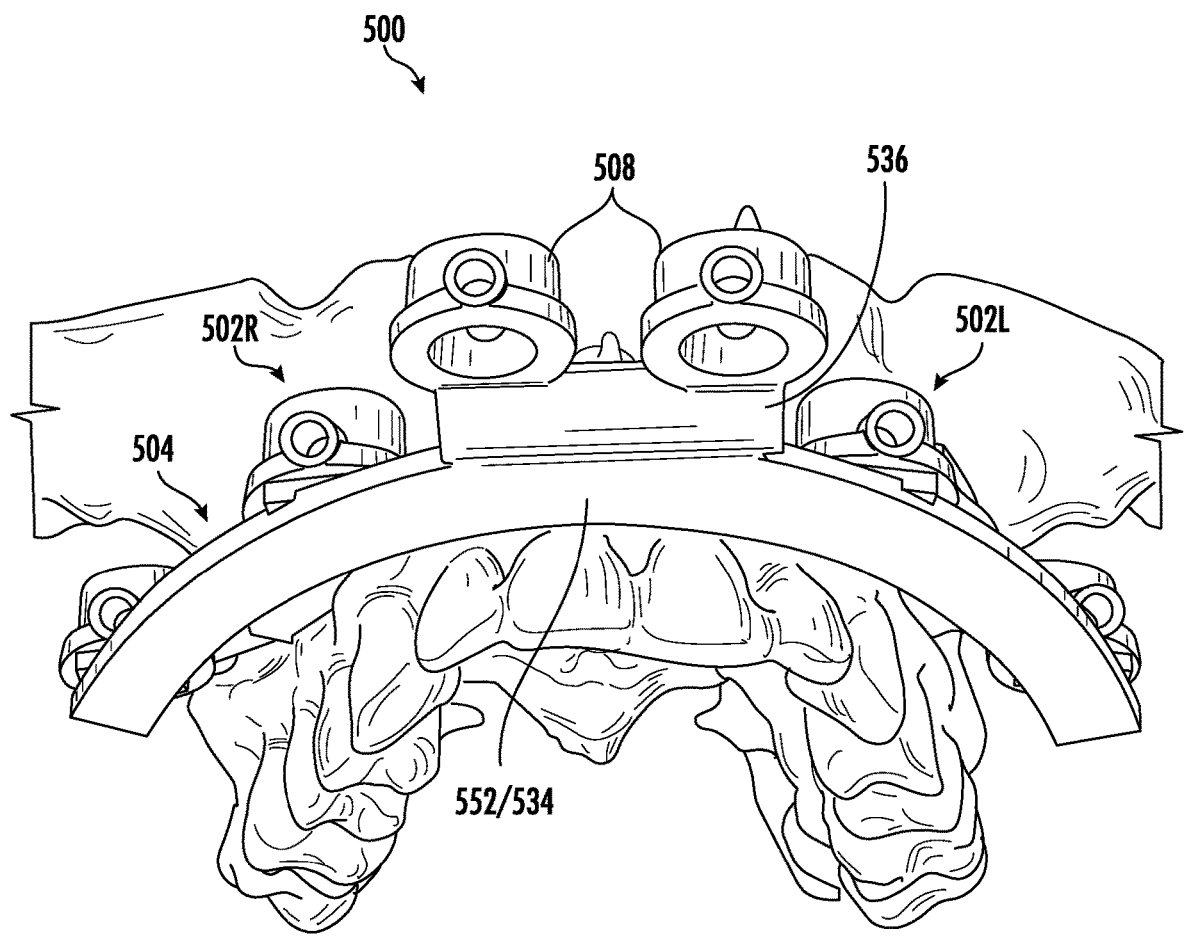
Figure 61:
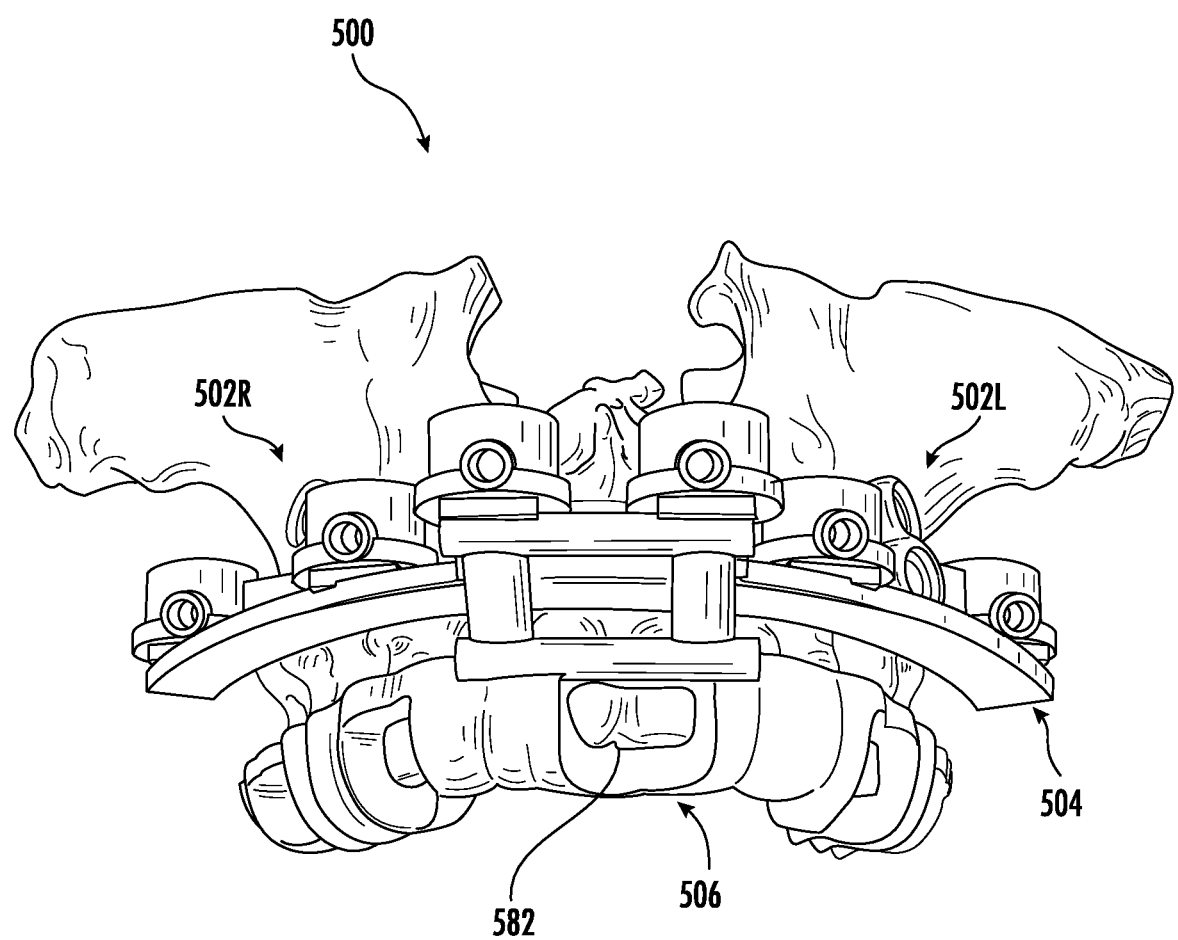
Figure 62:
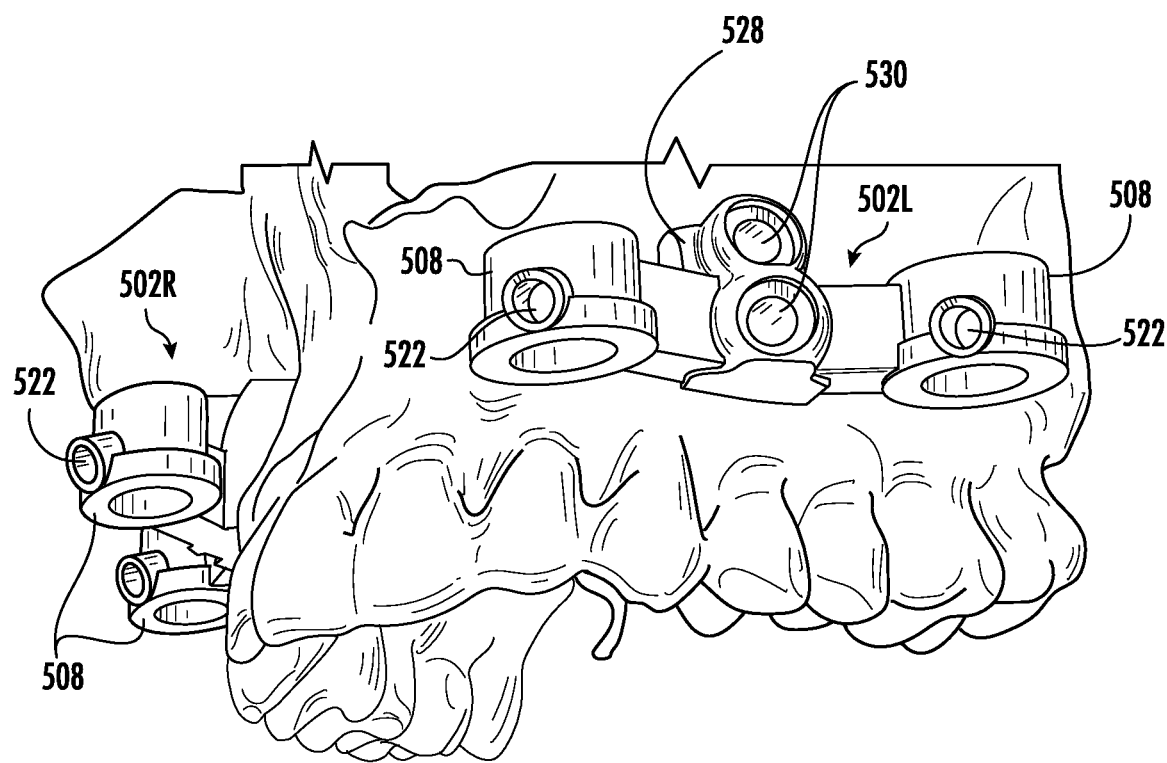
Figure 63:
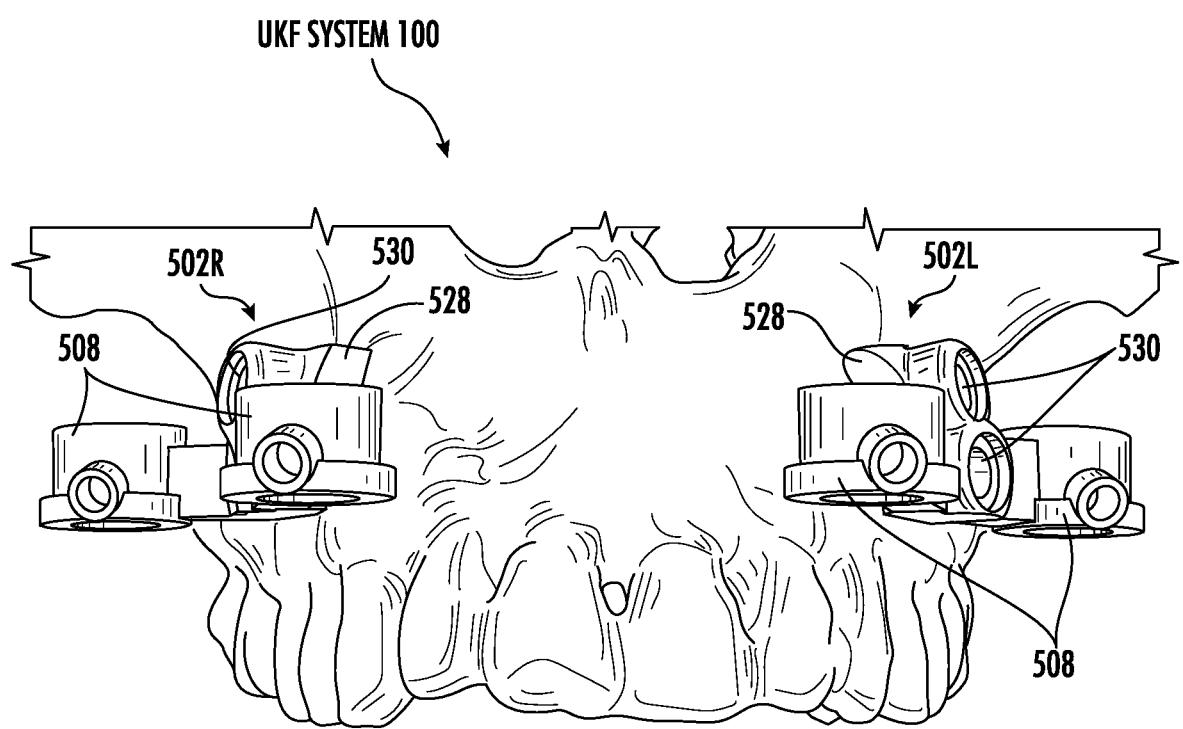
Figure 64:
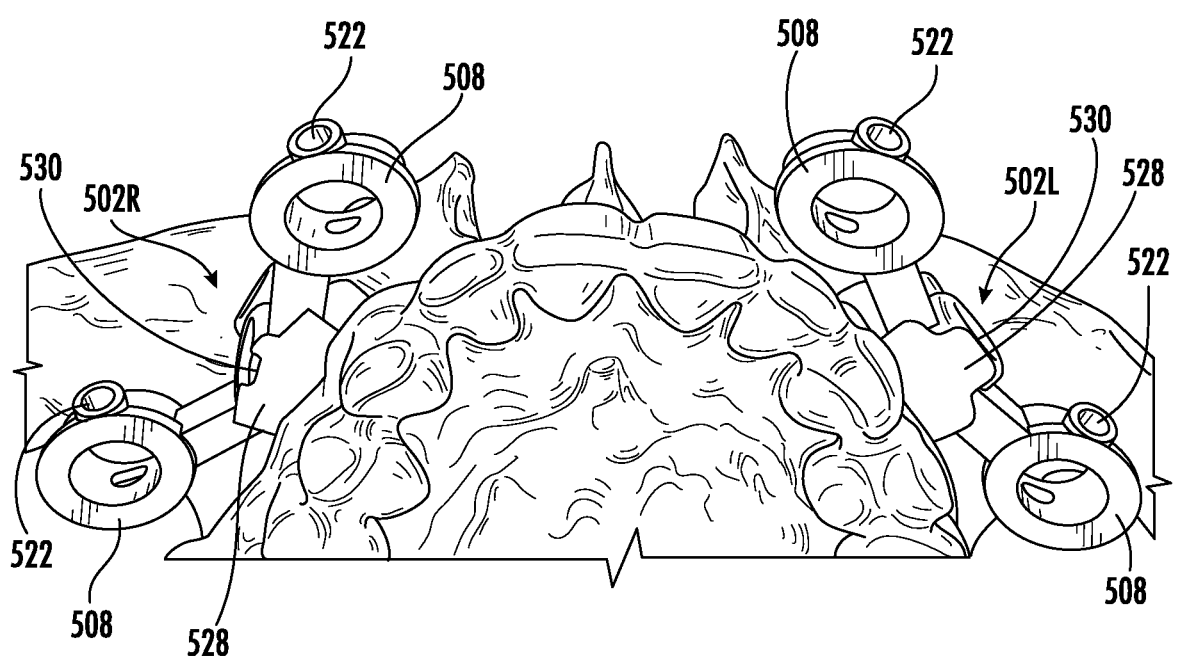
Figure 65:
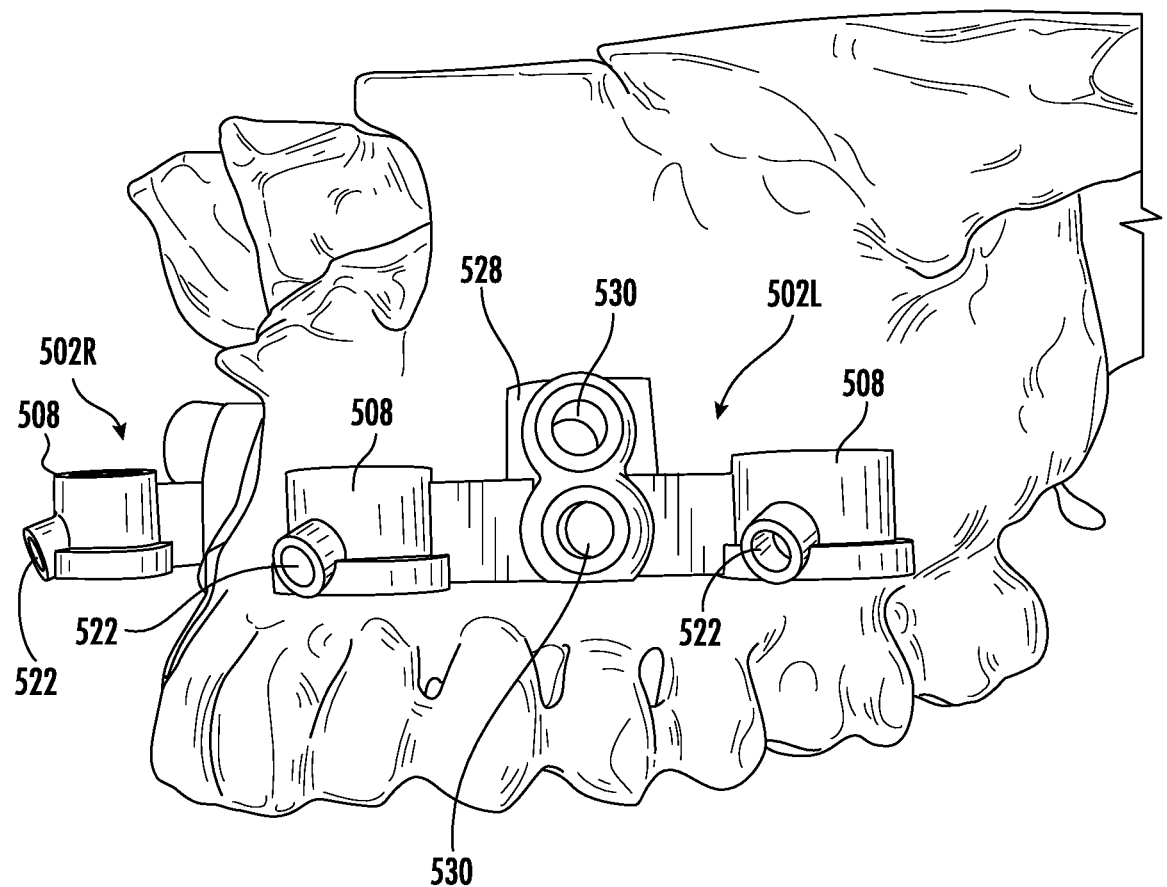
Figure 66:
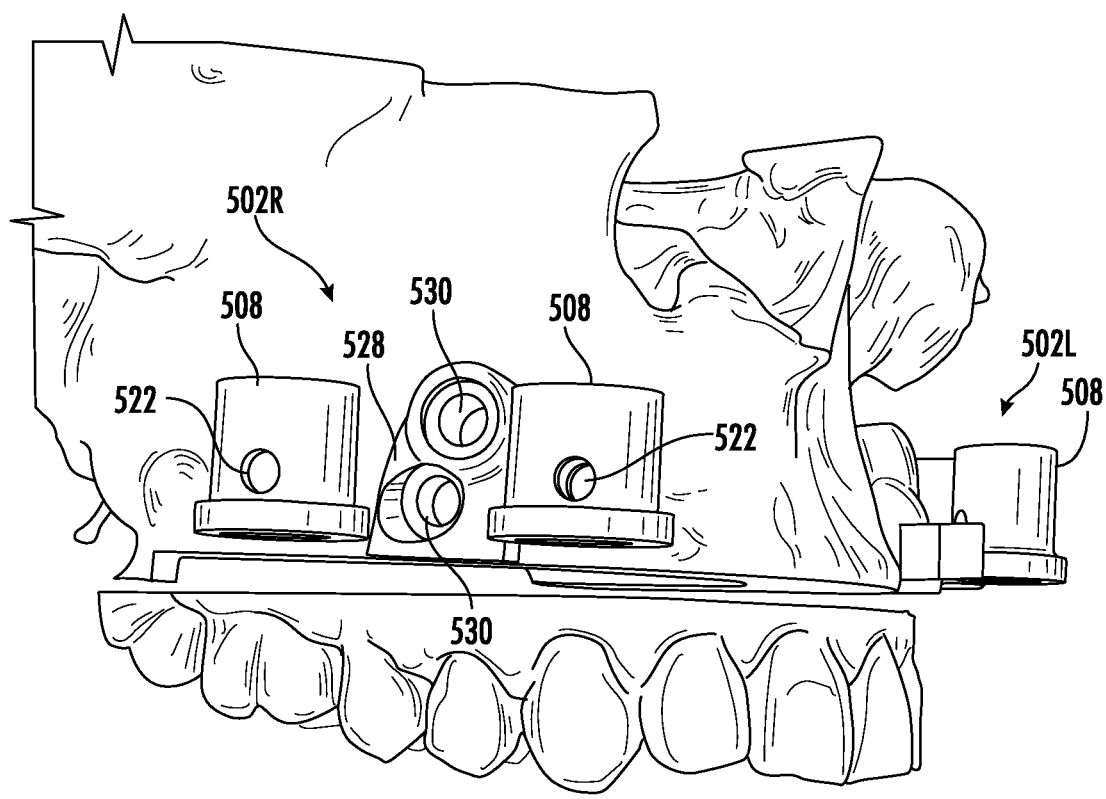
Figure 67:
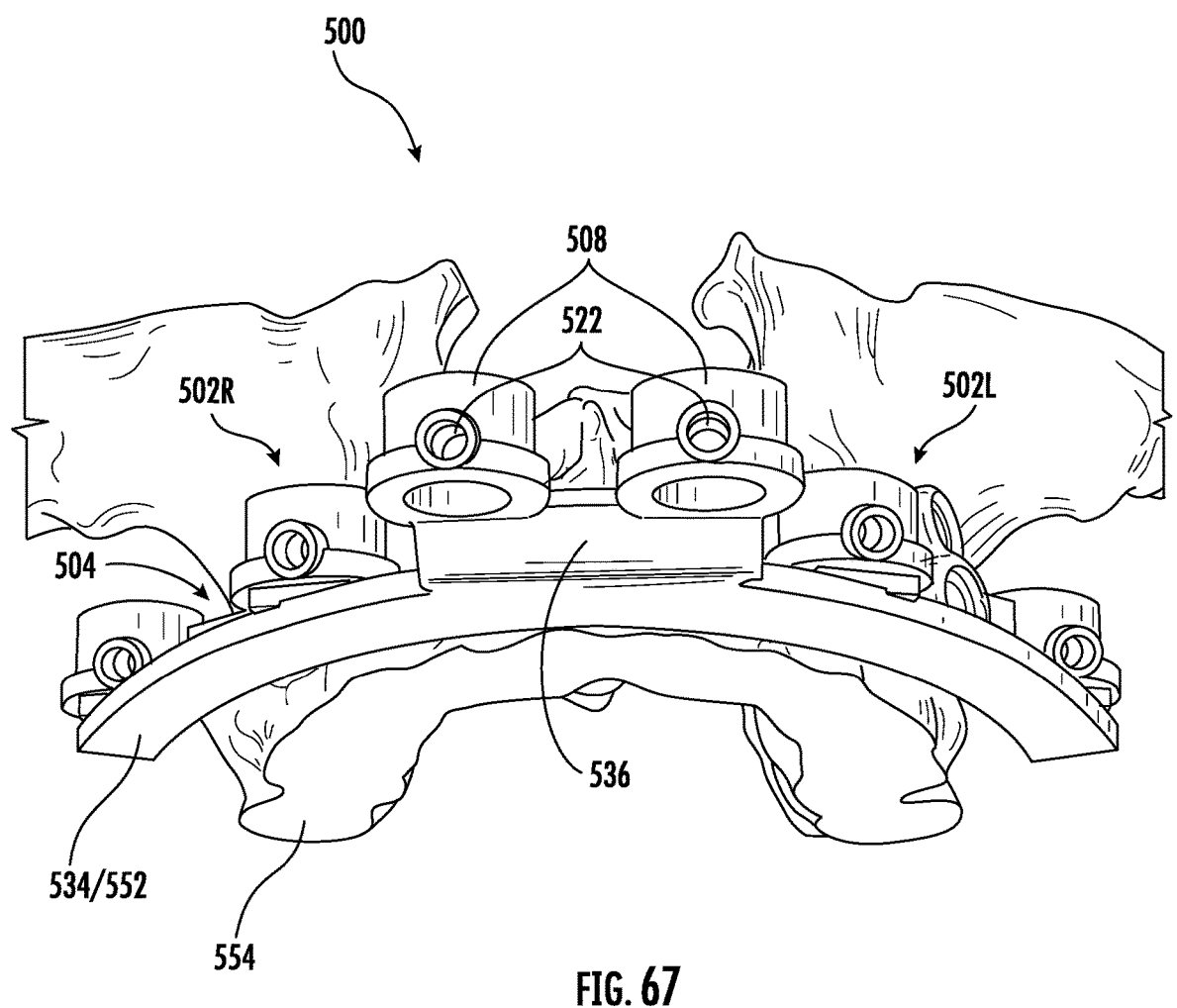
Figure 68:
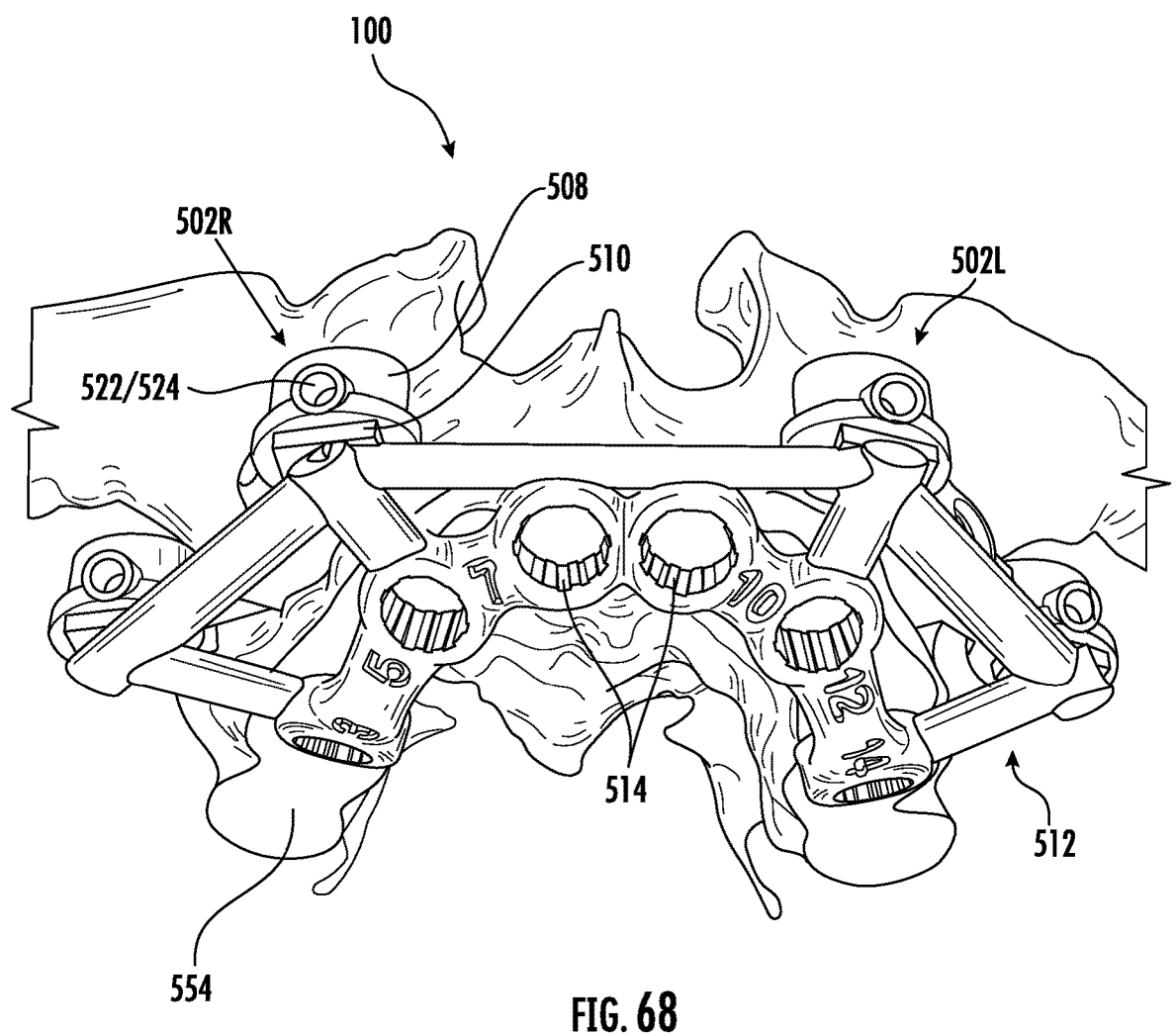
Figure 69:
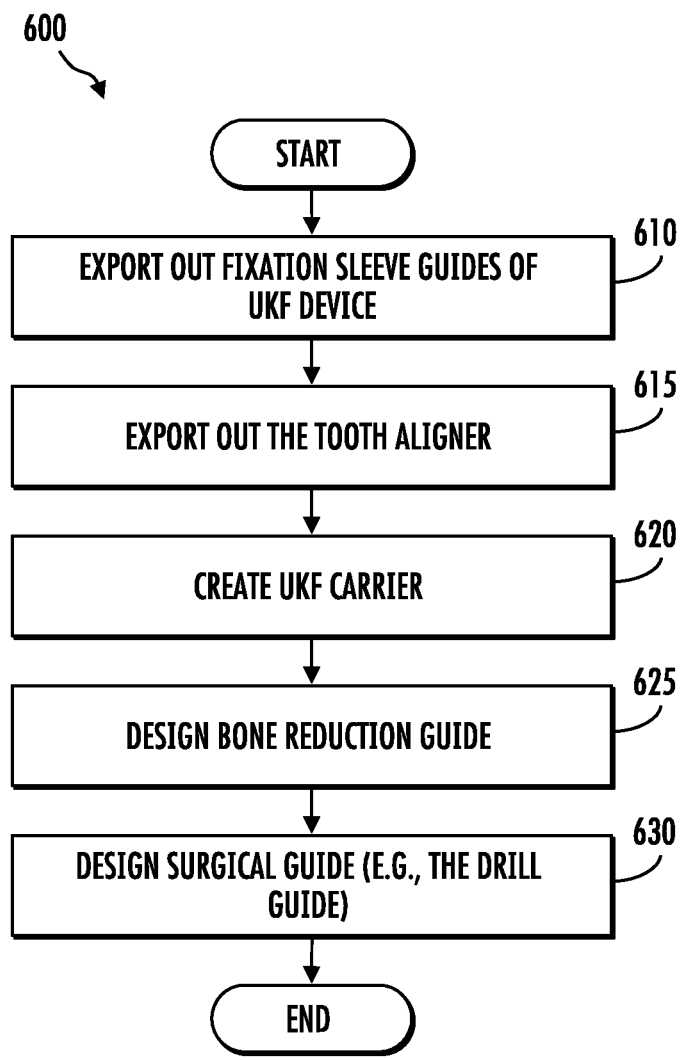
Figure 70:
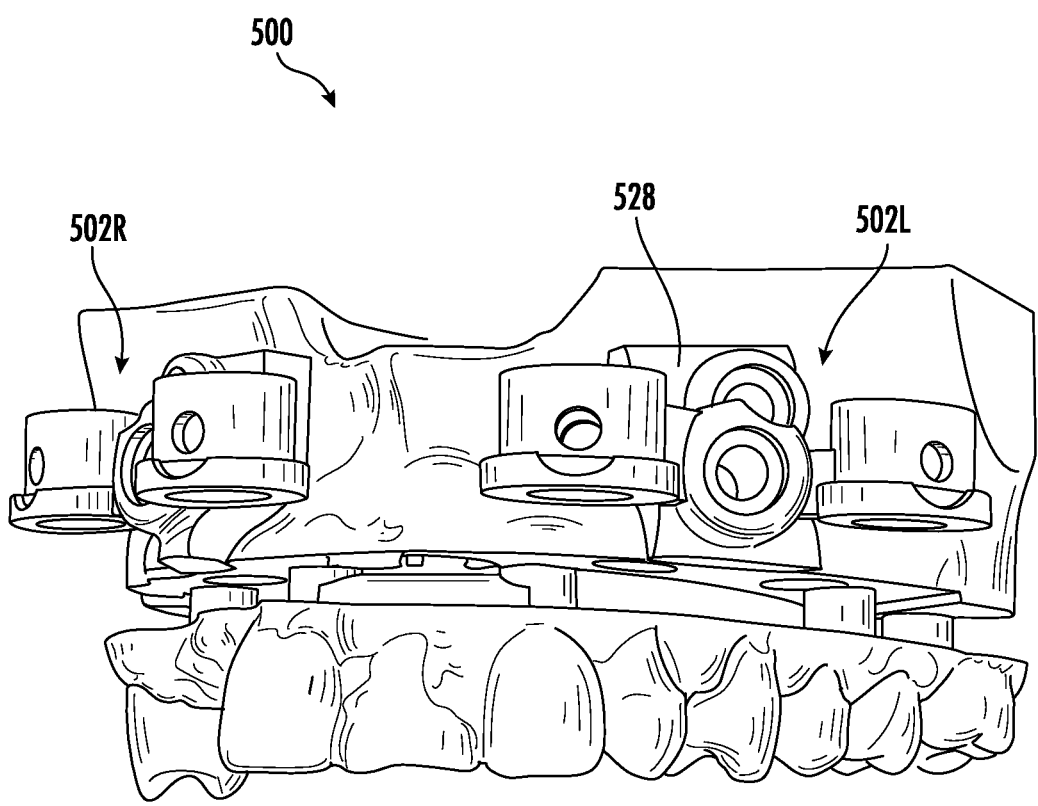
Figure 82:
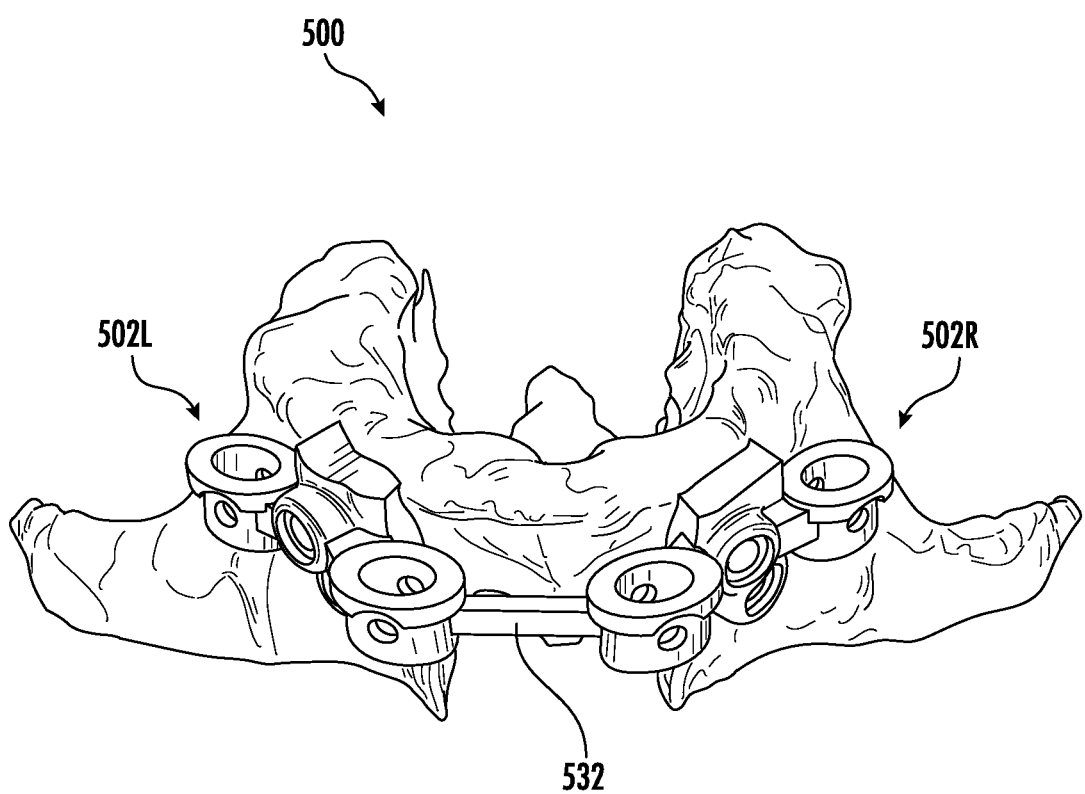
Figure 83:
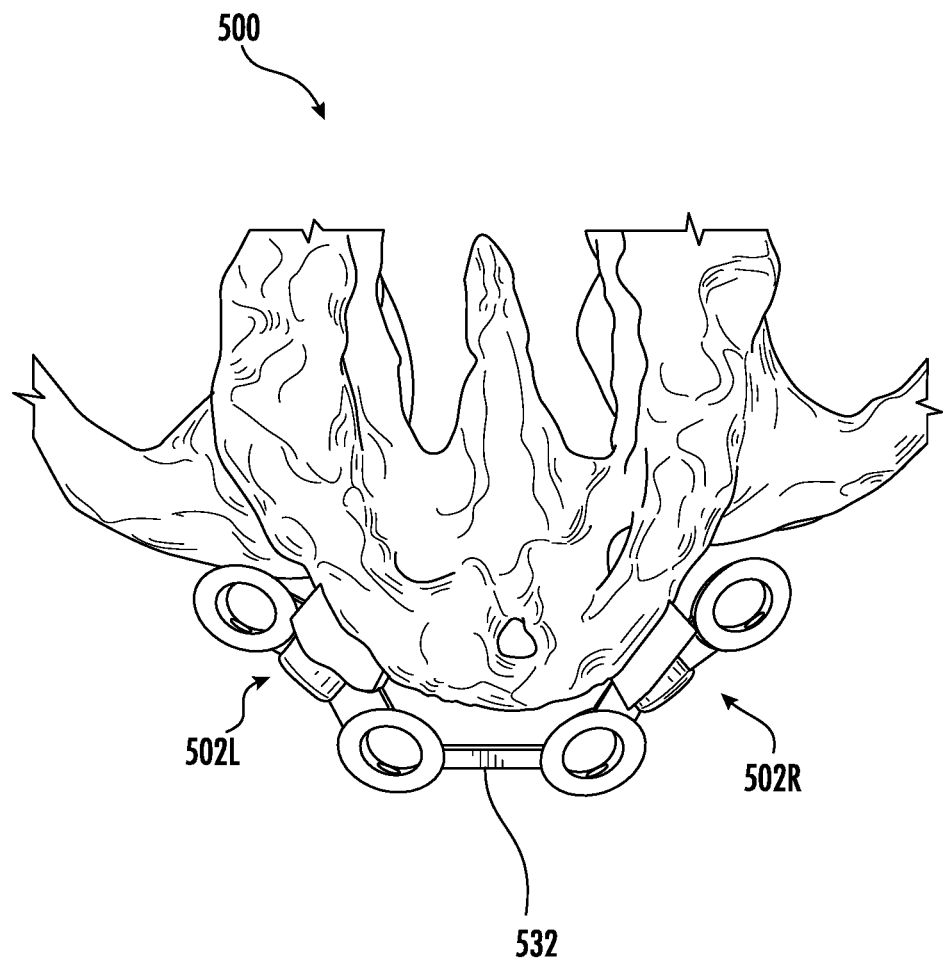
Figure 84:
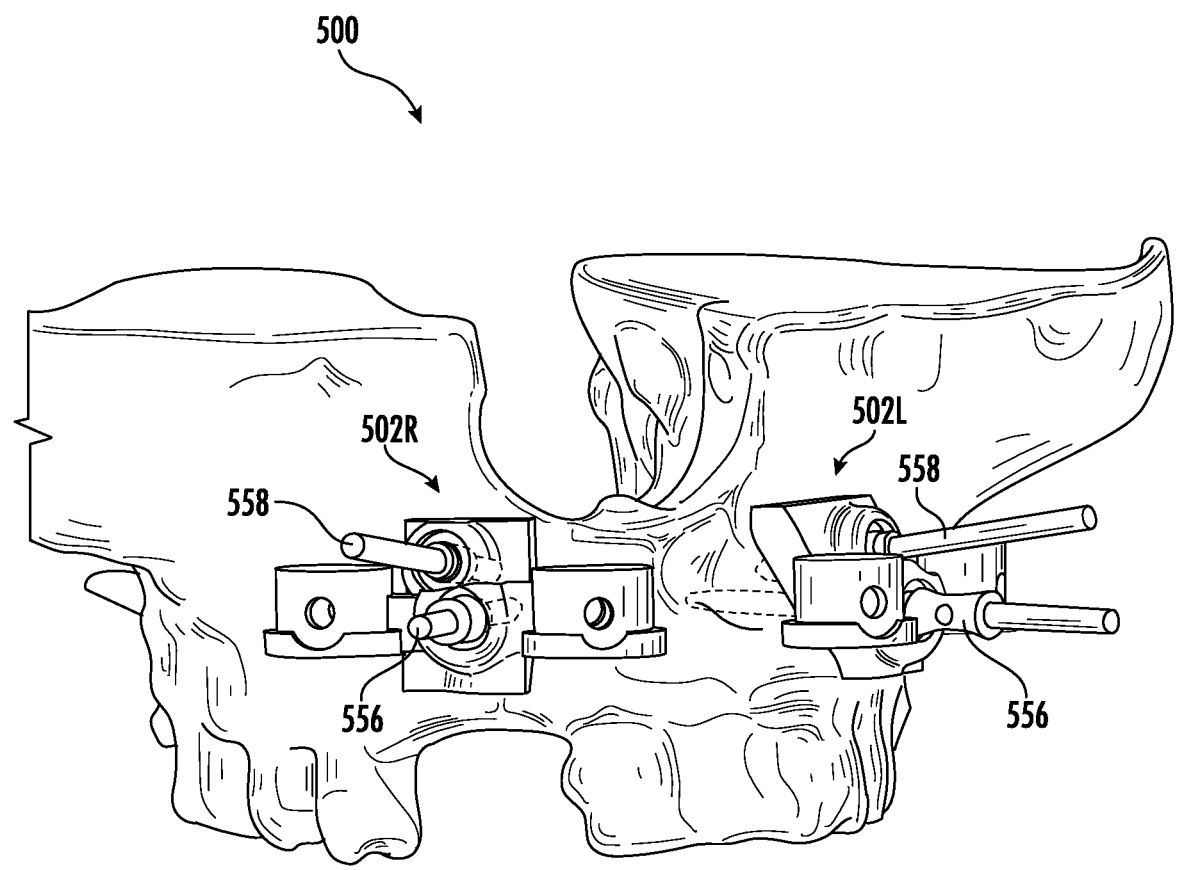
Figure 85:
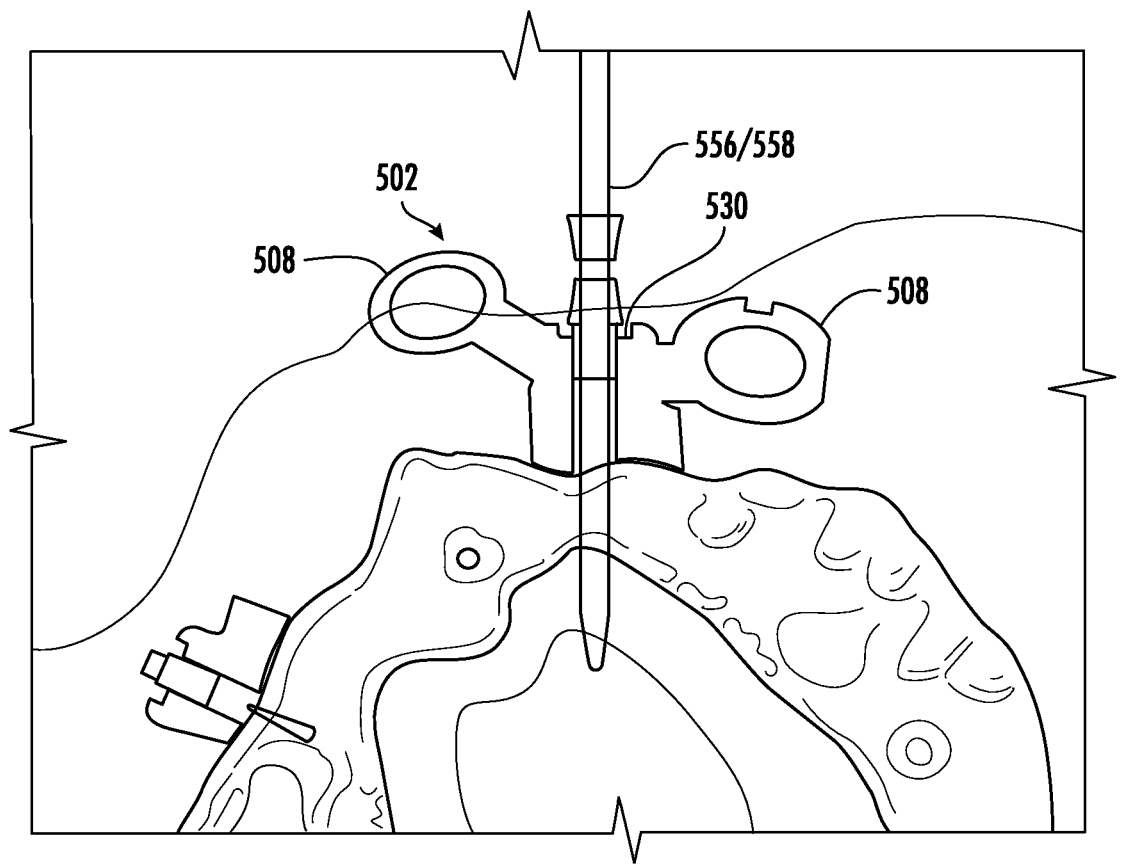
Figure 86:
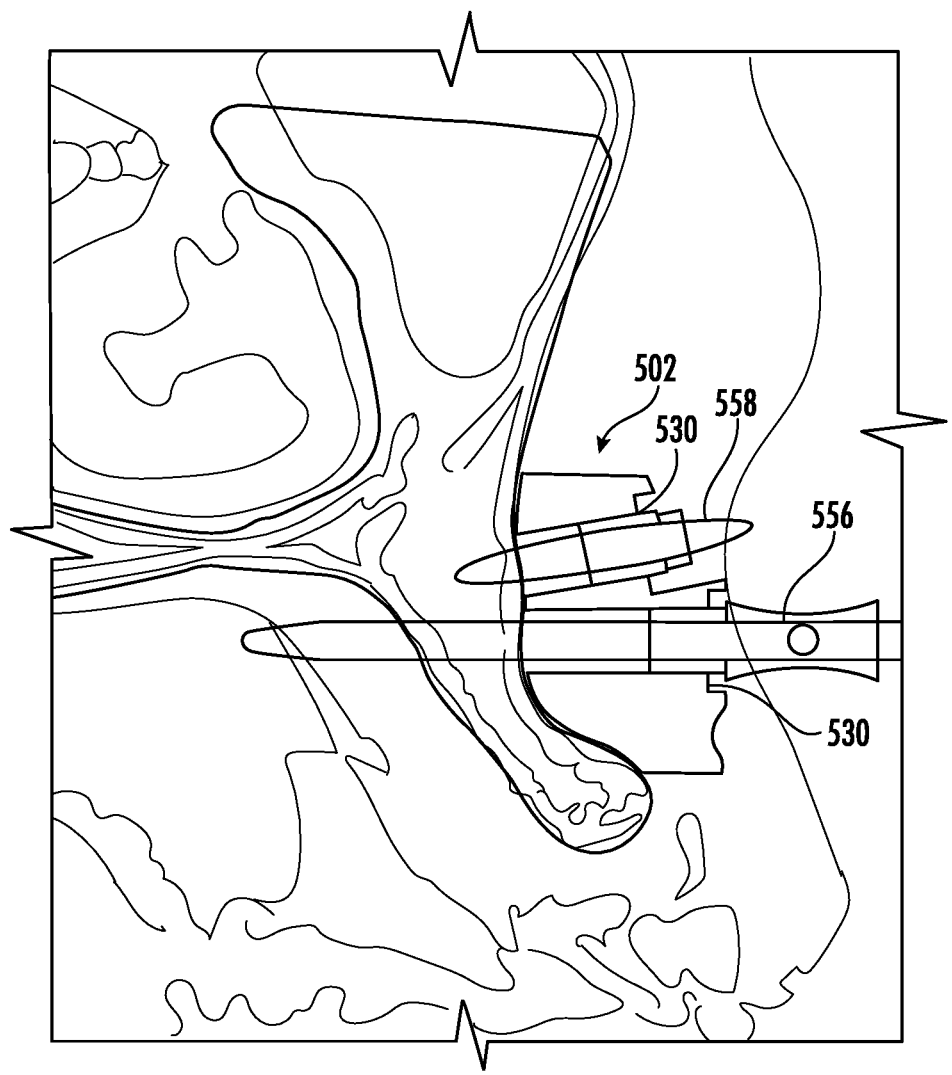
Figure 87:
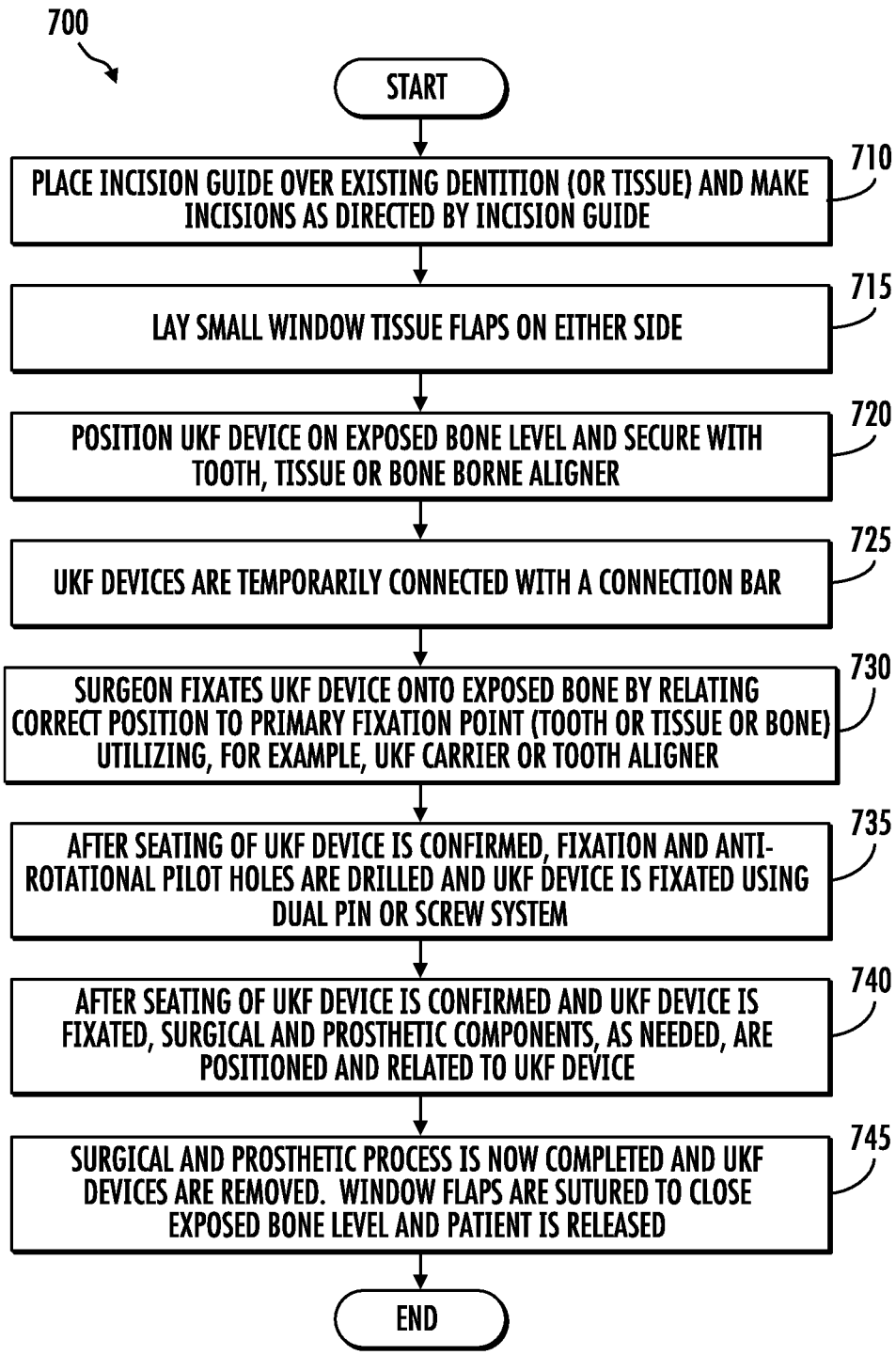
Figure 88A:
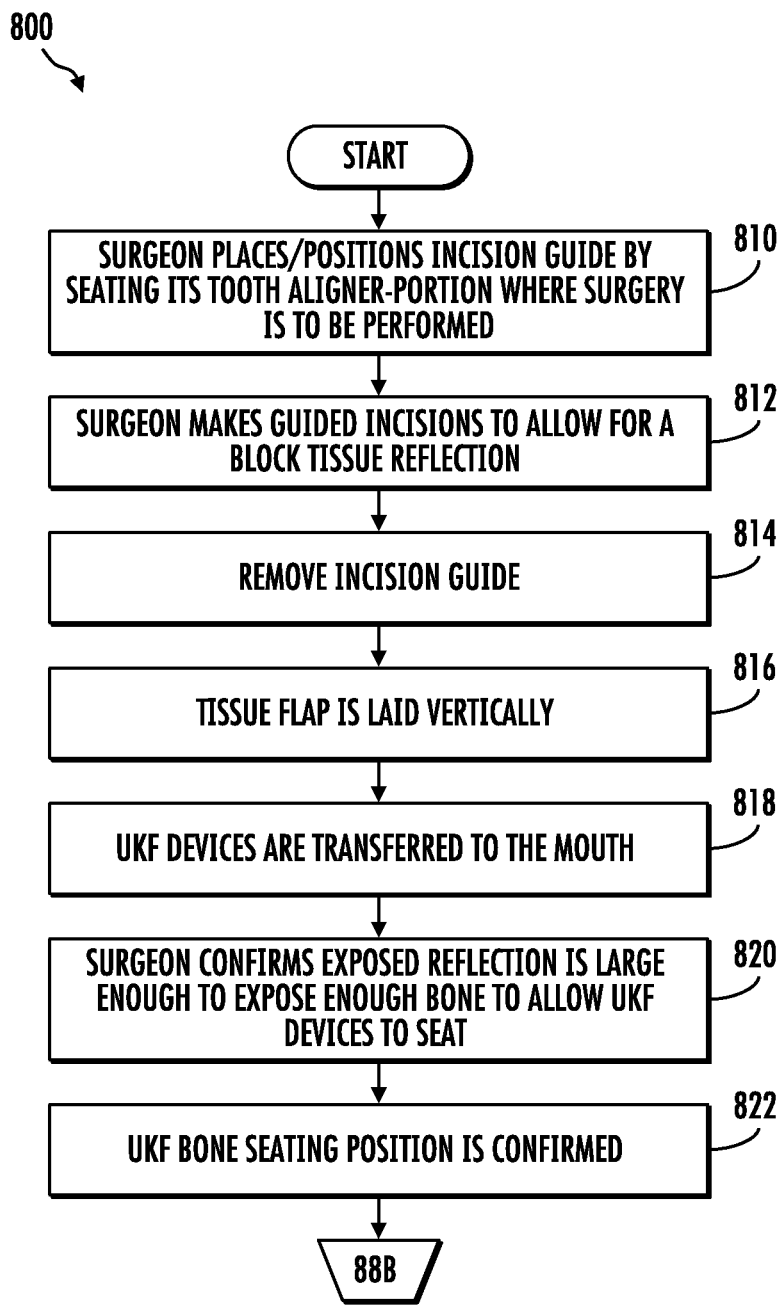
Figure 88B:
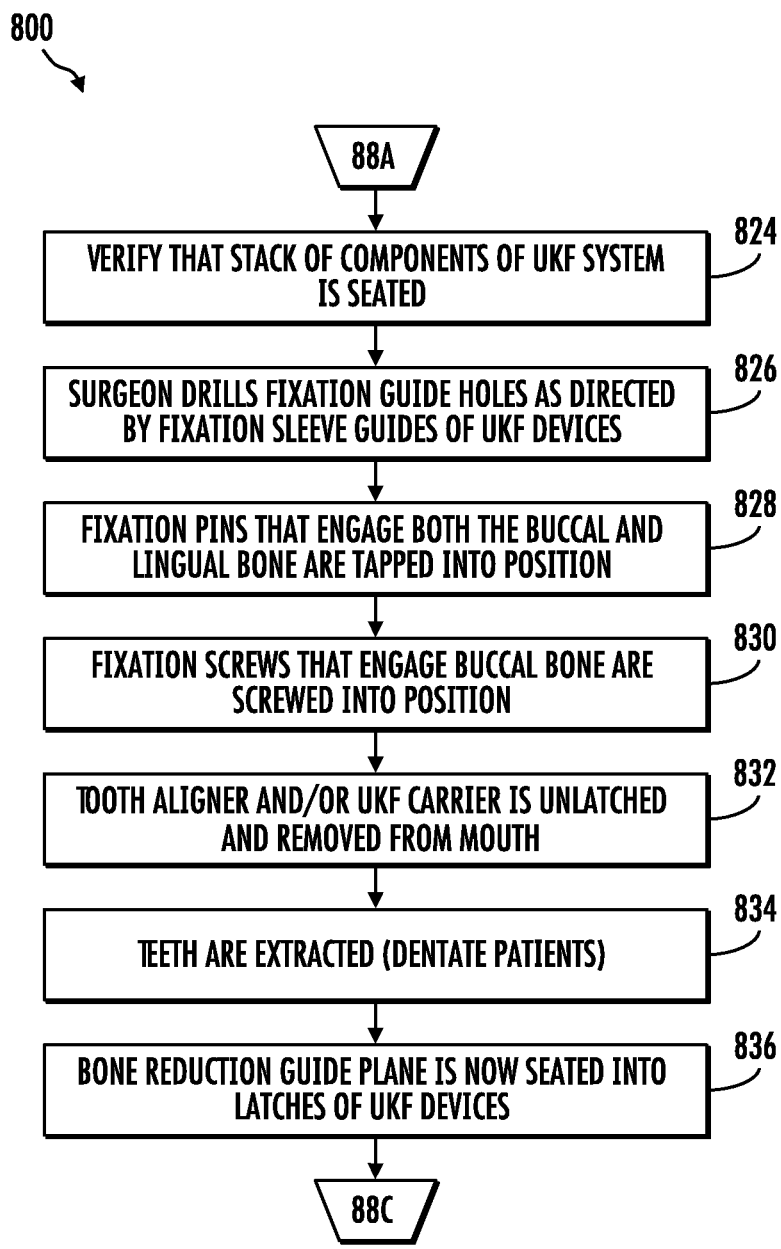
Figure 88C:
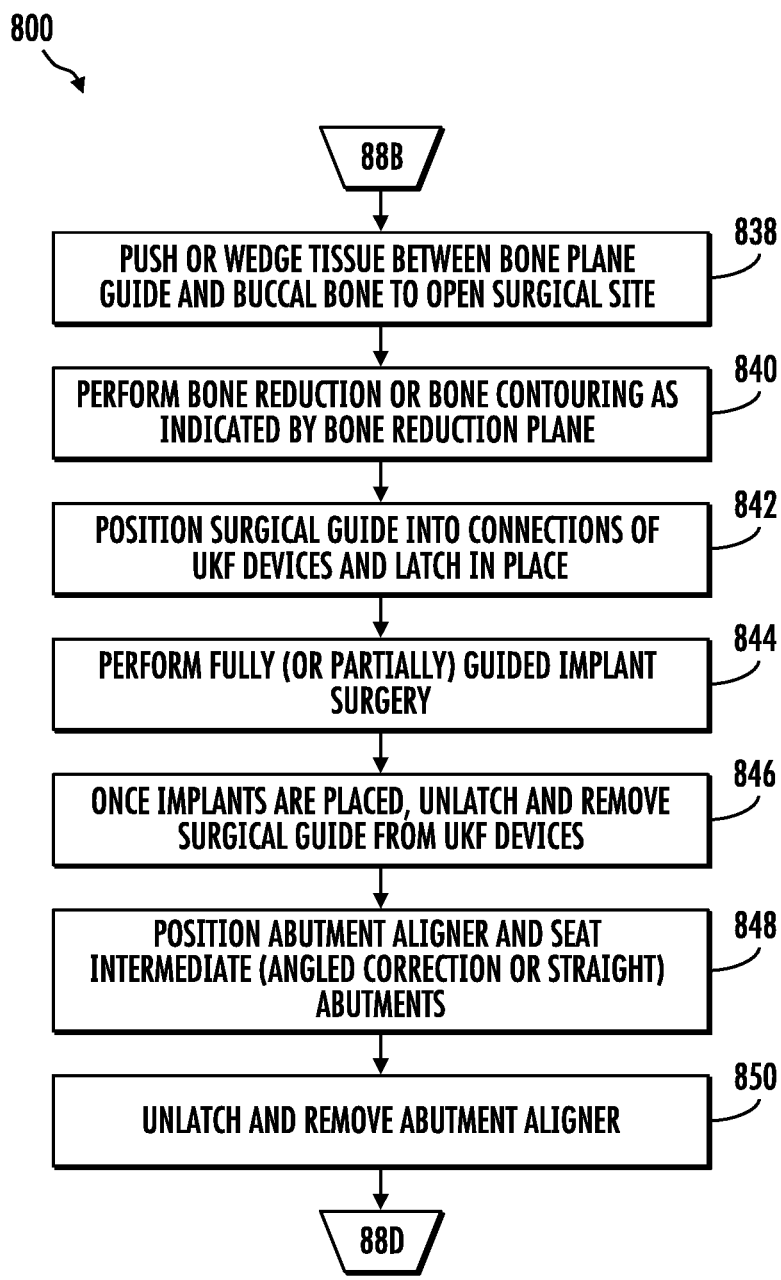
Figure 88D:
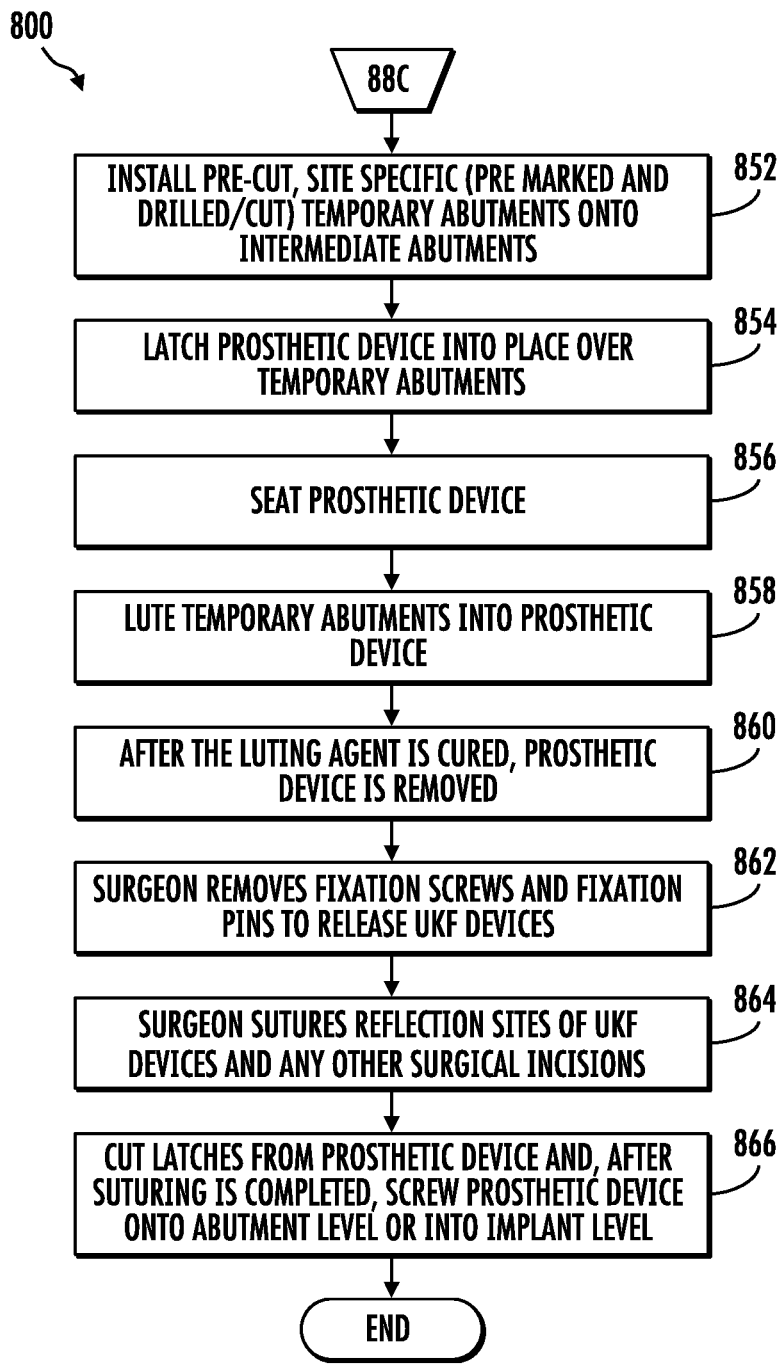
Figure 89:
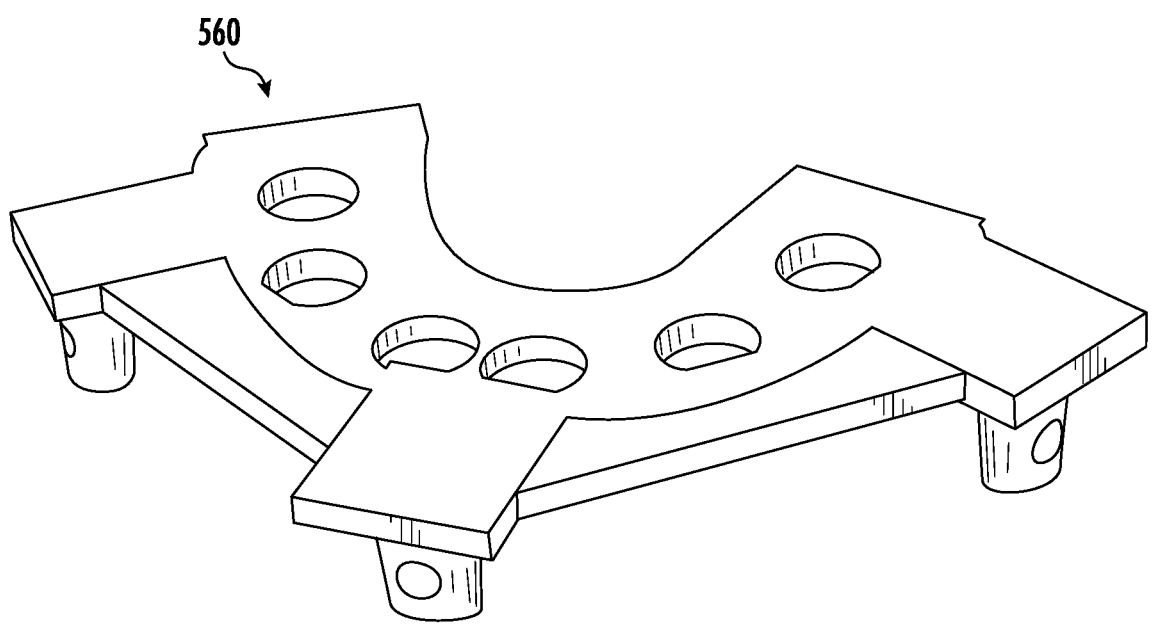
Figure 90:
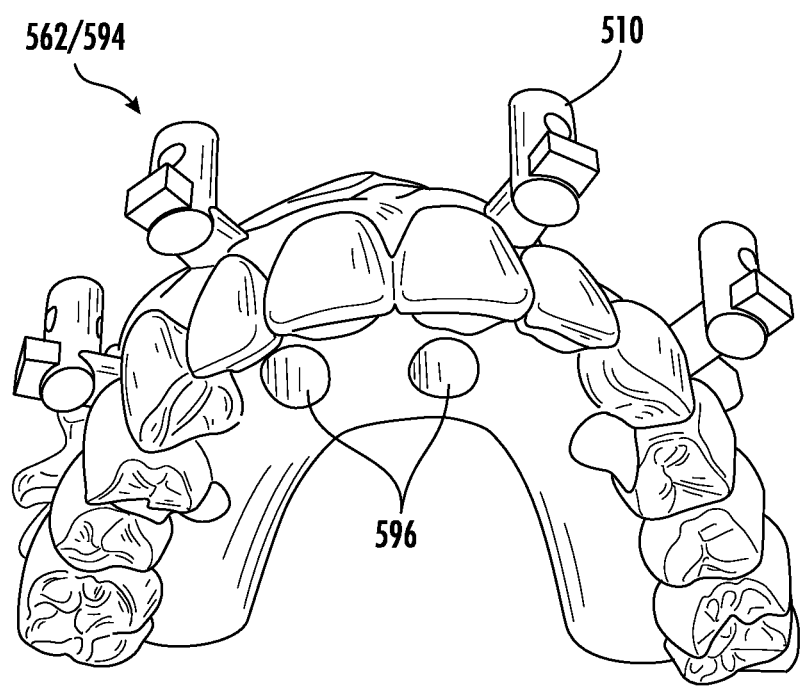
Figure 91:
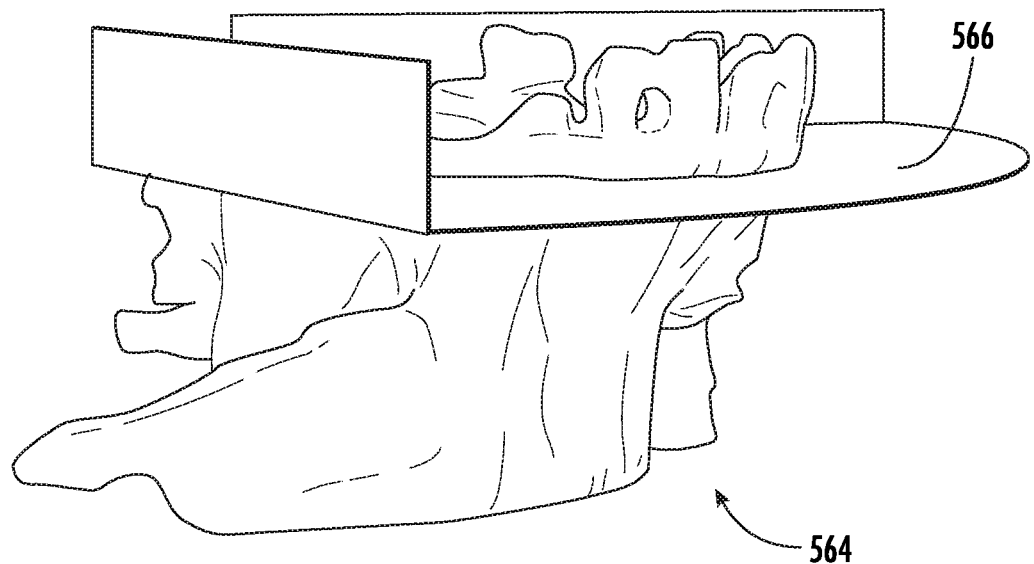
Figure 92:
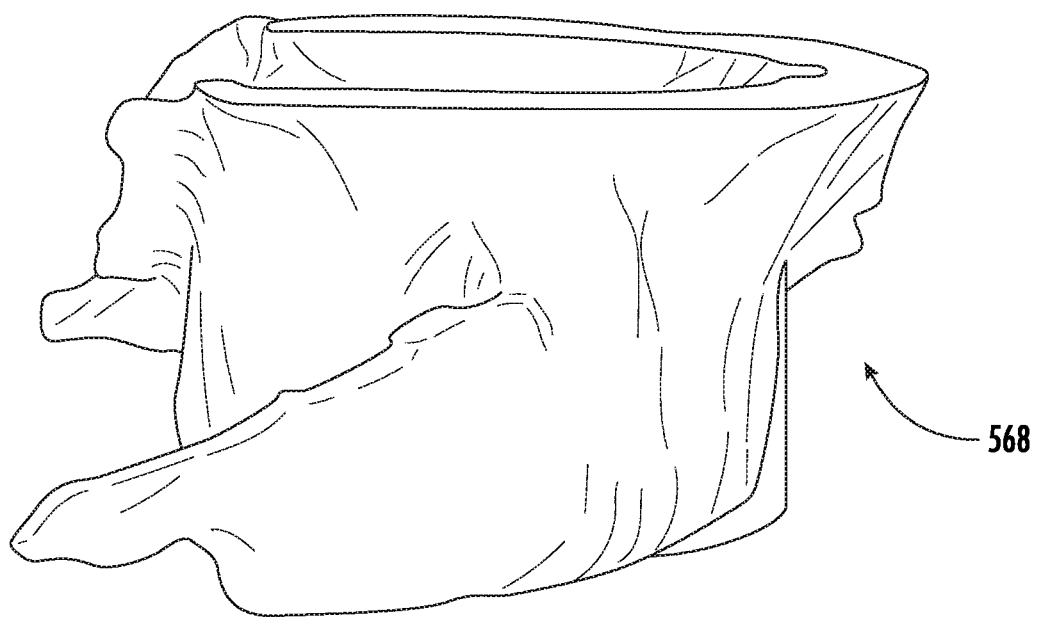
Figure 93:
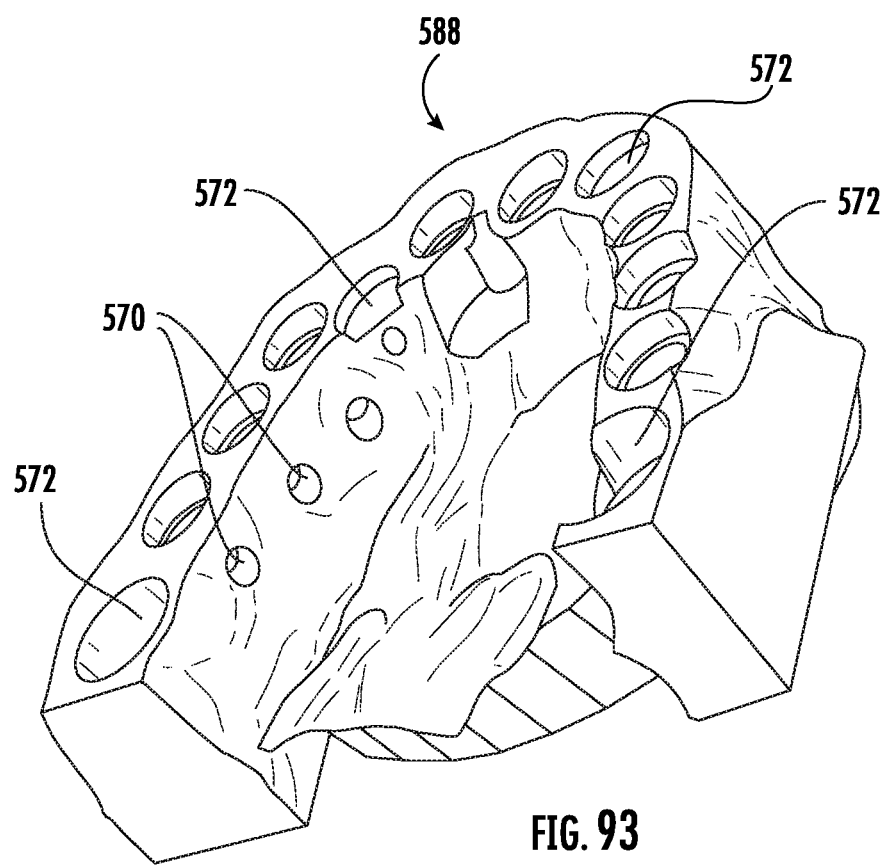
Figure 94:
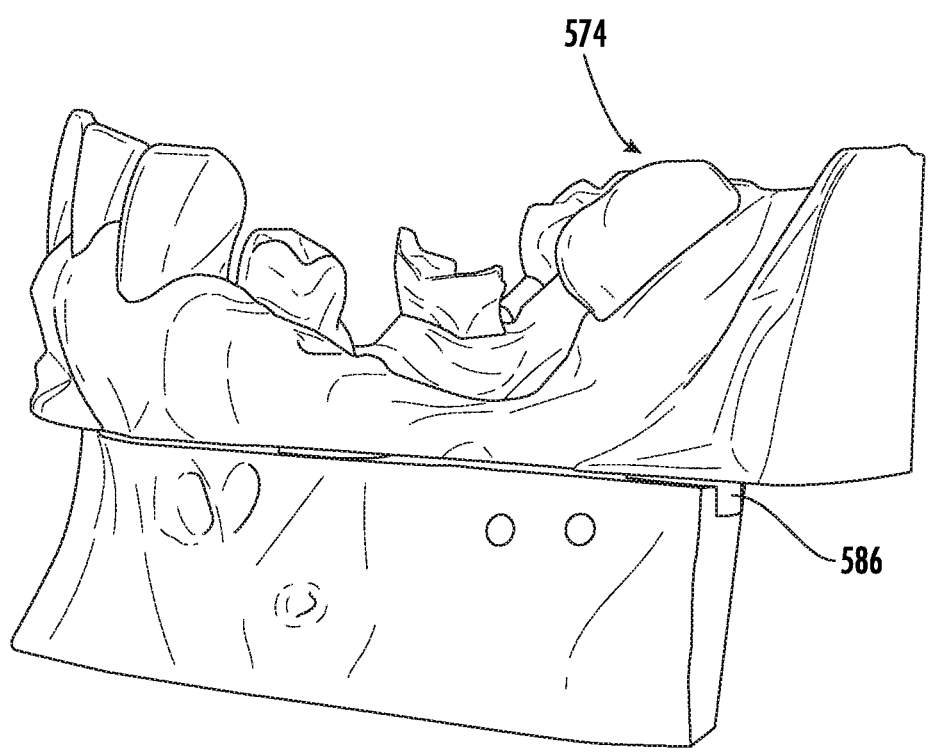
Figure 95:
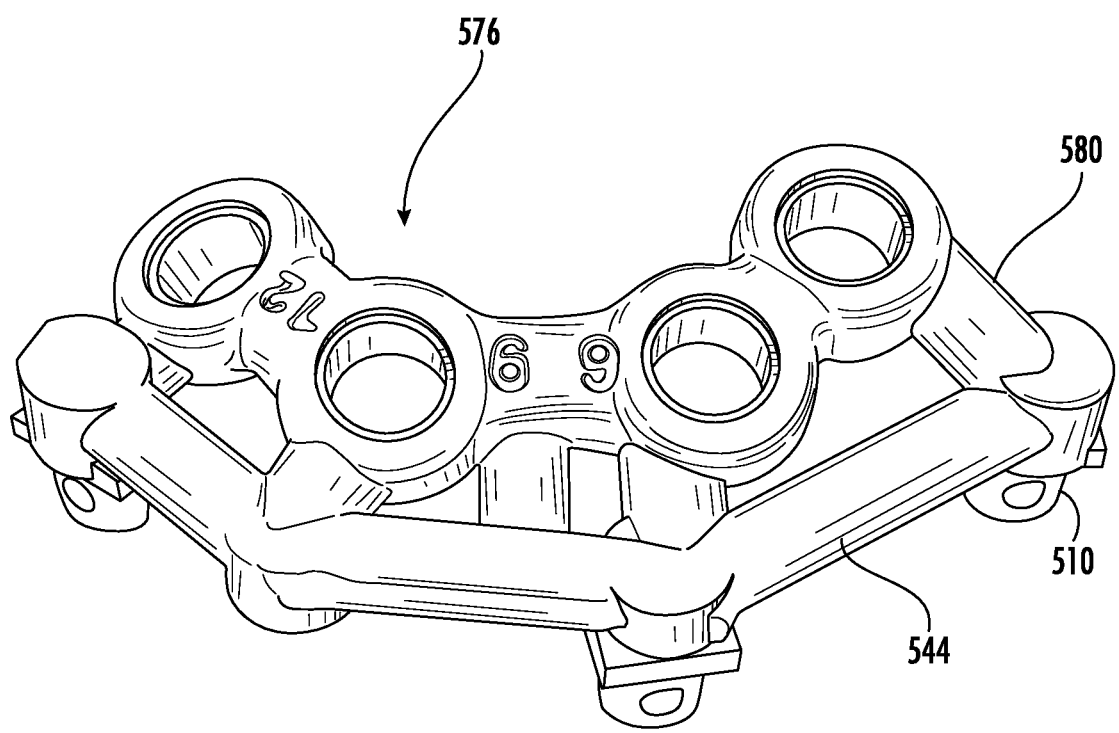
Figure 96:
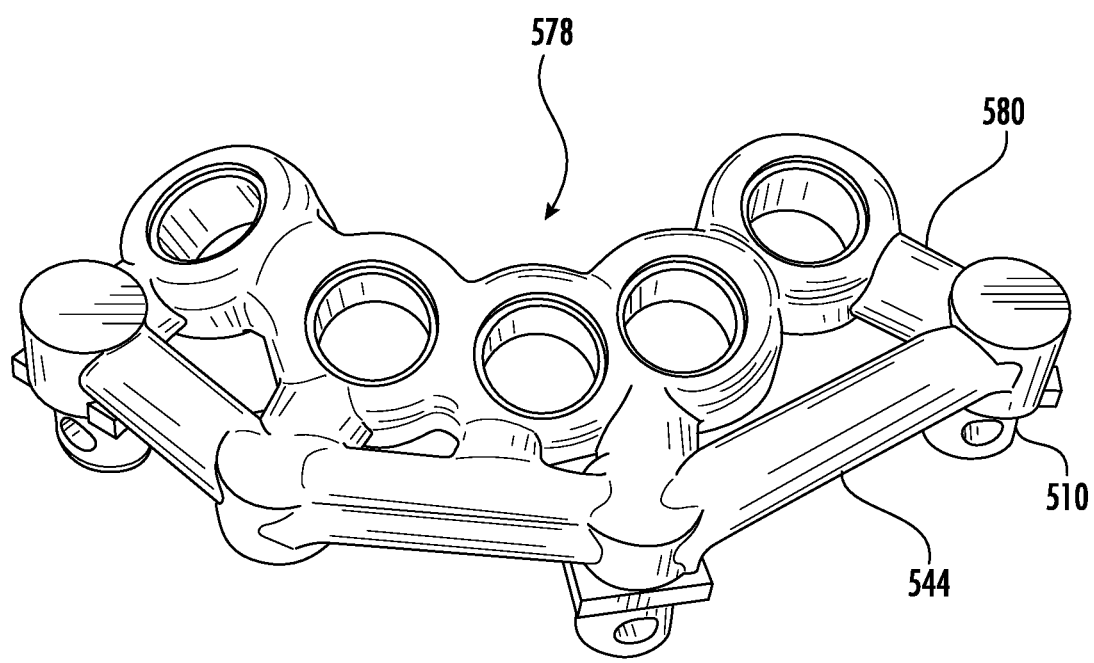
Figure 97:
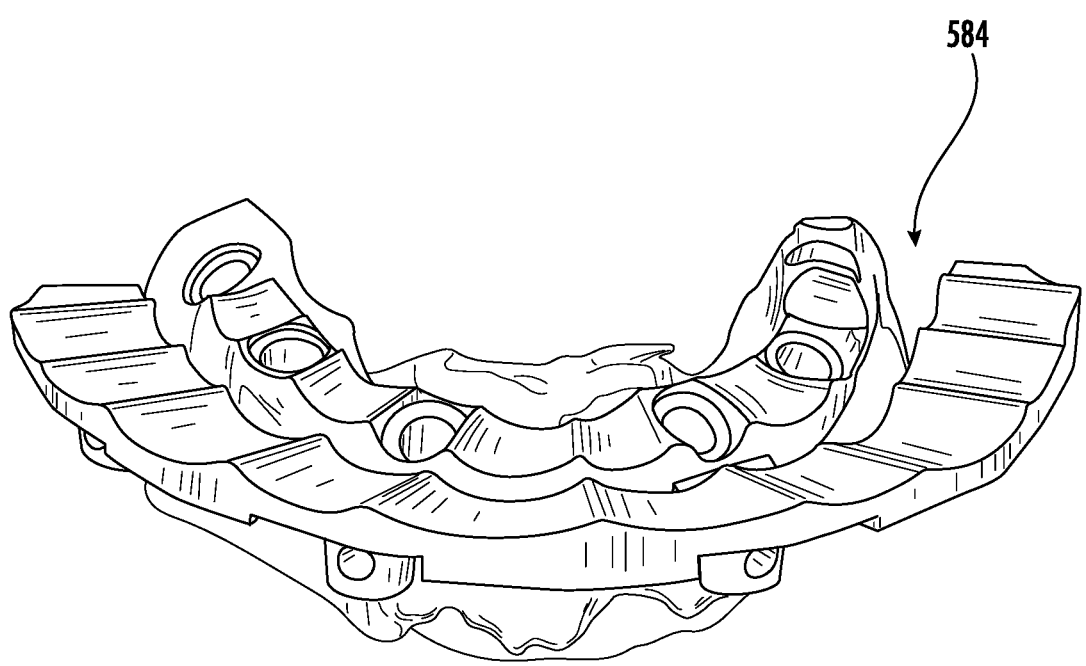
Figure 98:
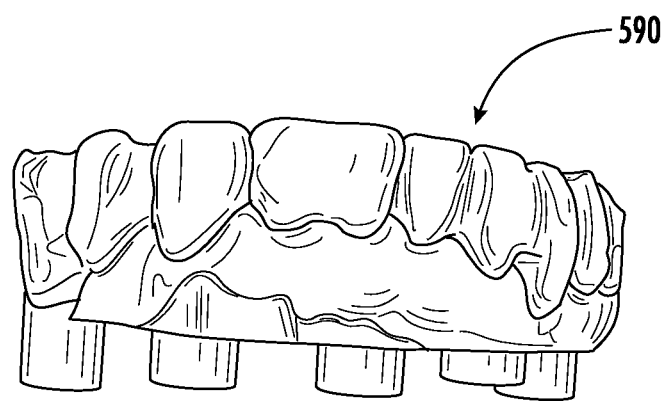
Figure 99:
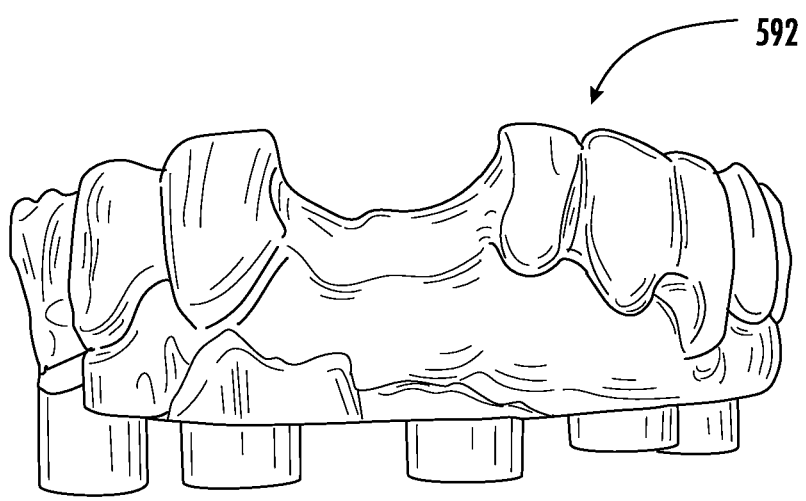
Figure 100:
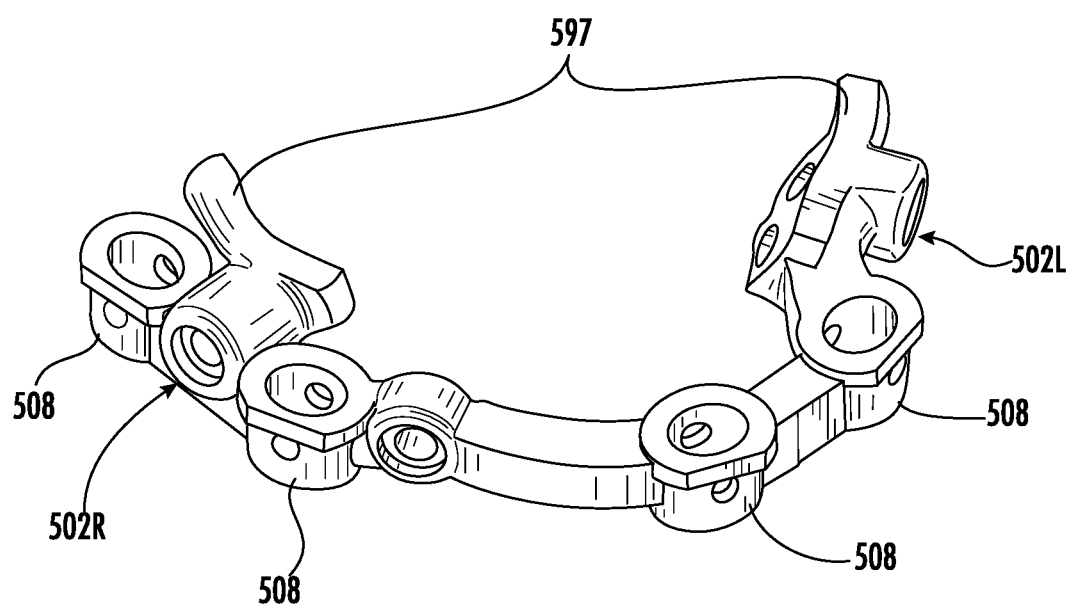
Figure 101:
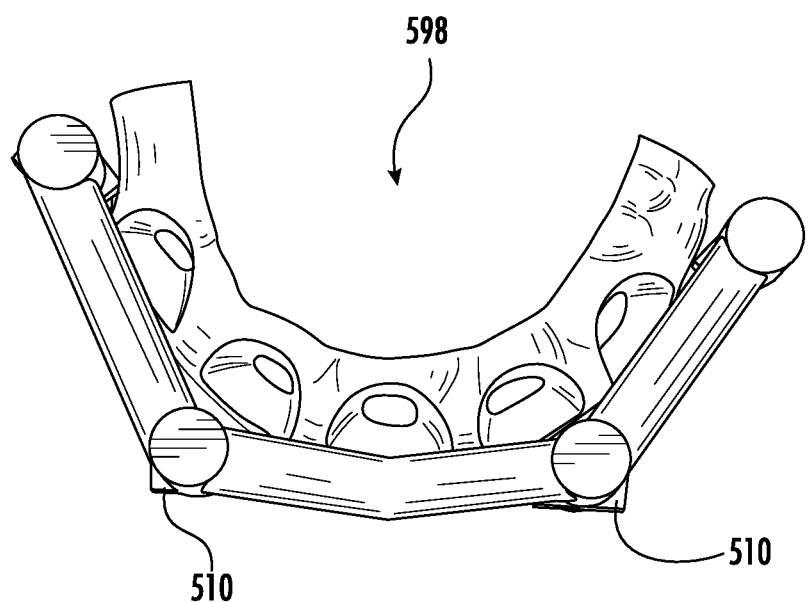
Figure 102:
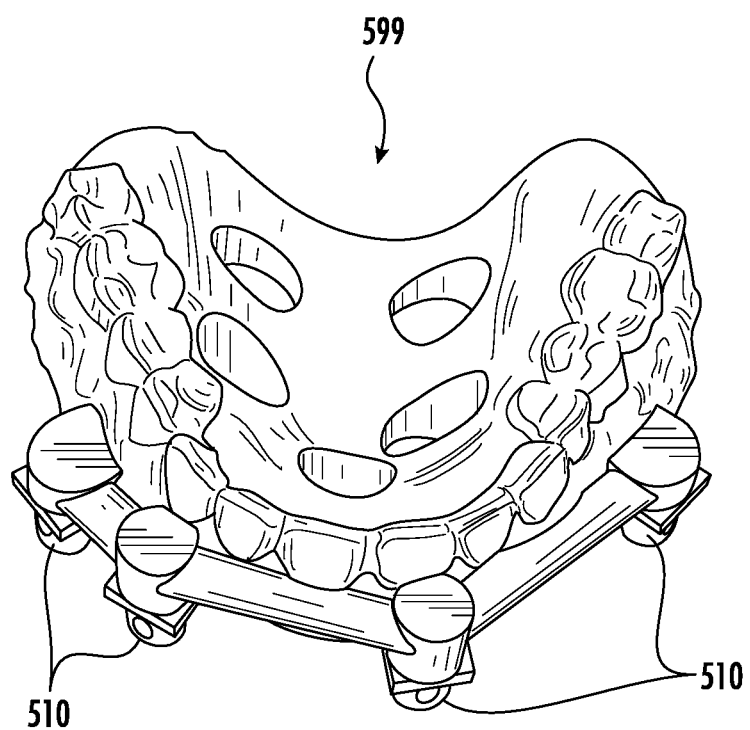
Figure 103:
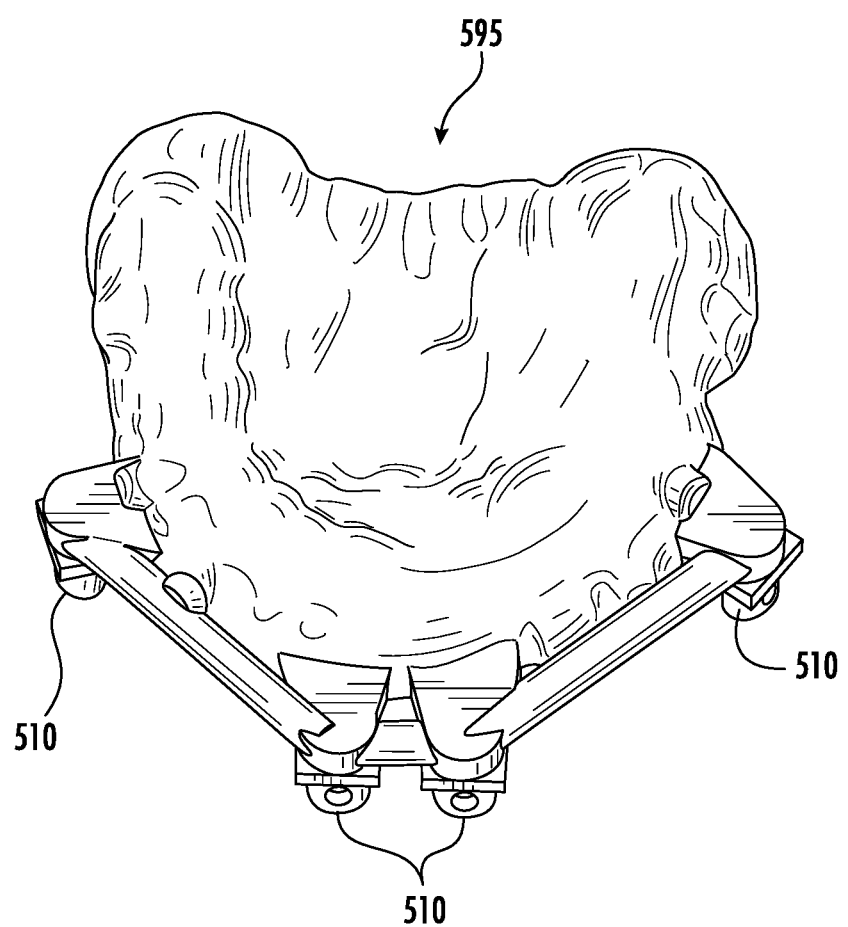

Having thus described the presently disclosed subject matter in general terms, reference will now be made to the accompanying drawings, which are not necessarily drawn to scale, and wherein:

FIGS. 1-4 illustrate various views of an example of a tissue borne fixation (TBF) device latched with a hinged tooth aligner guide in accordance with an embodiment of the invention;

FIGS. 5 and 6 illustrate perspective views of an example of a plug and jack system in accordance with an embodiment of the invention;

FIGS. 7A-9 illustrate various views of example TBF devices in accordance with an embodiment of the invention;

FIGS. 10A and 10B illustrate various views of a pair of TBF devices coupled via an example of a latch pin bridge in accordance with an embodiment of the invention;

FIGS. 11-13 illustrate various views of another example of a latch pin bridge in accordance with an embodiment of the invention;

FIGS. 14, 15A, and 15B illustrate various views of a pair of TBF devices coupled via a latch pin bridge and latched with a hinged tooth aligner guide in accordance with an embodiment of the invention;

FIGS. 16A, 16B, and 17 illustrate an example of a process of releasing an alignment guide from hinged members in accordance with an embodiment of the invention;

FIGS. 18A and 18B illustrate various views of an example of an aligner in relation to a patient's teeth, in relation to TBF devices, and absent hinged members in accordance with an embodiment of the invention;

FIGS. 19A and 19B illustrate various views of TBF devices latched with a drill guide in accordance with an embodiment of the invention;

FIGS. 20A, 20B, and 21 illustrate various views of TBF devices latched with a bone reduction guide in accordance with an embodiment of the invention;

FIG. 22 illustrates a flow diagram of an example of a fabrication process of components of the TBF system in accordance with an embodiment of the invention;

FIG. 23 illustrates a flow diagram of an example of a simplified method of performing a procedure using the TBF system in accordance with an embodiment of the invention;

FIGS. 24A-24D illustrate a flow diagram of an example of a detailed method of performing a procedure using the TBF system in accordance with an embodiment of the invention;

FIG. 25 illustrates an example of an abutment aligner that may be used with the TBF system in accordance with an embodiment of the invention;

FIG. 26 illustrates an example of a bone model with a bone reduction plane in accordance with an embodiment of the invention;

FIG. 27 illustrates an example of a bone reduced model in accordance with an embodiment of the invention;

FIG. 28 illustrates another example of a bone reduced model altered to show placement and depths of planned implants and/or fixations in accordance with an embodiment of the invention;

FIG. 29 illustrates an example of glue holes and peg holes formed in a bone reduced model in accordance with an embodiment of the invention;

FIG. 30 illustrates an example of a transfer model in accordance with an embodiment of the invention;

FIG. 31 illustrates an example of an analog model with tissue thickness indicator impressions in accordance with an embodiment of the invention;

FIG. 32 illustrates an example of a tissue alignment guide in accordance with an embodiment of the invention;

FIG. 33 illustrates an example of a denture alignment guide in accordance with an embodiment of the invention;

FIGS. 34 and 35 illustrate various views of portions of a hinged tooth aligner with a hinged receiver barrel and female ball detent in accordance with an embodiment of the invention;

FIGS. 36 and 37 illustrate various views of hinged members of a hinged tooth aligner with a hinged receiver barrel and male ball detent in accordance with an embodiment of the invention;

FIG. 38 illustrates a latched in hinged tooth aligner with a female and male ball detents locked in accordance with an embodiment of the invention;

FIG. 39 illustrates an example of a latched PMMA in accordance with an embodiment of the invention;

FIG. 40 illustrates an example of a waxup offset scallop model and an initial scallop guide in accordance with an embodiment of the invention;

FIG. 41 illustrates an example of an analog model in accordance with an embodiment of the invention;

FIG. 42 illustrates an example of a scallop transfer mount in accordance with an embodiment of the invention;

FIG. 43 illustrates an example of a scalloping guide in accordance with an embodiment of the invention;

FIGS. 44-46 illustrate an example of a unilateral key fixation (UKF) system and UKF devices for performing various intraoral guided surgery procedures in accordance with an embodiment of the invention;

FIG. 47 illustrates an example of an incision guide in accordance with an embodiment of the invention;

FIGS. 48-49 illustrate an example of a plug and jack system in accordance with an embodiment of the invention;

FIG. 50 illustrates an example UKF device in accordance with an embodiment of the invention;

FIG. 51 illustrates an example UKF carrier in accordance with an embodiment of the invention;

FIG. 52 illustrates an example tooth aligner in accordance with an embodiment of the invention;

FIG. 53 illustrates an example drill guide in accordance with an embodiment of the invention;

FIGS. 54-57 illustrate various views of an example incision guide in accordance with an embodiment of the invention;

FIG. 58 illustrates an example tooth aligner in accordance with an embodiment of the invention;

FIGS. 59-60 illustrate various views of an example UKF carrier in accordance with an embodiment of the invention;

FIG. 61 illustrates an example of a UKF carrier and tooth aligner in accordance with an embodiment of the invention;

FIGS. 62-66 illustrate various views of an example of a pair of UKF devices in accordance with an embodiment of the invention;

FIG. 67 illustrates an example of bone reduced to a bone reduction plane using a bone reduction plane guide/UKF carrier in accordance with an embodiment of the invention;

FIG. 68 illustrates an example of a drill guide latched to UKF devices in accordance with an embodiment of the invention;

FIG. 69 illustrates a flow diagram of an example of a UKF design workflow in accordance with an embodiment of the invention;

FIGS. 70-81 illustrate examples of the process steps of the UKF design workflow shown in FIG. 69;

FIGS. 82-83 illustrate an example of a one-piece UKF device wherein two UKF devices are connected by a bar in accordance with an embodiment of the invention;

FIGS. 84-86 illustrate various views of an example of the fixation of the UKF devices to a subject's bone in accordance with an embodiment of the invention;

FIG. 87 illustrates a flow diagram of an example of a simplified method of performing a procedure using the UKF system and UKF device in accordance with an embodiment of the invention;

FIG. 88A-FIG. 88D illustrate a flow diagram of an example of a detailed method of performing a procedure using the UKF system and UKF device in accordance with an embodiment of the invention;

FIG. 89 illustrates am example of an abutment aligner in accordance with an embodiment of the invention;

FIG. 90 illustrates an example of a PMMA in accordance with an embodiment of the invention;

FIG. 91 illustrates an example of a bone model with a bone reduction plane in accordance with an embodiment of the invention;

FIG. 92 illustrates an example of a bone reduced model in accordance with an embodiment of the invention;

FIG. 93 illustrates an example of glue holes and peg holes formed in a bone reduced model in accordance with an embodiment of the invention;

FIG. 94 illustrates an example of a transfer mount in accordance with an embodiment of the invention;

FIG. 95 illustrates an example of a sinus lift guide in accordance with an embodiment of the invention;

FIG. 96 illustrates an example of a depth control guide in accordance with an embodiment of the invention;

FIG. 97 illustrates a non-limiting example of a scalloping type guide that may be used with the UKF system;

FIG. 98 illustrates an example of a non-extracted transfer mount in accordance with an embodiment of the invention;

FIG. 99 illustrates an example of a planned extraction transfer mount in accordance with an embodiment of the invention;

FIG. 100 illustrates an example of a UKF device with a UKF extension in accordance with an embodiment of the invention;

FIG. 101 illustrates an example of a bone ridge alignment guide in accordance with an embodiment of the invention;

FIG. 102 illustrates an example of a denture alignment guide in accordance with an embodiment of the invention; and FIG. 103 illustrates an example of a tissue aligner in accordance with an embodiment of the invention.

DETAILED DESCRIPTION

The presently disclosed subject matter now will be described more fully hereinafter with reference to the accompanying drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides a tissue borne fixation (TBF) system, device, and methods of making and using same. For example, methods of performing intraoral guided surgical procedure using the presently disclosed TBF system and device is provided.

In some embodiments, the presently disclosed TBF system may include one or more TBF devices, wherein the TBF devices provide a common foundation or base to which other guides, prosthetic and/or surgical components, and/or any other devices required to perform intraoral guided surgery may be mounted.

In some embodiments, the presently disclosed TBF system may include one or more TBF devices, wherein the TBF devices may include tissue thickness indicators (TDI).

In some embodiments, the presently disclosed TBF system may include prosthetic and/or surgical components, such as, but not limited to, the one or more TBF devices, one or more tooth aligners, one or more drill guides, one or more bone reduction guides, and/or any other types of guides or carriers.

In some embodiments, the presently disclosed TBF system may include a plug and jack style connector system to support and relate prosthetic and/or surgical components intraorally. Namely, to register and seat prosthetic and/or surgical components.

In some embodiments, the presently disclosed TBF system and/or TBF device may be used to secure surgical and prosthetic components required to perform guided surgery in the correct relationship to the primary fixation point (e.g., pre-extracted teeth, tissue or bone).

In some embodiments, the presently disclosed TBF system includes a pair of TBF devices, which are fixation devices that can serve as the foundation or base of the presently disclosed TBF system.

In some embodiments, the TBF device of the presently disclosed TBF system includes a plurality of tissue thickness indicators that may be, for example, a set of conical pins that enters the patient's gum tissue and stops the TBF device at the correct offset from the buccal bone and thereby preserves the gum tissue.

In some embodiments, because the presently disclosed TBF system and/or TBF device is based on tissue borne fixation including tissue thickness indicators, the need for tissue reflection is substantially reduced or eliminated entirely and an intraoral guided surgery procedure is provided that is less invasive, faster, and safer, and that overall provides better patient care and recovery as compared with current methods, such as, but not limited to, bone fixated (bone touching/contacting) guide assisted surgical procedures.

Further, a fabrication process is provided for the presently disclosed TBF system and TBF device.

Further, a simplified method of performing surgery using the presently disclosed TBF system and TBF device is provided.

Further, a detailed method of performing surgery using the presently disclosed TBF system and TBF device is provided.

Figure 1:
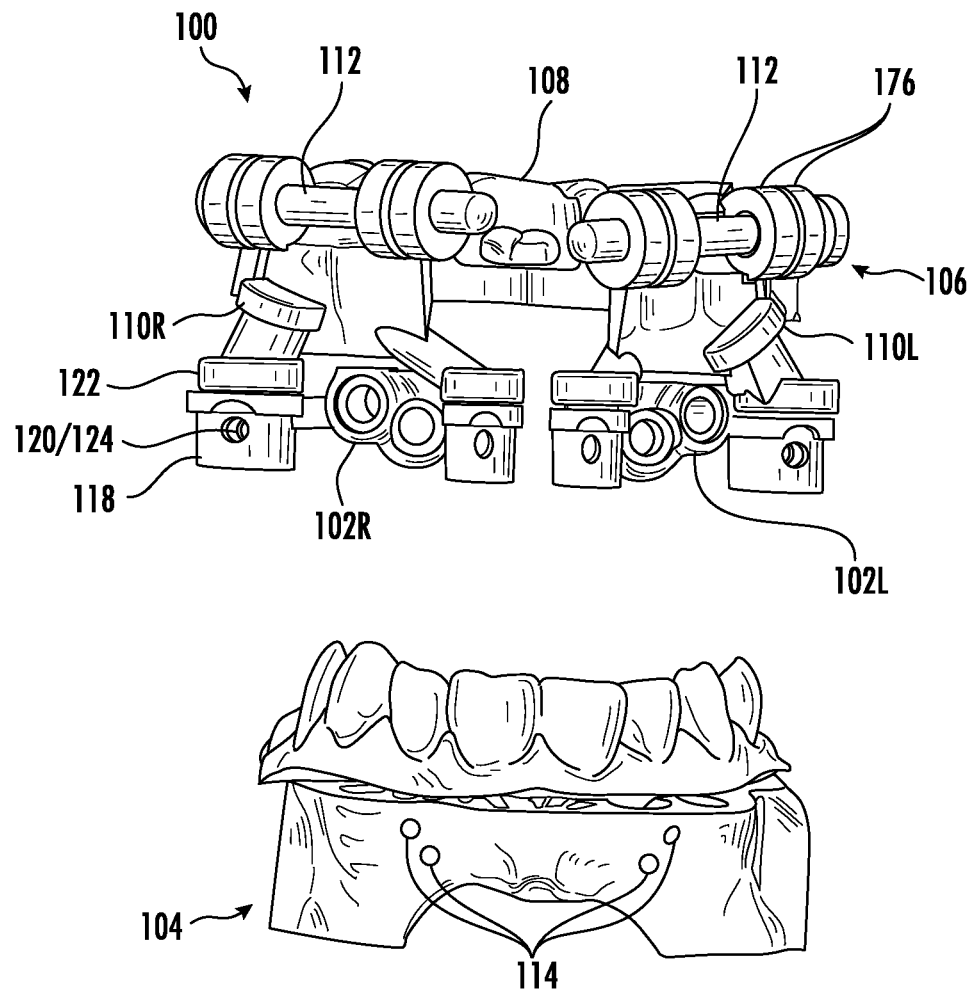
Figure 2:
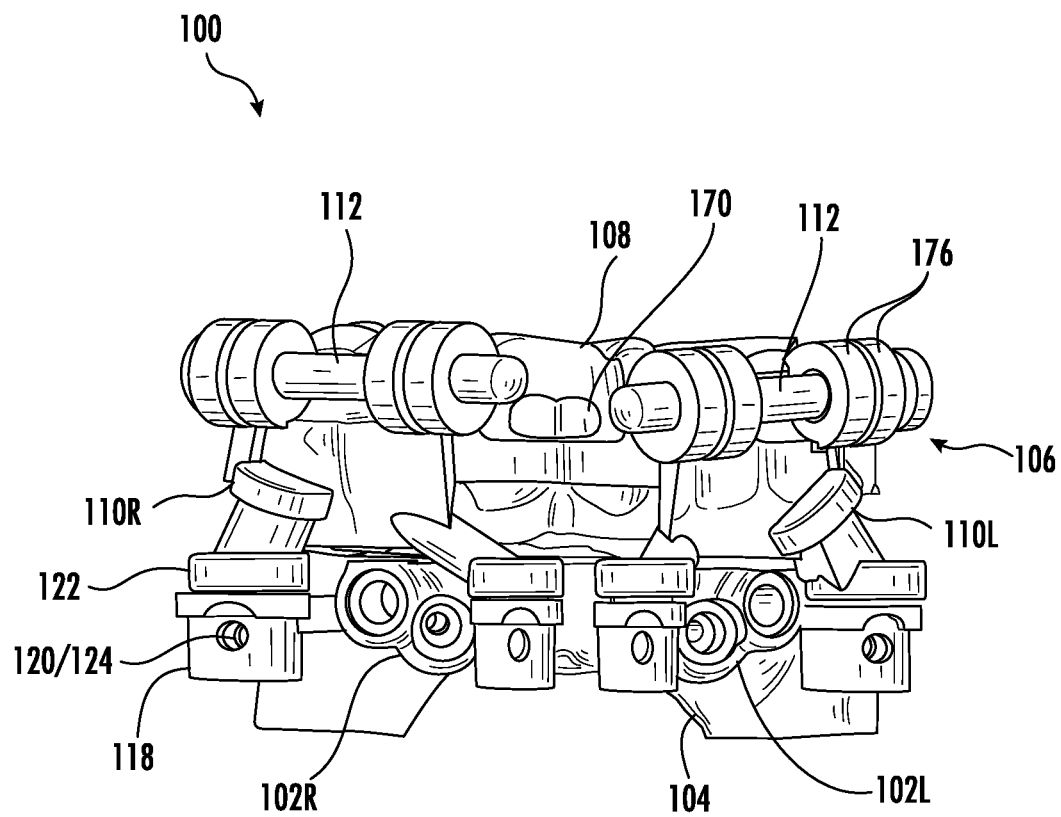
Figure 3:
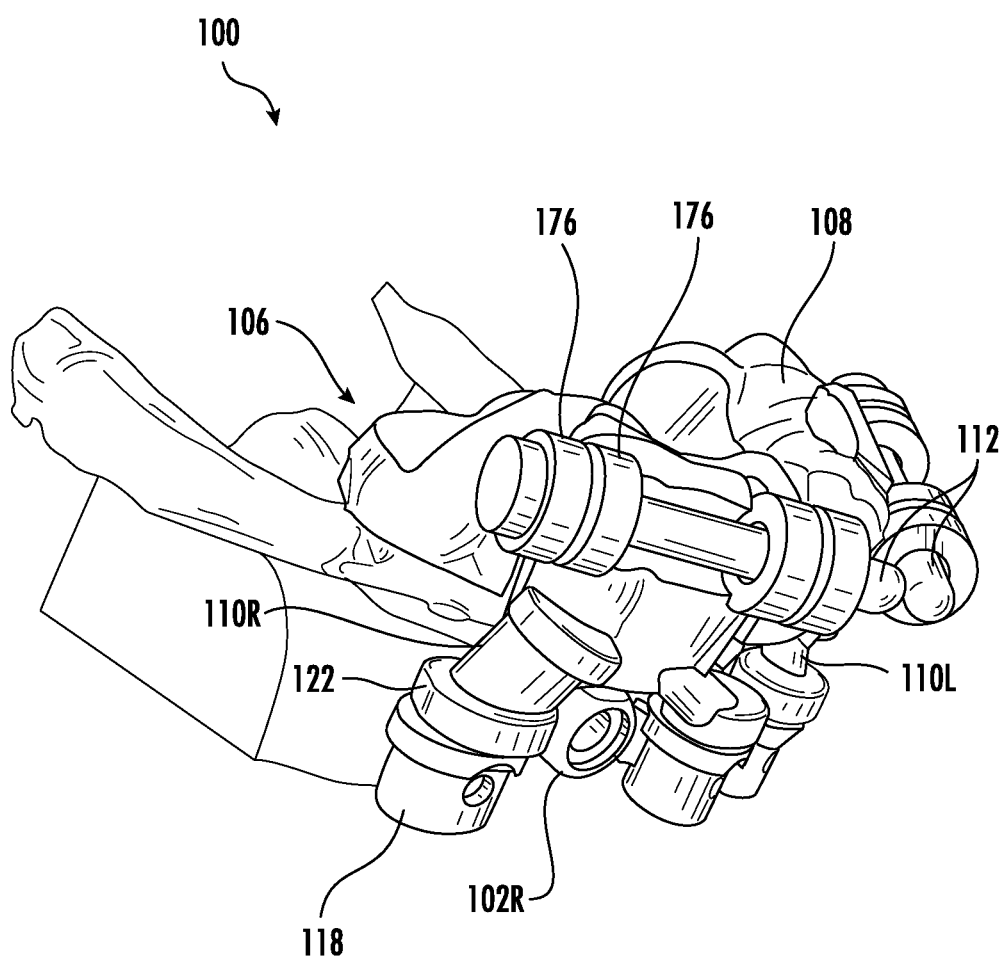

Referring now to FIGS. 1-4 illustrate various views of an example of TBF system 100 and TBF devices (or carrier) 102 for performing intraoral guided surgery. Namely, FIG. 1 shows an exemplary TBF system 100 in relation to, but separate from, a patient's jaw 104, while FIG. 2 and FIG. 3 show TBF system 100 engaged with the patient's jaw 104. In this example, TBF system 100 may include a pair of TBF devices 102 (i.e., a right TBF device 102R and a left TBF device 102L) to which a variety of other prosthetic and/or surgical components, and/or any other devices required to perform intraoral guided surgery may be mounted. FIGS. 1-4 illustrate TBF system 100 with a hinged tooth aligner guide 106 latched into TBF devices 102.

TBF device 102R may be custom to the right side of the patient's jaw 104 while TBF device 102L may be custom to the left side of the patient's jaw 104. Accordingly, TBF device 102R and TBF device 102L may be different, while each provide a pair of fixations in TBF system 100. More details of examples of TBF devices 102R and 102L are shown and described hereinbelow with reference to FIGS. 7A-9.

Figure 4:
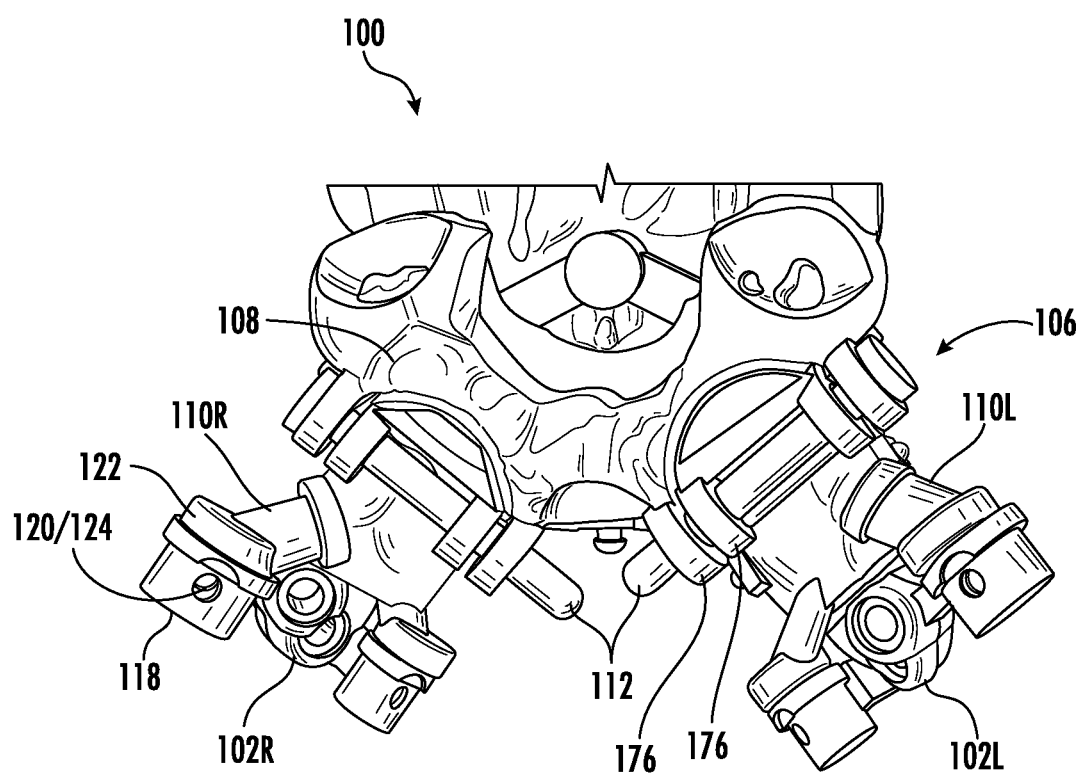

TBF system 100 may include, in one example, TBF devices 102R and 102L and a hinged tooth aligner guide 106 that, for example, may be seated on the patient's occlusal table and/or incisal edges of the pre-extracted arch (either maxilla or mandible) where, for example, a surgical procedure is to be performed. Hinged tooth aligner guide 106 may be a tooth aligner guide device that may be custom to the patient's preoperative teeth. Hinged tooth aligner guide 106 may include a tooth aligner portion 108 and one or more hinged members 110 (i.e., a right hinged member 110R and a left hinged member 110L). Tooth aligner portion 108 may be hingeably coupled to the pair of hinged members 110 via a pair of corresponding hinge pins 112. FIG. 4 shows a view of the hinged tooth aligner guide 106 with the tooth aligner portion 108 engaged with the patient's preoperative teeth, but with the two hinged members 110 (holding the two TBF devices 102) hinged out away from the patient's gums.

TBF devices 102R and 102L and hinged tooth aligner guide 106 provide guides that may be locked (latched) together using a plug and jack system and latch pins (see FIG. 5 and FIG. 6). This arrangement of hinged tooth aligner guide 106 engaged with the patient's jaw 104 and preoperative teeth and also engaged with TBF devices 102R and 102L allows, for example, a surgeon to accurately drill fixations of TBF devices 102R and 102L. For example, FIG. 1 shows four fixation holes 114 that may be drilled into the patient's buccal bone and then TBF devices 102R and 102L may be attached with pins and/or screws. The pins and/or screws referred to herein with regard to TBF system 100 may preferably be the same or substantially the same as fixation screws 556 and fixation pins 558 described below with regard to UKF system 500, and shown for example in FIGS. 85-87.

Hinged tooth aligner guide 106 may serve as a delivery device for positioning TBF devices 102 for fixation. Hinged tooth aligner guide 106 indexes firmly on the patient's existing teeth. Other aligners, such as tissue aligner (see, for example, tissue aligner 166 in FIG. 32), may be used in edentulous cases. The hinging action of hinged tooth aligner guide 106 allows TBF devices 102R and 102L to be delivered independently, and each may provide a pair of fixations. Once the fixations of TBF devices 102R and 102L are fully seated and secured, hinged tooth aligner guide 106 may be removed, leaving behind the TBF devices 102R and 102L as the foundation or base for other components of the TBF system 100.

Additionally, the TBF devices 102 may each include a plurality of tissue thickness indicators 116 (see FIG. 7A through FIG. 9). The tissue thickness indicators 116 may be, for example, a set of conical pins or spike like protrusions that are configured to enter a patient's gum tissue and indicate when the TBF device 102 is at the correct offset from the buccal bone and thereby preserves the gum tissue from being compressed and thereby damaged. Further, the tissue thickness indicators 116 obviate the need for a buccal flap (i.e., tissue reflection) as is required in current surgical procedures, such as, but not limited to, bone fixated (bone touching/contacting) guide assisted surgical procedures. More details of examples of TBF devices 102 that include tissue thickness indicators 116 are shown and described hereinbelow with reference to FIG. 7A through FIG. 9.

Each TBF device 102 may further include one or more (preferably a pair of) plug connectors (or plug keys) 118 and each having a plug latch pin hole 120. Hinged tooth aligner guide 106 (or other components of the TBF system 100), may include corresponding jack connectors (or jack keys) 122 (each having a jack latch pin hole 124) that plug into plug connectors (or plug keys) 1118 of TBF devices 102R and 102L, thereby latching the hinged tooth aligner guide 106 (or other components of the TBF system 100) into the TBF devices 102. Other following guides may be attached to TBF devices 102R and 102L by inserting latch pins (e.g., 2.5 mm latch pins, not shown) into plug connectors 118 and jack connectors 122. As each of the following guides set into the TBF devices 102R and 102L, an accurate fixation is necessary for a successful surgery and latched conversion occlusal. Plug connectors 118 and jack connectors 122 form the plug and jack system of TBF system 100. More details of an example of plug connectors (or plug keys) 118 and jack connectors (or jack keys) 122 are shown and described hereinbelow with reference to FIG. 5 and FIG. 6.

Referring now to FIG. 5 and FIG. 6 illustrate views of an example of a plug and jack system for use with the presently disclosed TBF system 100 and TBF device 102. The plug and jack system may include, for example, a plug connector (or plug key) 118 that has a plug latch pin hole 120, which may be angled or straight, and a jack connector (or jack key) 122 that has a jack latch pin hole 124, which may be angled or straight. Plug connector 118 may be, for example, a hollow cylinder-shaped member that is open at one or both ends. Plug connector 118 is preferably designed to receive jack connector 122, as shown, for example, in FIG. 6. Jack connector 122 may be, for example, a generally hollow cone-shaped member, or other suitable shape that may be partially or not hollow. Jack connector 122 (i.e., the male connector) is designed to be fitted into plug connector 118 (i.e., the female connector), as shown, for example, in FIG. 6, such that corresponding plug latch pin hole 120 and jack latch pin hole 124 align. Plug latch pin holes 120 and jack latch pin holes 124 may be digitally placed, printed or milled through the oval connecting components.

When plug connector 118 and jack connector 122 are fitted together, plug latch pin hole 120 of plug connector 1118 and jack latch pin hole 1124 of jack connector 122 are substantially aligned, as shown for example in FIG. 6. A latch pin (not shown) may be provided that may be inserted into both aligned plug latch pin hole 120 and jack latch pin hole 124 in order to secure plug connector 118 and jack connector 122 together. Namely, the latch pin secures plug connector 118 and jack connector 122 in a manner that ensures that they remain connected during surgery or associated procedure. The various prosthetic and/or surgical components and any other components of TBF system 100 may include any arrangement of plug connectors 118 and/or jack connectors 122 for fitting the components together. In one example, the latch pin may be in the range of about 2.5 mm.

Referring now to FIGS. 7A-9 illustrate various views of examples of TBF devices 102 of the presently disclosed TBF system 100. TBF devices 102R and 102L may include, for example, a mounting plate 126 that may include one or more fixation guide holes 128 therethrough, and one or more plug connectors 118 extending off mounting plate 126. Additionally, a set of tissue thickness indicators 116 may be provided on a tissue facing side of mounting plate 126.

Figure 9:
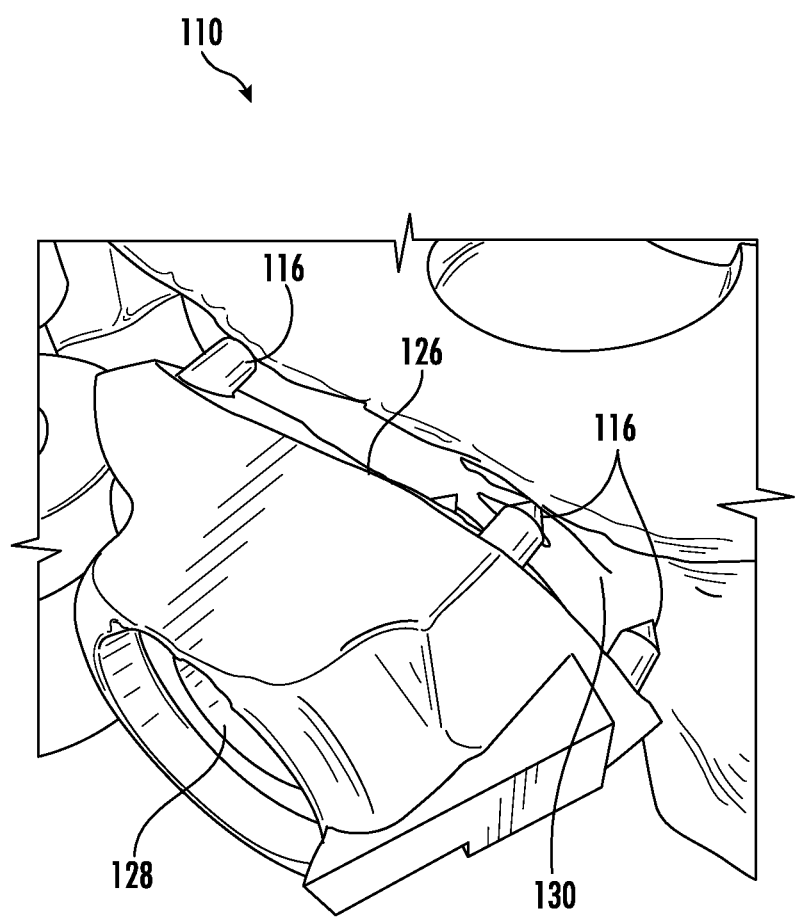

FIG. 9 is a closeup view showing more details of tissue thickness indicators 116 of TBF devices 102. TBF devices 102 are preferably seated on the buccal tissue using tissue thickness indicators 116. Tissue thickness indicators 116 may be, for example, a set of conical pins or spikes that enter the patient's gum tissue 130 and are sized to stop at the correct offset from the buccal bone and thereby preserves the gum tissue 130 from damage due to compression. Further, the presence of tissue thickness indicators 116 obviate the need for a buccal flap (i.e., tissue reflection) as required in current surgical procedures, such as, but not limited to, bone fixated (bone touching/contacting) guide assisted surgical procedures.

Tissue thickness indicators 116 (or tissue thickness seating indicators) function to show the correct mucosal seating position when fixating TBF devices 102 to avoid overtightening and compression of gum tissue 130, which can damage the gum tissue. Accordingly, each TBF device 102 provides a device for indicating tissue thickness of a patient and for supporting various prosthetic and/or surgical components and any other components (e.g., surgical components, aligners, provisional, and/or final dental prosthetics) during surgical procedures.

Tissue thickness indicators 116, in one example, protrude outward in a generally perpendicular direction from the tissue facing side of mounting plate 126 of TBF device 102. Tissue thickness indicators 116 are preferably shaped to facilitate insertion into a patient's gum tissue 130. In one example, tissue thickness indicators 116 may be generally conical in shape, tapering to a sharp point at their distal end. In one embodiment, tissue thickness indicators 116 may be localized in groups proximal to one or more of the fixation guide holes 128. As a non-limiting example, tissue thickness indicators 116 may be disposed generally about a periphery of the tissue facing side of the mounting plate 126 of the TBF device 102. In a non-limiting example, four (4) tissue thickness indicators 116 may be arranged around, and in proximity to, fixation guide holes 128. It should be understood that there may be more or less than four (4) tissue thickness indicators 116, and further the tissue thickness indicators 116 may be disposed at other portions and/or in various configurations or patterns on the tissue facing side of mounting plate 126 of TBF device 102.

Tissue thickness indicators 116 may vary in length depending on a specific patient. The length of tissue thickness indicators 116 for a particular patient may be determined by the depth of the patient's gum tissue 130. In one example, the length of the tissue thickness indicator 116 for a particular patient is determined by measuring the space between the outer surface of the patient's gum tissue 130 and their bone level below the gum tissue 130. The patient's gum tissue depth may be determined using any number of suitable techniques, for example, digital imaging and communications in medicine (DICOM), stereo lithography (STL), and/or polyvinyl siloxane (PVS) intra-oral modeling, which may be done during a digital design phase of TBF system 100.

The tissue thickness indicators 116 are preferably fabricated to be of a length that is slightly shorter than, or just equal to, the depth of the particular patient's gum tissue thickness, such that when it is fully set it does not engage (or penetrate) the patient's underlying bone. In one non-limiting example, the tissue thickness indicator 116 may be of a length, such that it is in the range of about 0.3 mm shorter than the depth of the particular patient's gum tissue thickness. Tissue thickness indicators 116 are preferably not used as bone stops and are preferably purposefully fabricated to be slightly shorter than, or just equal to, the thickness of the patient's gum tissue 130. The tissue thickness indicators 116 are preferably of a length, such that when TBF device 102 is fully and properly seated on a patient's gum tissue 130, the distal most ends of the tissue thickness indicators 116 fall short of engaging or penetrating the patient's underlying bone. Thereby, providing the surgeon with a guide to help prevent the surgeon from overtightening the guide, and compressing and damaging the gum tissue, when seating TBF device 102. That is, as the surgeon seats TBF device 102, he/she will know when to stop tightening based on the tissue thickness indicators 116, once the tissue thickness indicators 116 reach their full depth into the gum tissue 130 the surgeon knows to stop tightening.

The tissue facing side of mounting plate 126 of TBF devices 102 may be designed based on a combination of DICOM data and the STL of the tissue, and/or any other suitable technique. This allows for an intimate device to tissue fit. The length of the tissue thickness indicators 116 may be determined by the measured tissue thickness and offset by, for example, about 0.5 mm. This allows the surgeon to fixate TBF devices 102 without over-compressing the patient's gum tissue 130 and causing damage thereto.

Referring now to FIG. 10A and FIG. 10B show various views of TBF devices 102R and 102L absent hinged tooth aligner guide 106 and mechanically coupled via a latch pin bridge 132. For example, latch pin bridge 132 may include a pair of bridge latch pins 134, wherein one bridge latch pin 134 engages plug latch pin hole 120 of one plug connector (or plug key) 118 of TBF device 102R and the other bridge latch pin 134 engages plug latch pin hole 120 of one plug connector (or plug key) 118 of TBF device 102L. The purpose of latch pin bridge 132 is to ensure stability about the center axis of TBF system 100.

FIGS. 11-13 illustrate various views of another example of a latch pin bridge 136 for coupling together TBF devices 102R and 102L. Namely, the previously described latch pin bridge 132 is a one-piece device having two bridge latch pins 134 that are integrated with the body. FIGS. 11-13 illustrate a latch pin bridge 136 that has a crosslink member 138 and two separate bridge latch pins 140. Crosslink member 138 includes two openings or holes 142 for receiving the two bridge latch pins 140. FIG. 11 shows the crosslink member 138 only of latch pin bridge 136, absent the bridge latch pins 140. FIG. 12 shows the crosslink member 138 and bridge latch pins 140 in relation to TBF devices 102R and 102L but without the bridge latch pins 140 engaged. FIG. 13 shows the crosslink member 138 and the two bridge latch pins 140 fully engaged with the plug connectors 102 of TBF devices 102R and 102L. Latch pin bridge 136 would function in a similar manner as that of latch pin bridge 132. For example, as with latch pin bridge 132, latch pin bridge 136 provides additional stability about the center axis of TBF system 100, and may take the place of two latch pins across the center of TBF devices 102R and 102L. In one example, latch pin bridge 136 (or 132) may be used to hold hinged tooth aligner guide 106 (or other latched component) in TBF devices 102R and 102L.

FIG. 14, FIG. 15A and FIG. 15B illustrate various views of an example of using latch pin bridge 132 to hold hinged tooth aligner guide 106 in TBF devices 102R and 102L. Latch pin bridge 136 would function in much the same way to hold hinged tooth aligner guide 106 in TBF devices 102R and 102L.

FIG. 16A, FIG. 16B, and FIG. 17 illustrate an example of a process of releasing the tooth aligner portion 108 from hinged members 110R and 110L by removing hinge pins 112.

FIG. 18A and FIG. 18B illustrate various views of an example of a tooth aligner portion 108 of hinged tooth aligner guide 106 in relation to the patient's teeth, in relation to TBF devices 102R and 102L, and absent hinged members 110R and 110L.

In any of FIGS. 14-18B, latch pin bridge 136 could be substituted for latch pin bridge 132.

Referring now to FIG. 19A and FIG. 19B, TBF system 100 may include TBF devices 102R and 102L along with a drill guide 144. Drill guide 144 may latch into TBF devices 102R and 102L. For example, drill guide 144 may include one or more jack connectors (or jack keys) 122 that engage with the one or more plug connectors (or plug keys) 118 of TBF devices 102R and 102L.

Drilling sleeves 146 in drill guide 144 may reflect the patient's implant positions. Using drill guide 144, a surgeon may drill the osteotomies and place the implants. Each of the drilling sleeves 146 ensures the correct angle and depth for each drill. The surgeon then performs osteotomies as per the provided drill protocol. Implants may then be picked up and delivered using the same drill guide 144. Drill guide 144 may include timing marks to indicate the correct rotation of each implant.

Referring now to FIG. 20A, FIG. 20B, and FIG. 21, TBF system 100 may include TBF devices 102R and 102L latched with a bone reduction guide 148. Bone reduction guide 148 may latch into TBF devices 102R and 102L. For example, bone reduction guide 148 may include one or more jack connectors (or jack keys) 122 that engage with the one or more plug connectors (or plug keys) 118 of TBF devices 102R and 102L. Bone reduction guide 146 provides a surgeon with a reference for correct bone reduction. Bone reduction guide 146 may also serve to protect the patient's tissue and keep it away from the surgical site.

Referring now again to FIG. 1 through FIG. 21, the TBF system 100 and TBF devices 102 with tissue thickness indicators 116 may provide a unilateral buccal surgical fixation foundation with surgical carriers. Namely, TBF devices 102 provide a minimally invasive, tissue stabilized, surgical foundation with, for example, tissue thickness indicators (e.g., tissue thickness indicators 116).

TBF devices 102 with tissue thickness indicators 116 may act as a carrier for plug and jack connectors (plug connectors 118 and jack connectors 122) to support and secure surgical and prosthetic devices, e.g., incision guide, bone reduction plane, surgical guide, abutment aligner, prosthetic components, and/or other devices required to perform intraoral surgical procedures. TBF devices 102 may be positioned intraorally by engaging and verifying, for example, dual anatomical positioning points with the assistance of a tooth aligner (e.g., tooth aligner guide 106, tissue aligner 166). In one example, a primary point of stabilization may be the maxillary palatal tissue (tissue borne) or maxillary ridge and or palatal bone or mandibular bony ridge (bone borne) in edentulous patients. The tooth position (tooth borne) may be used in dentate patients or a combination of the above. The secondary point of stabilization may be on the buccal tissue using TBF devices 102.

In the process of positioning and fixation, TBF devices 102 may be transferred to the mouth using a tooth borne aligner (e.g., hinged tooth aligner guide 106). Hinged tooth aligner guide 106 may be designed with hinges to allow TBF devices 102 to engage the buccal undercut. TBF devices 102 may be designed with tissue thickness indicators 116 to allow the TBF devices 102 to be seated on the tissue without over compressing and cutting the blood flow to the tissue, thereby damaging the tissue, during surgery. Once TBF devices 102 are seated on the patient's tissue, TBF devices 102 may be cross arch stabilized by inserting, for example, a latch pin bridge 132 (or 136) into the most anterior latch pin holes 120/124 to bridge the seated pair of TBF devices 102. Latch pin bridge 132 (or 136) may act as the secondary, horizontal seating verification. After positioning and latching the unilateral TBF devices 102 with a tooth aligner delivery device (e.g., hinged tooth aligner guide 106), the fixation osteotomy may be drilled and a combination of fixation screws and/or fixation pins (for example fixation screws 556 and/or fixation pins 556, see FIGS. 85-87) may be used to fixate TBF devices 102 to the patient's tissue. TBF devices 102 may be fixated on the buccal tissue with one or more uni- or bi-cortical bone fixation screws or pins. Rotation may be stabilized with one or more anti-rotational stabilization screws or pins, these can engage uni- or bi-cortical bone. After fixation the tooth aligner delivery device (e.g., hinged tooth aligner guide 106) may be unlatched and removed from the mouth.

Other carrier variations are possible in the TBF system 100 and TBF devices 102. For example, TBF devices 102 may be splinted cross arch (bilateral) by a connection bar or TBF devices 102 may be transferred to the mouth with a carrier that can be removed after fixation. TBF devices 102 are not necessarily a surgical device or guide, in and of themselves, rather they are preferably a carrier or stabilizing device for surgical and other prosthetic components to be latched into. TBF devices 102 may be adapted to accommodate edentulous or dentate patients.

TBF devices 102 of TBF system 100 provide a tissue stabilized, minimally invasive, unilateral, independent foundation to carry latch plugs (plug connectors 118) for intraoral surgical and prosthetic components to latch into. The TBF devices 102 supports and stabilizes components, such as, but not limited to, bone reduction guides, aligners, surgical guides, provisional, and/or final dental prosthetics during surgical procedures.

TBF system 100 and TBF devices 102 provides an improvement to and can replace traditional "paper clip"

(bucco-lingual) and buccal bone engaging base or foundation guides. The presence of TBF devices 102 minimizes (or eliminates) the amount of surgical tissue reflection traditionally required to stabilize intraoral surgical devices. TBF system 100 and TBF devices 102 does not utilize a reflected buccal bone surface area for seating and therefore requires up to about 90% less tissue reflection than traditional bone engaging or floating guide carrier systems. For example, TBF system 100 and TBF devices 102 require about 90+% less tissue reflection than traditional "paperclip" buccolingual guides, and requires no lingual tissue reflection to seat the guide. Whereas, paperclip guides requires significant buccal as well as lingual tissue reflection.

TBF devices 102 are a carrier or stabilizing device for surgical and other prosthetic components. Other systems utilize the base guide as a dual use surgical bone reduction and component anchoring device. TBF system 100 and TBF devices 102 greatly reduces the traditional invasive nature of intra-oral dental implant surgical procedures and protocols and greatly reduces patient morbidity and post-surgical recovery time, by greatly reducing the amount of required tissue reflection and other tissue damage caused by over compression of the tissue when seating/fixating such guides and/or anchoring devices.

Generally, any components of TBF system 100 (e.g., TBF devices 102, hinged tooth aligner guide 106, tooth aligner portion 108, hinged members 110, hinge pins 112, latch pin bridge 132/136, drill guide 144, bone reduction guide 148) may be formed of polymers, fiber reinforced material, Teflon reinforced nylon, carbon reinforced nylon polymer, nylon, fiberglass, HSHT fiberglass, carbon fiber, onyx, Kevlar, cobalt chrome, polymers, alloys, zirconias, printed resin material, nylon carbon fiber reinforced, other printable and/or millable materials, and/or any other suitable material or combination of materials now known or known in the future. The components of TBF system 100 may be formed by printing, milling, casting, and/or any other suitable method/technique. The printing, milling, and/or casting of any components of TBF system 100 may be accomplished using various techniques/methods, such as, but not limited to, axis milling systems, selective laser milling, digital laser milling, selective laser melting (SLM), printed with resin based printer, centrifugal casted, digital precision metals (DPM), direct metal laser sintering (DMLS), and/or any other suitable methods and/or techniques. Further, any components of TBF system 100 may be planned from DICOM data in surgical planning software and guide design is done in multiple distinctive design software systems. Further, any components of TBF system 100 may be digitally designed with various suitable software packages and analog processed off, for example, SLT digital design files.

Referring still to FIG. 1 through FIG. 21, features of the presently disclosed TBF system 100 and TBF devices 102 with tissue thickness indicators 116 may include, for example, one or more of the following:
(1) the TBF devices 102 provide a fixated plug and jack carrier to support and relate surgical components intraorally;
(2) the TBF devices 102 reduce the invasiveness of bone fixated (bone touching/contacting) guide assisted surgical procedures by reducing the amount of tissue reflection required by about 90+%;
(3) the TBF devices 102 may be used to secure surgical and prosthetic components required to perform guided surgery in the correct relationship to the primary fixation point (pre-extracted teeth, tissue or bone);
(4) the TBF devices 102 provide a surgical foundation carrier that holds plug keys (e.g., female plug connectors 118) to register and seat surgical devices/components carrying the jack keys (e.g., male jack connectors 122) intraorally; and
(5) after fixating the TBF devices 102, other components (e.g., bone reduction guides, surgical guides, abutment aligner guides, restorative components) may be latched into the TBF devices 102 and guided surgery and/or other processes may be performed.

Referring still to FIG. 1 through FIG. 21, yet other features of the presently disclosed TBF system 100 and TBF devices 102 with tissue thickness indicators 116 may further include, for example, one or more of the following:
(1) the TBF device 102 is fixated to the tissue level;
(2) the TBF device 102 has tissue thickness indicators 116 to help fixate the device without compressing the patient's underlying tissue, which can cause trauma and tissue necrosis;
(3) the TBF device 102 is a plug and jack fixation carrier and is not, in and of itself, a device used for surgical procedures. By contrast, other conventional systems use the fixated device as base guide and/or bone reduction plane guide;
(4) the TBF device 102 may be a unilateral buccal only device and the individual device contacts less or no buccal bone therefore requiring no buccal tissue reflection most base guides typically engage exposed bone surfaces;
(6) the TBF device 102 may seat below the surgical/bone reduction level. Alternatively, the TBF device 102 may be seated at the bone reduction level, which may allow the TBF device 102 itself to serve as the bone reduction guide, and would remove the requirement for the fabrication of a separate bone reduction guide. This position varies depending on the height of the buccal plate. Measured, for example, from the vestibule to the cementoenamel junction (CEJ), the TBF device 102 may be planned from, for example, in the range of about 5 mm to about 10 mm below the surgical site. In case of a surgical emergency all plug and jack components are removed by releasing a simple latch-pin allowing the surgeon immediate unobstructed access to the surgical site. By contrast, other conventional systems have fixed buccal and lingual frames that can only be removed by unscrewing the fixation screws or by removing the fixation pins;
(7) the TBF system 100 may include two (or three in extreme cases) individual (or joined by a horizontal bar, e.g., latch pin bridge 132 or 136), TBF devices 102. By contrast, other conventional systems rely on a bilateral "paperclip" (buccal and lingual) base fixation guide or a unilateral one-piece bone fixation guide contacting the entire buccal surface area or touching the bone with individual bone stops. Some conventional systems utilize a floating buccal guide (not engaging the bone except through fixation pins) but still require full facial tissue reflection;
(8) the TBF device 102 offers enhanced stability with one bi-cortical fixation pin or screw and one anti-rotation uni-cortical fixation pin or screw as standard fixation. By contrast, other conventional systems rely on the fixation pins to create an undercut amongst each other and do not have anti-rotational fixation engagement for additional stability. If any of the fixation pins in other systems loosen the base guide will lose stability. The TBF device 102 is stabilized with dual pins/screws engaging bi- and uni-cortical bone. By contrast, other conventional systems only engage uni-cortical bone allowing for single bony plate engagement of the fixation. The TBF device 102 may engage, for example, 3 or 4 bony plates per site, or for example, 6 to 8 bony plate engagements with two TBF devices 102 as well as tissue stabilized on the tissue;

(9) the TBF device 102 covers about +/−20% of the surgical area only and after seating allows the surgeon full visual and working access to the surgical site. The anterior aspect of the surgical site is completely exposed and minimal tissue reflection, if any, is required in the surgical areas outside the TBF device 102 area. By contrast, other conventional buccal base guide systems require full buccal tissue reflection and contacts/attaches to the entire surgical bone surface area;

(10) a secondary bone reduction guide plane may attach to the TBF devices 102 through plug and jack connections (e.g., plug connectors 118 and jack connectors 122). The surgeon may use this guide to determine the planned and required bone reduction cut level. By contrast, other conventional systems utilize the base guide as the bone reduction level guide;

(11) the TBF device 102 may be positioned in relation to the primary fixation source (tooth or tissue or bone) by a titanium (or alloy/polymer) positioning frame that relates the TBF device 102 fixation position to the secondary fixation position. By contrast, other conventional systems relate the base guide only by the primary fixation source (exposed bone) or by touching the lingual and buccal bone with bone seating stops or indicators. Other conventional systems utilize the buccal and or lingual bone plane as primary fixation relation point for seating. In TBF system 100, the TBF device 102 utilizes the buccal bone only as fixation not as relation point. The primary relation point for fixation is the pre-extracted tooth position in dentate patients;

(12) the bone reduction plane guide may be free floating from the bone and not part of the TBF devices 102 fixated to the tissue. The bone reduction plane is only anchored with plug and jack connectors into the TBF devices 102. This feature allows the surgeon the freedom to determine the amount of distal tissue reflection the patient will be exposed to. Additionally, this feature greatly reduces the invasiveness of the surgery and assists in a faster post-surgical recovery. By contrast, other conventional systems dual-use the base guide as bone plane reduction guide, this requires aggressive tissue reflection into the posterior area;

(13) the TBF system 100 may latch the prosthesis in analog (not limited to digital like other systems) making it possible to cross-mount and verify pre-operative and post-occlusion; and

(14) the TBF system 100 relates its vertical occlusion position to the primary fixation point (existing pre-extracted teeth or bone level or tissue level). By contrast, other conventional systems check occlusion with occlusion check steps during the surgery process. The TBF system 100 has no occlusion check or verification steps during surgery. The TBF system 100 can therefore be used without compromise during orally intubated surgeries. By contrast, other conventional systems cannot check occlusion without removing the oral intubation.

Referring now to FIG. 22 is a flow diagram of an example of a fabrication process 200 of the presently disclosed TBF system 100 and TBF device 102. Fabrication process 200 may include, but is not limited to, the following steps.

At a step 210, DICOM data and STL or PVS of a patient's mouth may be imported into design software.

At a step 215, a diagnostic wax-up process may be performed.

At a step 220, the case may be surgically planned and reviewed with the surgeon and/or restorative clinician.

At a step 225, guides for the surgical procedure may be designed digitally and analog processed. For example, any components of TBF system 100 (e.g., TBF devices 102, tooth aligner guide 106, tooth aligner portion 108, hinged members 110, hinge pins 112, latch pin bridge 132/136, drill guide 144, bone reduction guide 148), may be designed digitally and analog processed.

At a step 230, in case of implant surgery, drill guides (e.g., drill guide 144) may be sleeved with the appropriate implant drilling sleeve guides 146 for fully guided or a pilot drill surgery procedure diagnostic.

At a step 235, plug connections (e.g., female plug connectors 118) are housed on the TBF carrier (e.g., TBF devices 102). Likewise, jack connections (e.g., male jack connectors 122) are housed on the surgical and prosthetic components (e.g., tooth aligner guide 106, drill guide 144, bone reduction guide 148).

At a step 240, coupling pin holes (e.g., latch pin holes 120, 124) may be digitally placed, and printed or milled through the oval connecting components (e.g., through female plug connectors 118 and male jack connectors 122). For example, when seating TBF devices 102 with hinged tooth aligner guide 106 these latch pin holes 120, 124 may be used to connect the unilateral TBF devices 102 for accuracy. Namely, a latch pin may be inserted into corresponding latch pin holes 120, 124 to hold the jack and plug connection in position during surgery.

Referring now to FIG. 23 is a flow diagram of an example of a simplified method 300 of performing a surgical procedure using the presently disclosed TBF system 100 and TBF devices 102. Method 300 may include, but is not limited to, the following steps.

At a step 310, two TBF devices 102 may be temporarily connected together using latch pin bridge 132 (or 136) as shown, for example, in FIG. 10A and FIG. 10B (or FIGS. 11-13). Optionally, the two TBF devices 102 may be cross-arch splinted using a fixed connecting bar for stability in lieu of a removable connecting bar (e.g., latch pin bridge 132 (or 136)) to form a one-piece TBF device 102. This variation may be used to supply rigidity and strength in specific anatomical make-ups or to satisfy surgeon preference.

At a step 315, the surgeon may fixate each of the two TBF devices 102 onto the buccal tissue level by tightening one or more fixation screws and/or fixation pins (e.g., fixation screws 556 and/or fixation pins 556, see FIGS. 85-87), to the appropriate depth as indicated by tissue thickness indicators 116 of TBF devices 102. The surgeon may relate the correct tissue seating position to the primary fixation point shown by Hinged tooth aligner 106. After seating of TBF device 102 is confirmed, the fixation and anti-rotational pilot holes are drilled and TBF device 102 may be fixated by using one, or preferably both, of fixation screws and/or fixation pins.

At a step 320, the temporary connection between the two TBF devices 102 may be removed. For example, the latch pin bridge 132 (or 136) between the two TBF devices 102 may be removed. Optionally, in the case of a one-piece TBF device 102 (e.g., similar to that shown as 502 in FIGS. 83 and 84), the surgeon may simply proceeds to the next step.

At a step 325, once the surgical and/or prosthetic process is complete the TBF device or devices 102 may be removed.

Referring now to FIG. 24A through FIG. 24D is a flow diagram of an example of a detailed method 400 of performing an example surgical procedure using the presently disclosed TBF system 100 and TBF device 102. In method 400, one or more TBF devices 102 may be used to anchor/support surgical components for full arch dental surgeries but can be utilized in quadrant application if required. Further, in method 400, little to no buccal incision or soft tissue reflection is required to seat TBF devices 102. Method 400 may include, but is not limited to, the following steps.

At a step 410, TBF devices 102 may be transferred to a patient's mouth. In one example, two TBF devices 102 may be loaded (latched in the plug and jack connectors) into the two respective hinged members 110 of a hinged tooth aligner guide 106.

At a step 412, the tissue seating position (i.e., secondary fixation point) of TBF devices 102 may be confirmed using the hinged position of hinged tooth aligner guide 106. Hinged tooth aligner guide 106 may be the primary fixation verification and tissue thickness indicators 116 of TBF devices 102 may be the secondary fixation verification.

At a step 414, the seating of the stack of components of TBF system 100 may be verified. For example, hinged tooth aligner guide 106 (tissue aligner guide 166 or bone ridge aligner in an edentulous case), may be positioned and two TBF devices 102 (which may be related to each other by hinged members 110) may be positioned on the tooth structure and tissue level (and may be interlocked using latch pin bridge 132 (or 136) with its latch pins 134 (or 140)), the stack (stack is defined as the engaged combination of, for example, hinged tooth aligner guide 106 and TBF devices 102 related to each other by latch pin bridge 132 (or 136)) is in undercut (undercut may be caused by the combination of the horizontal tooth position in relation with the vertical buccal bone undercut).

At a step 416, once the seating of the stack of components of TBF system 100 is verified (e.g., by visually inspecting the connection between the gum tissue and tissue thickness indicators 116 of TBF devices 102), the surgeon may drill the fixation holes 114 as directed by fixation guide holes 128 of TBF devices 102.

At a step 418, once the fixation holes 114 are drilled and finalized, the fixation pins/screws that engage bi-cortical bony plates (buccal and lingual) may be tapped into position. This primary fixation may be either done by using a fixation screw or fixation pin (e.g., fixation screws 556 and/or fixation pins 556, see FIGS. 85-87), depending on the bone quality and specific case and could be uni-cortical or bi-cortical. In one example, the fixation pins may be considered the primary TBF connectors.

At a step 420, after the fixation pins (if the primary TBF connector) are pinned, anti-rotational fixation screws that engage the buccal bone may be screwed into position to stabilize the TBF devices 102. In this example, the fixation screws may be considered the secondary TBF connectors. This secondary fixation may be done by using a fixation screw or fixation pin depending on the bone quality and specific case and could be uni-cortical or bi-cortical.

At a step 422, hinged tooth aligner guide 106 and latch pin bridge 132 (or 136) may be unlatched and removed from the patient's mouth. Namely, the various plug connectors 118 and jack connectors 122 may be disengaged. TBF devices 102 with their plug connectors 1118 may now be seated and ready to receive the sequential surgical and prosthetic components (prosthetic and surgical components with corresponding jack connectors 122 that latch in place with corresponding plug connectors 1118 using, e.g., latch pins). In particular, TBF devices 102 may be seated spaced from the surgical site (depth of seating depends on the amount of bone available).

At a step 424, if required for the procedure, teeth, as may be required, may now be extracted (dentate patients).

At a step 426, if bone reduction is required, a bone reduction guide 148 may be latched into plug connectors 118 of TBF devices 102. Bone reduction guide 148 is preferably a flat plane multi-use device. Bone reduction guide 148 indicates the bone reduction height (if bone reduction is required), and may act as a tissue retractor to expose the surgical site and manage the tissue reflected around the CEJ areas of the teeth.

At a step 428, after any required tooth extraction, and if required, the tissue may be pushed/wedged between the bone reduction guide 148 and the buccal bone to open the surgical site.

At a step 430, if required, bone reduction or bone contouring may be performed as indicated by the bone reduction guide 148.

At a step 432, after any needed bone reduction is completed, the surgical guide (e.g., drill guide 144) may be positioned into plug connectors 118 of TBF devices 102 and latched in place using latch pins. The surgical guide (e.g., drill guide 144) may be used for implant rotational, directional, and/or depth positioning.

At a step 434, fully (or partially) guided implant surgery may be performed depending on the surgeon's preferences.

At a step 436, once implants are placed, the surgical guide (e.g., drill guide 144) may be unlatched from TBF devices 102 and removed.

At a step 438, as/if required, an abutment aligner, such as abutment aligner 150 shown in FIG. 25, may be positioned (e.g., latched into TBF devices 102) and then intermediate (angled correction or straight) abutments may be seated using the abutment aligner (e.g., abutment aligner 150) to show the position of the screw access in relation to the hex position in the implant. The abutment aligner (e.g., abutment aligner 150) relates the rotation of the correction abutments to the screw-access position of in the pre-drilled transitional/conversion or even final prosthetic device.

At a step 440, after any required correction and straight dome abutments (not shown) positioned, the abutment aligner (e.g., abutment aligner 150) may be unlatched from TBF devices 102 and removed. The straight dome abutments may be screwed on to the implant after implant placed.

At a step 442, pre-cut, site specific (pre marked and drilled/cut) temporary dome abutments (not shown) may be screwed in place onto the intermediate abutments (not shown). In rare cases, the temporary dome abutments may be screwed directly into the implant interface-implant level restorative option.

At a step 444, the printed/milled/hand set-up prosthetic device (not shown) may now be positioned over the temporary abutments and latched into place using, for example, plug connectors 118 and/or jack connectors 122 that are milled and fixated (milled as one unit or luted) to the prosthetic device.

At a step 446, the prosthetic device may be seated. Seating may be done with all temporary abutments seated or individual temporary abutments placed to allow for draw into the screw access holes of the prosthetic device.

At a step 448, the temporary abutments may be luted into the prosthetic device. This process engages the prosthetic device into the implant positions in the correct position and relates back to the preoperative tooth or diagnostic position.

At a step 450, after the luting agent is cured with either light or chemical cure process, the prosthetic device may be removed by unlatching the latch pins and removing the device by disengaging the plug connectors 118 and jack connectors 122.

At a step 452, the surgeon may unscrew the TBF anti-rotational fixation screw, and/or pull (removes) the fixation pin to release TBF devices 102.

At a step 454, after removal of TBF devices 102, the surgeon may suture the reflections (if any) of TBF devices 102 and any other surgical incisions.

At a step 456, the latches may be cut from the prosthetic device and after suturing is completed the prosthetic device may be screwed onto the abutment level or screwed into the implant level. This prosthetic device is known as an immediately converted implant retained transitional prosthetic device.

In one example, a diagnostic design of a TBF system 100 and TBF devices 102 may include initially preparing a diagnostic wax-up, which will become a temporary prosthetic. A physical impression of a patient's current oral anatomy, or a digital scan of the same, may be provided, e.g., by the requestor/client. The physical impression may be poured and scanned, and a digital model may be printed and scanned or imported, resulting in a digital impression model. The diagnostic design may further include aligning the model of the patient's current oral anatomy to provided patient smile photos. Working within the parameters of the patient's existing dentition and bone structure, a prosthetic may be digitally planned to restore the patient's dental function and aesthetics.

The restorative doctor and/or surgeon preferably consults with lab designers on prescribed changes, patient expectations, and possible restorative options. Any changes to vertical dimension of occlusion (VDO) or midline, existing dentition, and/or need for restorative space are all considered during diagnostic wax-up design. The aesthetic qualities of the planned restoration are considered and mocked-up by superimposing the diagnostic wax-up onto the patient's smile photos and may be sent back to the requestor/client for approval.

While opening the VDO may be necessary, failing to achieve a modest range may cause discomfort for the patient. Chosen restoration type and available restorative space may impact options for adjustment. A dual-arch prosthetic may correct the upper and lower, idealizing the patient's bite. A single arch however, should preferably still be matched for occlusion against the patient's antagonist arch.

With regard to surgical planning, once the diagnostic wax-up is completed it may be imported by, for example, a guided surgery specialist to begin surgical planning. Surgical planning is based on laying a foundation for the prosthetic, which is derived from the diagnostic wax-up. In an embodiment, the TBF system 100 and TBF device 102 design process is prosthetically driven, and the planned surgery may be reverse engineered from the final prosthetic. Initially, the objective of the surgery is considered. For example, the final surgical plan may be for a removable, fixed hybrid, or partial restoration, which makes considerable differences in case planning. The patient's restorative space may determine the available room for the prosthetic, which may be increased by bone reduction if needed. For example, a removable implant-supported denture may require significantly more restorative space as compared to a fixed hybrid. In addition, cleanse-ability of the final prosthetic is also considered as a quality of life concern for the patient. Working within the parameters of the patient's existing dentition and bone structure, the prosthetic is digitally planned to restore the patient's dental function and aesthetics. At this stage, a technician preferably plans out the final bite created by the prosthetic. The final bite, created when the prosthetic is loaded into the patient's mouth, is expected to match the patient's prescribed bite. In one example, implant placement may begin with the patient's cone-beam computed tomography (CBCT) scan, sent as a DICOM file, which is imported into a suitable planning software. The digital impression model, along with the digital model of the diagnostic wax-up, may be imported and aligned to the CBCT scan. Planning considerations may include mapping out vital structures in the patient's mouth, such as nerves, blood vessels, and areas of insufficient bone density. An implant site is preferably planned in areas of sufficient bone density, providing the best possible chance of achieving primary stability. Diameter and length of each implant are determined by the doctor's prescription and/or indications provided by the implant manufacturer. Implant size and type will determine the implant analogs, sleeving, and drill protocol used in the creation of the TBF system 100 and TBF devices 102, stackable components, and/or models.

With regard to planning fixation, fixation points may be chosen to anchor TBF device 102 or devices to the patient's existing bone structure. As in implant placement, important and vital structures need to be avoided. In addition, bone density should be sufficient to stabilize the TBF system 100 across the patient's arch throughout the surgical procedure. Fixation points may be fixated using pins and/or screws, which may engage the patient's bone bi-cortically, and/or fixation screws, which may engage the patient's bone uni-cortically or vice versa. Fixation screws and pins may be for example, fixation screws 556 and/or fixation pins 556 shown in FIGS. 85-87. Should fixations be planned over the roots of preexisting teeth, the tooth would preferably be extracted prior to guide seating, which would be preferably communicated to the surgeon through documentation prior to surgery.

The TBF system 100 may be well suited for cases in which there is enough bone for bi-cortical and/or uni-cortical fixation, sufficient vestibule size, sufficient mouth opening, and scans and/or models of sufficient detail and accuracy. The TBF system 100 system's lack of required tissue reflection for guide seating may be well suited for cases with no or minimal bone reduction, as the total reflected area will be comparatively small. The TBF system 100 system preserves tissue that may be needed for scalloped or crown and bridge style cases, in which the prosthetic teeth sit directly on healed tissue.

With reference to FIGS. 26-31, in one example, a bone model 152 created from the CBCT scan, for example, may be constructed, imported, and aligned with the scan data. The bone model 152 may then be reduced to a bone reduction level by using a bone reduction plane 154 as a reference, creating a bone reduced model 156. This bone reduced model 156 may then be used in the creation of most guides (e.g., TBF devices 102) and other stackable components of the TBF system 100. The bone reduced model 156 may then be altered to reflect the exact placement and depths of planned implants and/or fixations. Glue holes 158 may be placed to allow implant analogs to be permanently positioned into the model. Peg holes 160, may be placed to allow for seating of a transfer mount 162 or mounts. This new model (analog model) may then be 3-D printed and used by technicians to test the guides (e.g., TBF device 102) and other stackable components of TBF system 100. In one example, impressions 164, for example of a depth in the range of about 0.2 mm, may be created in the model to allow for planned seating of tissue thickness indicators 116.

The initial TBF device 102 preferably may sit, for example, in the range of about 2 mm off the bone model 152 in order to be properly fixated during surgery. In order to create additional components for the TBF system 100, an additional bone model 152 may need to be created. A copy of the bone model 152 may be preferably created and offset by the same distance as planned for the TBF device 102. The model surface may then be extended and maintains topographical consistency. This model, which may be referred to as the offset model, may serve as a representation of the patient's tissue.

The TBF device 102 may be created by mapping fixation bodies (e.g., fixation guide holes 128) across the offset model. Fixation guide holes 128 may include a cylindrical opening, e.g., in the range of about 8 mm in diameter, surrounded with geometry mapped to the patient's tissue as it is represented in the offset model. This geometry covers the facial arc of the surgical site. The fixation guide holes 128 may serve as a fit for anchorage pieces such as fixation pins and/or screws.

For the purposes of creating and utilizing stackable guides (e.g., stackable components of the TBF system 100), plug (e.g., plug connectors 118) and jack (e.g., jack connectors 122) style latches/connectors may be formed on the facial arc of the bone model 152 with, for example, in the range of about 2-3 mm clearance. This allows a safe distance from the patient's tissue and bone structure. In some examples, the plug connectors 118 and jack connectors 122 may be respectively referred to as female and male latches/connectors. In an example, the latches/connectors may be placed an additional 3 mm, for example, from the occlusal in relation to below the implant plane, a plane defined by the crestal level of the planned implants. However, there may be occasions where the plug connector 118 latch surfaces will sit on the bone reduction plane. Such instances may occur when latch placement would fall within, for example, about 10 mm of the nasal spine. This will preferably allow for sufficient vestibule room for the TBF device 102 to seat comfortably. The latches/connectors raised to the bone reduction plane may now serve as a bone reduction guide. Latch/connector placement may also be determined upon hinge placement on, for example, the hinged tooth aligner guide 106.

Stackable latched guide components of the TBF system 100 that will not, or may not, be articulated by the same hinged members 110 (e.g., 110L, 110R), may need to be affixed by a removable latch pin bridge 132 or 136. Stackable latched guide components that may be articulated by the same hinged members 1110 are preferably securely attached to the TBF devices 102 using latches/connectors of a sufficient thickness, e.g., in the range of about 3 mm diameter. The jack connectors 122 of each of the stackable latched guide components may be removed and may be reused later in the creation of future stackable latched guide components of the TBF system 100.

Tissue thickness indicators 116, in one embodiment, may be spike-like protrusions and attached, for example, about each fixation guide hole 128. Tissue thickness indicators 116 are preferably configured to pierce through the patient's tissue and index onto the bone, but stopping prior to engaging the patient's underlying bone structure. The TBF device 102 may be affixed to the patient with little to no tissue reflection, greatly reducing the invasive nature of traditional surgical guides. The tissue thickness indicators 116 may be positioned on the lingual side (inner surface) of the TBF device 102 and carefully positioned so that they do not interfere with the fixation's trajectory. The angle of the tissue thickness indicators 116 relative to the tissue facing surface of the tissue thickness indicator 116, may differ depending on the type of guide component it is being installed on. In one example, the tissue thickness indicators 116 may be substantially perpendicular to the hinge axis of its related hinged members 110. The tissue thickness indicators 116 may act in conjunction with an aligner (such as a hinged tooth aligner guide 106) and a latch pin bridge 132 (or 136) to stabilize the TBF devices 102 during fixation. Fixation screws may be used to tighten the TBF devices 102 while the tissue thickness indicators 116 help prevent crushing of the patient's tissue due to overtightening of, for example, fixation screws.

Hinged seating guides may be created from a digital impression, which may include teeth, a tissue ridge, and/or a denture, or a converted CBCT model depicting the patient's relevant bone. This model may be aligned to the patient's existing dental anatomy as pictured in the CBCT. These models may then be used to create seating guides, which may include, for example, hinged tooth aligner guide 106, tissue alignment guide 166, denture alignment guide 168. The initial construction of such hinged seating guides may differ and non-limiting examples are described below.

In cases where a patient has existing teeth that are suitable for building guides, the digital impression model may be used to create a hinged tooth aligner guide 106. The initial hinged tooth aligner guide 106 may be created by enveloping the digital impression model with a polygonal mesh so that its internal structure matches the topography of the dentition with a defined offset, e.g., in the range of about 0.15 mm, in one example, its external structure may be in the range of about 3-4 mm in thickness. In some cases, it may be necessary to plan for tooth extraction before guide fixation. Instances where this is a factor may include situations where fixations may be placed through a tooth root, or where teeth are so badly damaged that they are unusable for the hinged tooth aligner guide 106. In these cases, either the .stl based on the patient's digital impression model should be altered to reflect these extractions, or special care should be taken to avoid these obstructions during the envelopment phase. For visibility, holes commonly referred to as "windows" (e.g., windows 170), may be cut into the guide, allowing the surgeon to see the patient's existing teeth and/or tissue, and allows confirmation of accurate seating. The hinged tooth aligner guide 106 may be cut on the lingual side in order to reduce the total guide size if needed. The distal edges may also be removed to reduce the hinged tooth aligner guide 106 size further if needed.

With reference to FIG. 32, in cases where the patient has no existing teeth for suitable guide building, a tissue alignment guide 166 may be created by enveloping the .stl model of the patient's CBCT scan with a polygonal mesh so that its internal structure matches to the patient's bone structure, with an offset typically in the range of about 0.15 mm. Its external structure, in one example, may be in the range of about 3-4 mm thick. Holes (windows) may be cut to allow the surgeon to see the bone structure and confirm accurate seating. The tissue alignment guide 166 may also be trimmed appropriately as/if needed.

With reference to FIG. 33, in cases where the patient has an existing and well-fitting denture, a denture alignment guide 168 may be used. A digitized scan of the patient's existing denture may be converted to a .stl mesh. Holes (windows) may then be cut into the denture alignment guide 168, allowing the surgeon to see the palatal tissue and confirm seating. Some trimming may be necessary; however, the denture's structure should be kept intact.

With reference to FIGS. 34-38 the hinged tooth aligner guide 106 may act as a delivery system for the TBF devices 102, which removes the need for tissue reflection beyond the planned surgical site. The hinged tooth aligner guide 106 may include a tooth aligner portion 108, hinge members 110, hinge pin or pins 112, female ball detent locks 172, and male ball detent locks 174. The hinged tooth aligner guide 106 may contain one or more (depending on the number of hinge members 110) sets of hinged receiver barrels 176, which may extend directly from the tooth aligner portion 108 itself and may be generally tubular in shape and may, in one example, have in the range of about a 4 mm internal diameter. These hinged receiver barrels 176 allow the insertion of a hinge pin 112, which have a smaller outer diameter than the inner diameter of the hinged receiver barrels 176. In one example, hinge pin 112 may be in the range of about a 0.1-0.25 mm lesser diameter than the inner diameter of the hinged receiver barrels 176. Beneath the hinged receiver barrel 176 may be a pair of female ball detent locks 172. The female ball detent locks 172 may extend outward from the tooth aligner portion 108, and lock together with corresponding male ball detents locks 174 on the hinge members 110. The placement and number of hinges is directly related to the number and position of the fixations and fixation bodies on the TBF devices 102. In a preferred embodiment there are two (2) hinges to provide sufficient stability. In one example, each of the TBF devices 102 may contain two plug connectors 118, and may rotate separately from one another.

For multi hinged stackable guide components of the TBF system 100, each hinge fixed onto the tooth aligner portion 108 may be on an angle roughly tangent to the curvature of the patient's bone at the fixation site, and may, in one example, be in the range of about 8 mm from the bone reduction plane 154. A stackable guide component of the TBF system 100 may preferably come with a hinged receiver barrel 176 accompanied by a set of female ball detent locks 172 for each TBF device 102. Additionally, a stackable guide component of the TBF system 100 may preferably come with a latch pin bridge, e.g., latch pin bridge 132 (or 136), to connect the TBF devices 102 and stackable guide component after delivery of the stackable guide component. The tissue thickness indicators 116 may be angled perpendicular to the center axis of the of its respective hinge member 110, which may be referred to as the hinge axis.

The hinge members 110 (e.g., 110R, 110L) may be constructed upon a set of jack connectors 122 and will seat in the TBF devices 102. In one example, cylinders in the range of about 5-8 mm in diameter may be used to form a strong base, the guide may be built vertically to the level of the hinged receiver barrel 176 on, for example, the hinged tooth aligner guide 106. On each side of the hinged receiver barrel 176, an additional hinged receiver barrel 176 may be attached to the hinge members 110 and a hinge pin 112 inserted. This creates an assembled hinge, for example, for a hinged tooth aligner guide 106. There may be one hinge member 110 unit for each hinge present.

Beneath each hinged receiver barrel 176 on each trunk of the hinge member 110 may be a male ball detent lock 174. The male ball detent lock 174 may include, for example, a substantially hemisphere like structure 178, which may be about in the range of 2 mm in diameter on an extension, which may be in the range of about 8 mm in length. The female ball detent lock 172 may include an extension of about a similar length to the extension of the male ball detent lock 174, and may further include a divot and trough 180 in which the hemisphere 178 of the male ball detent lock 174 may lock. Each of the male ball detent locks 174 preferably corresponds and fits with its related female ball detent lock 172 on the tooth aligner portion 108. When the female ball detent lock 172 and male ball detent lock 174 comes together, the rotation of the hinge is preferably halted. The hinge is preferably held closed by tension of the female ball detent lock 172 and male ball detent lock 174. This leaves the hinged tooth aligner guide 106 seated on the patient's tissue as planned. The latch pin bridge 132 (or 136) may then be inserted. It should be noted the above dimensions are examples only and a change in material or other factors, may require changes to dimensions.

With reference back to FIGS. 11-13, a latch pin bridge, such as latch pin bridge 136, may be of, in one example, a dogbone shaped (or other suitable shape) device which may include cylindrical ports 142 through which bridge latch pins 140 may be inserted. Bridge latch pins 140 may be placed through the ports 140. In one example, bridge latch pins 140 may be affixed in ports 142 via adhesive. In similar function to latch pins of the plug connectors 118 and jack connectors 122, the latch pin bridge 136 (or 132) may be inserted and removed with each stackable guide component latched to the TBF devices 102. The latch pin bridge 136 (or 132) may provide additional cross-arch stability during fixation and guide use.

The latch pin bridge 136 (or 132) may be designed as a solution for temporary locking of unconnected parallel plug and jack connector latches (e.g., plug connector 118 and jack connector 122). Plug and jack connector latches may normally be fixated together via, for example latch pins (e.g., 2 mm latch pins) inserted through aligned plug latch pin holes 120 and jack latch pin holes 124. The latch pin bridge 136 (or 132) preferably may provide the convenience of a temporary connection, and additionally it may provide a visual verification that the latched TBF component guide is seated securely and evenly, additionally during the seating phase and initial installation, it may secure the latched TBF component guide after it has been placed preventing further movement or rotation about the hinges.

With regard to assembly and delivery of TBF devices 102 everything is preferably assembled outside of the patient's mouth. In assembly, the hinged tooth aligner guide 106 fitted with hinged receiver barrels 176 may be aligned with those matching on the hinged members 110. They may then be pinned together with hinge pins 112. The hinged tooth aligner guide 106 may then be affixed to the hinged members 110 by placing, for example, latch pins through each seated plug and jack connector latch (e.g., plug connector 1118 and jack connector 122). The hinged members 110 may then be rotated facially, providing clearance for seating. The hinged tooth aligner guide 106 may then be placed securely on the patient's anatomy. The hinged members 110 may then be rotated lingually, delivering the tissue thickness indicators 116 of the TBF device 102 into the patient's gum tissue 130. The male ball detent locks 174 and female ball detent locks 176 may then combine and lock. The latch pin bridge 136 (or 132) may be installed to secure the placement of the hinged tooth aligner guide 106. Fixations may then be drilled and placed, the tissue thickness indicators 116 then seat into the patient's gum tissue 130 stopping just before engaging the patient's bone structure. Once the TBF devices 102 are fully seated, the hinge pins 112 may be pulled free, separating the hinged tooth aligner guide 106 and hinged members 110. In some instances this may be unnecessary and the entire hinged tooth aligner guide 106 may be removed as one piece. After the hinged tooth aligner guide 106 is removed from the patient. The latch pin bridge 136 (or 131) and pins 140 (or 134) may be removed unlocking the hinged members 110. The hinged members 110 may then be removed leaving only properly seated and fixated TBF devices 102 ready for receiving other stackable guide components of the TBF system 100.

With reference back to FIG. 30, transfer mount 162 may have pegs 182 corresponding to each punched port on the analog model. In one non-limiting example, each peg 182 may be in the range of about 1/10 of 1 mm smaller in diameter to its related port so that it fits securely after the transfer mount 162 has been affixed to the analog model. For testing the mounted analog and transfer mount 162 are fixed to a bite verification jig, the device fits and measures the mounted analog against a printed model of the patient's opposing arch. This measurement may be used to test the accuracy and effectiveness of the temporary prosthetic. If the prosthetic is accurate, the measurement will be the same.

The TBF devices 102 and hinged tooth aligner guide 106 may be tested in a manner similar to their surgical use. The transfer mount 162 may be inserted into the analog model, the hinged tooth aligner guide 106 assembled, and the TBF devices 102 may be latched and pinned to the hinged tooth aligner guide 106. This assembly may be used to deliver the TBF devices 102 onto the transfer mount 162 and analog model. When placed onto the analog model the tissue thickness indicators 116 will preferably fit into the tissue thickness indicator impressions 163 (see FIG. 31), approximating stability in tissue and providing an accurate representation of placement during surgery. The latch pin bridge 136 (or 132) may then be inserted, and the entire assembly is checked for correct seating and alignment. Due to fixation guide holes 128 already being created during the design phase, the TBF devices 102 may be fixated to the model with fixation pins and/or screws.

Each of the stackable guide components of TBF system 100 may be latched into the TBF devices 102 for testing and inspected for fit and functionality. Each combination of jack connector 122 on the stackable guide components of TBF system 100 may be latched to a corresponding plug connector 118 on the TBF device 102 using, for example, removable coupling/latch pins (e.g., 2 mm coupling/latch pins). This allows each stackable guide component of TBF system 100 to be firmly attached to the TBF devices 102 without fear of any unwanted movement during the surgery. In some cases, if the coupling/latch pin fit is too tight, it may be necessary using a hand piece or rotary tool to expand the diameter of the coupling/latch pin holes 120/124 on both the plug connectors 118 and/or the jack connectors 122. Basic functionality of each of the stackable guide components of TBF system 100 may also be tested.

In one example, for testing a stackable drill guide 144 component, the stackable drill guide 144 may be sleeved and test-fit by fixating the TBF devices 102 to the analog model and latching the stackable drill guide 144 into the TBF devices 102. Once accurate and secure seating has been confirmed the stackable drill guide 144 may be removed from the TBF devices 102, it is now possible to "time out" the case.

With reference to FIG. 39, as the TBF system 100 is prosthetically driven, the case can be "timed" with the use of a latched PMMA 184, as it may act as a stand-in for the temporary prosthetic. The TBF devices 102 may be fixated onto the analog model. Implant analogs may then be placed into the analog model, and any abutments and temporary cylinders may be attached. The latched PMMA 184 may be latched into the TBF devices 102. As the planned emergence is represented in emergence holes 186 through the latched PMMA 184, the technician may align the temporary cylinder with the emergence holes 186 by rotating the implant-abutment-temporary cylinder complex. Once each temporary cylinder matches its planned emergence hole 186, the implant analogs may be glued in position. The latched PMMA 184, temporary cylinders, and abutments may then be removed, leaving the implant analogs glued into the analog model at the correct planned rotation. The stackable drill guide 144 may then be latched into the TBF devices 102, an implant driver may be inserted through a drilling sleeve guide 146 into an implant. A marking may be made on the stackable drill guide 144 at each implant site corresponding to a marking on the implant driver. During surgery, the implant will be driven in, torqued, and the driver rotated to match this marking. This will set the emergence as planned.

In one example, for testing guides (e.g., seating guide, bone reduction guide, abutment alignment guide), they each may be separately fixated to the TBF devices 102 and checked for fit and sturdiness. Timing marks may be etched and stained into one or more of the guides as desired (e.g., abutment alignment guide). Once each piece has been verified for accuracy it may be removed and prepped to be shipped for the surgery.

For finishing bite verification with the latched PMMA 184, the transfer mount 162 may be removed from the analog model and a latched PMMA 184 may then be latched into the TBF devices 102. The analog model, fitted with the TBF devices 102 and latched PMMA 184, may then be inserted into the bite verification jig where it may be tested against the printed model of the patient's opposing arch. The measurement output should preferably not change from the prescribed bite. Each stackable guide component of TBF system 100 piece may be inspected and corrected if necessary. Finally, the finished temporary prosthetic may be set into the bite on the bite verification jig in place of the latched PMMA 184. Individual jack connectors 122 are preferably seat and pinned/latched into corresponding plug connectors 118 of the TBF devices 102 and may be cemented to the temporary prosthetic. This preferably allows the prosthetic to be delivered by latching into the TBF devices 102 and cementing in temporary cylinders. During surgery, once the temporary cylinders are cemented, the prosthetic may be removed from the mouth, the latches cut off, and the temporary prosthetic may be loaded onto the implants. Once the bite has been verified for accuracy and the entire TBF system 100 has passed quality control, all guides, models, and components may then be prepped and packed for shipping.

With reference to FIGS. 40-43, the following describes a system and process for the creation and utilization of a scalloping guide 188, which is an additional dental implant surgical guide that may be used with the TBF system 100. The creation of the scalloping guide 188 may include an all-digital workflow from wax up design to 3-D printing. The TBF system 100 requires minimal or no tissue reflection, and therefore it is ideally suited for cases in which the prosthetic teeth will seat into a patient's gumline, without artificial 'pink' (an acrylic material shaded to match the patient's tissue) revealing a prosthetic 'waterline' (e.g., where the visible line where the prosthetic meets the patient's tissue). Commonly called "crown and bridge style" or "scalloped," these conversions provide a seamless, natural smile fit for patients with high aesthetic requirements.

With the addition of the scalloping guide 188, the TBF system 100 can additionally support "scalloped" cases.

The scalloping guide 188, in one example, may take the place of a bone reduction guide 148 and may be used to profile the bone in advance of osteotomies, these profiled sites are referred to as 'scallops'. These scallops are the sites in which pontics of the prosthetic sit. Owing to biologic space requirements, the scallops will commonly provide in the range of about 1.5 mm of clearance between bone and restoration. In order to create this design, an STL model of the proposed restoration may be used as a starting point. By offsetting the surface of this model by the necessary distance, for example 1.5 mm, while maintaining topographic consistency, a model may be created to represent the desired profile (e.g., wax up offset model 190).

A model created from the CBCT scan (the bone model 152) may be constructed, imported, and aligned with the scan data. The bone model 152 for a scalloped case may be reduced beyond the implant plane, in one example in the range of about 2-5 mm, by using the bone reduction plane 154 (here, more accurately referred to as the 'implant plane') as a reference. Once reduced, this model will be referred to as the bone reduced model (e.g., bone reduced model 156). This bone reduced model 156 may then be used in the creation of most guide components for the TBF system 100. From this point the bone reduced model 156 may be altered to reflect the exact placement and depths of the implants and fixations. Glue holes 158 may be placed to allow the implant analogs to be permanently positioned into the model. Peg holes 160 may be placed to allow for seating of a transfer mount or mounts (e.g., transfer mount 192). This new model may be 3-D printed and used by technicians to test the guide components for the TBF system 100 and will be referred to as the scalloped analog model 194.

The scalloped analog model 194 may be an STL mesh created by subtracting the waxup offset model 190 from a bone ridge model. In edentulous cases, this initial bone model requires no further modification. In dentate cases, the teeth must be 'segmented out' of the scan in order to create a model of the expected bone ridge after extractions. After subtracting the waxup offset model 190, the model may be cut down to fit onto the analog model 194. Pegs 182, for example in the range of about 5-8 mm in diameter, may be set to match peg holes 160 in the analog model 194, allowing the scalloped transfer mount 192 to securely seat in the analog model 194 at the same location as in the patient's existing anatomy. The scalloped transfer mount 192 may preferably remain on the analog model 194 for the majority of case assembly.

The initial scallop guide 196 may be an STL mesh created by enveloping a model of the patient's bone ridge with a polygonal mesh so that its internal structure matches the topography of the bone with an offset for example typically in the range of about 0.3 mm. Its external structure may be in the typically range of about 2-4 mm in thickness. Using subtractive modeling, the waxup offset scallop model 190 may be removed from this mesh. This creates the scallop guide 188 that will rest on the patient's bone and continue the profile of the scalloped sites. The scallop guide 188 creates both a contour to be used as a visual reference for the surgeon, and a 'window' at each scallop area. The scallop guide 188 may be designed to accommodate both the buccal and lingual, or to only cover the buccal area, the scallop guide 188 may also be cut away from relevant structures such as the incisive canal. A reduction in height may also be made to minimize the vertical profile of the scallop guide 188.

Jack connectors 122 may be brought in to transform the scallop guide 188 into a stackable guide component that may be latched into the TBF devices 102. Each jack connectors 122 may preferably have a thick cylindrical base, e.g., in the range of about 7 mm, and horizontally each base cylinder may preferably be connected via a connection, for example, in the range of about 3-5 mm thick if possible. The low profile of the scallop guide 188 may preclude such horizontal connections. If necessary, the buccal and lingual sides of the scallop guide 188 may be bridged with connections, for example, in the range of about 3-7 mm, and other areas may be reinforced with such connections.

The scallop guide 188 may be printed from surgically acceptable material such as Cobalt-Chrome, MED610, or any other suitable material, including but not limited to any of the materials listed herein. In testing the scalloping guide 188, the scalloping guide 188 may be latched into the TBF device 102 on the analog model 194 with bone scallop transfer mount 192 attached. A technician may then test the accuracy of the scallop guide 188 by ensuring that each scallop on the scallop guide 188 matches those on the relevant scallop transfer mount 192. Once checked, the scallop guide 188 may then be removed from the TBF devices 102 and the latched PMMA 184 inserted. By checking for proper clearance between the latched PMMA 184 and scallop transfer mount 192, the accuracy of the final restoration is assured.

In an alternate embodiment, the subject matter of the invention provides a unilateral key fixation (UKF) system, device, methods of forming same, and methods for performing intraoral guided surgery.

In some embodiments, the UKF system may include one or more UKF devices, wherein the UKF devices provide a common foundation to which other prosthetic and/or surgical components, and/or any other devices required to perform intraoral guided surgery may be mounted.

In some embodiments, the UKF system may include prosthetic and/or surgical components, such as, but not limited to, the one or more UKF devices, one or more UKF carriers, one or more tooth aligners, one or more drill guides, one or more incision guides, and the like.

In some embodiments, the UKF system may include a plug and jack style connector system to support and relate prosthetic and/or surgical components intraorally.

Namely, to register and seat prosthetic and/or surgical components.

In some embodiments, the UKF system and/or UKF device may be used to secure surgical and prosthetic components required to perform guided surgery in the correct relationship to the primary fixation point (e.g., pre-extracted teeth, tissue or bone). In some embodiments, UKF system and/or UKF device may be used to reduce the invasiveness of bone fixated (bone touching/contacting) guide assisted surgical procedures by reducing the amount of tissue reflection required by up to about 60% to about 80%.

Further, a UKF design workflow method is provided for the UKF system and UKF device.

Further, a simplified method of performing surgery using the UKF system and UKF device is provided.

Further, a detailed method of performing surgery using the UKF system and UKF device is provided.

Referring now to FIGS. 44-46 illustrate various views of an example of UKF system 500 and UKF devices 502. For example, UKF system 500 may include a pair of UKF devices 502 (i.e., a right UKF device 502R and a left UKF device 502L) to which a variety of other prosthetic and/or surgical components, and/or any other devices that may be required for performing intraoral guided surgery may be mounted.

UKF system 500 may include UKF devices 502R and 502L, a UKF carrier 504, and a tooth aligner 506 that, in one example, may be seated on the subject's occlusal table and/or incisal edges of the pre-extracted arch (either maxilla or mandible) where surgery is to be performed. In this configuration, UKF devices 502R and 502L, UKF carrier 504, and tooth aligner 506 may provide three guides that may be locked together using a plug connector 508 and jack connector 510 system and latch pins, similar to plug connector 118 and jack connector 122 shown in FIGS. 5 and 6.

This configuration allows the surgeon to drill the fixation of UKF devices 502R and 502L. Once the fixation of UKF devices 502R and 502L are secured, UKF carrier 504 and tooth aligner 506 may be removed. More details of examples of UKF devices 502 are shown and described with reference to FIG. 50 and FIG. 62 through FIG. 66.

In UKF system 500, UKF carrier 504 may be both a UKF carrier and a bone reduction guide. The design of UKF carrier 504 may vary. More details of examples of UKF carrier 504 are shown and described with reference to FIG. 44, FIG. 59-60, and FIG. 67. Tooth aligner 506 is a tooth aligner device that is custom to the subject's preoperative teeth. More details of examples of tooth aligner 506 are shown and described with reference to FIG. 45, FIG. 52, FIG. 58, and FIG. 61.

Referring now to FIG. 46, UKF system 500 may include UKF devices 502R and 502L along with a drill guide 512. Openings 514 in drill guide 512 may reflect the subject's implant positions. Namely, using drill guide 514, a surgeon may drill the osteotomies and place the implants. More details of examples of drill guide 514 are shown and described with reference to FIG. 53 and FIG. 68.

Referring now to FIG. 47, UKF system 500 may include an incision guide 516. Incision guide 516 may include, for example, a custom tooth aligner body 518 and a pair of incision outline guides 520 (i.e., a right incision outline guide 520R and a left incision outline guide 520L). The positions of incision outline guides 520R and 520L substantially correspond to the desired positions of UKF devices 502R and 502L, respectively. Accordingly, incision guide 516 is provided to indicate to the surgeon the outline of the reflection sites for the fixation of UKF devices 502R and 502L. Each of the incision outline guides 520 may be, for example, a box-shaped member positioned off custom tooth aligner body 518. More details of examples of incision guide 516 are shown and described with reference to FIG. 54 through FIG. 57.

The plug and jack system may include, for example, a plug connector (or plug key) 508 that has a plug latch pin hole 522, which may be angled, and a jack connector (or jack key) 510 that has a jack latch pin hole 524, which may be angled. Plug connector 508 may be, for example, a hollow cylinder-shaped member that is open at one or both ends. Plug connector 508 is designed to receive jack connector 510. Jack connector 510 may be, for example, a hollow cone-shaped member. Jack connector 510 (the male connector) may be designed to be fitted into plug connector 508 (the female connector). Latch pin holes 522 and 524 may be digitally placed, printed or milled through the connecting components.

When plug connector 508 and jack connector 510 are fitted together, plug latch pin hole 522 and jack latch pin hole 524 are substantially aligned. A latch pin (not shown) may be provided that can be inserted into both plug latch pin hole 522 and jack latch pin hole 524 in order to secure plug connector 508 and jack connector 510 together. Namely, the latch pin (not shown) connects plug connector 508 and jack connector 510 in a manner that ensures that they remain connected during use (e.g., during a surgical procedure). The various prosthetic and/or surgical components and any other components of UKF system 500 may include any arrangement of plug connectors 508 and/or jack connectors 510 for fitting the stackable components of the UKF system 500 together.

Referring now to FIG. 50 through FIG. 68 are images showing various views of examples of the various components of the presently disclosed UKF system 500.

FIG. 50 shows an example of the presently disclosed UKF device 502. UKF device 502 may include, for example, a cross-member 526, a fixation plate 528 that may include one or more fixation guide holes 530, and one or more plug connectors 508 (e.g., two). In one example, one plug connector 508 may be at one end of cross-member 526 and another plug connector 508 may be at the opposite end of cross-member 526.

In one example, fixation plate 528 of UKF device 502 may be alloy printed using Select Laser Milled (SLM) or Digital Light Printing (DPL) fabrication techniques, or prefabricated steel guide sleeves may be fixed (cemented or glued) into a light cured printed material (fiber reinforced, Teflon reinforced nylon, carbon reinforced nylon polymer, nylon, fiberglass, HSHT fiberglass, carbon fiber, onyx, Kevlar, cobalt chrome, and/or any other suitable material now know or known in the future), guide using light cured printing techniques, or other suitable technique or mechanism now know or known in the future.

In UKF system 500, UKF devices 502 act as carrier devices with surgical keys to support and secure, for example, any type of UKF carrier 504, any type of tooth aligner 506, any type of drill guide 512, any type of prosthetic components, any type of surgical components, and/or any other devices required to perform intraoral guided surgery and/or procedure. UKF devices 502 provide a unilateral buccal fixation foundation with surgical keys. UKF devices 502 provide a surgical foundation that is minimally invasive and bone-stabilized.

Each of the UKF devices 502 may be positioned intraorally by engaging and verifying dual anatomical positioning points with the assistance of a tooth aligner/tissue aligner (e.g., tooth aligner 506 or tissue aligner 595) and/or bone aligner (e.g., UKF carrier 504). The primary point of stabilization may be the maxillary palatal tissue (tissue borne) or maxillary ridge and/or palatal bone or mandibular bony ridge (bone borne) in edentulous patients. The tooth position (tooth borne) may be used in dentate patients or a combination of the above. The secondary point of stabilization may be on the buccal bone. UKF devices 502 may fixated on the buccal bone with one or more unicortical or bicortical bone fixation screws and/or pins (e.g., fixation screws 556 and/or fixation pins 558, See for example FIGS. 84-86). Rotation may be stabilized with one or more anti-rotational stabilization screws and/or pins, these can engage unicortical or bicortical bone. Depending on the patient's anatomy the horizontal and vertical contact with the bone is minimized to reduce the required tissue reflection. More details of the fixation of UKF devices 502 is shown and described with reference to FIGS. 84-86.

Optionally, UKF devices 502R and 502L may be splinted cross arch (bi-lateral) by a connection bar 532 (see FIG. 82 and FIG. 83) or UKF devices 502R and 502L may be transferred to the mouth with a UKF carrier (e.g., UKF carrier 504) that may be removed after fixation (uni-lateral). In any case, the bone fixation remains uni-lateral. Optionally, the UKF carrier (e.g., UKF carrier 504) may be processed as one piece with UKF devices 502R and 502L.

Generally, UKF device 502 is a bone stabilized, minimally invasive, unilateral, independent foundation to carry keys (plug connectors 508) for intraoral surgical/procedural components. The key foundation carrier supports and stabilizes surgical components e.g., tissue/tooth aligner 506, drill guide 512, provisional and/or final dental prosthetics during surgical procedures.

UKF device 502 provides an improvement to, for example, a traditional "paperclip" (buccolingual) and buccal bone engaging base or foundation guides. UKF device 502 minimizes the amount of surgical tissue reflection traditionally required to stabilize intraoral surgical devices. For example, UKF device 502 may utilize from about 60% to about 80% less buccal bone surface area for engagement (and therefore 60% to 80% less tissue reflection is required) than traditional guides (e.g., "paperclip" buccolingual guides). Further, UKF device 502 requires from about 80% to about 90% less tissue reflection than traditional "paperclip" buccolingual guides and requires minimal, if any, lingual tissue reflection. Paperclip guides requires significant buccal as well as lingual tissue reflection. Further, UKF device 502 is a "plug and jack keyed" fixation carrier (e.g., plug connectors 508 and jack connectors 510). UKF device 502 is not necessarily in and of itself a surgical device or guide. Rather, UKF device 502 primarily acts as an anchor to carry plug and jack keys (e.g., plug connectors 508 and jack connectors 510 keys) used to stabilize surgical components (e.g., stackable guide components). By contrast, conventional systems utilize the base guide as a dual-use surgical and anchoring device. Further, UKF device 502 can be adapted to accommodate edentulous or dentate patients. Further, UKF device 502 greatly reduces the traditional invasive nature of intraoral dental implant surgical procedures and protocols and greatly reduces patient morbidity and post-surgical recovery time.

FIG. 51 shows one example of UKF carrier 504. In this example, UKF carrier 504 may include, for example, a substantially semicircular plate 534 and a front connecting plate 536 for holding plug connectors 508. Further, in this example, UKF carrier 504 may include jack connectors 510 that may be provided atop semicircular plate 534; including for example, two jack connectors 508 on each side of front connecting plate 536. The jack connectors 510 may be arranged to be fitted into the plug connectors 508 of UKF devices 502, and plug connectors 508 may be provided for receiving any other components, such as, but not limited to, tooth aligner 506.

UKF carrier 504 may be a dual-purpose component that serves as a stabilizing fixture or carrier and a bone reduction guide. Namely, UKF carrier 504 may define a bone reduction plane (see for example FIG. 60 and FIG. 69).

FIG. 52 shows one example of tooth aligner guide 506. In this example, tooth aligner guide 506 may include, for example, a tooth aligner body 538, a connecting structure 540, and two jack connectors 510 atop connecting structure 540. In one example, jack connectors 510 are provided for connection to the two plug connectors 508 of UKF carrier 504. Tooth aligner 506 is preferably custom to the subject's preoperative teeth.

FIG. 53 shows one example of drill guide 512. Drill guide 512 may include, for example, a custom drill guide body 542, a connecting structure 544, and jack connectors 510 arranged along connecting structure 544. In one example, jack connectors 510 may be provided for connection to the plug connectors 508 of UKF devices 502R and 502L. Additionally, openings 514 in custom drill guide body 542 correspond to the subject's implant positions. Namely, using openings 514 in drill guide 512, a surgeon may drill the osteotomy and place the implants.

FIGS. 54-57 show various views of one example of incision guide 516 that may include, for example, tooth aligner 506 and a pair of incision outline guides 520 (i.e., incision outline guides 520R and 520L). Again, the positions of incision outline guides 520R and 520L substantially correspond to the desired fixation positions of UKF devices 502R and 502L, respectively.

Figure 56:
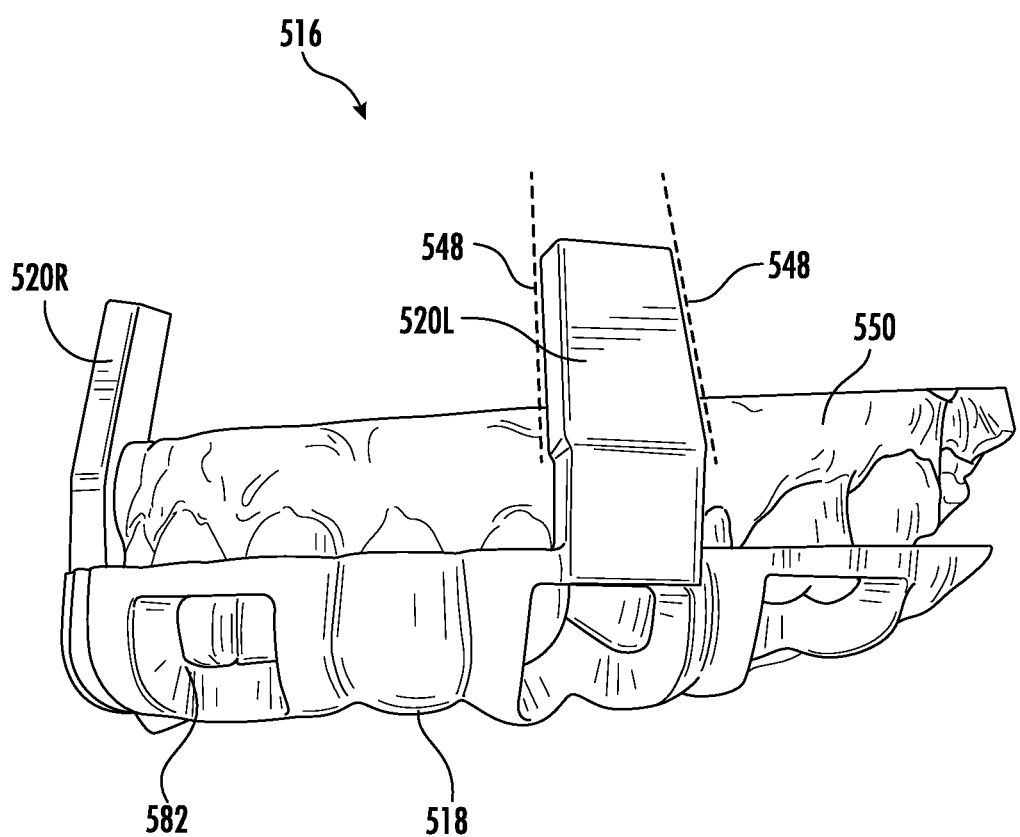
Figure 57:
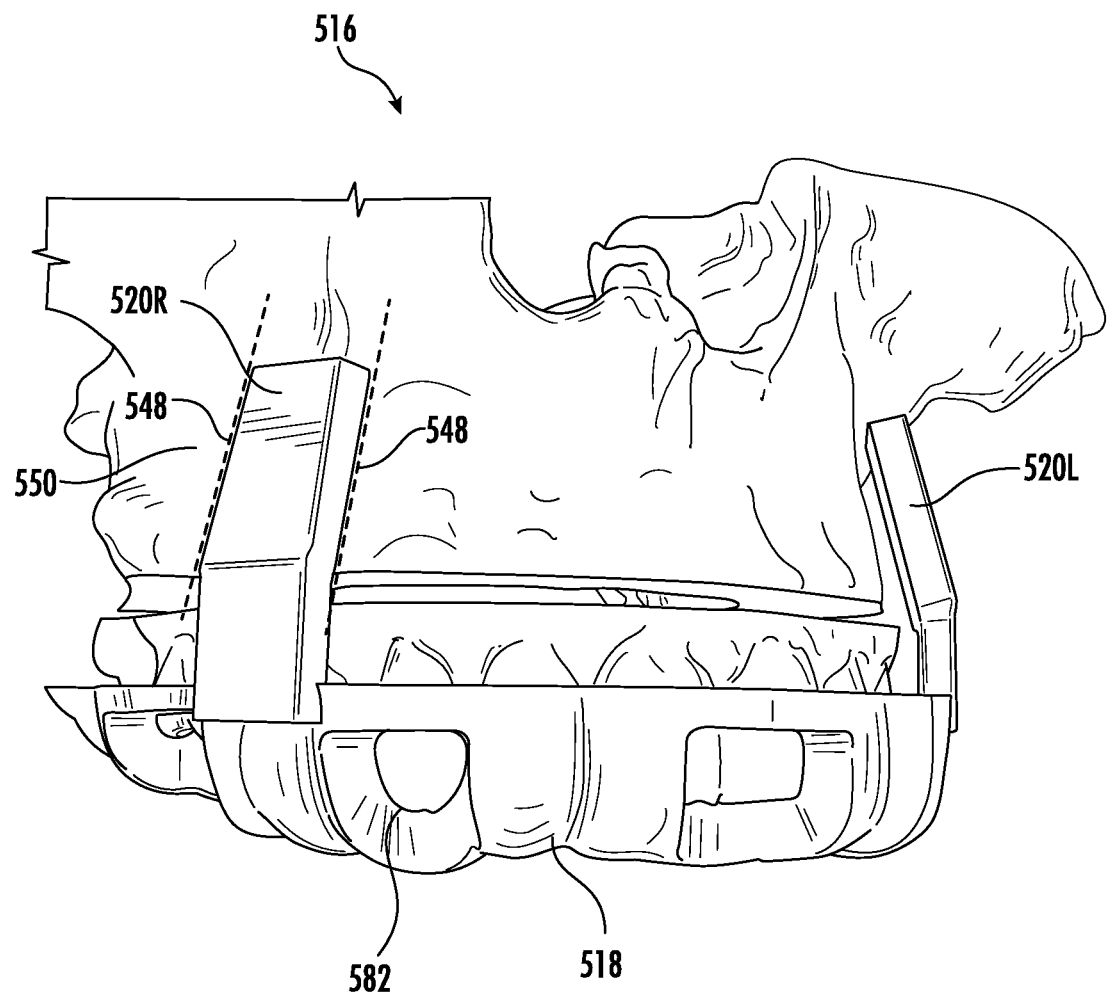

Incision guide 516 is provided to indicate to the surgeon the outline of the reflection sites for the fixation of UKF devices 502R and 502L. Each of the incision outline guides 520 may be used to "trace" the outside perimeter of the tissue to be reflected. Namely, each of the incision outline guides 520 provides a reflection pattern to the surgeon. The surgeon simply runs a scalpel, for example, on the outside of each incision outline guide 520. After tracing the vertical cuts, incision guide 516 may be removed. Then, the surgeon may reflect the tissue inside the lines. The box-shaped incision outline guides 520 may be designed slightly larger than the UKF devices 502 to allow for free/open bone reflection around the UKF devices 502. For example, FIG. 56 and FIG. 57 show an example of incisions 548 in tissue 550, wherein incisions 548 are guided by tracing the outline of incision outline guides 520R and 520L.

FIG. 58 shows another view of the tooth aligner 506 shown in FIG. 52, in a seated position. Tooth aligner 506 may serve as the primary fixation guide. Tooth aligner 506, latched together with UKF devices 502R and 502L and UKF carrier 504, enables the surgeon to accurately drill the fixation of UKF devices 502.

FIG. 59 and FIG. 60 show other views of the UKF carrier 504 shown in FIG. 44. Again, UKF carrier 504 may be both the UKF carrier and a bone reduction guide that defines a bone reduction plane 552 (which may be the surface face of semicircular plate 534). Namely, (1) UKF carrier 504 may be used to stabilize UKF devices 502 so that the fixation can be drilled, and/or (2) UKF carrier 504 may serve as the "plane" of reduction for the doctor/surgeon to follow when reducing bone.

FIG. 61 shows another view of the UKF system 500 shown in FIG. 51 that includes UKF devices 502, UKF carrier 504, and tooth aligner 506. Again, this configuration allows the surgeon to drill the fixation of UKF devices 502. Once the fixation of UKF devices 502 is secured, UKF carrier 504 and tooth aligner 506 may be removed.

FIGS. 62-66 show other views of the UKF devices 502 shown in FIG. 50, and in a fixated state. UKF devices 502 may be secured directly onto bone by a fixation pin and/or a fixation screw (see FIGS. 85-87). The UKF devices 502 may be fixated on the buccal bone with one or more uni or bi-cortical bone fixation screws and/or pins (e.g., fixation screws 556 and/or fixation pins 558). Rotation of the UKF devices 502 may be stabilized with one or more anti-rotational stabilization screws or pins (e.g., fixation screws 556 and/or fixation pins 558), these can engage uni or bi-cortical bone.

Each UKF device 502 may seat a distance away from the surgical/bone reduction level to provide easy/open access to the site. For example, the UKF device 502 may seat below the surgical/bone reduction level on the mandible and above the surgical/bone reduction level on the maxilla. This position may vary depending on the height of the buccal plate.

Measured from the vestibule to the cementoenamel junction (CEJ), the UKF device 502 can be planned from in the range of about 5 mm to about 10 mm below the surgical site. Another advantage of the present UKF system 500, in case of a surgical emergency, all jack and plug key components (e.g., plug connectors 508 and jack connectors 510) may be quickly and easily removed by releasing a simple latch-pin allowing the surgeon immediate unobstructed access to the surgical site. By contrast, conventional systems have fixed buccal and lingual frames that can be removed only by unscrewing the fixation screws 556 or by removing the fixation pins 558.

UKF system 500 may include two individual UKF devices 502 (or three UKF devices 502 in extreme cases) or, optionally, two UKF devices 502 joined by a horizontal connection bar 532 (see FIG. 82 and FIG. 83). By contrast, many conventional systems rely on a bilateral "paperclip" (buccal and lingual) base fixation guide or a unilateral one-piece bone fixation guide contacting the entire buccal surface area or touching the bone with individual bone stops. Some conventional systems utilize a floating buccal guide (not engaging the bone except through fixation pins) but still require full facial tissue reflection.

Each UKF device 502 of UKF system 500 may include a bicortical fixation pin or screw and an anti-rotation unicortical fixation pin or screw as standard fixation for enhanced stability. By contrast, conventional systems rely on the fixation pins to create an undercut amongst each other and do not have anti-rotational fixation engagement for additional stability. If any of the fixation pins in conventional systems loosen the base guide will lose stability. Each UKF device 502 is stabilized with preferably dual pins and/or engaging preferably bicortical bone and unicortical bone. By contrast, conventional systems engage unicortical bone only allowing for single bony plate engagement of the fixation. Each UKF device 502 may engage three or four bony plates per UKF device 502 fixation site, or may engage six to eight bony plate.

Each UKF device 502 preferably covers only about 20% of the surgical area and after seating allows the surgeon full visual and working access to the surgical site. The anterior aspect of the surgical site is completely exposed and minimal tissue reflection, if any, is required in the surgical areas outside the UKF device 502 area. By contrast, conventional buccal base guide systems require full buccal tissue reflection and contacts/attaches to the entire surgical bone surface area.

Referring now to FIG. 67, shows an example of a bone reduction guide plane 552 (e.g., UKF carrier 504) attached to UKF devices 502 through the plug and jack key components (e.g., plug connectors 508 and jack connectors 510). In this example, the surgeon may use UKF carrier 504 to determine the planned and required bone reduction cut level (i.e., bone reduction plane 554). FIG. 67 shows that the bone has been reduced to the bone reduction plane 554 by following bone reduction plane guide 552 that is defined using UKF carrier 504. By contrast, conventional systems may utilize the base guide as the bone reduction level guide.

FIG. 68 shows another view of the drill guide 512. In this example, jack connectors 510 of drill guide 512 are engaged with plug connectors 508 of UKF devices 502. Using openings 514 in drill guide 512, a surgeon may drill the osteotomy and place the implants.

Referring now again to FIG. 44 through FIG. 68, with respect to the fabrication of the components of UKF system 500, such as, but not limited to, UKF devices 502, UKF carriers 504, tooth aligners 506, drill guides 512, and incision guides 516, the devices may be planned from DICOM data in a conventional surgical planning software, and guide design may be done in multiple distinctive design software systems, which are conventional and well known. Namely, DICOM data and STL or PVS of a patient's mouth may be imported into the design software. Further, diagnostic wax-up may be performed. The components can, for example, be printed, milled, or casted with various techniques and varied materials (e.g., Axis milling systems, Selective laser milling (SLM), Digital laser milling (DPM), printed with resin-based printer, or centrifugal casted with alloys). Final product may be digitally designed and final processed in analog from STL digital design files.

Referring still to FIG. 44 through FIG. 68, with respect to the materials of the components of UKF system 500, such as, but not limited to, UKF devices 502, UKF carriers 504, tooth aligners 506, drill guides 512, and incision guides 516, depending on the patient, any device can be processed with fiber reinforced material, Teflon reinforced nylon, carbon reinforced nylon polymer, nylon, fiberglass, HSHT fiberglass, carbon fiber, onyx, Kevlar, cobalt chrome, polymers, alloys, zirconias, printed resin material, nylon carbon fiber reinforced, other printable and/or millable materials, and/or any other suitable material now know or known in the future.

The bone reduction plane guide 552 (also known as UKF carrier 504) may be free floating from the bone and not part of the UKF device 502 attached to the bone. The bone reduction plane guide 552 may be anchored with plug and jack connector (508, 510) attachments into UKF devices 502. This feature allows the surgeon the freedom to determine the amount of distal tissue reflection the patient will be exposed to. This greatly reduces the invasiveness of the surgery and assists in a faster post-surgical recovery. By contrast, conventional systems dual-use the base guide as bone plane reduction guide, this requires aggressive tissue reflection into the posterior area.

Referring still to FIG. 44 through FIG. 68, UKF system 500 may latch the prosthesis in analog (not digital like other systems) making it possible to cross-mount and verify pre-operative and post-occlusion. UKF system 500 preferably features an incision guide (e.g., incision guide 516) to direct the surgeon in making the window flap incisions 548 in the correct position and minimize unnecessary tissue reflection. Further, UKF system 500 requires only about 120 $mm^2$ (12 mm×10 mm) window incisions/flaps on each side of the posterior buccal bone. By contrast, conventional systems often require full anterior and partial to full posterior tissue reflection. Further, UKF system 500 relates its vertical occlusion position to the primary fixation point (existing pre-extracted teeth or bone level or tissue level). By contrast, conventional systems check occlusion with occlusion check steps during the surgery process. Further, UKF system 500 has no occlusion check or verification steps during surgery. Accordingly, UKF system 500 can therefore be used without compromise during orally intubated surgeries. By contrast, conventional systems cannot check occlusion without removing the oral intubation.

Referring now to FIG. 69 is a flow diagram of an example of a UKF design workflow 600 of the presently disclosed UKF system 500 and UKF device 502. Additionally, FIGS. 70-81 are diagrams showing examples of the process steps of UKF design workflow 600. UKF design workflow 600 may include, but is not limited to, the following steps.

At a step 610, fixation plates 528 of the UKF device 502 may be designed. For example, and referring now to FIG. 70, fixation plates 528 of UKF device 502 of UKF system

Figure 71:
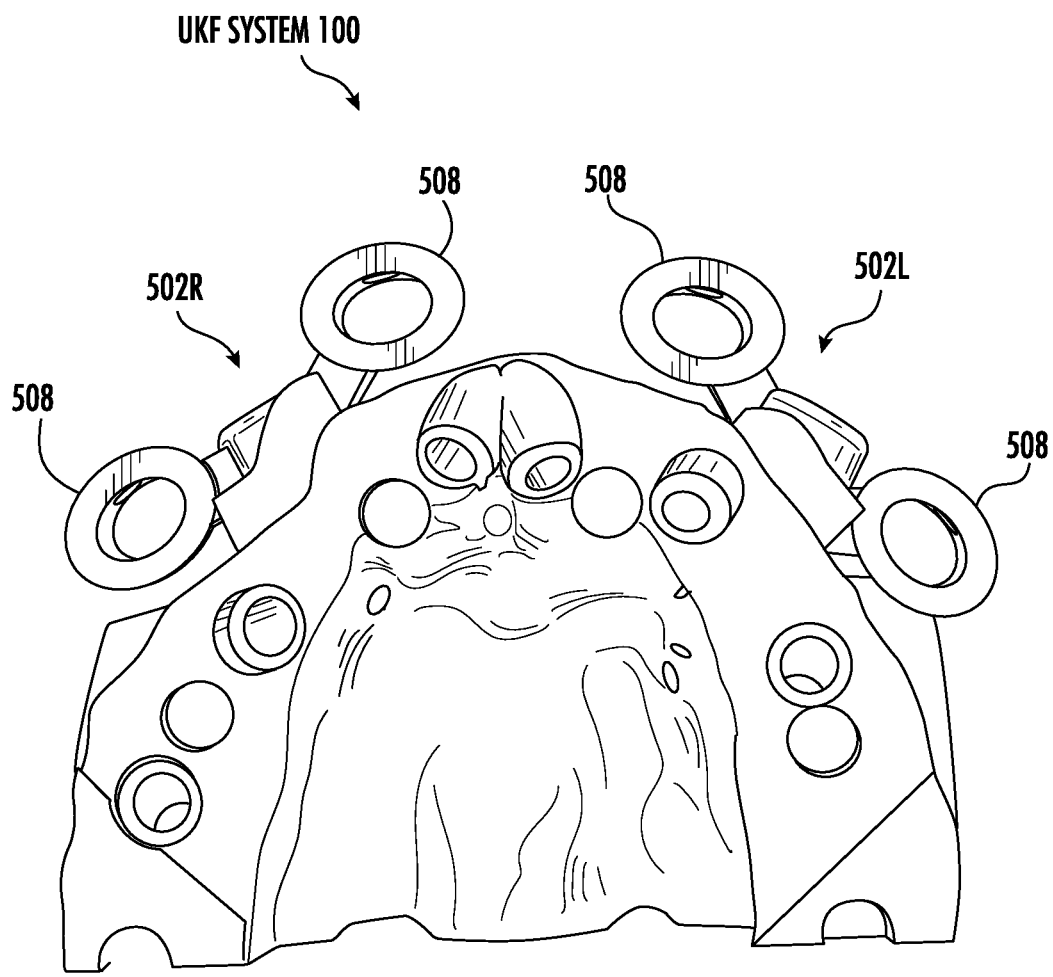
Figure 72:
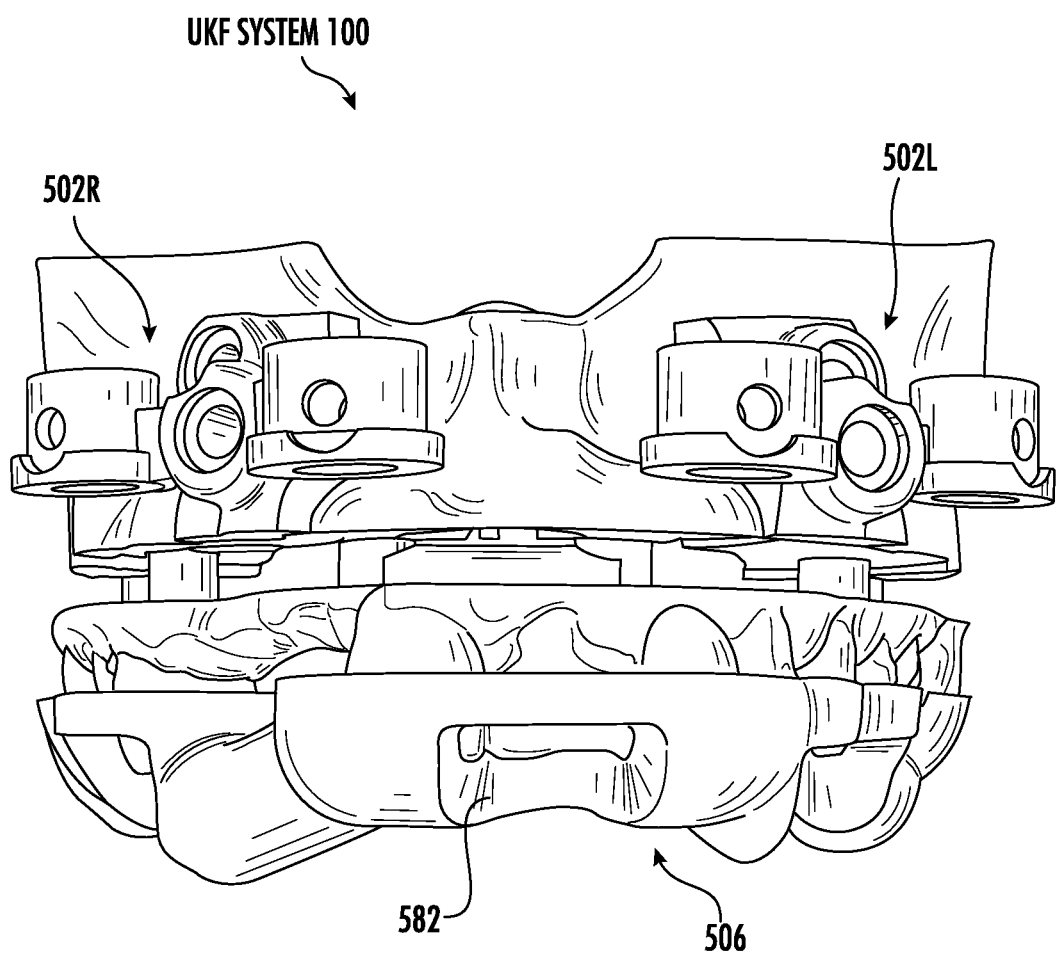
Figure 73:
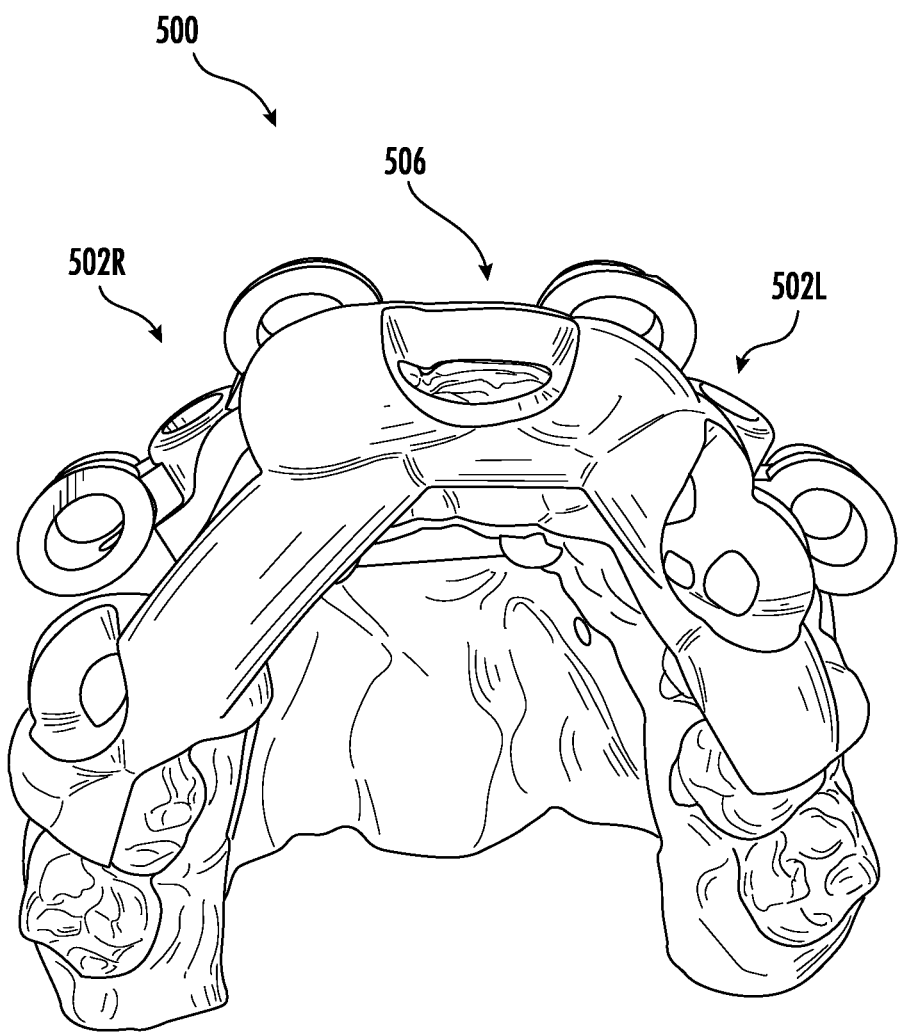

500 may be designed (e.g., digitally), and may be exported out of the design software. Referring now to FIG. 71, looking at the axial view of the surgical site, it is determined where to place the plug connectors 508. The posterior plug connector 508, in one example, may be positioned closer to the tissue. This would be to minimize proximity to the cheek. The anterior plug connector 508 may be used to open the a-p spread (of the jack connectors 510) and build out the surgical platform anteriorly. These plug connectors 508 are configured to, in one example, to stabilize a bone reduction guide (e.g., UKF carrier 504) and a surgical guide (e.g., drill guide 512).

At a step 615, a tooth aligner may be designed. For example and referring now to FIG. 72 and FIG. 73, tooth aligner 506 of UKF system 500 may be designed (e.g., digitally), and may be exported out of the design software. Tooth aligner 506 may be used as three different guides as follows.

Figure 74:
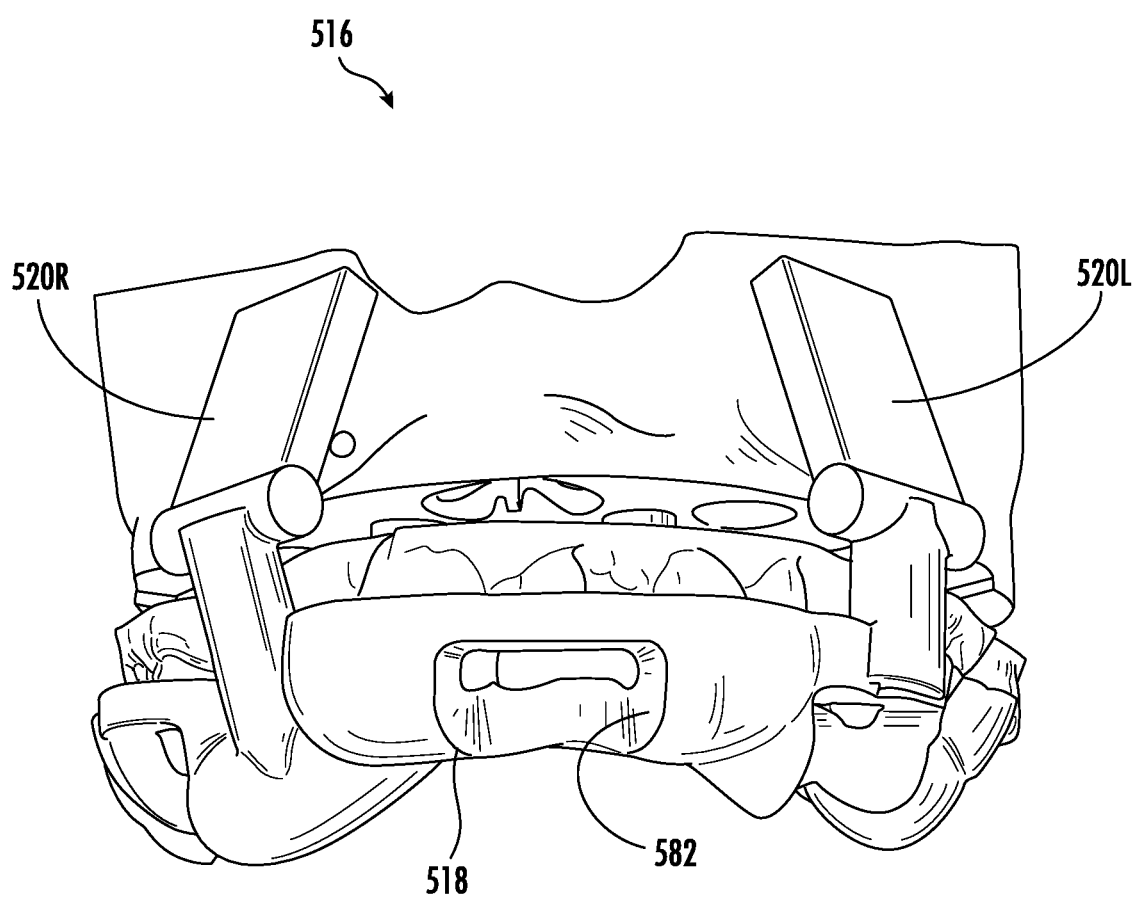

(1) The first guide may be used as an incision guide 516, for example, as shown in FIG. 74. Incision guide 516 allows the surgeon to accurately flap the tissue and expose the bone on which the UKF device 502 will ultimately fixate onto. Incision guide 516 may include incision outline guides 520 (e.g., 520R, 520L), which may be, in one example, substantially rectangular shaped, or any other suitable shape. The planes are preferably set far enough away from the surgical sight to be able to fit without any pre-operative actions.

Figure 75:
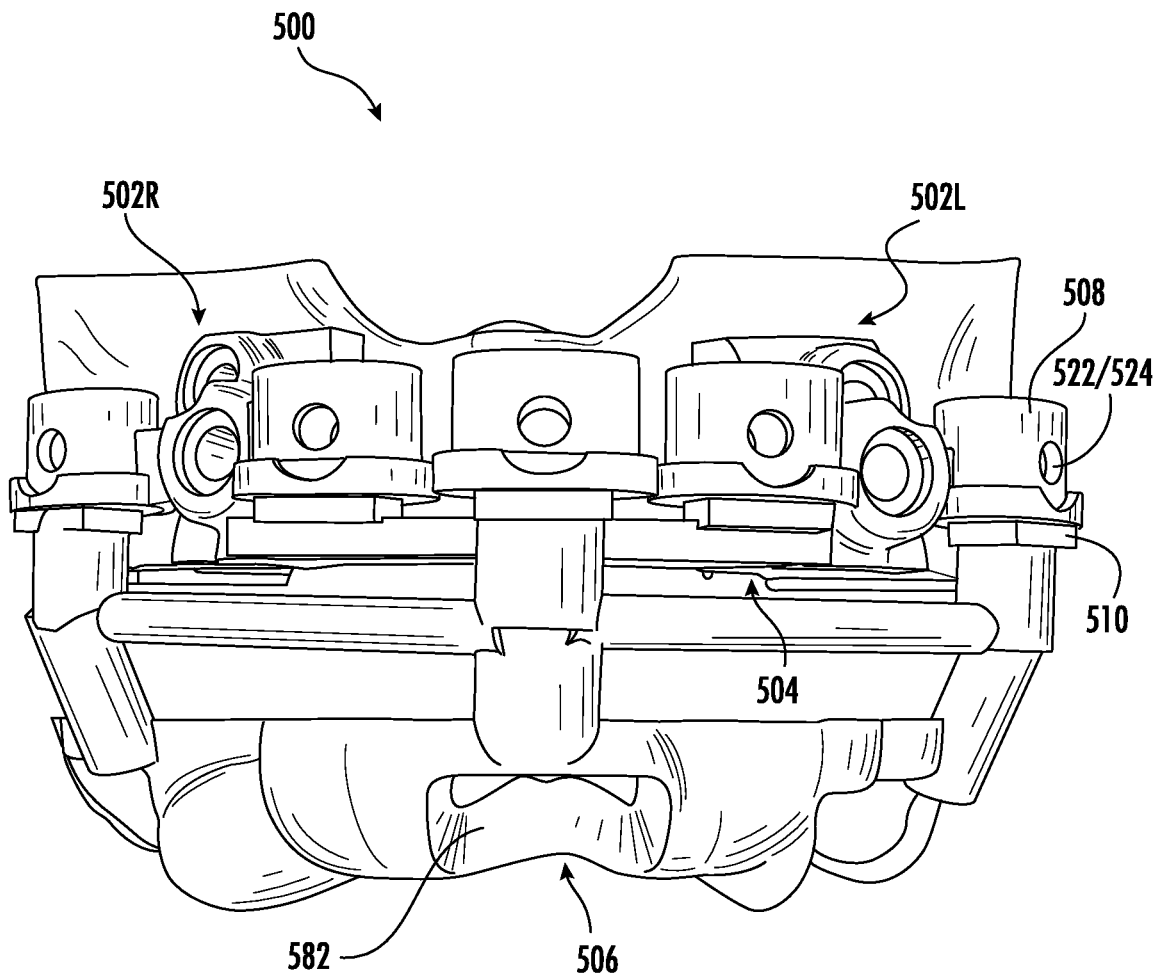

(2) The second may be tooth aligner 506, and may work in tandem with UKF devices 502 and a UKF carrier 504 as shown for example in FIG. 75. This guide may serve as a secondary verification tool for the surgeon to confirm the seating position of UKF carrier 504.

Figure 76:
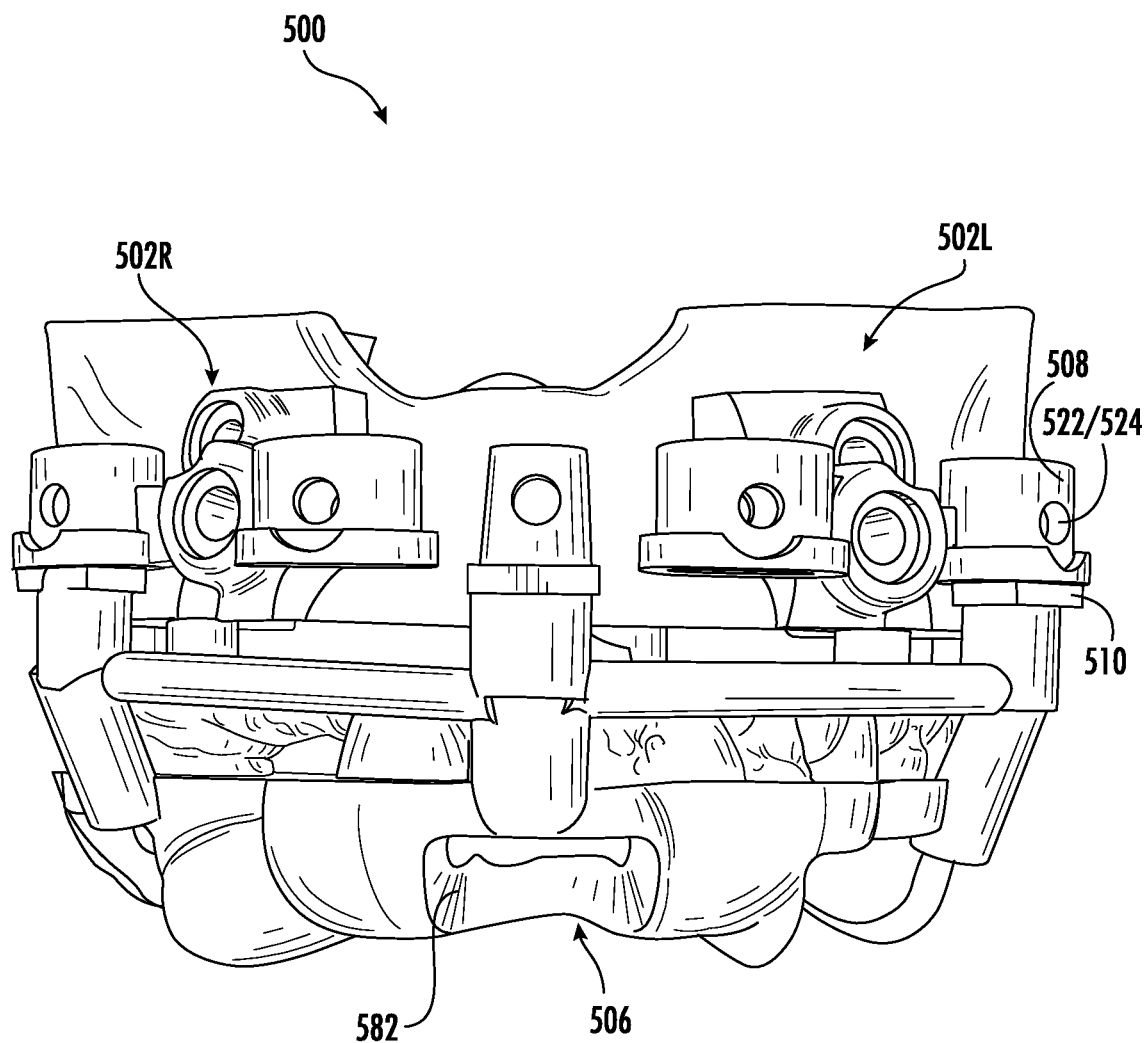

(3) The third may be a tooth aligner 506 and may plug into plug connectors 508 of UKF devices 502 (absent UKF carrier 504) and delivers the UKF guides into the mouth as shown in FIG. 76. This guide (e.g., absent UKF carrier 504) may be used when there is not sufficient room for UKF carrier 504.

Figure 77:
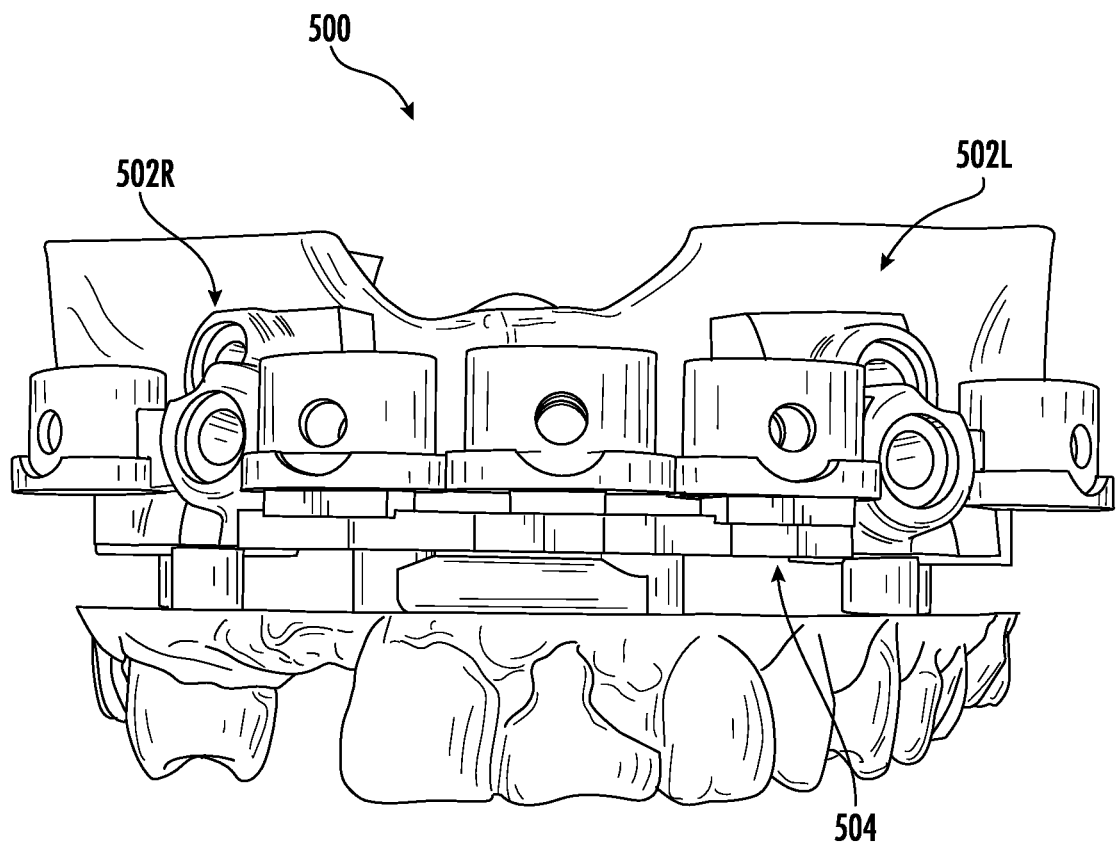
Figure 78:
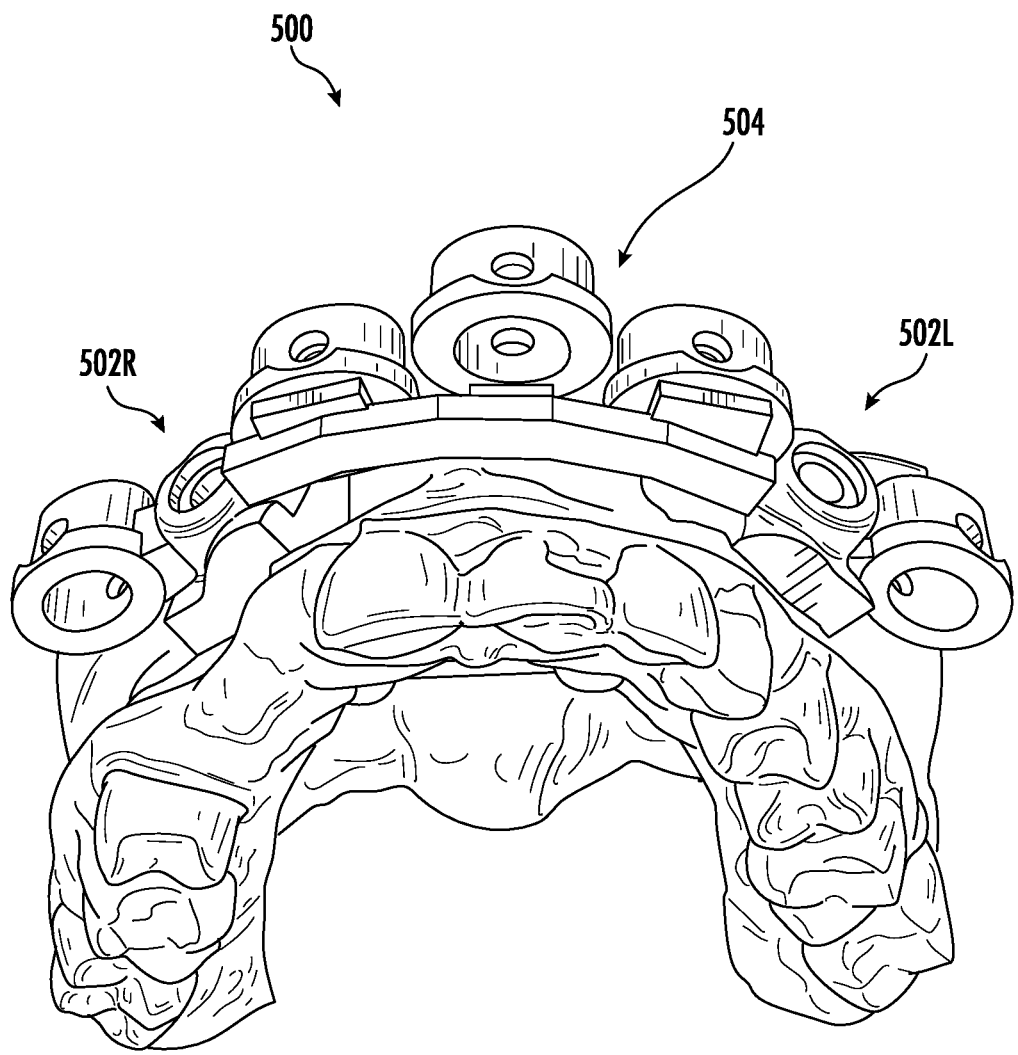

At a step 620, a UKF carrier may be designed. For example, UKF carrier 504 may be created as shown in FIG. 77 and FIG. 78. In one example, UKF carrier 504 may be created after tooth aligner 506 and UKF devices 502 are designed. UKF carrier 504 may be designed uniquely based on how much space is available at the surgical site. UKF carrier 504 preferably stabilizes the two UKF devices 502 along a lateral axis. UKF carrier 504 preferably allows for the primary verification of seating the UKF devices 502. The UKF devices 502, combined with UKF carrier 504, preferably lock into the buccal undercut. Tooth aligner 506 may be the secondary verification.

The method steps 610, 615, and 620 may be performed to design the components to fixate the UKF devices 502 onto the bone. The following method steps 625 and 630 may be performed to design components to level out the bone surface and placement of implants.

Figure 79:
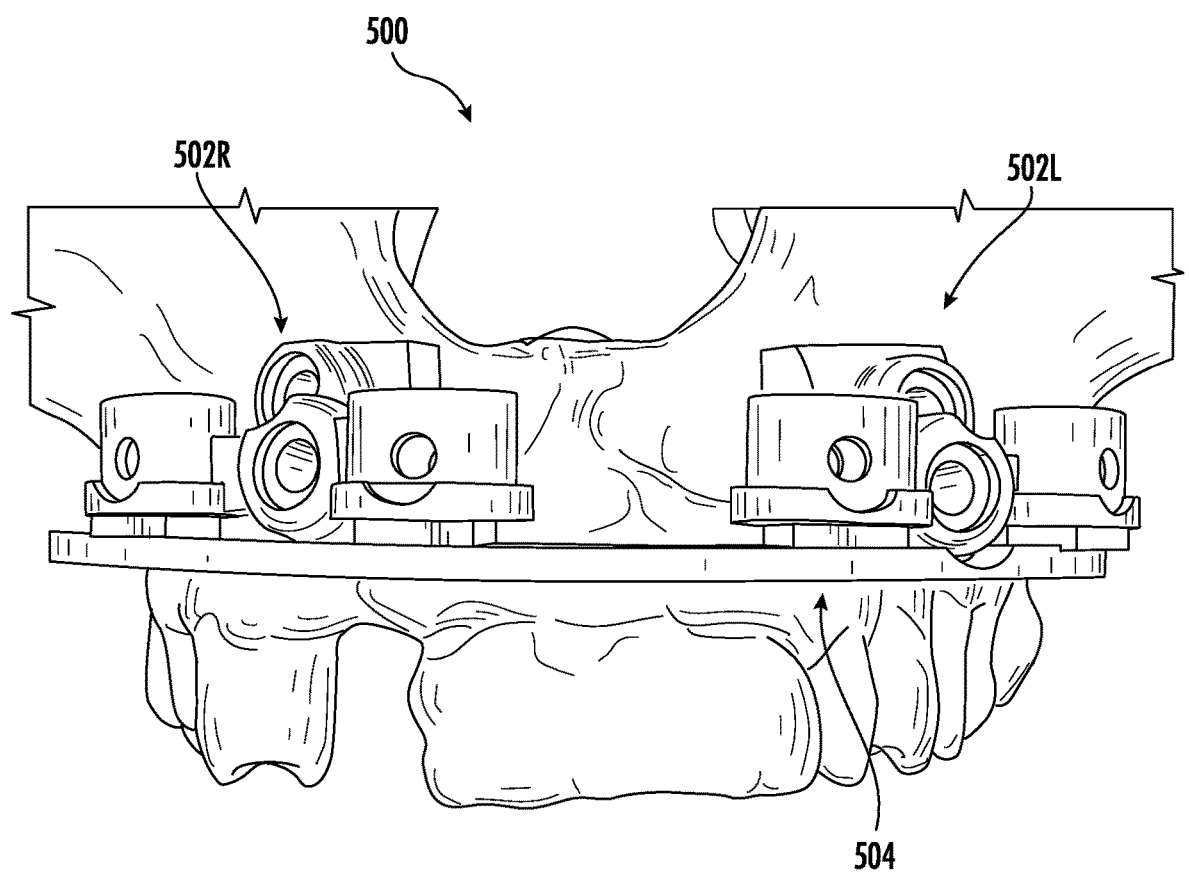
Figure 80:
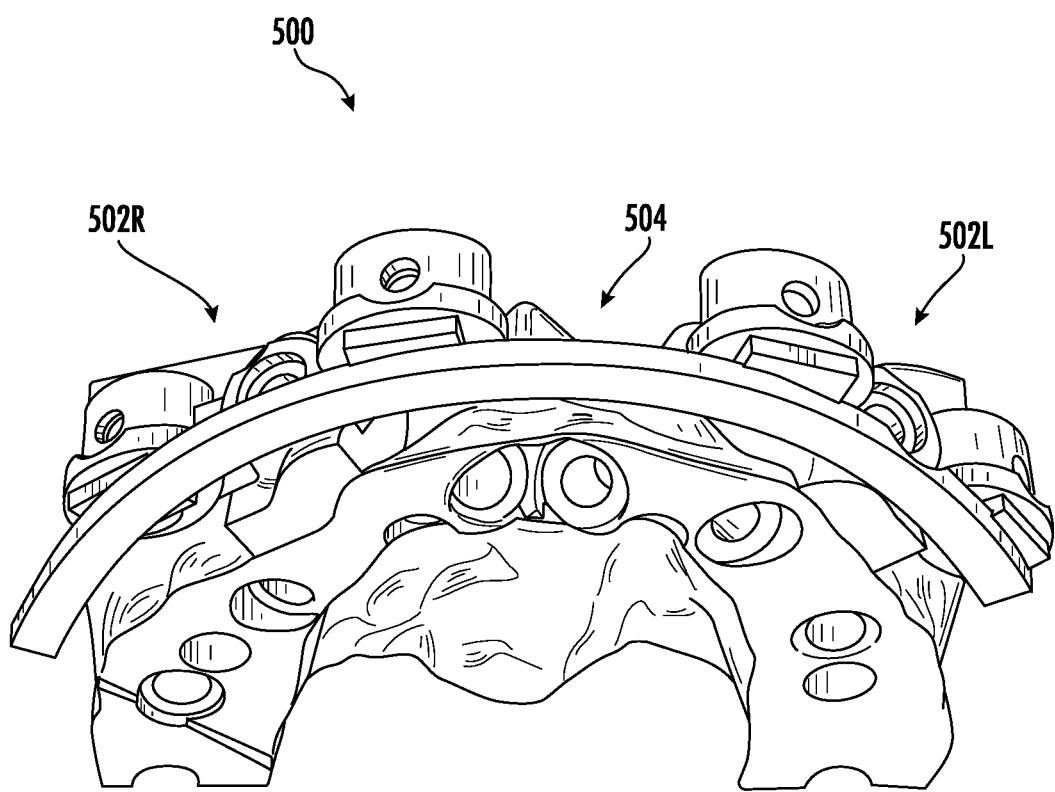
Figure 81:
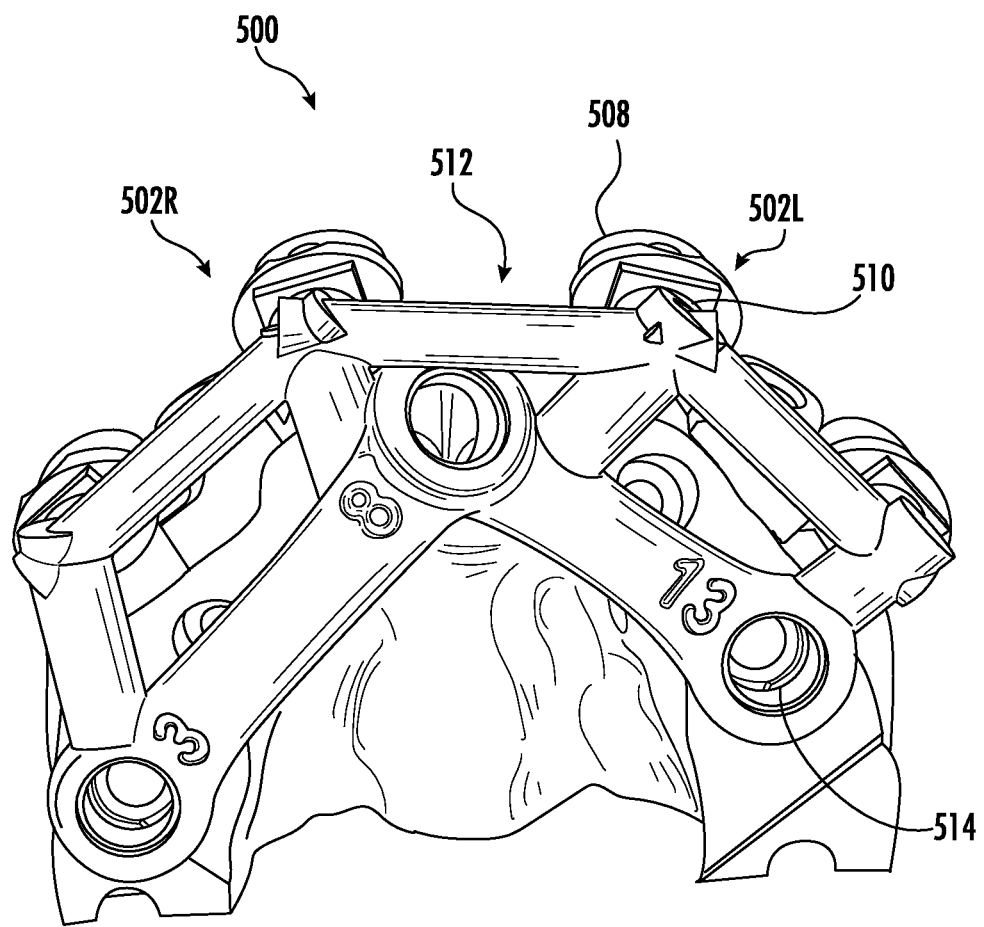

At a step 625, a bone reduction guide may be designed. For example, UKF carrier 504 may be designed as a bone reduction guide, for example, as shown in FIG. 79 and FIG. 81. Based on where plug connectors 508 of UKF devices 502 are situated along the arch, the bone reduction guide (e.g., UKF carrier 504) may be designed along those surfaces. The bone reduction guide placement along the vertical axis is determined by the bone plane of reduction.

At a step 630, a surgical guide may be designed. For example, drill guide 512 may be designed as shown in FIG. 81. Once the implant sleeves are set in space relative to the proposed placement of implants, the raw drill guide 512 design is exported out. Implant sleeves are typically specific to the type/brand of implant being placed. The openings 514 are preferably designed to be an open architecture being compatible with/receive most if not all implant sleeves on the market. Various shapes may be engineered to reinforce drill guide 512. Jack connectors 510 may be provided along drill guide 512 relative to the placement of plug connectors 508 of UKF devices 502.

Referring now to FIG. 82 and FIG. 83 are images showing an example of a one-piece UKF device 502 wherein two UKF devices 502 are connected by a bar. In this example, UKF devices 502R and 502L may be mechanically connected via a fixed connection bar 532.

Referring now to FIGS. 84-86 are images showing various views of an example of the fixation of the presently disclosed UKF device 502 to a subject's bone. In this example, a fixation screw 556 may be passed through a first fixation guide hole 530 and secured into the bone. Fixation screw 556 may be unicortical and work to stabilize UKF device 502. Additionally, a fixation pin 558 may be passed through a second fixation guide hole 530 and secured into the bone. Fixation pin 558 may be bicortical.

Fixation pin 558 may, in one example, go through both bony plates to horizontally stabilize/secure UKF device 502 to the bone. Fixation pin 558 may use friction to hold in place, wherein the fixation guide hole 530 for fixation pin 558 may be drilled slightly smaller than the fixation pin 558 diameter. Fixation pin 558 may be hammered or tapped into the bone. Fixation screw 556, in one example, may engage the outside "buccal" bony plate and may be physically screwed into the bone. This second fixation point is preferably provided to stop UKF device 502 from rotating and also to vertically secure UKF device 502.

In UKF system 500, each UKF device 502 may be positioned in relation to the primary fixation source (tooth or tissue or bone) by a positioning frame that relates the UKF device 502 fixation position to the secondary fixation position (buccal bone). By contrast, conventional systems relate the base guide only by the primary fixation source (exposed bone) or by touching the lingual and buccal bone with bone seating stops or indicators. Further, conventional systems utilize the buccal and or lingual bone plane as primary fixation relation point for seating. UKF system 500 utilizes the buccal bone only as fixation not as relation point. The primary relation point for fixation is the pre-extracted tooth position in dentate patients.

Another example of a UKF design workflow of the presently disclosed UKF system 500 and UKF device 502 may include first receiving one or more of a digitally computed tomography (CT) pre-operative scan of at least a part of a patients' intra oral bony structure and a digital intra oral scan in STL file (or other convertible format) of the patients' pre-operative oral structure or part thereof; a physical model of at least a part of the pre-operative oral structure or physical impression of at least part of the oral structure to be poured in dental stone then converted by digitally scanning the model to replicate the patients oral structure and tissue in a digital file format; or receiving a computed tomography (CT) pre-operative scan of an edentulous patient scanned with a patient specific denture/prosthetic device marked and scanned with radiopaque markers and a computed tomography (CT) scan of the prosthetic device with radiopaque markers to be used as model match device (dual scan protocol).

Next, the process may include superimposing the digital file of the intra oral cavity over the digital file of the computed tomography by model matching the bony/tooth structures between the two files. The UKF system 500 preferably utilizes the pre-operative model for model matching of the diagnostic in the correct relationship to the patient.

Then the process may include, designing digitally a guide appliance with design coordinates using the computed tomography data. In an edentulous patient, the CT denture scan is matched with intra-oral CT dual scan protocol. Then the digital file of the oral structure or denture with radiopaque markers in edentulous patients may be exported into a diagnostic design software. A digital diagnostic design may then be performed, and then model matching the pre-operative digital file/model to the patient smile pictures by lining up the tooth positions.

Then the process may include, superimposing the diagnostic design into patient pictures by model matching the pre-operative file with the patient pictures and diagnostic design file with the pre-operative file. The digital diagnostic file may then be exported into an implant planning software and performing virtual implant planning and placement within the parameters shown by the diagnostic wax-up file superimposed over the CT of the pre-operative of the bony structures in relation to the approved digital wax-up.

The process may further include, exporting the surgical implant plan and preoperative CT scan from the implant planning software into a modelling software and engineering a structurally sound UKF device carrier 504 to support surgical and prosthetic components. The UKF system 500, surgical, and prosthetic design files may then be exported into a printer or milling unit to create the devices in analog.

Referring now to FIG. 87 is a flow diagram of an example of a simplified method 700 performing an example surgical procedure using the presently disclosed UKF system 500 and UKF device 502. Method 700 may include, but is not limited to, the following steps.

At a step 710, incision guide 516 may be placed over the existing dentition (or tissue) and incisions 548 are made as directed by incision guide 516, as shown for example in FIG. 56 and FIG. 57.

At a step 715, small window tissue flaps are laid on either side of the patient's jaw.

At a step 720, a fixation plate 528 of UKF device 502 is positioned on the exposed bone level with tooth, tissue, and/or bone borne aligner (e.g., UKF carrier 504, tooth aligner 506).

At a step 725, the two UKF devices 502 may be temporarily connected together, such as UKF carrier 504 shown in FIG. 75 and FIG. 77. In another example, a one-piece UKF device 502 with fixed connection bar 532 (see FIG. 82 and FIG. 83) may be used. The connection bar 532 connecting the two UKF devices 502 may be made of CoCr/Titanium or any other suitable material, such as, but not limited to, materials previously listed herein.

At a step 730, a surgeon fixates UKF device 502 onto the exposed bone by relating the correct position to the primary fixation point (tooth or tissue or bone) utilizing, for example, UKF carrier 504 and/or tooth aligner 506.

At a step 735, after seating of UKF device 502 is confirmed, the fixation and/or anti-rotational pilot holes may be drilled and UKF device 502 may be fixated by using the dual pin and/or screw system, such as fixation screws 556 and/or fixation pins 558, as shown for example in FIGS. 84-86. After seating of UKF devices 502 is confirmed, the removable carrier (e.g., UKF carrier 504) may be removed. In the case of the one-piece UKF device 502, simply proceed to the next step.

At a step 740, after seating of UKF device 502 is confirmed and UKF device 502 is fixated, the surgical and/or prosthetic components, as needed, may be positioned and related to UKF device 502.

At a step 745, the surgical and/or prosthetic process is now completed and the UKF devices 502 may be removed. The window flaps may then be sutured to close the exposed bone and the procedure concludes.

Referring now to FIGS. 88A-88D is a flow diagram of an example of a more detailed method 800 of performing an example surgical procedure using the presently disclosed UKF system 500 and UKF device 502. Method 800 may include, but is not limited to, the following steps.

At a step 810, after a patient is sedated, a surgeon may place/position an incision guide 516 by, for example, seating a tooth aligner 506 portion on an occlusal table and/or incisal edges of the pre-extracted arch (either maxilla or mandible) where the surgery is to be performed. Incision guide 516 carries incision outline guides 520 showing the outlines of the area where the surgical reflection tissue flap is to be laid.

At a step 812, after positive seating of incision guide 516 is confirmed (this may be done by visually confirming occlusal table or incisal edge seating through one or more window cut outs in the incision guide 516 and/or tooth aligner 506), the surgeon makes guided incisions 548 to allow for a block tissue reflection, as shown for example in FIG. 56 and FIG. 57.

At a step 814, after all the incisions 548 are made (by "tracing" incision outline guides 520 with a surgical scalpel or blade on the carrier), incision guide 516 may be removed.

At a step 816, the tissue flap may be laid vertically by releasing the tissue from the CEJ or ridge area down towards the vestibule area.

At a step 818, after the tissue is reflected and bone is exposed and confirmed clear from any tissue, UKF devices 502 may be transferred to the mouth. In one example, two UKF devices 502 are loaded (latched in place using the plug 508 and jack 510 connectors) into UKF carrier 504. In another example, a one-piece UKF device 502 may be placed on the bone level.

At a step 820, the surgeon confirms that the exposed reflection as indicated by incision guide 516 is large enough to expose enough bone to allow UKF devices 502 to seat properly (e.g., without any tissue contact).

At a step 822, the UKF bone seating position may be confirmed by feel (tactile) and primarily confirmed accurate by engaging the pre-extracted dentition (or tissue/mucosa in edentulous patients) with the tooth or tissue aligner (e.g., UKF carrier 504 tooth aligner 506, tissue aligner 595) that fixates laterally into plug connectors 508 of UKF devices 502. This tooth or tissue aligner is preferably the primary fixation verification with the tactile bone position as the secondary. The intaglio surfaces of UKF devices 502 may be designed from, for example, the DICOM image of the subject's buccal bone allowing for an intimate guide to bone fit.

At a step 824, the seating of the stack of components of UKF system 500 is verified. For example, once tooth aligner 506 (tissue aligner in edentulous) is positioned and UKF devices 502 (e.g., related to each other by UKF carrier 504) are positioned on the tooth structure and exposed bone level (and interlocked using the retaining latch pins), the stack (stack may be the engaged combination of UKF devices 502 and UKF devices 502 related to each other by UKF carrier 504) is in undercut (undercut is caused by the combination of the horizontal tooth position in relation with the vertical buccal bone undercut). The stack may be verified by visually inspecting the connection between UKF devices 502 and the exposed bone or by running, for example, an explorer on the interface to confirm an intimate integration.

At a step 826, once the seating of the stack of components of UKF system 500 is verified, the surgeon may drill fixation guide holes as directed by fixation plate 528 of UKF devices 502.

At a step 828, once the fixation pilot drills are finalized, fixation pins 558 that, for example, engage bicortical bony plates (buccal and lingual) may be tapped into position. Fixation pins 558 may, in one example, be considered the primary UKF connectors. This primary fixation may be either done by using a screw and/or fixation pin depending on the bone quality and specific case and could be unicortical or bicortical.

At a step 830, in one example, after fixation pins 558 (e.g., major UKF connector) are pinned, anti-rotational fixation screws 556 that engage the buccal bone may be screwed into position to stabilize UKF devices 502. Fixation screws 556 may be considered the secondary UKF connectors. This secondary fixation may be done by either using a screw or fixation pin (e.g., fixation screw 556, fixation pin 558) depending on the bone quality and specific case and could be unicortical or bicortical.

At a step 832, tooth aligner 506 and UKF carrier 504 may be unlatched and removed from the patient's mouth. Namely, the various plug connectors 508 and jack connectors 510 may be disengaged. UKF devices 502 with their plug connectors 508 are now fully seated and ready to receive the sequential surgical and prosthetic components (prosthetic and surgical components with corresponding jack connectors 510 that latch in place with UKF devices 502 using latch pins for example). UKF devices 502 may be seated and spaced from the surgical site (depth of seating depends on the amount of bone available).

At a step 834, if required for the procedure, the patient's teeth may now extracted (dentate patients).

At a step 836, if bone reduction is required, the bone reduction plane guide 552 (e.g., the plane of plate 534 of UKF carrier 504) may be seated into plug connectors 508 of UKF devices 502. The bone reduction plane guide 552 (e.g., UKF carrier 504 with plate 534) is a flat plane multi-use device. This device indicates the bone reduction height (if bone reduction is required) and may also act as a tissue retractor to expose the surgical site and manage the tissue reflected around the CEJ areas of the teeth.

At a step 838, after tooth extraction, and if required, the tissue may be pushed/wedged between the bone reduction plane guide 552 (e.g., the plane of plate 534 of UKF carrier 504) and the buccal bone to open the surgical site.

At a step 840, if required, bone reduction or bone contouring may be performed as indicated by the bone reduction plane guide 552 (e.g., the plane of plate 534 of UKF carrier 504).

At a step 842, after any needed bone reduction is completed, the surgical guide (e.g., drill guide 512) may be positioned into plug connectors 508 of UKF devices 502 and latched in place using latch pins. The surgical guide (e.g., drill guide 512) may be used for implant rotational, directional, and/or depth positioning.

At a step 844, fully (or partially) guided implant surgery may be performed depending on the surgeon's preferences.

At a step 846, once any required implants are placed, the surgical guide (e.g., drill guide 512) may be unlatched from UKF devices 502 and removed.

At a step 848, as/if required an abutment aligner 560 (for example as shown in FIG. 89), may be positioned and intermediate (angled correction or straight) abutments are seated using the abutment aligner 560 to show the position of the screw access in relation to the hex position in the implant. The abutment aligner 560 relates the rotation of the correction abutments to the screw-access position of the pre-drilled transitional/conversion or even final prosthetic device.

At a step 850, after correction and straight dome abutments (not shown) are positioned, the abutment aligner 560 may be unlatched from UKF devices 502 and removed. The straight dome abutments are screwed on to the implant after implant placed.

At a step 852, pre-cut, site specific (pre marked and drilled/cut) temporary dome abutments (not shown) may be screwed in place onto the intermediate abutments (not shown). In rare cases, the temporary dome abutments may be screwed directly into the implant interface-implant level restorative option.

At a step 854, the printed/milled/hand set-up prosthetic device 562 (for example as shown in FIG. 90), may now be positioned over the temporary abutments and latched into place using, for example, plug connectors 508 and jack connectors 510 that are milled and fixated (milled as one unit or luted) to the prosthetic device.

At a step 856, the prosthetic device 562 may be seated. Seating may be done with all temporary abutments seated or individual temporary abutments placed to allow for draw into the screw access holes of the prosthetic device 562.

At a step 858, the temporary abutments may be luted into the prosthetic device 562. This process engages the prosthetic device 562 into the implant positions in the correct position and relates back to the preoperative tooth or diagnostic position.

At a step 860, after the luting agent is cured with either light or chemical cure process, the prosthetic device 562 may be removed by unlatching the latch pins and removing the device by disengaging the plug connectors 508 and jack connectors 510.

At a step 862, the surgeon may unscrew the UKF anti-rotational fixation screws (e.g., fixation screws 556) and pulls (removes) the fixation pins (e.g., fixation pins 558) to release UKF devices 502.

At a step 864, after removal of UKF devices 502, the surgeon may suture the reflection sites of UKF devices 502 and any other surgical incisions.

At a step 866, any latches (e.g., jack connectors 510) may be cut from the prosthetic device and after suturing is completed the prosthetic device 562 may be screwed onto the abutment level or screwed into the implant level. This prosthetic device 562 is known as an immediately converted implant retained transitional prosthetic device.

In one example, a diagnostic design of a UKF system 500 and UKF device 502 may include initially preparing a diagnostic wax-up, which will become a temporary prosthetic. A physical impression of a patient's current oral anatomy, or a digital scan of the same, may be provided, e.g., by the requestor/client. The physical impression may be poured and scanned, and a digital model may be printed and scanned or imported, resulting in a digital impression model. The diagnostic design may further include aligning the model of the patient's current oral anatomy to provided patient smile photos. Working within the parameters of the patient's existing dentition and bone structure, a prosthetic may be digitally planned to restore the patient's dental function and aesthetics. The restorative doctor and/or surgeon preferably consults with lab designers on prescribed changes, patient expectations, and possible restorative options. Any changes to vertical dimension of occlusion (VDO) or midline, existing dentition, and/or need for restorative space are all considered during diagnostic wax-up design. The aesthetic qualities of the planned restoration are considered and mocked-up by superimposing the diagnostic wax-up onto the patient's smile photos and may be sent back to the requestor/client for approval.

While opening the VDO may be necessary, failing to achieve a modest range may cause discomfort for the patient. Chosen restoration type and available restorative space may impact options for adjustment. A dual-arch prosthetic may correct the upper and lower, idealizing the patient's bite. A single arch however, should preferably still be matched for occlusion against the patient's antagonist arch.

With regard to surgical planning, once the diagnostic wax-up is completed it may be imported by, for example, a guided surgery specialist to begin surgical planning. Surgical planning is based on laying a foundation for the prosthetic, which is derived from the diagnostic wax-up. In an embodiment, the UKF system 500 and UKF device 502 design process is prosthetically driven, and the planned surgery may be reverse engineered from the final prosthetic. Initially, the objective of the surgery is considered. For example, the final surgical plan may be for a removable, fixed hybrid, or partial restoration, which makes considerable differences in case planning. The patient's restorative space may determine the available room for the prosthetic, which may be increased by bone reduction if needed. For example, a removable implant-supported denture may require significantly more restorative space as compared to a fixed hybrid. In addition, cleanse-ability of the final prosthetic is also considered as a quality of life concern for the patient. Working within the parameters of the patient's existing dentition and bone structure, the prosthetic is digitally planned to restore the patient's dental function and aesthetics. At this stage, a technician preferably plans out the final bite created by the prosthetic. The final bite created when the prosthetic is loaded into the mouth and is expected to match the patient's prescribed bite. In one example, implant placement may begin with the patient's cone-beam computed tomography (CBCT) scan, sent as a DICOM file, which is imported into a suitable planning software. The digital impression model, along with the digital model of the diagnostic wax-up, may be imported and aligned to the CBCT scan. Planning considerations may include mapping out vital structures in the patient's mouth, such as nerves, blood vessels, and areas of insufficient bone density. An implant site is preferably planned in areas of sufficient bone density, providing the best possible chance of achieving primary stability. Diameter and length of each implant are determined by the doctor's prescription and/or indications provided by the implant manufacturer. Implant size and type will determine the implant analogs, sleeving, and drill protocol used in the creation of the UKF system 500 and UKF devices 502, stackable components, and/or models.

With regard to planning fixation, fixation points may be chosen to anchor UKF device 502 or devices to the patient's existing bone structure. As in implant placement, important and vital structures need to be avoided. In addition, bone density should be sufficient to stabilize the UKF system 500 across the patient's arch throughout the surgical procedure. Fixation points may be fixated using pins and/or screws, such as fixation pins 558, which may engage the patient's bone bi-cortically, and/or fixation screws 556, which may engage the patient's bone uni-cortically or vice versa. Should fixations be planned over the roots of preexisting teeth, the tooth would preferably be extracted prior to guide seating, which would be preferably communicated to the surgeon through documentation prior to surgery.

The UKF system 500 may be well suited for cases in which there is enough bone for bi-cortical and/or uni-cortical fixation, a need for bone reduction, and scans and/or models of sufficient detail and accuracy. The UKF system 500 may also be well suited for dual-arch cases, as the UKF system 500 does not require bite verification during surgery and does not require each arch to be converted independently. Surgeries conducted using the UKF system 500 are expected to be much shorter (e.g., in the range of about 1.5 to 2.5 hours per arch), as compared to 3 to 5 hours for non-sequential guides and 6 to 8 hours in non-guided 'freehand' cases. The UKF system 500 may also be well suited for sinus-lift cases. The UKF system 500 allows separate guidance of osteotomies and implant depth control, which makes it possible to drill osteotomies, perform sinus grafting, and place implants in the same surgery. The UKF system 500 may also be well suited for zygomatic cases. The UKF system 500 supports latched zygomatic drill guides, using individual drill guides for each zygomatic implant site. Also, in cases requiring multiple planes of reduction, where a case may require two or more unique planes of bone reduction due to available bone or implant placement UKF system 500 may be 'stepped' to accommodate this possibility. Further, UKF system 500 allows for immediate conversion, that is, a surgery using the UKF system 500 commonly ends with the loading of a fixed temporary healing prosthesis, which allows the patient to have functional dentition immediately after surgery.

Once the case is properly planned, e.g., the guided surgery specialist has reviewed the case with the client doctor after the completed pre-planning and any changes needed are made and the doctor approves the case, guide design would preferably begin.

The UKF system 500 may include various stackable guide components, for example UKF devices 500, drill guide 512, seating guide (e.g., tooth aligner guide 530), incision guide 516, bone reduction guide (e.g., UKF carrier 504), and/or other necessary stackable guides, and may culminate in a temporary prosthetic to be loaded concluding the surgery.

With reference to FIGS. 91-94, in one example, a bone model 564 created from the CBCT scan may be constructed, imported, and aligned with the scan data. The bone model 564 may then be reduced to a bone reduction level by using a bone reduction plane 566 as a reference, creating a bone reduced model 568. This bone reduced model 568 may then be used in the creation of most guides (e.g., UKF devices 502) and other stackable components of the UKF system 500. The bone reduced model 568 may then be altered to reflect the exact placement and depths of planned implants and/or fixations. Glue holes 570 may be placed to allow implant analogs to be permanently positioned into the model. Peg holes 572, may be placed to allow for seating of a transfer mount 574 or mounts. This new model (analog model) may then be 3-D printed and used by technicians to test the guides (e.g., UKF device 502) and other stackable components of UKF system 500.

With regards to designing UKF devices 502, the one or more fixation guide holes 530 may be created on the bone reduced model 568. These fixation guide holes 530 preferably fit to the bone reduced model 568 at fixation points with, for example, an offset in the range of about 0.15 mm, which preferably enables fit for anchorage such as pins or screws (e.g., fixation screws 556 and/or fixation pins 558). The fixation guide holes 530 may then be trimmed in order to reduce the amount of surface area of the UKF devices 502 that is touching the patient's bone structure. This reduces the amount of tissue that may be needed to be reflected in order to seat the UKF devices 502, and further decreases the patient's overall healing time. In a case where fixation would ideally be placed in a location where tissue reflection would be undesirable, a 'floating' fixation may be used, which would be a fixation guide hole 530 that does not contact the patient's bone.

Referring to FIG. 100, depending on implant placement it may be necessary to add UKF extensions 597 on the UKF device 502. These UKF extensions 597 may also be created from the CBCT scan model by mimicking the patient's bone surface with, for example, an offset of in the range of about 0.15 mm. The UKF extensions 597, in one example, extend to the distal-most implants and may be cut facially to prevent interference with any stackable guide components. These UKF extensions 597 may work in conjunction with a centralized bone reduction guide in reducing the patient's bone level. UKF extensions 597, or other sections of the UKF device 502, may also exist on different planes into order to accommodate multiple planes of bone reduction.

For the purposes of creating and utilizing stackable guides for use with the UKF system 500, plug (female) connector 502 and jack (male) connector 506 style latches may be placed around the facial arc of the bone model 564 with, for example, a preferred minimum clearance of in the range of about 3 mm, to allow a safe distance from the patient's tissue and bone structure. In some cases the plug connector 508 and jack connector 510 style latches may also respectively be colloquially referred to as female and male latches. In one example, the latches may be placed, for example, in the range of about an additional 3 mm from the occlusal in relation to the bone reduction plane 554, however there may be occasions where the jack connector 510 surfaces (or plug connector 508 surfaces) may sit on the bone reduction plane 554. Such instances may occur when latch placement may fall, for example, within about in the range of 10 mm of the patient's nasal spine. This will allow sufficient vestibule room for a latched guide to seat comfortably. The latches raised to the bone reduction plane 554 may now serve as a bone reduction guide, which would remove the need for a separate guide.

The latches may then be securely attached to the UKF device 502, using connections, typically square in cross-section, of a preferred minimum in the range of about 3 mm thickness. The male (jack) section of each of the latches may be reused in the creation of stackable guides. Should the latches be placed at the bone reduction plane 554, the connections will also be constructed at the bone reduction plane 554 and assist in the bone reduction process. Connections may be trimmed to allow for clearance at fixation sites, and will preferably not interfere with female (plug) latches, other guides, or UKF device 502 seating.

The final UKF device 502 may be crafted from metal by Selective Laser Melting (SLM), printed in surgically acceptable guide materials such as MED610, or manufactured from any other appropriate processes and made of any other suitable material, including but not limited to any of the materials listed herein. In one example, if the UKF device 502 is printed in MED610 or other similar resin, the connections should preferably be designed for a thickness of in the range of about 5 mm. Such a planned increase in connection diameter during the planning phase preferably ensures for increased durability of structurally sound guides and reducing the likelihood of fracturing and or breakage of finished guides.

A drill guide 512 may be defined by the placement of proprietary and/or non-proprietary drill sleeves at the implant sites. Consisting of connected cylindrical ports for each drill sleeve, the inner diameter of each opening 514 may be determined by the selected drill sleeve for each implant site. The outer diameter of each opening 514, may, as an example, be in the range of about 10-15 mm, as strength of the drill guide 512 needs to be balanced with bulk and ease of access. The height of each opening 514 may, in one example, be set to in the range of about a minimum of 5 mm to ensure that the drill guide 512 is strong enough to withstand drilling forces. The vertical position of each opening 514 may be determined by the prolongation of the drill which can be measured as the distance from the bottom of the drill sleeve to the crestal level of the implant. Numbers may be placed by each opening 514 referencing its corresponding tooth number. Once the main body of the drill guide 512 is completed, it may then be attached to a set of male jack connector 510 latches and converted into a stackable guide component that may be latched into UKF devices 502.

In surgical cases requiring sinus lifts, the UKF system 500 allows separate guidance of osteotomies and implant depth control. It is then possible to drill osteotomies, perform sinus grafting, and place implants in the same surgical procedure. This may take the form of a sinus lift guide 576 (FIG. 95) and a depth control guide 578 (FIG. 97). Each of these guides may preferably share the same design methods as the drill guide 560. Drilling preferably occurs through the sinus lift guide 576 and implant placement occurs through the depth control guide 578.

If the structure of the drill guide 512 may intersect the patient's tissue or bone, the drill guide 512 itself may be trimmed. For example, the drill guide 512 may be trimmed in the range of about 0.5-1 mm from the bone reduction plane 554 to ensure no contact with the patient's anatomy.

A finished drill guide 512 needs to have the structural integrity necessary to withstand the forces of drilling and implant placement. Also, while drill guide 512 is in use, the surgeon will need some visibility to the surgical site. Additionally, the drilling process causes temperature increase in the bone, and will commonly be irrigated for cooling of the bone. Therefore, sufficient space will preferably be provided between structural components of the drill guide 512 to allow for irrigation and visibility. To construct the final drill guide 512, a set of plug connector 508 and jack connector 510 style latches are brought in so that the final drill guide 512 can be seated in the UKF devices 502. In one example, each jack (male) connector 510 latch may have a cylindrical base in the range of about 7 mm thick, and horizontally each base cylinder may be connected via a connection bar in the range of about 3-5 mm thick, and each base cylinder may be connected to the closest opening 514 with connection bars 580 in the range of about 4-5 mm thick. These dimensions may be typical to connection bars on guides of the UKF system 500.

The drill guide 512 may be printed in surgically acceptable materials such as MED610, or any other suitable material, including but not limited to any of the materials listed herein. The printed drill guide 512 may fitted with corresponding sleeves by cementing or heat-setting, or any other suitable mechanism or technique. A technician may fit the drill guide 512 into the UKF device 502 to test the depth and seating of the implant drivers and implant analogs.

Seating Guides may be created from a digital impression, which may include teeth, a tissue ridge, and/or a denture, or a converted CBCT model depicting the patient's relevant bone. This model may be aligned to the patient's existing dental anatomy as pictured in the CBCT. These models may then be used to create seating guides, which may include, for example, tooth aligner guide 506, ridge alignment guide 598, denture alignment guide 599. The initial construction of such seating guides may differ and non-limiting examples are described below.

In cases where a patient has existing teeth that are suitable for building guides, the digital impression model may be used to create a tooth aligner 506 guide. The initial tooth aligner 506 may be created by enveloping the digital impression model with a polygonal mesh so that its internal structure matches the topography of the dentition with a defined offset, e.g., in the range of about 0.15 mm, in one example, its external structure may be in the range of about 3-5 mm in thickness. In some cases, it may be necessary to plan for tooth extraction before guide fixation. Instances where this is a factor may include situations where fixations may be placed through a tooth root, or where teeth are so badly damaged that they are unusable for the tooth aligner 506. In these cases, either the .stl based on the patient's digital impression model should be altered to reflect these extractions, or special care should be taken to avoid these obstructions during the envelopment phase. For visibility, cylindrical holes commonly referred to as "windows" (e.g., windows 582), may be cut into the tooth aligner 506 guide, allowing the surgeon to see the patient's existing teeth and/or tissue, and allows confirmation of accurate seating. The tooth aligner 506 may then be cut on the lingual side in order to reduce the total guide size if needed. The distal edges may also be removed to reduce the tooth aligner 506 size further if needed.

With reference to FIG. 101, illustrates an example ridge alignment guide 598. In cases where the patient has no existing teeth for suitable guide building, a ridge alignment guide 598 may be created by enveloping the .stl model of the patient's CBCT scan with a polygonal mesh so that its internal structure matches to the patient's bone structure, with an offset typically in the range of about 0.15 mm. Its external structure, in one example, may be in the range of about 3-5 mm thick. Windows 582 (which may for example be cylindrical holes) may then be cut, allowing the surgeon to see the bone structure and confirm accurate seating. The ridge alignment guide 598 may also be trimmed appropriately as/if needed.

With reference to FIG. 102, illustrate an example denture alignment guide 599. In cases where the patient has an existing and well-fitting denture, a denture alignment guide 599 may be used. A digitized scan of the patient's existing denture may be converted to a .stl mesh. Windows 582 (which may for example be cylindrical holes) may then be cut into the denture alignment guide 599, allowing the surgeon to see the palatal tissue and confirm seating. Some trimming may be necessary; however, the denture's structure should be kept intact.

The seating guide body (e.g., 518/538) may also be used to create a separate guide that may not be stackable called the incision guide 516. In one embodiment, for mandible cases a reflection guide may be made. The reflection guide is substantially the same incision guide 516 except it includes markings (e.g., circular markings), that let the doctor/surgeon know where the mental foramina are so they know where not to cut.

The incision guide 516 indicates where the surgeon will reflect tissue to expose bone. The UKF device 502 will contact this exposed bone at the fixation sites. The incision guide 516 may contain in the range of about a 3.5 to 4 mm thick block (incision outline guides 520R, 520L) for each UKF device 502 fixation site. The width of each incision outline guide 520 may be slightly greater than the width of its corresponding UKF device 502 fixation site, which may, in one example be in the range of about 2-4 mm. Incision outline guides 520 may be angled inward lingually to preferably match the slope and profile of the patient's digital impression model. Each incision outline guide 520 may be fixated to the incision guide 516 by a cylindrical shape to improve structural integrity of the guide.

Latches are brought in to transform the seating guide body (e.g., 518/538) into a stackable guide component of the UKF system 500 capable of latching into the UKF devices 502. Each male (Jack connector 510) latch may preferably have a cylindrical base in the range of about 7 mm thick, and horizontally each base cylinder may preferably be connected via a connection bar (e.g., 580) in the range of about 3-5 mm thick. The base cylinders may be connected to the seating guide via connection bars (e.g., 580) in the range of about 3-5 mm thick. Oval or cylindrical shapes may additionally be added to bolster the connected surface area of the guide and its connections.

The seating guides (e.g., 506) and incision guides (e.g., 516) may be printed in surgically acceptable materials such as MED610, or any other suitable material, including but not limited to any of the materials listed herein. In testing, a technician may place the seating guide onto its corresponding transfer mount 574. When a technician is satisfied that the seating guide fits correctly, the process may be repeated for the incision guide 516.

The working surface of a bone reduction guide (e.g., 552) is defined by the plane of reduction (523). The bone reduction guide 552 may be created digitally with an offset from the bone model, typically in the range of about 1-3 mm in the facial direction, and may be in the range of 3 mm or less in vertical thickness. The bone reduction guide 552 may generally follow the contour of the patient's bone along the facial anatomy, ending slightly beyond the distal-most implant site. This defines a generally 'horseshoe' shape. Male jack connectors 510 latches for the 'plug-and-jack' system may then be attached. In use, the bone reduction guide 552 latches into the UKF devices 502 and provides a reference level for bone reduction. If the path of fixation for the UKF device 502 conflicts with the profile of the bone reduction guide 552 the digital model of the bone reduction guide 552 may be reshaped as to allow for clearance of fixation and seating into the UKF device 502.

Furthermore, the above reshaping of the bone reduction guide 552 may result in a loss of reduction-level surface area on the bone reduction guide 552. If this loss of surface area is too great it can leave the most distal sections of the bone reduction guide 552 too small to be used as a proper bone reduction guide, a UKF extension 597 may be used and this distal portion of the bone reduction guide 552 may be removed. The UKF extension 597 is preferably part of the UKF device 502 and follows the profile of the bone.

A case may require separate planes of bone reduction to accommodate implant placement or bone structure. In these cases, the working surface of the bone reduction guide 552 may include a 'step' from one plane to another. In some maxillary cases the patient's vestibule may be too small vertically, (typically 10 mm or fewer) as measured from the nasal spine to the surgical site, to fit the UKF device 502 and bone reduction guide 552. In this case, the latches of the UKF device 502 are raised to sit on the reduction plane 554 which may obviate the need for the bone reduction guide 552.

Where treatment planning includes a scalloped case, the bone reduction guide 552 may not be used, and may be replaced by a scalloping guide 584 (See as a general example FIG. 97). The scalloping guide 584 follows a 'horseshoe' shape similar to the bone reduction guide 552. However, the working surface of the scalloping guide 584 is defined by the planned bone scalloping. The construction of a scalloping guide 584 may include offsetting the diagnostically created waxup teeth by, for example, in the range of about 3 mm. These offset teeth may then be imported into a suitable guide planning software where they may be enveloped in guide material. The result leaves a scalloping guide 584 constructed by the contours and recessions of the offset teeth. The scalloping guide 584 may then be placed on a set of plug connector 508 and jack connector 510 style latches. The scalloping guide 584 may then be trimmed lingually and facially so that its edges are removed, and preferably only the profiles of each individual tooth remains. Each curve on the scalloping guide 584 follows the profile of the original waxup teeth. Each curve of the scalloping guide 584 should follow nearly exactly on the corresponding tooth on the original waxup. This gives the surgeon a visual representation of exactly where to scallop the bone, and greatly reduces the overall bone reduction during surgery.

The final bone reduction guide 552 may be crafted from metal by Selective Laser Melting (SLM), printed in surgically acceptable guide materials such as MED610, or manufactured from other appropriate processes, techniques, or mechanisms. Bone reduction guide 552 may be made of any other suitable material, including but not limited to any of the materials listed herein. Should the guide be printed in material such as MED610, connections may be preferably thickened appropriately. A technician may test the bone reduction guide 552 for secure and accurate connection into the UKF device 502 and will verify that the bone reduction guide 552 presents a surface level with the surgical site.

The transfer mount 574 (FIG. 94) begins with the digital model of a segment of the patient's existing anatomy, which may include tissue, bone, and/or teeth. Any teeth to be extracted pre-fixation in the surgical plan are typically extracted from the digital model. Pegs 586 (which may be cylindrical), typically in the range of about 5-8 mm in diameter, are set to match peg holes 572 in the analog model 588 (FIG. 93), allowing the transfer mount 574 to securely seat in the analog model 588 at the same location as in the patient's existing anatomy. This transfer mount 574 may also serve as a method of testing the alignment guide 588 while assembling the case.

In edentulous cases, a patient may have an existing denture. In such cases it may be necessary to create more than one transfer mount 574. A first transfer mount 574 capturing the patient's existing tissue or bone ridge will allow testing of the alignment guide during assembly, and an additional transfer mount 574 made from the denture may be used to preserve the patient's bite. In a case wherein the pre-fixation tooth extractions reduce the incisal area of the transfer mount 574, it may be necessary to create both a non-extracted transfer mount 590 (FIG. 98) and a planned extractions transfer mount 592 (FIG. 99).

The final transfer mount may be printed in acceptable materials such as, but not limited to, MED620, or any other suitable material or manufactured from any other appropriate processes, technique, or mechanism. A technician may test the guide for secure and accurate connection into the analog model 588 and may verify that the alignment guide or guides seat correctly on the final transfer mount.

The temporary prosthetic, worn by the patient during the healing process, is typically milled or printed in Poly(methyl methacrylate) (PMMA) after digital design. As such, this temporary prosthetic is commonly called a 'PMMA.' The PMMA 594 digital design process may begin with a digital model of the waxup teeth, as prepared during the diagnostic design stage. That model may be reinforced for strength. It is possible for this digital model to extend distally of the implant sites, this creates a cantilever which can put unfavorable stresses on freshly loaded implants. In these cases, it may be necessary to trim the model to reduce this cantilever. Holes, typically in the range of about 6 mm in diameter, may be punched through the model to provide room for temporary cylinders. The angle and position of these holes may be a result of the 'emergence', the combination of the rotation of the implant and angle of the attached abutment. This emergence sets the position for temporary cylinders, which may be cemented into the prosthetic before being fastened onto the implants. As the emergence has been planned based on the final prosthetic, it is possible to load the temporary prosthetic at the end of surgery with a minimum of time and effort. This digital model is then milled and finished.

A scalloped case may require that the bone be contoured to the prosthetic teeth. This contour, typically in the range of about 3 mm deeper than the future prosthetic, allows the tissue to heal around the prosthetic. This is aesthetically preferable for some patients, as there is no artificial gum line. A scalloped PMMA may require reinforcement between the cervicals of the teeth and on the lingual side. This results in a PMMA of notably thinner profile as compared to a common case. Holes for temporary cylinders may also need to be smaller in these cases.

A latched PMMA 594 may perform a function similar to the transfer mount 574. Male jack connector 510 latches are attached to a copy of the finished digital PMMA model. This model is printed in an appropriate material such as MED620, or any other suitable material, including but not limited to materials listed herein. The latched PMMA 594 can then 'stack' into the UKF device 502. This allows the final bite to be tested and compared with the original during the assembly process. A technician may test for discrepancy between the bit created by the transfer mount 574 and that created by the latched PMMA 594.

An abutment aligner (e.g., abutment aligner 560) may serve as a reference for the connection between the implant and the abutment itself. This connection may be of a generally hexagonal shape. With an angled abutment, a hex connection may allow the abutment to connect at an incorrect index. An abutment aligner (e.g., abutment aligner 560) is designed to reduce the possibility of this occurrence. The abutment aligner 560 may be marked with the screw axis of each implant. This mark allows the surgeon to correctly index and insert the abutment into the implant. This mark also provides a reference for the insertion of a screw and screwdriver. Digital design of the abutment aligner 560 may begin with a flat primitive shape, typically in the range of about 1.5 mm-2.5 in thickness, and of enough width and length to cover all relevant implant sites. This shape may be placed with a typical offset from the bone reduction plane 554 of in the range of about 0.5-1 mm. The same holes as used in the PMMA 594 may be punched through this shape, male jack connector 510 style latches may be attached, and the lingual section may be cut out. This results in a generally 'horseshoe' shape covering the surgical sites, with remainder removed from the lingual at the punched holes. As non-angled abutments do not require a specific index on the hex connection, no alignment mark may be required for a straight abutment, and no abutment aligner may be required for a case including only non-angled abutments. Male jack connector 510 style latches may be added to the abutment aligner 560, it is then printed in surgically acceptable guide materials such as MED610 or any other suitable materials, or manufactured from any other appropriate processes. A technician may test the abutment aligner 560 for secure and accurate connection into the UKF device 502 and mark the abutment aligner 560 appropriately.

In manufacturing, a guide designer exports a final guide and model designs after a digital quality control review. The guide designer commonly completes a checklist of guides and models to be manufactured and communicates this information to manufacturing personnel. Manufacturing personnel may then complete the nesting, layout, and other preparation for guides and models. The guides and models may then be printed or otherwise manufactured from suitable materials and may be cleaned, cured and/or otherwise finished before the assembly process.

For mounting, assembly, and quality control, the UKF device 502 may be placed onto the analog model 588 where it should fit firmly against the surface of the model, as the UKF devices 502 fixation sites are modeled on the exact same topology as the analog model 588. Due to fixation guide holes 530 being created during the design phase, the UKF device 502 can be fixated to the analog model 588 with pins and/or screws.

The transfer mount 574 may have pegs 586 corresponding to each punched hole (e.g., peg holes 572) on the analog model 588. Each peg 586 may preferably be in the range of about 1/10 of 1 mm smaller in diameter to its related hole so that it fits securely after the transfer mount 574 has been affixed to the analog model 588. The mounted analog model 588 and transfer mount 574 may be fixed to, for example, an articulator, the device preferably fits and measures the mounted analog model against a printed model of the patient's opposing arch. This measurement may be used to test the accuracy and effectiveness of the temporary prosthetic. If the prosthetic is accurate, the measurement will preferably be the same.

To test the incision guide 516, the incision guide 516 may be firmly and securely placed onto the transfer mount 574 where it may be inspected for imperfections. When the guide has passed quality control, it may be removed and prepped to be shipped for the surgery.

To test the stackable guides of the UKF system 500, each of the stackable guides may be inserted into the UKF devices 502 and inspected for fit and functionality. Each of the stackable guides may be latched into the UKF device 502 using removable latch coupling pins, in one example a 2 mm coupling pin, to secure the plug connectors 508 and jack connectors 510 together. This preferably allows for each stackable guide of the UKF system 500 to be firmly attached to the UKF devices 502 without fear of any unwanted movement during the surgery. In some cases, the latch coupling pin may fit too tightly. In such a case, it may be necessary using a handpiece or rotary tool to expand the diameter of the holes on both the plug connectors 508 and jack connectors 510 latches. Basic Functionality of each of the guides is also tested.

To test the drill guide 512, the drill guide 512 may be sleeved and test-fit by fixating the UKF device 502 to the analog model 588 and latching the drill guide 512 into the UKF device 502. Once accurate and secure seating has been confirmed the drill guide 512 may be removed from the UKF device 502, it may now be possible to 'time out' the case.

As the UKF system 500 is prosthetically driven, the case can be "timed" with the use of a latched PMMA 594, as it may act as a stand-in for the temporary prosthetic. The UKF devices 502 may be fixated onto the analog model 588. Implant analogs may then be placed into the analog model 588, and any abutments and temporary cylinders may be attached. The latched PMMA 594 may be latched into the UKF devices 502. As the planned emergence is represented in emergence holes 596 through the latched PMMA 594, the technician may align the temporary cylinder with the emergence holes 596 by rotating the implant-abutment-temporary cylinder complex. Once each temporary cylinder matches its planned emergence, the implant analogs may be glued in position. The latched PMMA 594, temporary cylinders, and abutments may then be removed, leaving the implant analogs glued into the analog model 588 at the correct planned rotation. The stackable drill guide 512 may then be latched into the UKF devices 502, an implant driver may be inserted through a sleeve guide into an implant. A marking may be made on the stackable drill guide 512 at each implant site corresponding to a marking on the implant driver. During surgery, the implant will be driven in, torqued, and the driver rotated to match this marking. This will set the emergence as planned.

In one example, for testing guides (e.g., seating guide, bone reduction guide, abutment alignment guide), they each may be separately fixated to the UKF devices 502 and checked for fit and sturdiness. Screw axis marks may be etched and stained into one or more of the guides as desired (e.g., abutment alignment guide 560). Once each piece has been verified for accuracy it may be removed and prepped to be shipped for the surgery.

For finishing bite verification with the latched PMMA 594, the transfer mount 574 may be removed from the analog model 588 and the latched PMMA 594 may then be latched into the UKF devices 502. The analog model 588, fitted with the UKF devices 502 and latched PMMA 594, may then be inserted into the articulator where it may be tested against the printed model of the patient's opposing arch. The measurement output should preferably not change from the prescribed bite. Each stackable guide component of UKF system 500 piece may be inspected and corrected if necessary. Finally, the finished temporary prosthetic may be set into the bite on the verification jig in place of the latched PMMA 594. Individual jack connectors 510 are preferably seat and pinned/latched into corresponding plug connectors 508 of the UKF devices 502 and may be cemented to the temporary prosthetic. This preferably allows the prosthetic to be delivered by latching into the UKF devices 502 and cementing in temporary cylinders. During surgery, once the temporary cylinders are cemented, the prosthetic may be removed from the mouth, the latches cut off, and the temporary prosthetic may be loaded onto the implants. Once the bite has been verified for accuracy and the entire UKF system 500 has passed quality control, all guides, models, and components may then be prepped and packed for shipping.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments ±100%, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

The subject treated by the presently disclosed devices and methods in their many embodiments is desirably a human subject, although it is to be understood that the methods described herein are effective with respect to all vertebrate species, which are intended to be included in the term "subject."

A "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A surgical guide foundation system, comprising:
   a. a first surgical guide foundation device and a second surgical guide foundation device separate and spaced apart from the first surgical guide foundation device, the first surgical guide foundation device and the second surgical guide foundation device each comprising:
      i. a main body portion;
      ii. a first fixation port and a second fixation port formed in the main body portion and forming a passage therethrough, and wherein the first fixation port and the second fixation port are disposed generally adjacent to one another;
      iii. a first carrier connector and a second carrier connector connected to the main body portion; and
         wherein, the first foundation device is configured to be installed to a first side of a mouth of a patient and the second foundation device is configured to be installed to a second side of the mouth of the patient; and
   b. a guide component, the guide component configured to be engageable with the first carrier connector and the second carrier connector of each of the first surgical guide foundation device and the second surgical guide foundation device.

2. The system of claim 1, wherein the main body portion of each of the first surgical guide foundation device and the second surgical guide foundation device comprises protrusions formed on an inner facing surface thereof and extending in a generally perpendicular direction therefrom.

3. The system of claim 2, wherein the protrusions comprise generally conical shaped bodies tapering to a point at a distal end.

4. The system of claim 2, wherein one or more of the protrusions are disposed proximate to one or both of the first fixation port and the second fixation port of one or both of the first surgical guide foundation device and the second surgical guide foundation device.

5. The system of claim 2, wherein the protrusions are localized in groups proximal to one or more of the one or more fixation ports.

6. The system of claim 2, wherein the protrusions comprise a length, such that when at least the first foundation device or the second foundation device is seated on a patient's gum tissue, the distal most ends of the protrusions are at a depth slightly less than or equal to a thickness of the patient's gum tissue.

7. The system of claim 1, wherein the fixation ports are each configured to receive a fixation mechanism therethrough, and wherein the fixation mechanism is configured for anchoring its respective surgical guide foundation device to a maxillary or mandibular bone of a patient.

8. The system of claim 7, wherein the fixation mechanism comprises one or more of a fixation pin and fixation screw.

9. The system of claim 1, wherein the carrier connector extends laterally from a first side of the main body portion and the second carrier connector extends laterally from a second opposing side of the main body portion.

10. The system of claim 1, wherein each of the carrier connectors comprise a connection sleeve, the connection sleeve comprising a lengthwise passageway therethrough.

11. The system of claim 10, wherein each of the carrier connectors comprise a coupling hole, the coupling hole comprising a widthwise passageway therethrough, and wherein the coupling hole intersects with the lengthwise passageway of the connection sleeve.

12. The system of claim 1, wherein an inner facing surface of the main body portion is configured to be generally of the same contour as that of a gum tissue surface of a patient.

13. The system of claim 1, further comprising a connector bridge, wherein the connector bridge is configured to connect the first surgical guide foundation device and the second surgical guide foundation device together.

14. The system of claim 13, wherein the connector bridge is configured to engage with one of the carrier connectors of the first surgical guide foundation device and an adjacent one of the carrier connectors of the second surgical guide foundation device.

15. The system of claim 13, wherein the connector bridge comprises a crossbar portion and two connector pins positioned at opposing end portions of the crossbar, and wherein the two connector pins extend generally perpendicular relative to the crossbar portion.

16. The system of claim 13, wherein the connector bridge comprises a crossbar portion; two openings formed through opposing end portions of the crossbar portion; and removable bridge pins, wherein the bridge pins are configured to be inserted at least partially through the openings.

17. The system of claim 1 wherein the guide component comprises a component body portion and one or more component connectors.

18. The system of claim 17 wherein the component connectors are spaced about an outer edge portion of the component body portion.

19. The system of claim 17, wherein the component connectors each comprise a coupling hole, the coupling hole comprising a widthwise passageway therethrough.

20. The system of claim 19, wherein the carrier connectors and component connectors are configured such that when engaged the component connectors seat into voids formed in corresponding ones of the carrier connectors, wherein the carrier connectors comprise coupling holes and wherein when the component connectors are seated into corresponding carrier connectors, their respective coupling holes are substantially aligned.

21. The system of claim 20, wherein the guide component is securable to one or more of the surgical guide foundation devices via one or more coupling mechanisms inserted through their substantially aligned coupling holes.

22. The system of claim 1, wherein the guide component is configured to facilitate a dental procedure.

23. The system of claim 1, wherein the guide component comprises any of a surgical guide, an alignment guide, or a prosthetic.

24. The system of claim 1, wherein the guide component comprises a hingeable component comprising one or more hinged members, wherein the one or more hinged members are configured to engage with one or more of the surgical guide foundation devices via one or more of the carrier connectors.

25. The system of claim 24, wherein the one or more hinged members comprise one or more hinge member carrier connectors, and wherein one or more component connectors are configured to be engageable with the one or more hinge member carrier connectors.

26. The system of claim 24, wherein the hingeable component further comprises a releasable component body hingeably attached to the one or more hinged members.

27. The system of claim 26, wherein the releasable component body comprises an alignment guide.

28. A surgical guide foundation device, comprising:
   a. a main body portion configured to fit the mouth of a patient;
   b. two fixation ports formed in the main body portion, wherein the two fixation ports are disposed generally adjacent to one another, and wherein each fixation port forms a passage through the main body portion; and
   c. two carrier connectors, each of the carrier connectors comprise a connection sleeve, the connection sleeve comprising a lengthwise passageway therethrough, wherein a first one of the two carrier connectors extending from a first end edge of the main body portion and a second one of the two carrier connectors extending from a second end edge of the main body portion, and wherein the first one of the two carrier connectors is generally adjacent a first one of the two adjacent fixation ports and a second one of the two carrier connectors is generally adjacent to a second one of the two adjacent fixation ports.

29. The device of claim 28, further comprising protrusions formed on an inner facing surface of the main body portion and extending in a generally perpendicular direction therefrom.

30. The device of claim 29, wherein the protrusions comprise generally conical shaped bodies tapering to a point at a distal end.

31. The device of claim 29, wherein one or more of the protrusions are disposed proximate to one or more of the fixation ports.

32. The device of claim 29, wherein the protrusions are localized in groups proximal to one or more of the fixation ports.

33. The device of claim 29, wherein the protrusions comprise a length, such that when the foundation device is seated on a patient's gum tissue, the distal most ends of the protrusions are at a depth slightly less than or equal to a thickness of the patient's gum tissue.

34. The device of claim 28, wherein each of the fixation ports are configured to receive a fixation mechanism therethrough, and wherein the fixation mechanism is configured for anchoring its respective foundation device to a maxillary or mandibular bone of a patient.

35. The device of claim 34, wherein the fixation mechanism comprises one or more of a fixation pin and fixation screw.

36. The device of claim 28, wherein each of the carrier connectors comprise a coupling hole, the coupling hole comprising a widthwise passageway therethrough, and wherein the coupling hole intersects with the lengthwise passageway of the connection sleeve.

37. The device of claim 28, wherein an inner facing surface of the main body portion is configured to be generally of the same contour as that of a gum tissue surface of a patient.

38. The device of claim 28, wherein each of the carrier connectors are configured to be engageable with a guide component.

39. The device of claim 38, wherein the guide component comprises:
   a. a component body; and
   b. component connectors spaced about an outer edge portion of the guide body, wherein the component connectors are configured to engage with the carrier connectors.

40. The device of claim 38, wherein the guide component comprises a hingeable component comprising one or more hinged members, wherein the one or more hinged members are configured to be engageable with the one or more carrier connectors.

41. A method of making a surgical guide foundation system component, the method comprising:
   a. modeling a patient's mouth;
   b. planning a desired surgical procedure based on the model of the patient's mouth;
   c. designing and fabricating at least one surgical guide foundation device based on the planned surgical procedure, wherein the designed surgical guide foundation device comprises
      i. a main body portion;
      ii. two fixation ports formed in the main body portion, wherein the two fixation ports are disposed generally adjacent to one another, and wherein each fixation port forms a passage through the main body portion; and
      iii. two carrier connectors, each of the carrier connectors comprise a connection sleeve, the connection sleeve comprising a lengthwise passageway therethrough, wherein a first one of the two carrier connectors extending from a first end edge of the main body portion and a second one of the two carrier connectors extending from a second end edge of the main body portion, and wherein the first one of the two carrier connectors is generally adjacent a first one of the two adjacent fixation ports and a second one of the two carrier connectors is generally adjacent to a second one of the two adjacent fixation ports.

42. The method of claim 41, wherein the surgical guide foundation device further comprises protrusions formed on an inner facing surface of the main body portion and extending in a generally perpendicular direction therefrom.

43. The method of claim 42, wherein the protrusions comprise generally conical shaped bodies tapering to a point at a distal end.

44. The method of claim 42, wherein the protrusions comprise a length, such that when the foundation device is seated on a patient's gum tissue, the distal most ends of the protrusions are at a depth slightly less than or equal to a thickness of the patient's gum tissue.

45. The method of claim 41, further including designing and fabricating one or more corresponding guide components as required based on the planned surgical procedure.

46. The method of claim 45, wherein the one or more guide components are configured to be engageable with the foundation guide.

47. A method of using a surgical guide foundation system, the method comprising:
   a. positioning one or more surgical guide foundation devices in a patient's oral cavity, wherein the one or more surgical guide foundation devices each comprise
      i. a main body portion;
      ii. two fixation ports formed in the main body portion, wherein the two fixation ports are disposed generally adjacent to one another, and wherein each fixation port forms a passage through the main body portion; and
      iii. two carrier connectors, each of the carrier connectors comprise a connection sleeve, the connection sleeve comprising a lengthwise passageway therethrough, wherein a first one of the two carrier connectors extending from a first end edge of the main body portion and a second one of the two carrier connectors extending from a second end edge of the main body portion, and wherein the first one of the two carrier connectors is generally adjacent a first one of the two adjacent fixation ports and a second one of the two carrier connectors is generally adjacent to a second one of the two adjacent fixation ports;
   b. seating and fixating the one or more surgical guide foundation devices on the patient's gum tissues;
   c. positioning and securing a guide component to the one or more surgical guide foundation devices as required for a planned procedure;
   d. conducting the planned procedure; and
   e. removing the guide component and the one or more surgical guide foundation devices from the patient's oral cavity.

48. The method of claim 47, wherein the surgical guide foundation device further comprises protrusions formed on an inner facing surface of the main body portion and extending in a generally perpendicular direction therefrom.

49. The method of claim 48, wherein the protrusions comprise generally conical shaped bodies tapering to a point at a distal end.

50. The method of claim 48, wherein the protrusions comprise a length, such that when the foundation device is seated on a patient's gum tissue, the distal most ends of the protrusions are at a depth slightly less than or equal to a thickness of the patient's gum tissue.

* * * * *